(12) United States Patent
Chu et al.

(10) Patent No.: US 6,756,359 B2
(45) Date of Patent: Jun. 29, 2004

(54) C12 MODIFIED ERYTHROMYCIN MACROLIDES AND KETOLIDES HAVING ANTIBACTERIAL ACTIVITY

(75) Inventors: Daniel Chu, Santa Clara, CA (US); Matthew Burger, Albany, CA (US); Xiaodong Lin, Walnut Creek, CA (US); Georgia Law Carroll, Walnut Creek, CA (US); Jacob Plattner, Berkeley, CA (US); Alice Rico, Berkeley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/190,431

(22) Filed: Jul. 3, 2002

(65) Prior Publication Data

US 2003/0125266 A1 Jul. 3, 2003

Related U.S. Application Data

(60) Provisional application No. 60/302,825, filed on Jul. 3, 2001.

(51) Int. Cl.[7] .................. A61K 31/70; C07H 17/08
(52) U.S. Cl. .................. 514/29; 536/7.2; 536/7.3; 536/7.4
(58) Field of Search .................. 514/29; 536/7.2, 536/7.3, 7.4

(56) References Cited

U.S. PATENT DOCUMENTS

| | | | |
|---|---|---|---|
| 5,656,607 A | 8/1997 | Agouridas et al. | |
| 5,750,510 A | 5/1998 | Elliott et al. | |
| 5,866,549 A | 2/1999 | Or et al. | |
| 6,063,561 A | 5/2000 | Katz et al. | |
| 6,075,011 A | 6/2000 | Or et al. | |

FOREIGN PATENT DOCUMENTS

| | | |
|---|---|---|
| EP | 0 303 471 A2 | 2/1989 |
| EP | 0 945 459 A1 | 9/1999 |
| WO | WO98/42720 A1 | 10/1998 |
| WO | WO99/35157 A1 | 7/1999 |

OTHER PUBLICATIONS

Hauske, J.R., et al., "Aglycon Modifications of Erythromycin A: Regiospecific and Sterospecific Elaboration of the C–12 Position," *J. Org. Chem.* 52(20):4622–4625, 1987.

Jacobson, J.R., et al., "Precursor–Directed Biosynthesis of 12-Ethyl Erythromycin," *Bioorganic & Medicinal Chemistry* 6:1171–1177, 1998.

Lartey, P.A., et al., "Synthesis and Activity of C–21 Alkylamino Derivatives of (9R)–Erythromycylamine," *Journal of Antibiotics* 45(3):380–385, 1992.

*Primary Examiner*—Elli Peselev
(74) *Attorney, Agent, or Firm*—Dennis K. Shelton; Steven W. Collier; Robert P. Blackburn

(57) ABSTRACT

Antimicrobial macrolide compounds are provided having formulas II:

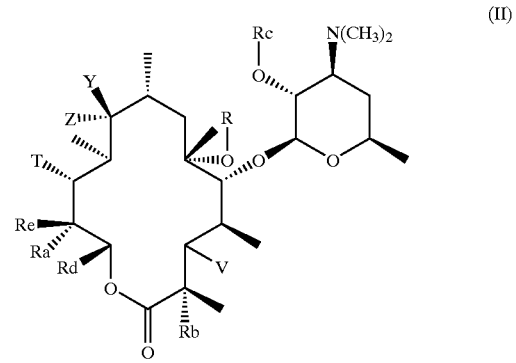

as well as pharmaceutically acceptable salts, esters or prodrugs thereof; pharmaceutical compositions comprising such compounds; methods of treating bacterial infections by the administration of such compounds; and processes for the preparation of the compounds.

10 Claims, No Drawings

C12 MODIFIED ERYTHROMYCIN MACROLIDES AND KETOLIDES HAVING ANTIBACTERIAL ACTIVITY

This application claims the benefit of U.S. Provisional Application Serial No. 60/302,825 filed Jul. 3, 2001.

FIELD OF THE INVENTION

This invention relates to novel semi-synthetic macrolides and ketolides having antibacterial activity, to pharmaceutical compositions comprising these compounds, and to a medical method of treatment. More particularly, this invention concerns to C12 modified erythromycin macrolides and ketolide derivatives, compositions containing these compounds, methods of producing the compounds and methods of treating bacterial infections.

BACKGROUND OF THE INVENTION

Erythromycins A through D, represented by formula (I):

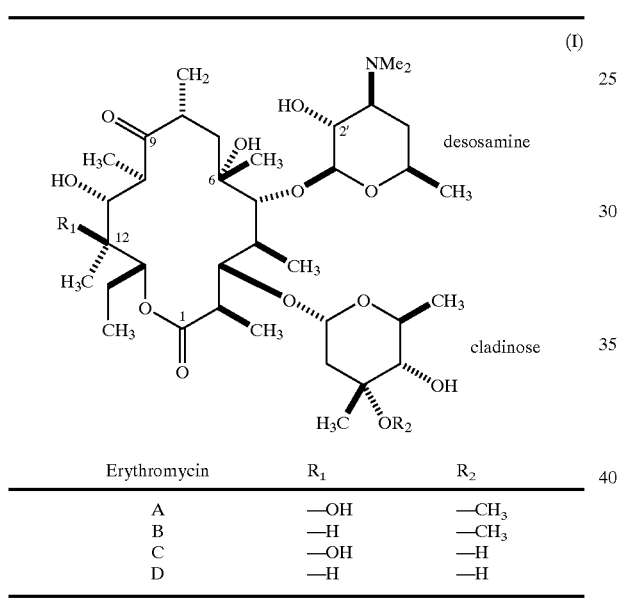

| Erythromycin | $R_1$ | $R_2$ |
|---|---|---|
| A | —OH | —$CH_3$ |
| B | —H | —$CH_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess Gram-negative activity, or which possess unexpected selectivity against target microorganisms. Consequently, numerous investigators have prepared chemical derivatives of erythromycin in an attempt to obtain analogs having modified or improved profiles of antibiotic activity. For example, the compound 6-OMe erythromycin A, or clarithromycin, has found widespread use. However, even this compound is beginning to lose its effectiveness and other erythromycin derivatives having improved activity are needed. Other 6-O-substituted erythromycin compounds have also been proposed for this purpose. For example, PCT application WO 92/09614, published Jun. 11, 1992, discloses tricyclic 6-O-methylerythromycin A derivatives. U.S. Pat. No. 5,444,051 discloses 6-O-substituted-3-oxoerythromycin A derivatives in which the substituents are selected from alkyl, —$CONH_2$, —CONHC(O)alkyl and —$CONHSO_2$ alkyl. PCT application WO 97/10251, published Mar. 20, 1997, discloses 6-O-methyl 3-descladinose erythromycin derivatives. European Patent Application 596802, published May 11, 1994, discloses bicyclic 6-O-methyl-3-oxoerythromycin A derivatives.

More recently, a class of 3-O ketolide erythromycin derivatives have been disclosed in U.S. Pat. Nos. 6,147,197 and 5,635,485. Representative lead compounds in this class include, for example ABT-773 disclosed in U.S. Pat. No. 6,147,197 and telithromycin disclosed in U.S. Pat. No. 5,635,485. The structures of these compounds are as follows:

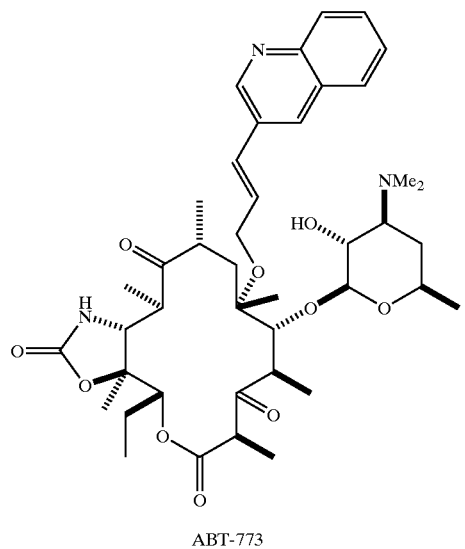

ABT-773

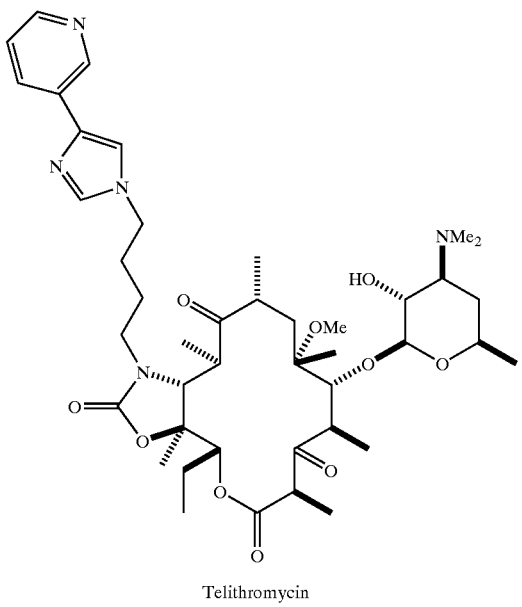

Telithromycin

Other modifications that have shown promise include modifications at C2, including, for example, those shown in U.S. Pat. No. 6,124,269 and International Application Publication No. WO 00/69875, the disclosures of which are incorporated herein by reference.

Despite much activity in designing 14-membered macrolide derivatives, few examples of modifications at C12 exist, especially with regards to the C12–C21 bond. U.S. Pat. No. 4,857,641 (Hauske) discloses that when the C9–C11 erythromycin positions are protected as cyclic thiocarbonates, the C12 OH can be selectively activated and eliminated over the C6 OH to give an exocyclic double bond, and the thiocarbonate protecting group can then be removed reductively with NaBH. Stereoselective dihydroxylation is disclosed as the sole olefin modification. U.S. Pat. No. 5,217,960 (Lartey), discloses that the above C12 exocyclic alkene formation of Hauske can also be effected with a protected amino group at C9 and a formate ester at C11. However, elimination at C6 did occur, suggesting that the C9 amino substituent does not provide as great a steric impediment to C6 OH activation as does the Hauske C9 thiocarbonate. The desired C12 olefin could be separated and isolated, and is disclosed as participating in stereoselective epoxidation, dihydroxylation, and hydroboration reactions, wherein all reagents attack the same face of the olefin (top face if the macrolide is drawn as shown above). Of these products, only the epoxide is disclosed as being derivatized by ring opening with alkyl amines. (Ring opening with other nucleophiles is suggested, but only generally, and no specific examples are given). It should be noted that the C12 modified compounds of Hauske and Lartey exhibit minimal antibacterial activity.

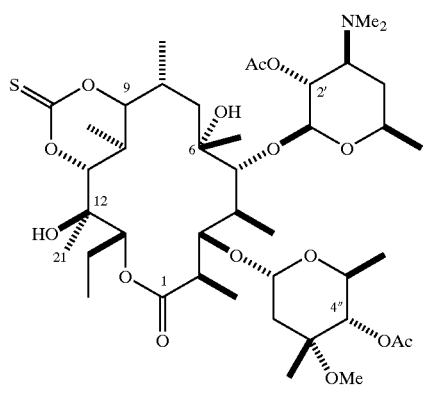

Hauske olefin precursor

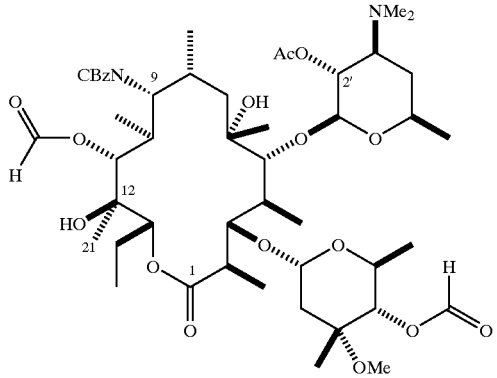

Lartey olefin precursor

Efficient strategies for synthetic modifications involving the C12–C21 bond rely, in part, on the ability to selectively differentiate between the aglycon alcohols of erythromycin A. The differentiation appears to be dependent upon the identity of the C9 substituent, although the order and degree of selectivity can be difficult to predict. For example, the reactivity of the aglycon alcohols generally decrease when comparing C11 to C6 to C12. However as seen in the Hauske and Lartey examples above, the C12 OH can become more reactive than the C6 OH if the C9 ketone is modified in a particular manner. Alternatively when the C9 ketone is functionalized as various oximes (see U.S. Pat. No. 6,147,195), the C6 OH can be selectively alkylated over both C12 and C11. Finally, it has been shown that when erythromycin A is treated with $NaBH_4$ to form a bis-erythromycin A borate ester followed by alkylation with MeI, selective methylation occurs at C12 over both C11 and C6 (JOC, 1999, p. 2107).

SUMMARY OF THE INVENTION

The present invention provides novel 14 membered macrolide and ketolide antibiotics containing C12 modifications, useful common intermediates for introducing C12 modifications, methods for their synthesis, and methods of use of the compounds for the treatment and/or prophylaxis of diseases, especially bacterial infections.

In one embodiment, the present invention provides compounds of the following formula (II):

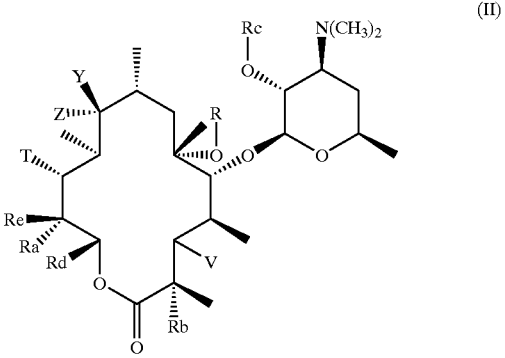

(II)

or a pharmaceutically acceptable salt, ester or prodrug thereof, wherein

A. V is —$OCOR_x$, carbonyl, or a cladinose moiety of the formula:

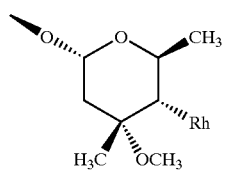

wherein $R_x$ is H, alkyl, —O-alkyl, —N(H)-alkyl, or —N(alkyl)$_2$;

B. either Y and Z taken together define a group X, wherein X is selected from the group consisting of
(1) =O,
(2) =N—OH,
(3) =N—O—$R^1$ where $R^1$ is selected from the group consisting of
(a) $C_1$–$C_{12}$-alkyl,
(b) $C_1$–$C_{12}$-alkyl substituted with alkoxy,
(c) $C_1$–$C_{12}$-alkyl substituted with aryl,
(d) $C_1$–$C_{12}$-alkyl substituted with substituted aryl,
(e) $C_1$–$C_{12}$-alkyl substituted with heteroaryl,
(f) $C_1$–$C_{12}$-alkyl substituted with substituted heteroaryl,
(g) $C_3$–$C_{12}$-cycloalkyl, and
(h) —Si—($R^2$)($R^3$)($R^4$) wherein $R^2$, $R^3$, $R^4$ are each independently selected from $C_1$–$C_{12}$-alkyl and aryl; and (4) =N—O—C(R$^5$)(R$^6$)—O—R$^1$ wherein R$^1$ is as previously defined and R$^5$ and R$^6$ are each independently selected from the group consisting of
(a) hydrogen,
(b) $C_1$–$C_{12}$-alkyl,
(c) $C_1$–$C_{12}$-alkyl substituted with aryl,
(d) $C_1$–$C_{12}$-alkyl substituted with substituted aryl,
(e) $C_1$–$C_{12}$-alkyl substituted with heteroaryl, and
(f) $C_1$–$C_{12}$-alkyl substituted with substituted heteroaryl;
or R$^5$ and R$^6$ taken together with the atoms to which they are attached form a $C_3$–$C_{12}$-cycloalkyl ring;
or
Y and Z are =N— when taken together with T to form a moiety of the structure:

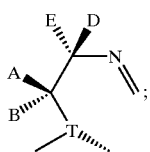

or
one of Y and Z is hydrogen and the other is selected from a group consisting of
(1) hydroxy,
(2) protected hydroxy, and
(3) NR$^7$R$^8$ wherein R$^7$ and R$^8$ are independently selected from hydrogen and alkyl, subsituted alkyl, or R$^7$ and R$^8$ are taken with the nitrogen atom to which they are connected to form a 3- to 7-membered ring which, when the ring is a 5- to 7-membered ring, may optionally contain a hetero function selected from the group consisting of —O—, —NH, —N($C_1$–$C_6$-alkyl)-, —N(aryl)-, —N(aryl-$C_1$–$C_6$-alkyl-)-, —N(substituted-aryl-$C_1$–$C_6$-alkyl-)-, —N(heteroaryl)-, —N(heteroaryl-$C_1$–$C_6$-alkyl-)-, —N(substituted-heteroaryl-$C_1$–$C_6$-alkyl-)-, and —S— or S(O)$_n$— wherein n is 1 or 2;
C. T is selected from the group consisting of —O—Rg, —O—, —NH—, N(W—Rf)—, and —CH(W—Rf)—, wherein
(1) W is absent or is selected from the group consisting of —O—, NH—CO—, —N=CH—, —NH— and —CH$_2$—; and
(2) Rf is selected from the group consisting of
(a) hydrogen,
(b) alkyl, alkenyl or alkynyl,
(c) alkyl, alkenyl or alkynyl substituted with one or more substituents selected from the group consisting of
(i) aryl,
(ii) substituted aryl,
(iii) heteroaryl,
(iv) substituted heteroaryl,
(v) hydroxy,
(vi) $C_1$–$C_6$-alkoxy,
(vii) —NR$^7$R$^8$ wherein R$^7$ and R$^8$ are as defined previously, and
(viii) —M—R$^9$, wherein M is selected from the group consisting of:
(a) —C(O)—NH—,
(b) —NH—C(O)—,
(c) —NH—,
(d) —N=,
(e) —N(CH$_3$)—,
(f) —NH—C(O)—O—,
(g) —NH—C(O)—NH—,
(h) —O—C(O)—NH—,
(i) —O—C(O)—O—,
(j) —O—,
(k) —S(O)$_n$—, wherein n is 0, 1 or 2,
(l) —C(O)—O—,
(m) —O—C(O)—,
(n) —C(O)—; and
and R$^9$ is selected from the group consisting of:
(a) alkyl optionally substituted with a substituent selected from the group consisting of
(aa) aryl,
(bb) substituted aryl,
(cc) heteroaryl, and
(dd) substituted heteroaryl,
(b) aryl,
(c) substituted aryl,
(d) heteroaryl,
(e) substituted heteroaryl, and
(f) heterocycloalkyl,
D. R is selected from the group consisting of
(1) hydrogen;
(2) methyl substituted with a moiety selected from the group consisting of
(a) CN,
(b) F,
(c) —CO$_2$R$^{10}$ wherein R$^{10}$ is $C_1$–$C_3$-alkyl or aryl substituted $C_1$–$C_3$-alkyl, or heteroaryl substituted $C_1$–$C_3$-alkyl,
(d) —S(O)$_n$R$^{10}$—, wherein n is 0, 1 or 2 and R$^{10}$ is as previously defined,
(e) —NH—C(O) R$^{10}$, wherein R$^{10}$ is as previously defined,
(f) —NH—C(O)N R$^{11}$ R$^{12}$ wherein R$^{11}$ and R$^{12}$ are independently selected from hydrogen, $C_1$–$C_3$-alkyl, $C_1$–$C_3$-alkyl substituted with aryl, substituted aryl, heteroaryl, substituted heteroaryl,
(g) aryl,
(h) substituted aryl,
(i) heteroaryl, and
(j) substituted heteroaryl;
(3) alkyl;
(4) $C_2$–$C_{12}$-alkyl substituted with one or more substituents selected from the group consisting of
(a) halogen,
(b) hydroxy,
(c) $C_1$–$C_3$-alkoxy,
(d) $C_1$–$C_3$-alkoxy-$C_1$–$C_3$-alkoxy,
(e) oxo,
(f) O—SO$_2$-(substituted $C_1$–$C_6$-alkyl),
(g) —N$_3$,
(h) —CHO,
(i) —NR$^{13}$R$^{14}$ wherein R$^{13}$ and R$^{14}$ are selected from the group consisting of
(i) hydrogen,
(ii) C1–C12-alkyl,
(iii) substituted C1–C12-alkyl,
(iv) C2–C12-alkenyl,
(v) substituted C2–C12-alkenyl,
(vi) C2–C12-alkynyl,
(vii) substituted C2–C12-alkynyl,
(viii) aryl,
(ix) C3–C8-cycloalkyl,
(x) substituted C3–C8-cycloalkyl,
(xi) substituted aryl,
(xii) heterocycloalkyl, (xiii) substituted heterocycloalkyl,
(xiv) C1–C12-alkyl substituted with aryl,
(xv) C1–C12-alkyl substituted with substituted aryl,
(xvi) C1–C12-alkyl substituted with heterocycloaryl,
(xvii) C1–C12-alkyl substituted with substituted heterocycloaryl,
(xviii) C1–C12-alkyl substituted with C3–C8-cycloalkyl,
(xix) C1–C12-alkyl substituted with substituted C3–C8-cycloalkyl,
(xx) heteroaryl,
(xxi) substituted heteroaryl,
(xxii) C1–C12-alkyl substituted with heteroaryl, and
(xxiii) C1–C12-alkyl substituted with substituted heteroaryl;

or $R^{13}$ and $R^{14}$ are taken together with the atom to which they are attached form a 3- to 10-membered heterocycloalkyl ring which may optionally be substituted with one or more substituents independently selected from the group consisting of
(i) halogen,
(ii) hydroxy,
(iii) C1–C3-alkoxy,
(iv) C1–C3-alkoxy-C1–C3-alkoxy,
(v) oxo,
(vi) C1–C3-alkyl,
(vii) halo-C1–C3-alkyl, and
(viii) C1–C3-alkoxy-C1–C3-alkyl;
(j) —$CO_2R^{10}$ wherein $R^{10}$ is as previously defined,
(k) —$C(O)R^{11}R^{12}$ wherein $R^{11}$ and $R^{12}$ are as previously defined,
(l) =N—O—$R^{10}$ wherein $R^{10}$ is as previously defined,
(m) —CN,
(n) —O—$S(O)_nR^{10}$ wherein n is 0, 1 or 2 and $R^{10}$ is as previously defined,
(o) aryl,
(p) substituted aryl,
(q) heteroaryl,
(r) substituted heteroaryl,
(s) $C_3$–$C_8$-cycloalkyl,
(t) substituted $C_3$–C8-cycloalkyl,
(u) $C_1$–$C_{12}$-alkyl substituted with heteroaryl,
(v) heterocycloalkyl,
(w) substituted heterocycloalkyl,
(x) —NH—$C(O)R^{10}$ wherein $R^{10}$ is as previously defined,
(y) —NH—$C(O)NR^{11}R^{12}$ wherein $R^{11}$ and $R^{12}$ are as previously defined,
(z) =N—$NRC^{13}R^{14}$ wherein $R^{13}$ and $R^{14}$ are as previously defined,
(aa) =N—$R^9$ wherein $R^9$ is as previously defined,
(bb) =N—NH—$C(O)R^{10}$ wherein $R^{10}$ is as previously defined, and
(cc) =N—NH—$C(O)NR^{11}R^{12}$ wherein $R^{11}$ and $R^{12}$ are as previously defined;
(5) $C_3$-alkenyl substituted with a moiety selected from the group consisting of
(a) halogen,
(b) —CHO,
(c) —$CO_2R^{10}$ wherein $R^{10}$ is as previously defined,
(d) —$C(O)NR^{11}R^{12}$ wherein $R^{11}$ and $R^{12}$ are as previously defined,
(e) —$C(O)R^9$ wherein $R^9$ is as previously defined,
(f) —CN,
(g) aryl,
(h) substituted aryl,
(i) heteroaryl,
(j) substituted heteroaryl,
(k) $C_3$–$C_8$-cycloalkyl, and
(l) $C_1$–$C_{12}$-alkyl substituted with heteroaryl;
(6) $C_4$–$C_{10}$-alkenyl;
(7) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^{10}$ wherein $R^{10}$ is as previously defined,
(f) —$C(O)NR^{11}R^{12}$ wherein $R^{11}$ and $R^{12}$ are as previously defined,
(g) $NR^{13}R^{14}$ wherein $R^{13}$ and $R^{14}$ are as previously defined,
(h) =N—O—$R^{10}$ wherein $R^{10}$ is as previously defined,
(i) —CN,
(j) —O—$S(O)_nR^{10}$ wherein n is 0, 1 or 2 and $R^{10}$ is as previously defined,
(k) aryl,
(l) substituted aryl,
(m) heteroaryl,
(n) substituted heteroaryl,
(o) $C_3$–$C_8$-cycloalkyl,
(p) $C_1$–$C_{12}$-alkyl substituted with substituted heteroaryl,
(q) —NH—$C(O)R^{10}$ wherein $R^{10}$ is as previously defined,
(r) —NH—$C(O)NR^{11}R^{12}$ wherein $R^{11}$ and $R^{12}$ are as previously defined,
(s) =N—$NR^{13}R^{14}$ wherein $R^{13}$ and $R^{14}$ are as previously defined,
(t) =N—$R^9$ wherein $R^9$ is as previously defined,
(u) =N—NH—$C(O)R^{10}$ wherein $R^{10}$ is as previously defined, and
(v) =N—NH—$C(O)NR^{11}R^{12}$ wherein $R^{11}$ and $R^{12}$ are as previously defined;
(8) $C_3$–$C_{10}$-alkynyl;
(9) $C_3$–$C_{10}$-alkynyl substituted with one or more substituents selected from the group consisting of
(a) trialkylsilyl,
(b) aryl,
(c) substituted aryl,
(d) heteroaryl, and
(e) substituted heteroaryl; and
(10) $C(O)NR^7R^8$ where $R^7$ and $R^8$ are previously defined;

E. Ra is selected from a group consisting of
(1) hydrogen;
(2) $C_1$ alkyl further substituted with a one or more substituents selected from a group consisting of
(a) hydroxyl,
(b) halogen,
(c) thiol, which can be further subsituted with and alkyl or subsituted alkyl group
(d) $C_1$–$C_{12}$-alkyl which can be further substituted by halogen, hydroxyl alkoxy, or amino,
(e) $C_1$–$C_3$-alkoxy,
(f) $C_1$–$C_3$-thioalkoxy,
(g) amino,
(h) alkylamino,
(i) dialkylamino, (j) nitrile,
(k) nitro,
(l) amido,
(m) carboxylic acid,
(n) ester,
(o) azido,
(p) =N—O—$R^{10}$, wherein $R^{10}$ is as previously defined,
(q) =N—$R^9$, wherein $R^9$ is as previously defined,
(r) =N—$NR^{13}R^4$, wherein $R^{13}$ and $R^{14}$ are as previously defined,
(s) =N—NH—C(O)$R^{10}$, wherein $R^{10}$ is as previously defined, and
(t) =N—NH—C(O)$NR^{11}R^{12}$, wherein $R^{11}$ and $R^{12}$ are as previously defined;
(3) $C_2$–$C_4$-alkenyl, which can be further substituted With $C_1$–$C_{12}$-alkyl and one or more halo groups;
(4) —$C_2$–$C_4$-alkynyl, which can be further substituted with $C_1$–$C_{12}$-alkyl and one or more halo groups;
(5) aryl, which can be further substituted with $C_1$–$C_{12}$-alkyl and one or more halo groups;
(6) CHO;
(7) —$CO_2H$;
(3) —CN;
(9) —$CO_2R^{10}$, wherein $R^{10}$ is as previously defined;
(10) —C(O)$NR^{11}R^{11}R^{12}$, wherein $R^{11}$ and $R^{12}$ are as previously defined;
(11) —C(O)$R^9$ wherein $R^9$ is as previously defined; and
(12) thioester;
with the proviso that in formula II, when Z is amino or substituted amino, then Ra can not be —$CH_2OH$, —$NR^4R^6$, or —(CH2)n $NR^4R^6$, wherein $R^4$ and $R^6$ are selected from the group consisting of hydrogen, loweralkyl and aralkyl;
F. Rb is hydrogen, halogen or $C_1$–$C_{12}$-alkyl which can be further substituted by one or more halo groups, or Rb can be taken together with V to form a double bond;
G. Rc is hydrogen or a hydroxy protecting group;
H. Rd is selected from the group consisting of
(1) $C_1$–$C_{12}$-alkyl,
(2) $C_1$–$C_{12}$-alkyl substituted with one or more substituents selected from the group consisting of
(a) halogen,
(b) hydroxy, and
(c) $C_1$–$C_3$-alkoxy,
(3) $C_3$–$C_7$-cycloalkyl,
(4) $C_2$–$C_4$-alkenyl, and
(5) $C_2$–$C_4$-alkynyl;
I. Re is hydroxyl, amino, or alkylamino; or Re and Ra may be taken together to form an epoxide, a carbonyl, an olefin, or a subsituted olefin; or Re and Ra when taken together with the atom to which they are attached form a Spiro ring consisting of $C_3$–$C_7$-carbocyclic, carbonate or carbamate wherein the nitrogen atom can be unsubstituted or substituted with an alkyl group; or Re and T when taken together with the carbon atoms to which they are attached form a ring of the structure:

wherein L is methylene or carbonyl and P is —O—, —NH— or —$NR^1$— wherein $R^1$ is as previously defined; provided that when L is methylene, T is —O— and P is —O—;

J. Rg is hydrogen, R where R is as previously defined; or Rg may be taken together with Y, separated by a linker of the formula —C(=O)— or —C($CH_3$)$_2$—, to form a cyclic moiety;
K. Rh is selected from the group consisting of
(1) hydrogen,
(2) —ORj, where Rj is hydrogen or a hydroxy protecting group,
(3) halogen,
(4) OC(O)NHRi wherein Ri is selected from a group consisting of
(a) $C_1$–$C_4$ alkyl,
(b) $C_1$–$C_4$ aminoalkyl where the amino group is substituted with one or two groups selected from
(i) $C_1$–$C_4$ alkyl,
(ii) $C_1$–$C_4$ alkyl substituted with halogen,
(iii) $C_1$–$C_4$ alkyl substituted with alkoxy,
(iv) $C_1$–$C_4$ alkyl substituted with hydroxyl,
(v) $C_1$–$C_4$ alkyl substituted with aryl,
(vi) $C_1$–$C_4$ alkyl substituted with substituted aryl,
(vii) $C_1$–$C_4$ alkyl substituted with heteroaryl,
(viii) $C_1$–$C_4$ alkyl substituted with substituted heteroaryl,
(ix) $C_3$–$C_6$ cycloalkyl; and
L. A, B, D, and E are independently selected from the group consisting of:
(1) hydrogen;
(2) $C_1$–$C_6$-alkyl optionally substituted with one or more substituents selected from the group consisting of:
(a) aryl,
(b) substituted aryl,
(c) heteroaryl,
(d) substituted heteroaryl,
(e) heterocycloalkyl,
(f) hydroxy,
(g) $C_1$–$C_6$-alkoxy,
(h) halogen selected from the group consisting of Br, Cl, F or I, and
(i) $NR^7R^8$ where $R^7$ and $R^8$ are as previously defined;
(3) $C_3$–$C_7$-cycloalkyl;
(4) aryl;
(5) substituted aryl;
(6) heteroaryl;
(7) substituted heteroaryl;
(8) heterocycloalkyl; and
(9) a group selected from option (2) above further substituted with —M—$R^9$, wherein M and $R^9$ are as previously defined; or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2, —C(O)—NH, —C(O)—$NR^{12}$, wherein $R^{12}$ is as previously defined, —NH—C(O)—, —$NR^{12}$—C(O)—, wherein $R^{12}$ is as previously defined, and —C(=NH)—NH—; with the provision that at least two of A, B, D, and E are hydrogen.

In another embodiment, the present invention provides compounds of formula (II) above having the structure of the following formula (III):

(III)

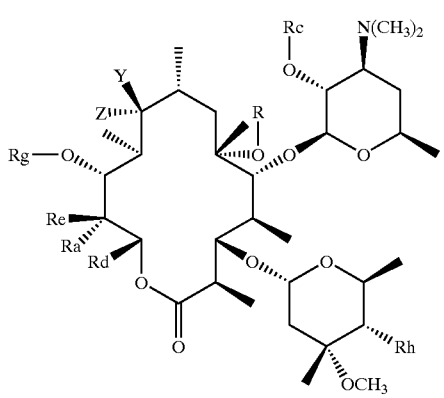

or a pharmaceutically acceptable salt, ester or prodrug thereof, wherein Y, Z, R, Ra, Rc, Rd, Re, Rg and Rh have the meanings defined above.

In another embodiment, the present invention provides compounds of formula (II) above having the structure of the following formula (IV):

(IV)

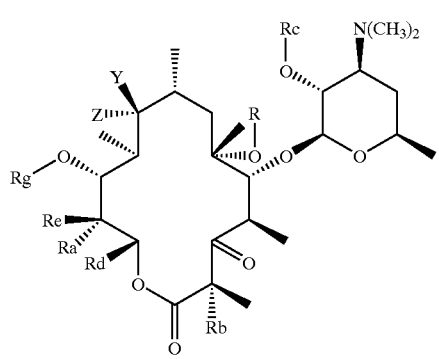

or a pharmaceutically acceptable salt, ester or prodrug thereof, wherein Y, Z, R, Ra, Rb, Rc, Rd, Re, and Rg have the meanings defined above.

In another embodiment, the present invention provides compounds of formula (II) above having the structure of the following formula (V):

(V)

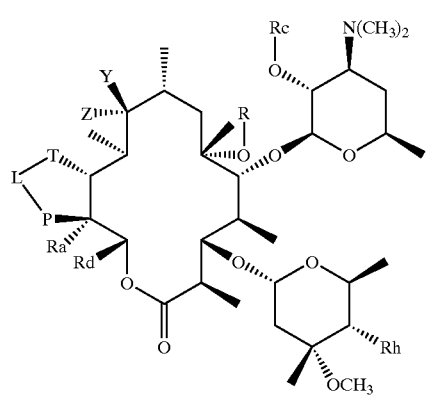

or a pharmaceutically acceptable salt, ester or prodrug thereof, wherein L, P, T, Y, Z, R, Ra, Re, Rd, and Rh have the meanings defined above.

In another embodiment, the present invention provides compounds of formula (II) above having the structure of the following formula (VI):

(VI)

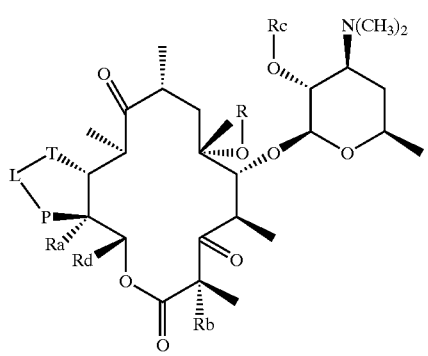

or a pharmaceutically acceptable salt, ester or prodrug thereof, wherein L, P, T, R, Ra, Rb, Rc, and Rd have the meanings defined above.

In another embodiment, the present invention provides compounds of formula (II) above having the structure of the following formula (VII):

(VII)

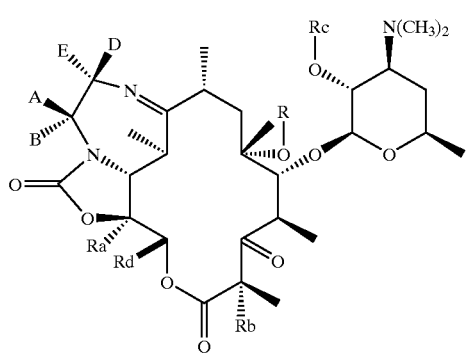

or a pharmaceutically acceptable salt, ester or prodrug thereof, wherein A, B, D, E, R, Ra, Rb, Rc, and Rd have the meanings defined above.

In another embodiment, the present invention provides compounds of formula (II) above having the structure of the following formula (VIII):

(VIII)

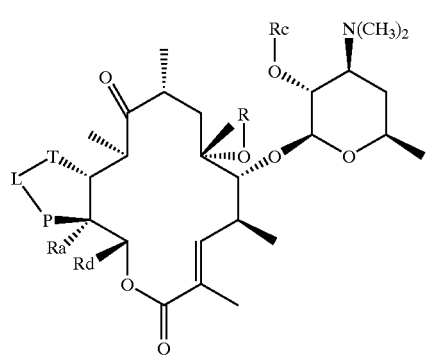

or a pharmaceutically acceptable salt, ester or prodrug thereof, wherein L, P, T, R, Ra, Rc, and Rd have the meanings defined above.

The present invention also provides pharmaceutical compositions which comprise a therapeutically effective amount of a compound as defined above in combination with a pharmaceutically acceptable carrier.

The invention further relates to methods of treating bacterial infections in a host mammal in need of such treatment comprising administering to a mammal in need of such treatment a therapeutically effective amount of a compound of the invention as defined above.

In a further aspect of the present invention are provided processes for the preparation of macrolide derivatives of Formulas (II), (III), (IV), (V), (VI), (VII) and (VIII), above.

DETAILED DESCRIPTION OF THE PREFERRED EMBODIMENT

In one embodiment, the present invention provides compounds of the following formula (II):

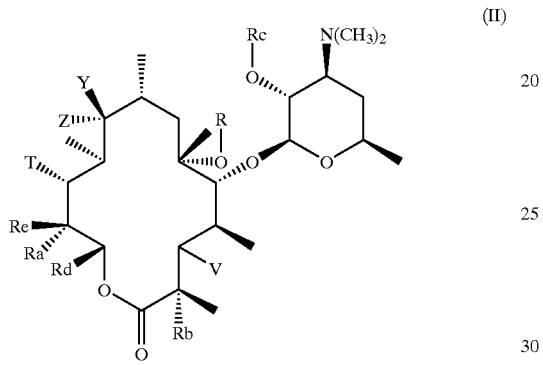

(II)

or a pharmaceutically acceptable salt, ester or prodrug thereof, wherein

A. V is —OCOR$_x$, carbonyl, or a cladinose moiety of the formula:

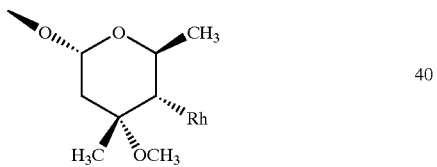

wherein R$_x$ is H, alkyl, —O-alkyl, —N(H)-alkyl, or —N(alkyl)$_2$;

B. either Y and Z taken together define a group X, wherein X is selected from the group consisting of
  (1) =O,
  (2) =N—OH,
  (3) =N—O—R$^1$ where R$^1$ is selected from the group consisting of
    (a) C$_1$–C$_{12}$-alkyl,
    (b) C$_1$–C$_{12}$-alkyl substituted with alkoxy,
    (c) C$_1$–C$_{12}$-alkyl substituted with aryl,
    (d) C$_1$–C$_{12}$-alkyl substituted with substituted aryl,
    (e) C$_1$–C$_{12}$-alkyl substituted with heteroaryl,
    (f) C$_1$–C$_{12}$-alkyl substituted with substituted heteroaryl,
    (g) C$_3$–C$_{12}$-cycloalkyl, and
    (h) —Si—(R$^2$)(R$^3$)(R$^4$) wherein R$^2$, R$^3$, R$^4$ are each independently selected from C$_1$–C$_{12}$-alkyl and aryl; and
  (4) =N—O—C(R$^5$)(R$^6$)—O—R$^1$ wherein R$^1$ is as previously defined and R$^5$ and R$^6$ are each independently selected from the group consisting of
    (a) hydrogen,
    (b) C$_1$–C$_{12}$-alkyl,
    (c) C$_1$–C$_{12}$-alkyl substituted with aryl,
    (d) C$_1$–C$_{12}$-alkyl substituted with substituted aryl,
    (e) C$_1$–C$_{12}$-alkyl substituted with heteroaryl, and
    (f) C$_1$–C$_{12}$-alkyl substituted with substituted heteroaryl;
    or R$^5$ and R$^6$ taken together with the atoms to which they are attached form a C$_3$–C$_{12}$-cycloalkyl ring; or Y and Z are =N— when taken together with T to form a moiety of the structure:

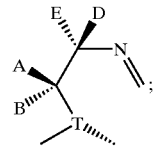

or
one of Y and Z is hydrogen and the other is selected from a group consisting of
  (1) hydroxy,
  (2) protected hydroxy, and
  (3) NR$^7$R$^8$ wherein R$^7$ and R$^8$ are independently selected from hydrogen and alkyl, subsituted alkyl, or R$^7$ and R$^8$ are taken with the nitrogen atom to which they are connected to form a 3- to 7-membered ring which, when the ring is a 5- to 7-membered ring, may optionally contain a hetero function selected from the group consisting of —O—, —NH, —N(C$_1$–C$_6$-alkyl)-, —N(aryl)-, —N(aryl-C$_1$–C$_6$-alkyl-)-, —N(substituted-aryl-C$_1$–C$_6$-alkyl-)-, —N(heteroaryl)-, —N(heteroaryl-C$_1$–C$_6$-alkyl-)-, —N(substituted-heteroaryl-C$_1$–C$_6$-alkyl-)-, and —S— or S(O)$_n$— wherein n is 1 or 2;

C. T is selected from the group consisting of —O—Rg, —O—, —NH—, N(W—Rf)—, and —CH(W—Rf)—, wherein
  (1) W is absent or is selected from the group consisting of —O—, NH—CO—, —N=CH—, —NH— and —CH$_2$—; and
  (2) Rf is selected from the group consisting of
    (a) hydrogen,
    (b) alkyl, alkenyl or alkynyl,
    (c) alkyl, alkenyl or alkynyl substituted with one or more substituents selected from the group consisting of
      (i) aryl,
      (ii) substituted aryl,
      (iii) heteroaryl,
      (iv) substituted heteroaryl,
      (v) hydroxy,
      (vi) C$_1$–C$_6$-alkoxy,
      (vii) —NR$^7$R$^8$ wherein R$^7$ and R$^8$ are as defined previously, and
      (viii) —M—R$^9$, wherein M is selected from the group consisting of:
        (a) —C(O)—NH—,
        (b) —NH—C(O)—,
        (c) —NH—,
        (d) —N=,
        (e) —N(CH$_3$)—,
        (f) —NH—C(O)—O—,
        (g) —NH—C(O)—NH—,
        (h) —O—C(O)—NH—,
        (i) —O—C(O)—O—, (j) —O—,
(k) —S(O)$_n$—, wherein n is 0, 1 or 2,
(l) —C(O)—O—,
(m) —O—C(O)—,
(n) —C(O)—; and and R$^9$ is selected from the group consisting of:
(a) alkyl optionally substituted with a substituent selected from the group consisting of
  (aa) aryl,
  (bb) substituted aryl,
  (cc) heteroaryl, and
  (dd) substituted heteroaryl,
(b) aryl,
(c) substituted aryl,
(d) heteroaryl,
(e) substituted heteroaryl, and
(f) heterocycloalkyl, D. R is selected from the group consisting of
(1) hydrogen;
(2) methyl substituted with a moiety selected from the group consisting of
  (a) CN,
  (b) F,
  (c) —CO$_2$R$^{10}$ wherein R$^{10}$ is C$_1$–C$_3$-alkyl or aryl substituted C$_1$–C$_3$-alkyl, or heteroaryl substituted C$_1$–C$_3$-alkyl,
  (d) —S(O)$_n$ R$^{10}$—, wherein n is 0, 1 or 2 and R$^{10}$ is as previously defined,
  (e) —NH—C(O) R$^{10}$, wherein R$^{10}$ is as previously defined,
  (f) —NH—C(O)N R$^{11}$R$^{12}$ wherein R$^{11}$ and R$^{12}$ are independently selected from hydrogen, C$_1$–C$_3$-alkyl, C$_1$–C$_3$-alkyl substituted with aryl, substituted aryl, heteroaryl, substituted heteroaryl,
  (g) aryl,
  (h) substituted aryl,
  (i) heteroaryl, and
  (j) substituted heteroaryl;
(3) alkyl;
(4) C$_2$–C$_{12}$-alkyl substituted with one or more substituents selected from the group consisting of
  (a) halogen,
  (b) hydroxy,
  (c) C$_1$–C$_3$-alkoxy,
  (d) C$_1$–C$_3$-alkoxy–C$_1$–C$_3$-alkoxy,
  (e) oxo,
  (f) O—SO$_2$-(substituted C$_1$–C$_6$-alkyl),
  (g) —N$_3$,
  (h) —CHO,
  (i) —NR$^{13}$R$^{14}$ wherein R$^{13}$ and R$^{14}$ are selected from the group consisting of
    (i) hydrogen,
    (ii) C1–C12-alkyl,
    (iii) substituted C1–C12-alkyl,
    (iv) C2–C12-alkenyl,
    (v) substituted C2–C12-alkenyl,
    (vi) C2–C12-alkynyl,
    (vii) substituted C2–C12-alkynyl,
    (viii) aryl,
    (ix) C3–C8-cycloalkyl,
    (x) substituted C3–C8-cycloalkyl,
    (xi) substituted aryl,
    (xii) heterocycloalkyl,
    (xiii) substituted heterocycloalkyl,
    (xiv) C1–C12-alkyl substituted with aryl,
    (xv) C1–C12-alkyl substituted with substituted aryl,
    (xvi) C1–C12-alkyl substituted with heterocycloaryl,
    (xvii) C1–C12-alkyl substituted with substituted heterocycloaryl,
    (xviii) C1–C12-alkyl substituted with C3–C8-cycloalkyl,
    (xix) C1–C12-alkyl substituted with substituted C3–C8-cycloalkyl,
    (xx) heteroaryl,
    (xxi) substituted heteroaryl,
    (xxii) C1–C12-alkyl substituted with heteroaryl, and
    (xxiii) C1–C12-alkyl substituted with substituted heteroaryl;
  or R$^{13}$ and R$^{14}$ are taken together with the atom to which they are attached form a 3- to 10-membered heterocycloalkyl ring which may optionally be substituted with one or more substituents independently selected from the group consisting of
    (i) halogen,
    (ii) hydroxy,
    (iii) C1–C3-alkoxy,
    (iv) C1–C3-alkoxy-C1–C3-alkoxy,
    (v) oxo,
    (vi) C1–C3-alkyl,
    (vii) halo-C1–C3-alkyl, and
    (viii) C1–C3-alkoxy-C1–C3-alkyl;
  (j) —CO$_2$R$^{10}$ wherein R$^{10}$ is as previously defined,
  (k) —C(O)R$^{11}$R$^{12}$ wherein R$^{11}$ and R$^{12}$ are as previously defined,
  (l) =N—O—R$^{10}$ wherein R$^{10}$ is as previously defined,
  (m) —CN,
  (n) —O—S(O)$_n$R$^{10}$ wherein n is 0, 1 or 2 and R$^{10}$ is as previously defined,
  (o) aryl,
  (p) substituted aryl,
  (q) heteroaryl,
  (r) substituted heteroaryl,
  (s) C$_3$–C$_8$-cycloalkyl,
  (t) substituted C$_3$–C$_8$-cycloalkyl,
  (u) C$_1$–C$_{12}$-alkyl substituted with heteroaryl,
  (v) heterocycloalkyl,
  (w) substituted heterocycloalkyl,
  (x) —NH—C(O)R$^{10}$ wherein R$^{10}$ is as previously defined,
  (y) —NH—C(O)NR$^{11}$R$^{12}$ wherein R$^{11}$ and R 2 are as previously defined,
  (z) =N—NR$^{13}$R$^{14}$ wherein R$^{13}$ and R$^{14}$ are as previously defined,
  (aa) =N—R$^9$ wherein R$^9$ is as previously defined,
  (bb) =N—NH—C(O)R$^{10}$ wherein R$^{10}$ is as previously defined, and
  (cc) =N—NH—C(O)NR$^{11}$R$^{12}$ wherein R$^{11}$ and R$^{12}$ are as previously defined;
(5) C$_3$-alkenyl substituted with a moiety selected from the group consisting of
  (a) halogen,
  (b) —CHO,
  (c) —CO$_2$R$^{10}$ wherein R$^{10}$ is as previously defined,
  (d) —C(O)NR$^{11}$R$^{12}$ wherein R$^{11}$ and R$^{12}$ are as previously defined,
  (e) —C(O)R$^9$ wherein R$^9$ is as previously defined,
  (f) —CN,
  (g) aryl,
  (h) substituted aryl,
  (i) heteroaryl, (j) substituted heteroaryl,
(k) $C_3$–$C_8$-cycloalkyl, and
(l) $C_1$–$C_{12}$-alkyl substituted with heteroaryl;
(6) $C_4$–$C_{10}$-alkenyl;
(7) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^{10}$ wherein $R^{10}$ is as previously defined,
(f) —$C(O)NR^{11}R^{12}$ wherein $R^{11}$ and $R^{12}$ are as previously defined,
(g) $NR^{13}R^{14}$ wherein $R^{13}$ and $R^{14}$ are as previously defined,
(h) =N—O—$R^{10}$ wherein $R^{10}$ is as previously defined,
(i) —CN,
(j) —O—$S(O)_nR^{10}$ wherein n is 0, 1 or 2 and $R^{10}$ is as previously defined,
(k) aryl,
(l) substituted aryl,
(m) heteroaryl,
(n) substituted heteroaryl,
(o) $C_3$–$C_8$-cycloalkyl,
(p) $C_1$–$C_{12}$-alkyl substituted with substituted heteroaryl,
(q) —NH—$C(O)R^{10}$ wherein $R^{10}$ is as previously defined,
(r) —NH—$C(O)NR^{11}R^{12}$ wherein $R^{11}$ and $R^{12}$ are as previously defined,
(s) =N—$NR^{13}R^{14}$ wherein $R^{13}$ and $R^{14}$ are as previously defined,
(t) =N—$R^9$ wherein $R^9$ is as previously defined,
(u) =N—NH—$C(O)R^{10}$ wherein $R^{10}$ is as previously defined, and
(v) =N—NH—$C(O)NR^{11}R^{12}$ wherein $R^{11}$ and $R^{12}$ are as previously defined;
(8) $C_3$–$C_{10}$-alkynyl;
(9) $C_3$–$C_{10}$-alkynyl substituted with one or more substituents selected from the group consisting of
(a) trialkylsilyl,
(b) aryl,
(c) substituted aryl,
(d) heteroaryl, and
(e) substituted heteroaryl; and
(10) $C(O)NR^7R^8$ where $R^7$ and $R^8$ are previously defined;
E. Ra is selected from a group consisting of
(1) hydrogen;
(2) $C_1$ alkyl further substituted with a one or more substituents selected from a group consisting of
(a) hydroxyl,
(b) halogen,
(c) thiol, which can be further subsituted with and alkyl or subsituted alkyl group
(d) $C_1$–$C_{12}$-alkyl which can be further substituted by halogen, hydroxyl alkoxy, or amino,
(e) $C_1$–$C_3$-alkoxy,
(f) $C_1$–$C_3$-thioalkoxy,
(g) amino,
(h) alkylamino,
(i) dialkylamino,
(j) nitrile,
(k) nitro,
(l) amido,
(m) carboxylic acid,
(n) ester,
(o) azido,
(p) =N—O—$R^{10}$, wherein $R^{10}$ is as previously defined,
(q) =N—$R^9$, wherein $R^9$ is as previously defined,
(r) =N—$NR^{13}R^{14}$, wherein $R^{13}$ and $R^{14}$ are as previously defined,
(s) =N—NH—$C(O)R^{10}$, wherein $R^{10}$ is as previously defined, and
(t) =N—NH—$C(O)NR^{11}R^{12}$, wherein $R^{11}$ and $R^{12}$ are as previously defined;
(3) $C_2$–$C_4$-alkenyl, which can be further substituted with $C_1$–$C_{12}$-alkyl and one or more halo groups;
(4) -$C_2$–$C_4$-alkynyl, which can be further substituted with $C_1$–$C_{12}$-alkyl and one or more halo groups;
(5) aryl, which can be further substituted with $C_1$–$C_{12}$-alkyl, and one or more halo groups;
(6) CHO;
(7) —$CO_2H$;
(8) —CN;
(9) —$CO_2R^{10}$, wherein $R^{10}$ is as previously defined;
(10) —$C(O)NR^{11}R^{12}$, wherein $R^{11}$ and $R^{12}$ are as previously defined;
(11) —$C(O)R^9$ wherein $R^9$ is as previously defined; and
(12) thioester;
with the proviso that in formula II, when Z is amino or substituted amino, then Ra can not be —$CH_2OH$, —$NR^4R^6$, or —$(CH2)n\ NR^4R^6$, wherein $R^4$ and $R^6$ are selected from the group consisting of hydrogen, loweralkyl and aralkyl;
F. Rb is hydrogen, halogen or $C_1$–$C_{12}$-alkyl which can be further substituted by one or more halo groups, or Rb can be taken together with V to form a double bond;
G. Rc is hydrogen or a hydroxy protecting group;
H. Rd is selected from the group consisting of
(1) $C_1$–$C_{12}$-alkyl,
(2) $C_1$–$C_{12}$-alkyl substituted with one or more substituents selected from the group consisting of
(a) halogen,
(b) hydroxy, and
(c) $C_1$–$C_3$-alkoxy,
(3) $C_3$–$C_7$-cycloalkyl,
(4) $C_2$–$C_4$-alkenyl, and
(5) $C_2$–$C_4$-alkynyl;
I. Re is hydroxyl, amino, or alkylamino; or Re and Ra may be taken together to form an epoxide, a carbonyl, an olefin, or a subsituted olefin; or Re and Ra when taken together with the atom to which they are attached form a spiro ring consisting of $C_3$–$C_7$-carbocyclic, carbonate or carbamate wherein the nitrogen atom can be unsubstituted or substituted with an alkyl group; or Re and T when taken together with the carbon atoms to which they are attached form a ring of the structure

wherein L is methylene or carbonyl and P is —O—, —NH— or —$NR^1$— wherein $R^1$ is as previously defined; provided that when L is methylene, T is —O— and P is —O—;
J. Rg is hydrogen, R where R is as previously defined; or Rg may be taken together with Y, seperated by a linker of the formula —C(=O)— or —$C(CH_3)_2$—, to form a cyclic moiety;

K. Rh is selected from the group consisting of
  (1) hydrogen,
  (2) —ORj, where Rj is hydrogen or a hydroxy protecting group,
  (3) halogen,
  (4) OC(O)NHRi wherein Ri is selected from a group consisting of
     (a) $C_1$–$C_4$ alkyl,
     (b) $C_1$–$C_4$ aminoalkyl where the amino group is substituted with one or two groups selected from
        (i) $C_1$–$C_4$ alkyl,
        (ii) $C_1$–$C_4$ alkyl substituted with halogen,
        (iii) $C_1$–$C_4$ alkyl substituted with alkoxy,
        (iv) $C_1$–$C_4$ alkyl substituted with hydroxyl,
        (v) $C_1$–$C_4$ alkyl substituted with aryl,
        (vi) $C_1$–$C_4$ alkyl substituted with substituted aryl,
        (vii) $C_1$–$C_4$ alkyl substituted with heteroaryl,
        (viii) $C_1$–$C_4$ alkyl substituted with substituted heteroaryl,
        (ix) $C_3$–$C_6$ cycloalkyl; and
L. A, B, D, and E are independently selected from the group consisting of:
  (1) hydrogen;
  (2) $C_1$–$C_6$-alkyl optionally substituted with one or more substituents selected from the group consisting of:
     (a) aryl,
     (b) substituted aryl,
     (c) heteroaryl,
     (d) substituted heteroaryl,
     (e) heterocycloalkyl,
     (f) hydroxy,
     (g) $C_1$–$C_6$-alkoxy,
     (h) halogen selected from the group consisting of Br, Cl, F or I, and
     (i) $NR^7R^8$ where $R^7$ and $R^8$ are as previously defined;
  (3) $C_3$–$C_7$-cycloalkyl;
  (4) aryl;
  (5) substituted aryl;
  (6) heteroaryl;
  (7) substituted heteroaryl;
  (8) heterocycloalkyl; and
  (9) a group selected from option (2) above further substituted with —M—$R^9$, wherein M and $R^9$ are as previously defined; or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2, —C(O)—NH, —C(O)—$NR^{12}$, wherein $R^{12}$ is as previously defined, —NH—C(O)—, —$NR^{12}$—C(O)—, wherein $R^{12}$ is as previously defined, and —C(=NH)—NH—; with the provision that at least two of A, B, D, and E are hydrogen.

In another embodiment, the present invention provides compounds of formula (II) above having the structure of the following formula (III):

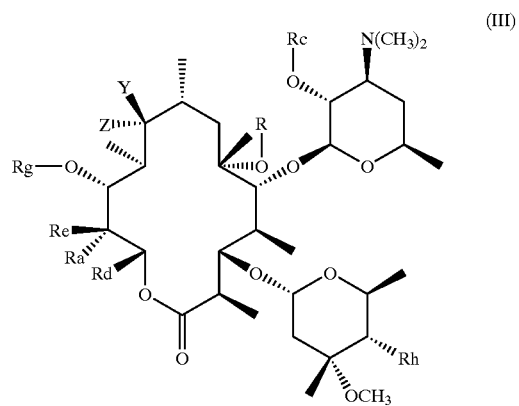
(III)

or a pharmaceutically acceptable salt, ester or prodrug thereof, wherein Y, Z, R, Ra, Rc, Rd, Re, Rg and Rh have the meanings defined above.

In another embodiment, the present invention provides compounds of formula (II) above having the structure of the following formula (IV):

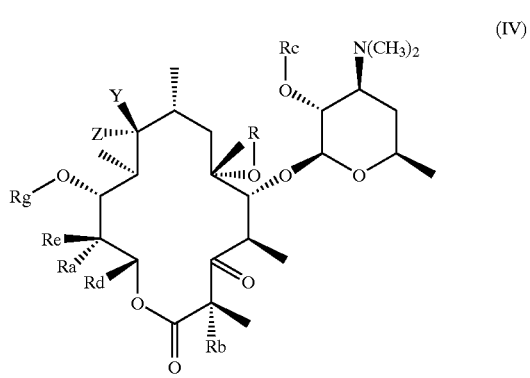
(IV)

or a pharmaceutically acceptable salt, ester or prodrug thereof, wherein Y, Z, R, Ra, Rb, Rc, Rd, Re, and Rg have the meanings defined above.

In another embodiment, the present invention provides compounds of formula (II) above having the structure of the following formula (v):

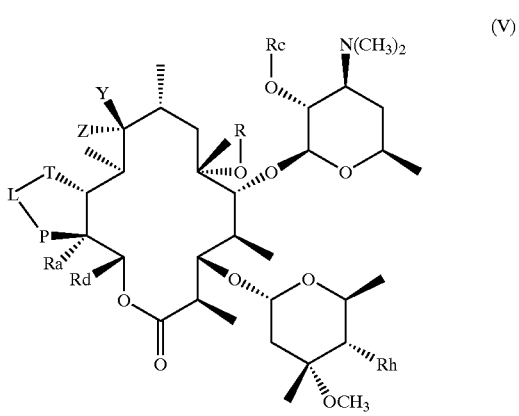
(V)

or a pharmaceutically acceptable salt, ester or prodrug thereof, wherein L, P, T, Y, Z, R, Ra, Re, Rd, and Rh have the meanings defined above.

In another embodiment, the present invention provides compounds of formula (II) above having the structure of the following formula (VI):

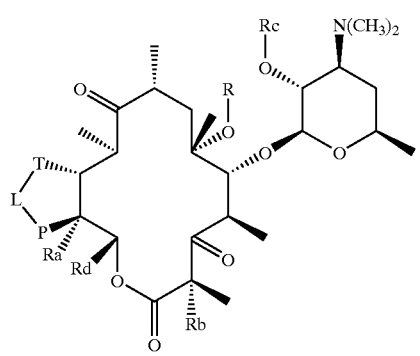
(VI)

or a pharmaceutically acceptable salt, ester or prodrug thereof, wherein L, P, T, R, Ra, Rb, Rc, and Rd have the meanings defined above. In another embodiment, illustrative compounds of formula (VI) have the structure of formula (VIa):

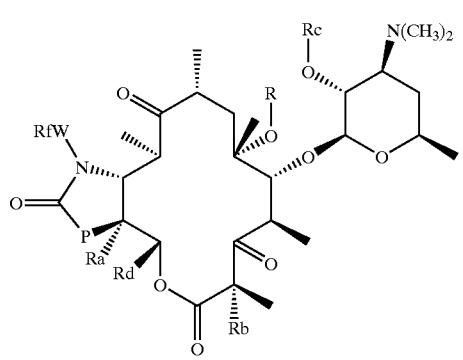
(VIa)

or a pharmaceutically acceptable salt, ester or prodrug thereof, wherein W, Rf, R, Ra, Rc, and Rd have the meanings defined above. Illustrative, but nonlimiting examples include, without limitation, compounds of formula (VIa(1)):

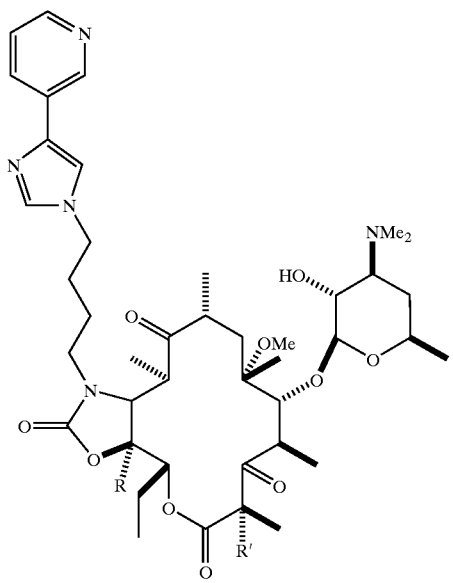
(VIa(1))

wherein R is H, ethyl or vinyl, and R' is H or F;

compounds of formula (VIa(2)):

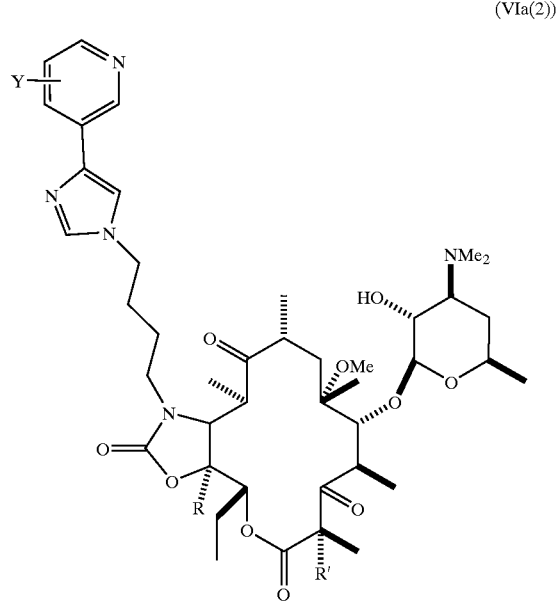
(VIa(2))

wherein R is H, ethyl or vinyl, R' is H or F, and Y is H, halogen, amino, C1–C4 alkyl, hydroxy, alkoxy, alkylamino, cyano or substituted C1–C4 alkyl;

compounds of formula (VIa(3)):

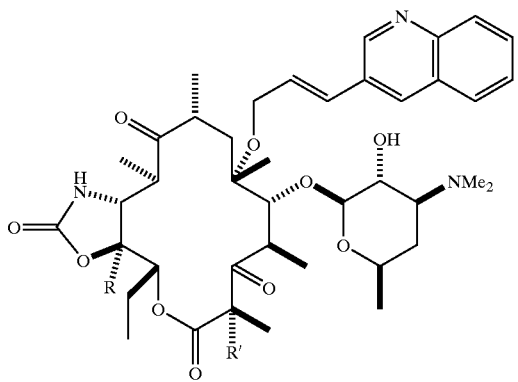
(VIa(3))

wherein R is H, $CF_3$, ethyl or vinyl, and R' is H or F;

compounds of formula (VIa(4)):

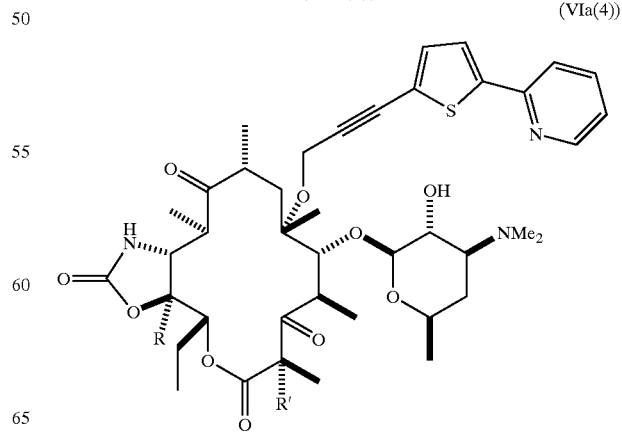
(VIa(4))

wherein R is H, CF$_3$, ethyl or vinyl, and R' is H or F; and compounds of formula (VIa(5)):

(VIa(5))

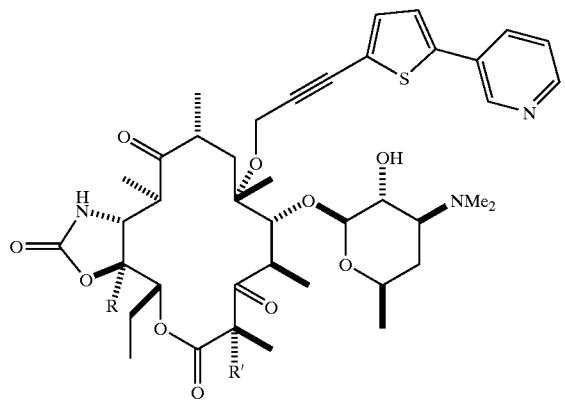

wherein R is H, CF$_3$, ethyl or vinyl, and R' is H or F.

In another embodiment, the present invention provides compounds of formula (II) above having the structure of the following formula (VII):

(VII)

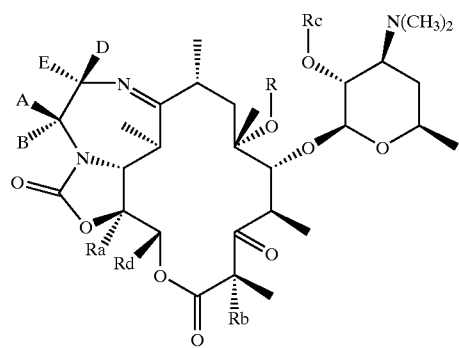

or a pharmaceutically acceptable salt, ester or prodrug thereof, wherein A, B, D, E, R, Ra, Rb, Rc, and Rd have the meanings defined above.

In another embodiment, the present invention provides compounds of formula (II) above having the structure of the following formula (VIII):

(VIII)

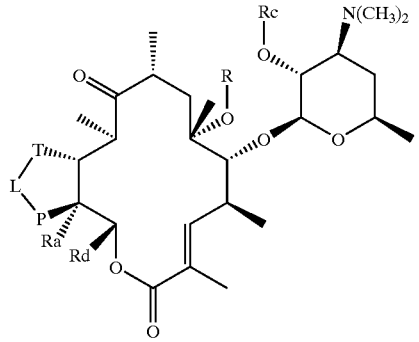

or a pharmaceutically acceptable salt, ester or prodrug thereof, wherein L, P, T, R, Ra, Rc, and Rd have the meanings defined above.

In certain aspects, representative compounds of formulas II, III, IV, V, VI, VII, or hydrogen, substituted or unsubstituted C$_1$–C$_{12}$-alkyl, C$_2$–C$_4$-alkenyl, —C$_2$–C$_4$-alkynyl, aryl or thioester; X is =O; L is CO; P is =O; T is NH or N(W—Rf) wherein W is as previously defined and Rf is an alkyl or subsituted alkyl group, which may be further subsituted by a heteroaryl selected from but not limited to

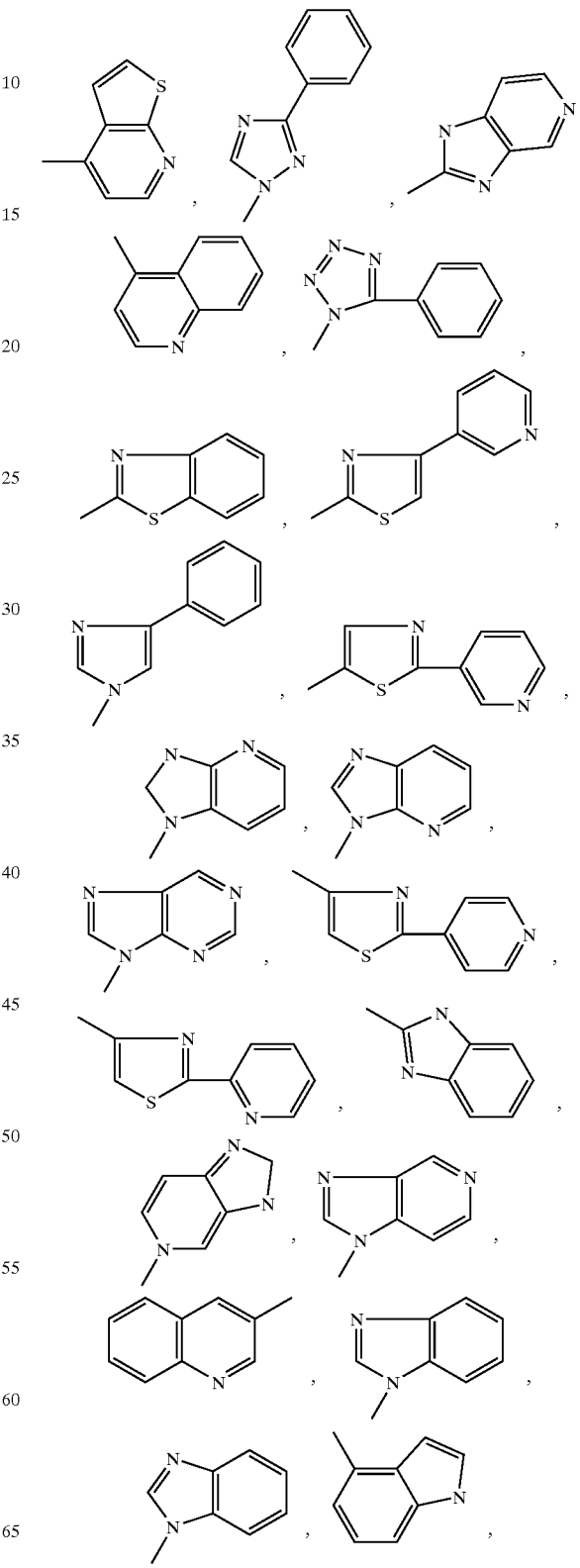

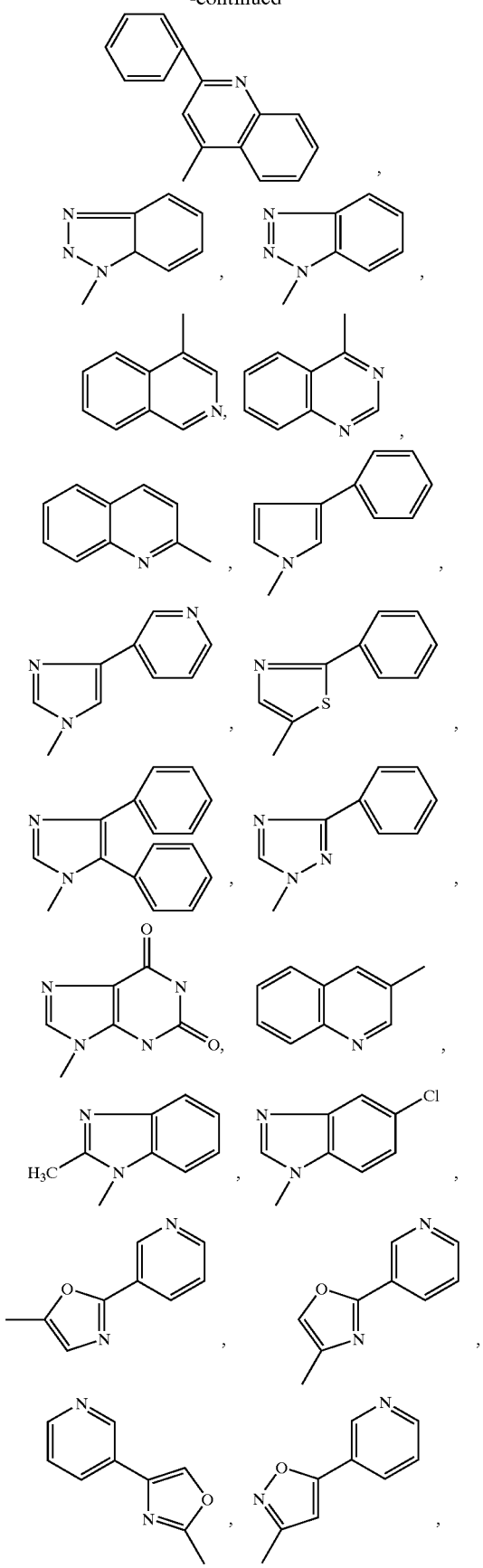

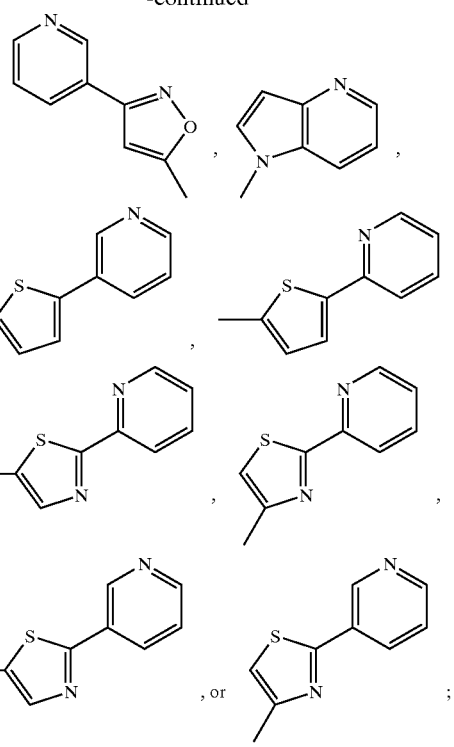

A, B, D, and E are H; and R is methyl, allyl, propyl, —CH₂CHO, —CH₂CH=NOH, —CH₂CH=NOH, —CH₂CN, —CH₂CH₂NH₂, —CH₂CH₂NHCH₂-phenyl, —CH₂CH₂-NHCH₂CH₂-phenyl, —CH₂CH₂—NHCH—(CO₂CH₃)CH₂-phenyl, —CH₂CH₂NHCH₂-(4-pyridyl), —CH₂CH₂NHCH₂-(4-quinolyl), —CH₂CH=CH-phenyl, —CH2CH2CH2phenyl, —CH₂CH=CH-(4-methoxyphenyl), —CH₂CH=CH-(4-chlorophenyl), —CH₂CH=CH-(3-quinolyl), —CH₂CH₂CH₂OH, —CH₂C(O)OH, —CH₂CH₂ HCH₃, —CH₂CH₂NHCH₂OH, —CH₂CH₂N(CH₃)₂, —CH₂CH₂(1-morpholinyl), —CH₂C(O)NH₂, —CH₂NHC(O)NH₂, —CH₂NHC(O)CH₃, —CH₂F, —CH₂CH₂OCH₃, —CH₂CH₃, —CH₂CH=CH(CH₃)₂, —CH₂CH₂CH(CH₃)CH₃, —CH₂CH₂OCH₂CH₂OCH₃, —CH₂SCH₃, -cyclopropyl, —CH₂OCH₃, —CH₂CH₂F, —CH₂-cyclopropyl, —CH₂CH₂CHO, —C(O)CH₂CH₂CH₃, —CH₂-(4-nitrophenyl), —CH₂-(4-chlorophenyl), —CH₂-(4-methoxyphenyl), —CH₂-(4-cyanophenyl), —CH₂CH=CHC(O)OCH₃, —CH₂CH=CHC(O)OCH₂CH₃, —CH₂CH=CHCH₃, —CH₂CH=CHCH₂CH₃, —CH₂CH=CHCH₂CH₂CH₃, —CH₂CH=CHSO₂-phenyl, —CH₂C≡C—Si(CH₃)₃, —CH₂C≡CCH₂CH₂—CH₂CH₂CH₃, —CH₂ C≡CCH₃, —CH₂-(2-pyridyl), —CH₂-(3-pyridyl), —CH₂-(4-pyridyl), —CH₂-(4-quinolyl), —CH₂NO₂, —CH₂C(O)OCH₃, —CH₂C(O)-phenyl, —CH₂C(O)CH₂CH₃, —CH₂Cl, —CH₂S(O)₂-phenyl, —CH₂CH==CHBr, —CH₂ CH=CH-(4-quinolyl), —CH₂ CH₂ CH₂-(4-quinolyl), —CH₂ CH=CH-(5-quinolyl), —CH₂CH₂CH₂-(5-quinolyl), —CH₂CH=CH-(4-benzoxazolyl), —CH₂CH=CH-(7-benzimidazolyl), —CH₂-(3-iodophenyl), —CH₂-(2-naphthyl), —CH₂—CH=CH-(4-fluorophenyl), —CH₂—CH(OH)—CN, —CH₂CH=CH-(quinoxalin-6-yl), —CH₂CH=CH-([1,8]-naphthyridin-3-yl), —CH₂CH=CH-([1,5]-naphthyridin-3-yl), —CH₂CH=CH-(5-pyridin-2-yl-thiophen-2-yl), —CH$_2$CH=CH-(5-pyridin-3-yl-thiophen-2-yl),
—CH$_2$CH=CH-(5-(6-methylpyridin-3-yl)-thiophen-2-yl),
—CH$_2$CH=CH-(5-thiazol-2-yl-thiophen-2-yl),
—CH$_2$CH=CH-(5-thiazol-5-yl-thiophen-2-yl),
—CH$_2$CH=CH-(5-pyrimidin-2-yl-thiophen-2-yl),
—CH$_2$CH=CH-(5-pyrazin-2-yl-thiophen-2-yl),
—CH$_2$C≡C-(quinolin-3-yl), —CH$_2$C≡C-(quinoxalin-6-yl), —CH$_2$C≡C-([1,8]-naphthyridin-3-yl), —CH$_2$C≡C-([1,5]-naphthyridin-3-yl), —CH$_2$C≡C-(5-pyridin-2-yl-thiophen-2yl), —CH$_2$C≡C-(5-pyridin-3-yl-thiophen-2-yl), —CH$_2$C≡C-(5-(6-methylpyridin-3-yl)-thiophen-2-yl), —CH$_2$C≡C-(5-thiazol-2-yl-thiophen-2-yl), —CH$_2$C≡C-(5-thiazol-5-yl-thiophen-2-yl), —CH$_2$C≡C-(5-pyrimidin-2-yl-thiophen-2-yl), or —CH$_2$C≡C-(5-pyrazin-2-yl-thiophen-2-yl).

Definitions

As used throughout this specification and the appended claims, the following terms have the meanings specified.

The term "alkyl" refers to saturated, straight- or branched-chain hydrocarbon groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Alkyl also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

The phrase "substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group.

The terms "$C_1$–$C_3$-alkyl", "$C_1$–$C_6$-alkyl", and "$C_1$–$C_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$–$C_3$-alkyl radicals include methyl, ethyl, propyl and isopropyl, examples of $C_1$–$C_6$-alkyl radicals include, but are not limited to, methyl, ethyl, propyl, isopropyl, n-butyl, tert-butyl, neopentyl and n-hexyl. Examples of $C_1$–$C_{12}$-alkyl radicals include, but are not limited to, all the foregoing examples as well as n-heptyl, n-octyl, n-nonyl, n-decyl, n-undecyl and n-docecyl.

The term "$C_1$–$C_6$-alkoxy" as used herein refers to a $C_1$–$C_6$-alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_2$–$C_{12}$-alkenyl" denotes a monovalent group derived from a hydrocarbon moiety containing from two to twelve carbon atoms and having at least one carbon-carbon double bond by the removal of a single hydrogen atom. Alkenyl groups include, for example, ethenyl, propenyl, butenyl, 1-methyl-2-buten-1-yl, and the like.

The term "$C_2$–$C_{12}$-alkynyl" as used herein refers to a monovalent group derived from a hydrocarbon moiety containing from two to twelve carbon atoms and having at least one carbon-carbon triple bond by the removal of a single hydrogen atom. Representative alkynyl groups include ethynyl, propynyl and the like.

The term 14-member macrolide antibiotics used herein include the natural products erythromycin, narbomycin, lakamycin, and oleandomycin, as well as derivatives such as roxithromycin, clarithromycin, dirithromycin, flurithromycin, and the ketolides (telithromycin, HMR 3004, TE-802, TE-810, ABT 773).

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "$C_1$–$C_3$-alkylamino" as used herein refers to one or two $C_1$–$C_3$-alkyl groups, as previously defined, attached to the parent molecular moiety through a nitrogen atom. Examples of $C_1$–$C_3$-alkylamino include, but are not limited to methylamino, dimethylamino, ethylamino, diethylamino, and propylamino.

The term "oxo" denotes a group wherein two hydrogen atoms on a single carbon atom in an alkyl group as defined above are replaced with a single oxygen atom (i.e. a carbonyl group).

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "$C_3$–$C_{12}$-cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptyl, and bicyclo[2.2.2]octyl.

The terms "halo" and "halogen" as used herein refer to an atom selected from fluorine, chlorine, bromine and iodine.

The term "alkylamino" refers to a group having the structure —NHR' wherein R' is alkyl, as previously defined. Examples of alkylamino include, but are not limited to, methylamino, ethylamino, iso-propylamino.

The term "dialkylamino" refers to a group having the structure —NR'R" wherein R' and R" are independently selected from alkyl, as previously defined. Additionally, R' and R" taken together may optionally be —(CH$_2$)$_k$— where k is an integer of from 2 to 6. Examples of dialkylamino include, but are not limited to, dimethylamino, diethylamino, diethylaminocarbonyl, methylethylamino, methylpropylamino, and piperidino.

The term "haloalkyl" denotes an alkyl group, as defined above, having one, two, or three halogen atoms attached thereto and is exemplified by such groups as chloromethyl, bromoethyl, trifluoromethyl and the like.

The term "alkoxycarbonyl" represents an ester group; i.e. an alkoxy group, attached to the parent molecular moiety through a carbonyl group such as methoxycarbonyl, ethoxycarbonyl and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —CO$_2$H.

The term "carboxamide" as used herein refers to a group of formula —CONHR'R" wherein R' and R" are independently selected from hydrogen or alkyl, or R' and R" taken together may optionally be —(CH$_2$)$_k$— where k is an integer of from 2 to 6.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl. Representative examples of heteroaryl moieties include, but not limited to, pyridin-3-yl-1H-imidazol-1-yl, phenyl-1H-imidazol-1-yl, 3H-imidazo[4,5-b]pyridin-3-yl, quinolin-4-yl, 4-pyridin-3-yl-1H-imidazol-1-yl, quinolin-2-yl, 2-methyl-4-pyridin-3-yl-1H-imidazol-1-yl, 5-methyl-4-pyridin-3-yl-1H-imidazol-1-yl, 1H-imidazo[4,5-b]pyridin-1-yl, pyridin-3-ylmethyl, 3H-imidazo[4,5-b]pyridin-3-yl, 4-pyrimidin-5-yl-1H-imidazol-1-yl, 4-pyrazin-2-yl-1H-imidazol-1-yl, 4-pyridin-3-yl-1H-imidazol-1-yl, 4-pyridin-4-yl-1H-imidazol-1-yl, 4-(6-methylpyrid-3-yl)-1H-imidazol-1-yl, 4-(6-fluoropyridin-3-yl)-1H-imidazol-1-yl, 5-(3-aminophenyl)-1,3-thiazol-2-yl, 3-pyridin-3-ylphenoxy, 4-pyridin-3-ylphenoxy, 3H-imidazo[4,5-b]pyridin-3-yl, 4-phenyl-1H-imidazol-1-yl, 1H-pyrrolo[3,2-b]pyridin-1-yl, quinolin-3-yl, 2-methylquinolin-4-yl, trifluoromethyl)quinolin-4-yl, 8-(trifluoromethyl)quinolin-4-yl, 2-phenoxyethoxy, 4-pyridin-3-ylphenoxy, 3-pyridin-3-ylphenoxy, 5-phenyl-1,3-thiazole, 5-(2,4-difluorophenyl)-1,3-thiazol-2-yl, 5-(3-aminophenyl)-1,3-thiazol-2-yl, (3,3'-bipyridin-5-ylmethyl)(methyl)amino, (6-methylpyridin-3-yl)-1H-imidazol-1-yl, methyl(quinolin-3-ylmethyl)amino, 3-phenylisoxazol-5-yl, 3-(4-methylphenyl)isoxazol-5-yl and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heteroarylalkyl" as used herein, refers to a heteroaryl group as defined above attached to the parent molecular moiety through an alkylene group wherein the alkylene group is of one to four carbon atoms.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, Protective Groups in Organic Synthesis, 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reaction during synthetic procedures and to be selectively removable. The use of ketone-protecting groups is well known in the art for protecting groups against undesirable reaction during a synthetic procedure and many such protecting groups are known, cf., for example, T. H. Greene and P. G. M. Wuts, Protective Groups in Organic Synthesis, 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "substituted aryl" as used herein refers to an aryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Synthetic Methods

Synthesis of the compounds of the invention can be broadly summarized as follows. 1) The free alcohols on the sugars and the reduced C9 ketone are protected in a fashion that allows for the relatively efficient elimination of the C12 hydroxy group (i.e., without burdensome competing side products) to form an alkene intermediate. 2) The alkene intermediate is converted to an epoxide, diol, or ketone intermediate. 3) The epoxide, diol, and ketone is then used to introduce new C12 substituents. 4) Further manipulations are then carried out as needed to generate the desired final products.

1. Useful Intermediates for Producing Useful C12 Olefins

The above-described disclosure of the Lartey patent (U.S. Pat. No. 5,217,960) is limited, because the C9 amine disclosed therein cannot be converted to a ketone to access C9-keto analogs combined with C12 modifications. The unavailability of this option is unfortunate in view of the fact that compounds lacking the C9-keto group generally show weak antibacterial activity. Alternatively the disclosure of the Hauske patent (U.S. Pat. No. 4,857,641) typically leads to a complex mixture of products. Thus, Hauske does not show or suggest synthetically reasonable routes to address the deficiencies of Lartey.

Thus, in one aspect, the invention provides macrolide and ketolide synthesis procedures having advantages over the prior teachings of Hauske and Lartey.

Surprisingly, the inventors have found that the C9 and C11-diols, when protected as acid labile acetonides or base labile carbonates, provide relatively efficient elimination at C12 over C6. Moreover, the inventors have discovered that the elimination reaction to form the C12 alkene can be more efficiently carried out when acetates are not used to protect the 2' and 4" positions of the associated sugars as is taught by the prior art. Representative protecting groups used in the novel and surprisingly effective synthesis methodologies provided by the present invention include, but are not limited to, benzyl esters and TMS ethers. This invention also provides still other alternative protecting groups that lead to useful C12 alkene intermediates. For example, the five illustrative compounds below have been found to be useful precursors for the elimination reaction to form the corresponding C12 alkenes.

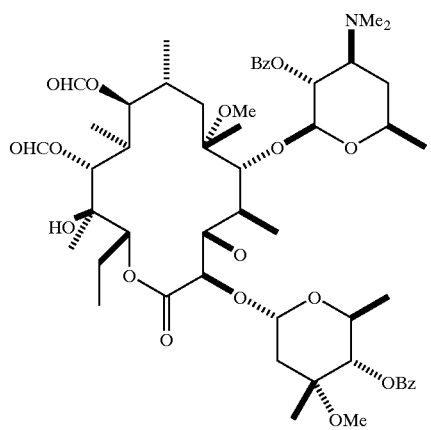

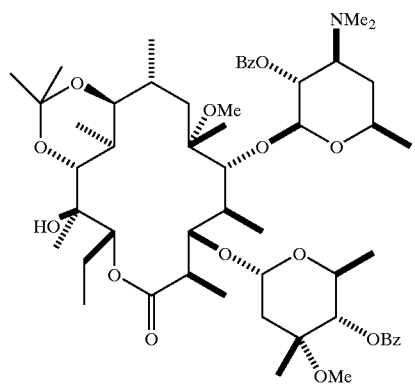

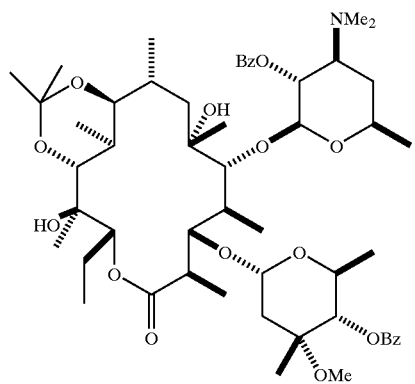

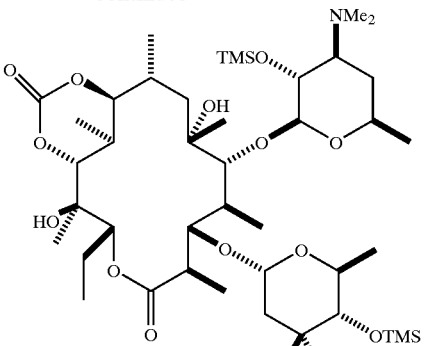

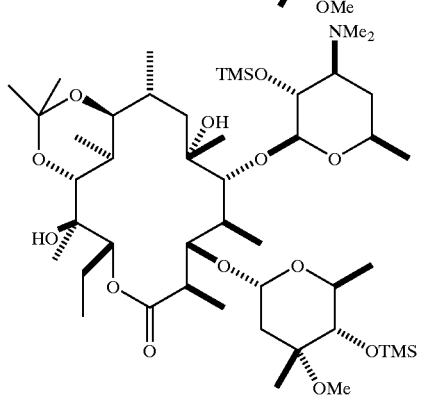

2. New Macrolide and Ketolide Antibiotics Arising from an Epoxide Intermediate

In one aspect, this invention provides means for functionalizing the macrolide C12 methyl group with optionally substituted alkyl, alkenyl, alkynyl, and aryl groups to give a new, monosubstituted C12 methyl group. It has been found that the alkyl and aryl cuprates $LiMe_2Cu$ and $LiPh_2Cu$ can be efficiently added to a C12 epoxide to produce, effectively, the respective ethyl and benzyl substituents at C12. This invention also contemplates a number of novel substituents at C12 that may be similarly introduced via the reagents shown below:

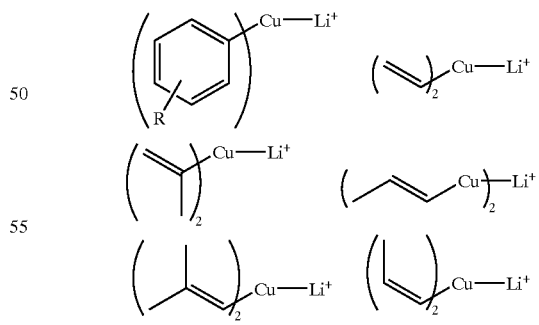

$R_2CuLi$ where R=perfluoroalkyl, F—, CN—, $CNCH_2$—, CNCHR—

In addition to the above carbanion equivalents, nucleophiles (such as azides and thiolates) known to react with epoxides are also included with the methods and compounds provided by the invention.

3. New C12 Ketone Intermediate

In other aspects, the present invention relates to methods for introducing a ketone at the C12 position. In this aspect, a C12 olefin can undergo ozonolysis to form the corresponding ketone. This procedure can be efficiently carried out if the amino group on the desosamine sugar is preferably protonated to minimize generating unwanted side products. This invention also contemplates other methods for producing a ketone at C12 such as treatment of the alkene with $RuO_4$ or dihydoxylating the precursor olefin followed by diol cleavage with $NaIO_4$.

4. Method for Generating New Macrolides and Ketolides from Ketone Intermediate.

A. Addition of Nucleophiles from Top Face

Unlike the epoxide route that only allows access to monosubstituted C12 methyl groups, this procedure further relates to methods for replacing the C12 methyl group entirely with substituents such as H or $CF_3$, such as shown in Scheme A, below.

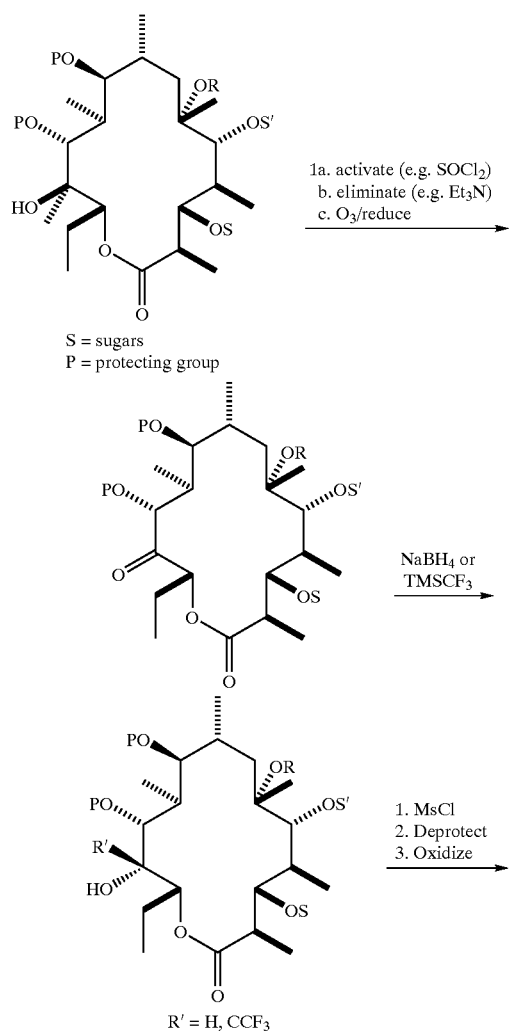

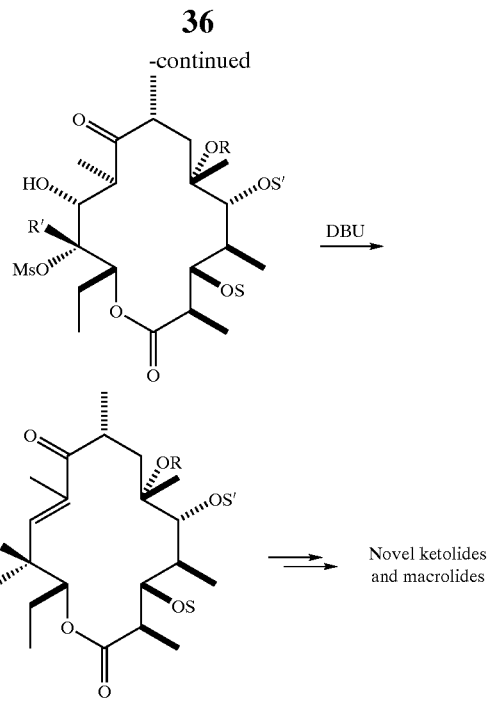

B. Introduction of a Tertiary Amine at C12

The C12 ketone moiety is useful in the synthesis of derivatives with a C12 amine. The following "reverse carbamate" analog containing a 4" benzoate has been synthesized.

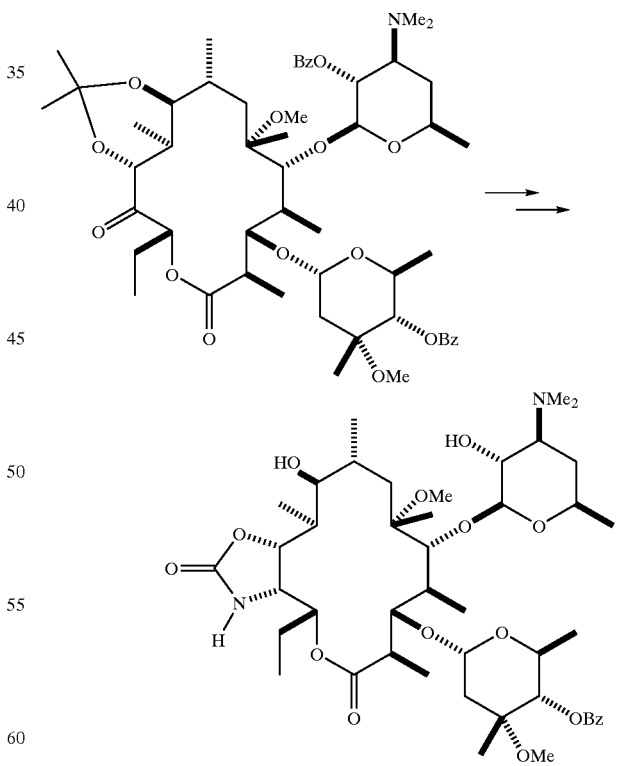

5. Representative Examples of Other C12 modified Compounds

Further examples of analogs that may be synthesized using the above methods are described in the following section.

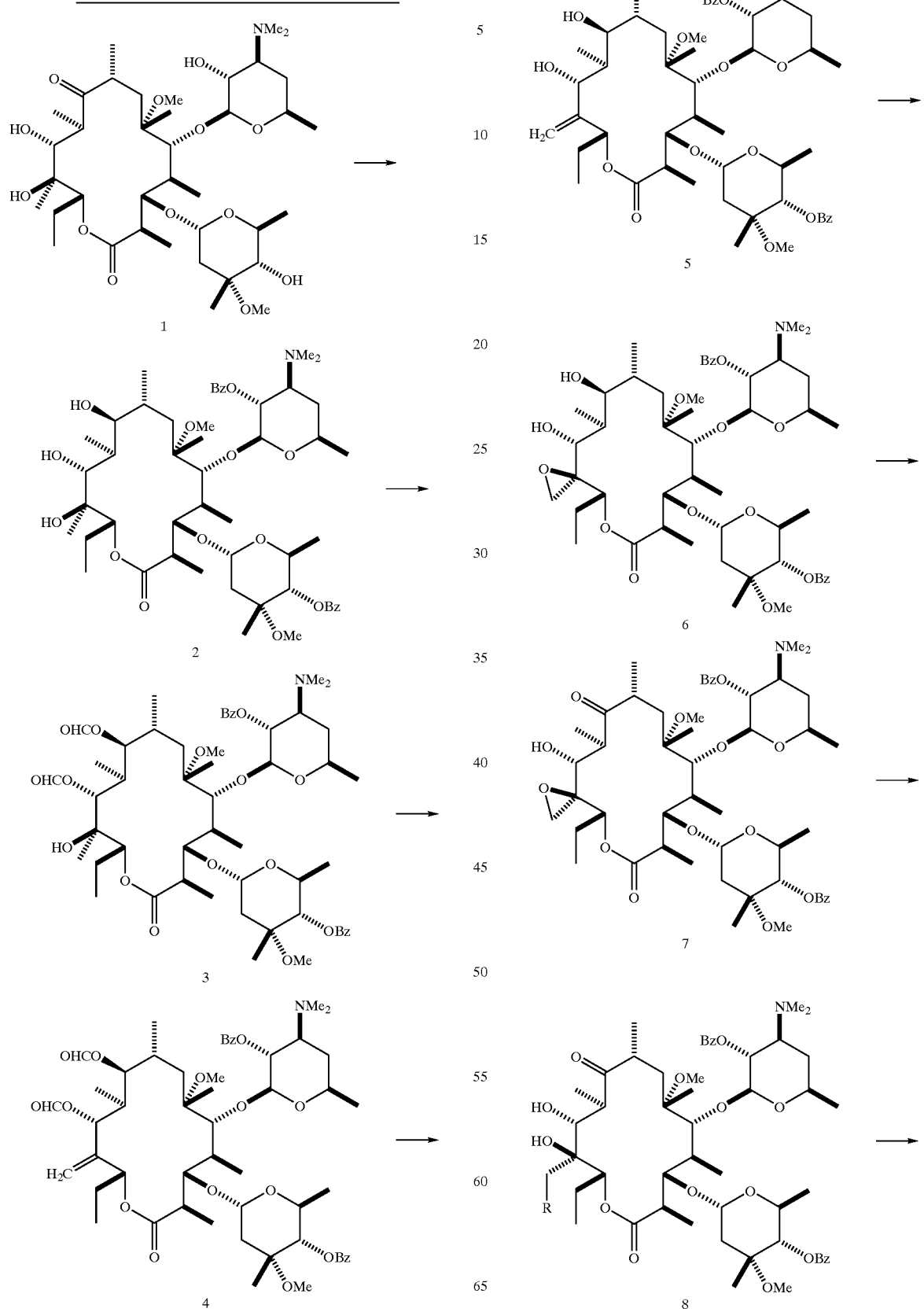
Scheme 1a.
C12 analogs where R = N₃, SMe via epoxide opening

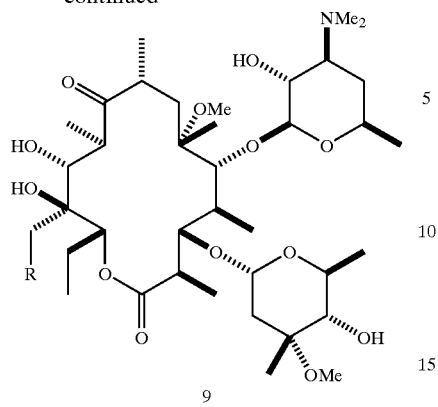

9

R = N₃, SMe

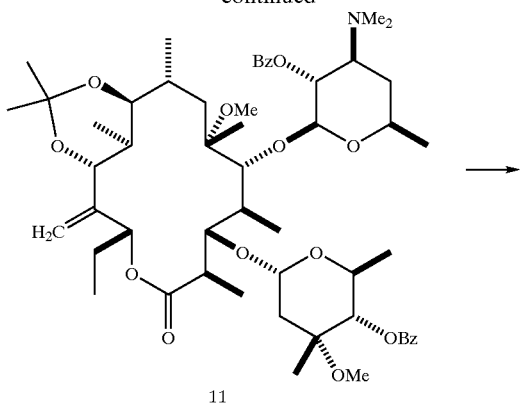

11

Scheme 1a illustrates one embodiment of the invention, whereby novel C12 modifications may be introduced via an epoxide intermediate. Starting with compound 1, the free hydroxyl groups on the sugar moieties may be protected as benzyl esters followed by stereoselective reduction of the C9 ketone to give compound 2. After protecting the two remaining secondary alcohols as their formate esters, the C12 tertiary alcohol 3 may be treated with thionyl chloride and an amine base to form the exocyclic alkene 4. The formate protecting groups may then be removed by treatment with MeOH. These conditions may also result in deprotection of the benzyl esters, which can be overcome by an additional protection step to reinstall the benzyl protecting groups, if necessary. Olefin 5 may then be epoxidized and the resulting C9 alcohol 6 selectively reoxidized back to the ketone 7. Ring opening of epoxide 7 with a nucleophile to give 8 followed by global removal of the sugar protecting groups furnishes analog 9 with a new C21 substituent.

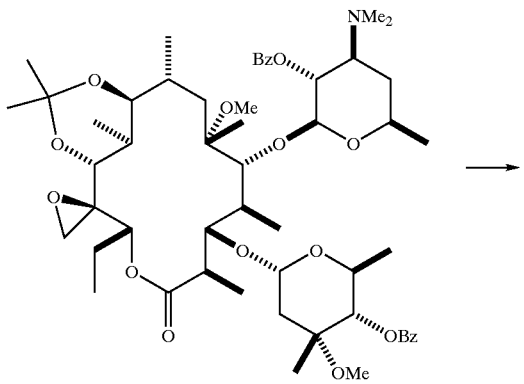

Scheme 1b.
C12 analogs where R = Me, Ph via epoxide

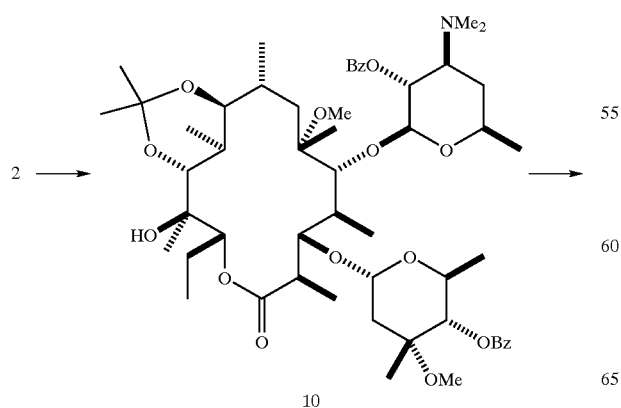

10

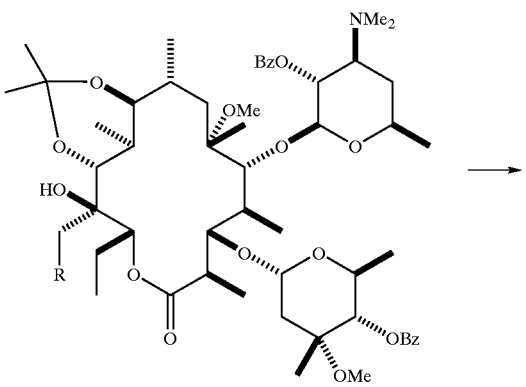

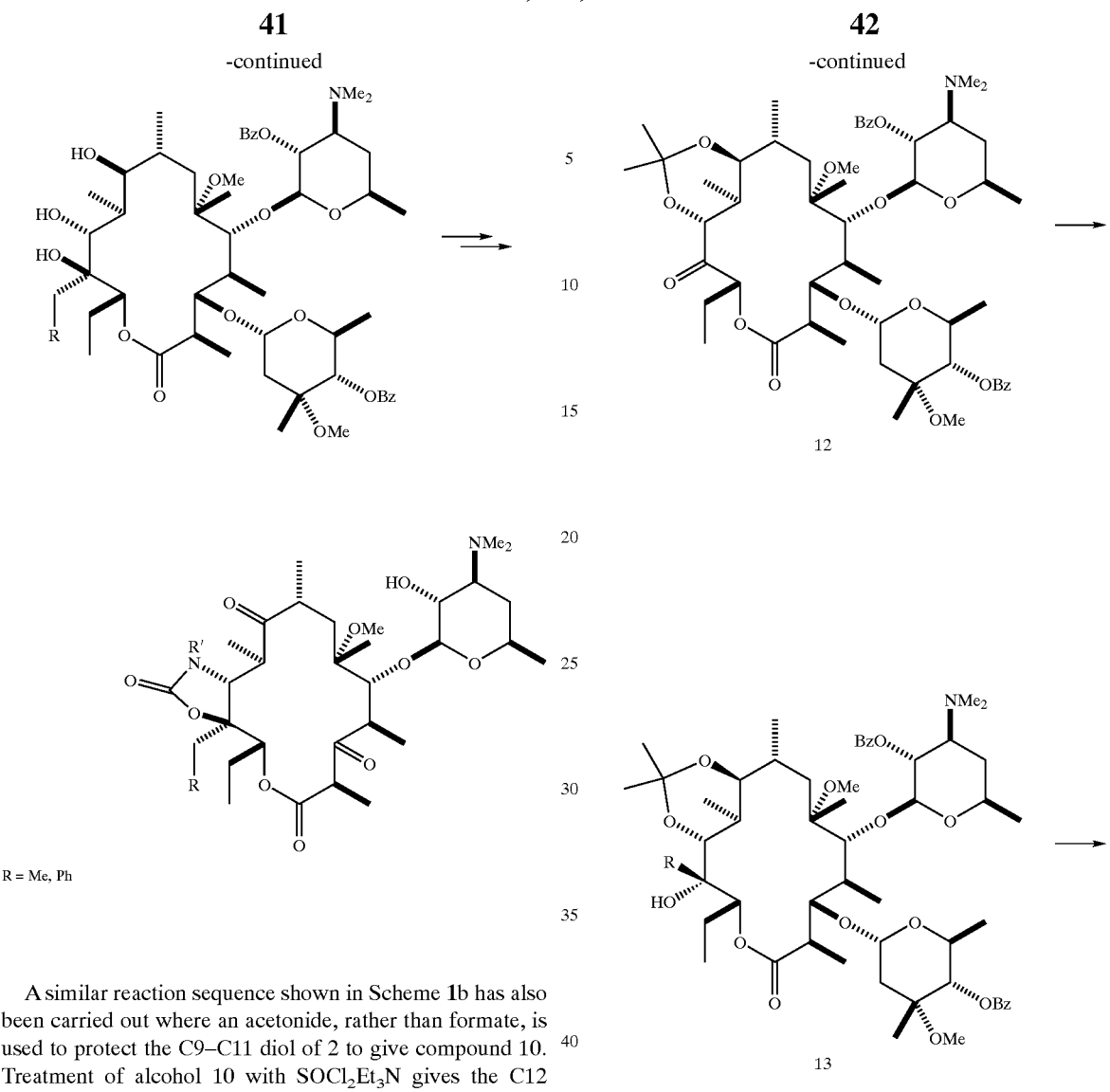

A similar reaction sequence shown in Scheme 1b has also been carried out where an acetonide, rather than formate, is used to protect the C9–C11 diol of 2 to give compound 10. Treatment of alcohol 10 with SOCl$_2$Et$_3$N gives the C12 olefin 11 that is then epoxidized. The epoxide ring opening may be successfully carried out with LiMe$_2$Cu and LiPh$_2$Cu. The resulting intermediates are useful for accessing C12 telithromycin analogs and demonstrate the viability of cuprate mediated C12 epoxide openings.

Scheme 2a. C12 modification via ketone intermediate to generate ketolides (C3 ketone).

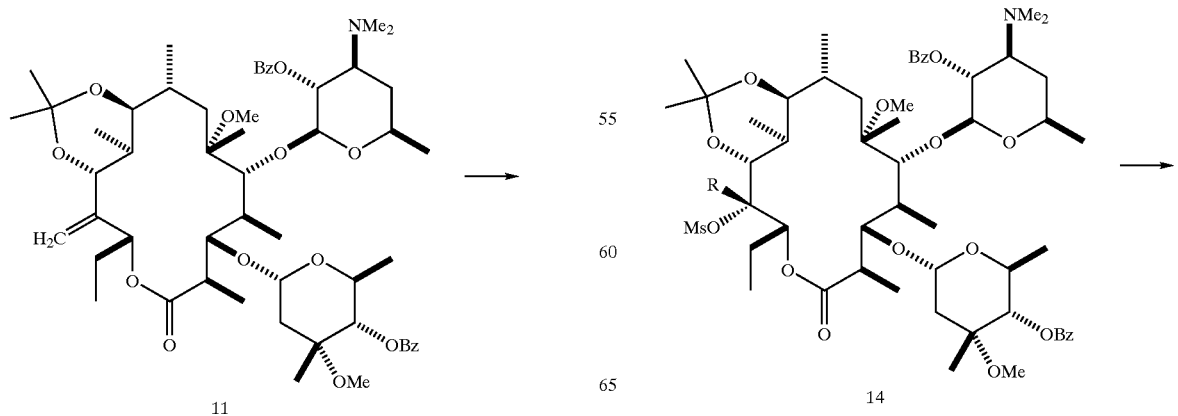

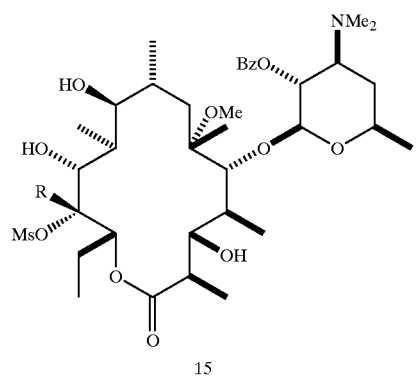
15
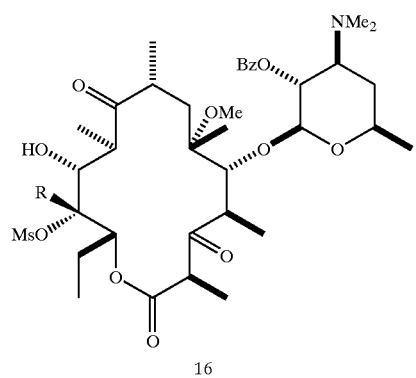
16
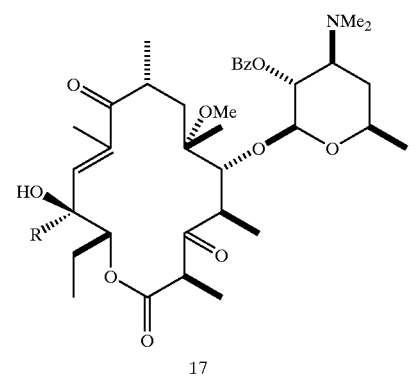
17
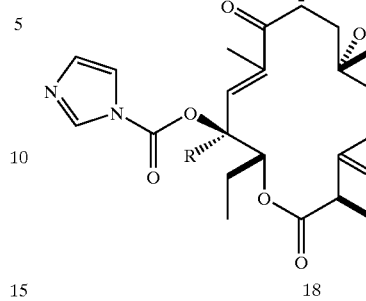
18
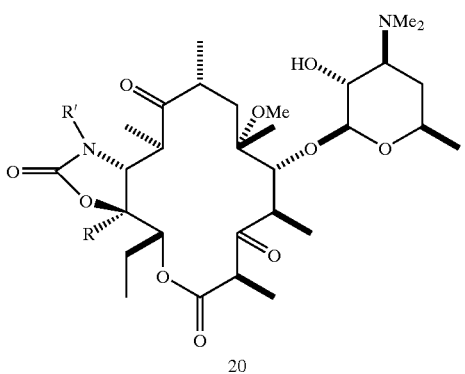
19
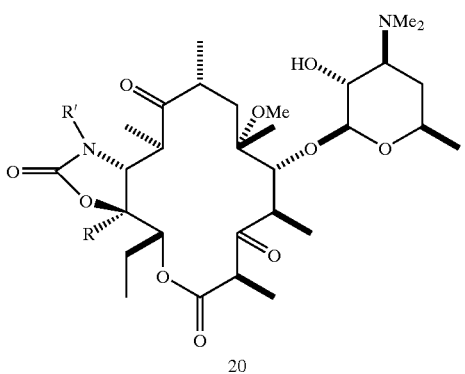
20
R = H Scheme 2b. C12 modification via ketone intermediate to generate analogs with a C3 sugar

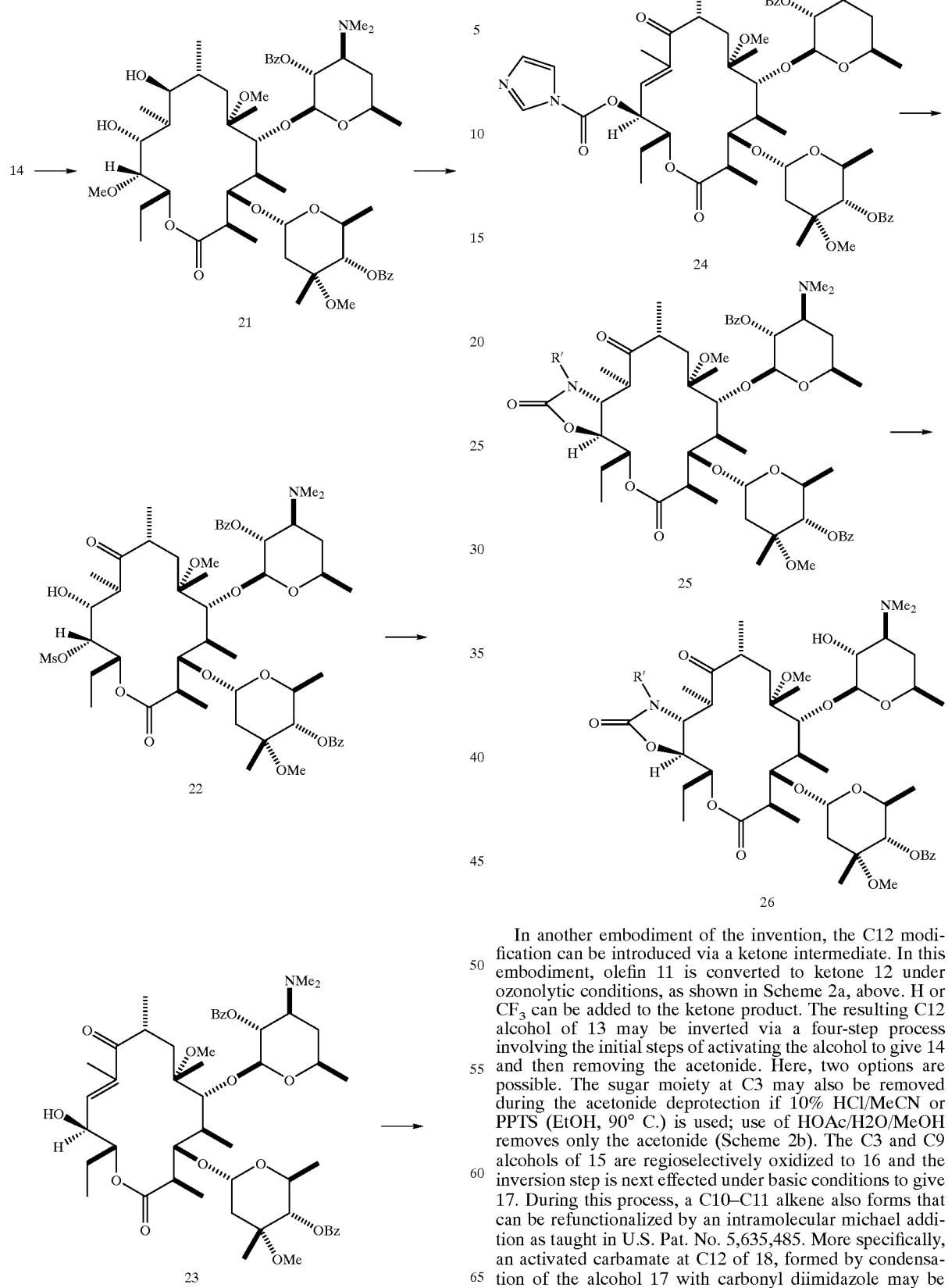

In another embodiment of the invention, the C12 modification can be introduced via a ketone intermediate. In this embodiment, olefin 11 is converted to ketone 12 under ozonolytic conditions, as shown in Scheme 2a, above. H or $CF_3$ can be added to the ketone product. The resulting C12 alcohol of 13 may be inverted via a four-step process involving the initial steps of activating the alcohol to give 14 and then removing the acetonide. Here, two options are possible. The sugar moiety at C3 may also be removed during the acetonide deprotection if 10% HCl/MeCN or PPTS (EtOH, 90° C.) is used; use of HOAc/H2O/MeOH removes only the acetonide (Scheme 2b). The C3 and C9 alcohols of 15 are regioselectively oxidized to 16 and the inversion step is next effected under basic conditions to give 17. During this process, a C10–C11 alkene also forms that can be refunctionalized by an intramolecular michael addition as taught in U.S. Pat. No. 5,635,485. More specifically, an activated carbamate at C12 of 18, formed by condensation of the alcohol 17 with carbonyl diimidazole may be coupled to a variety of alkyl amines. The resulting intermediate then cyclizes in situ to form the cyclic carbamate 19.

Removal of the remaining protecting groups yields the novel ketolides 20. A similar route as utilized for the C12-hydrogen series, is outline in Scheme 3 for the C12-trifluoromethyl series.
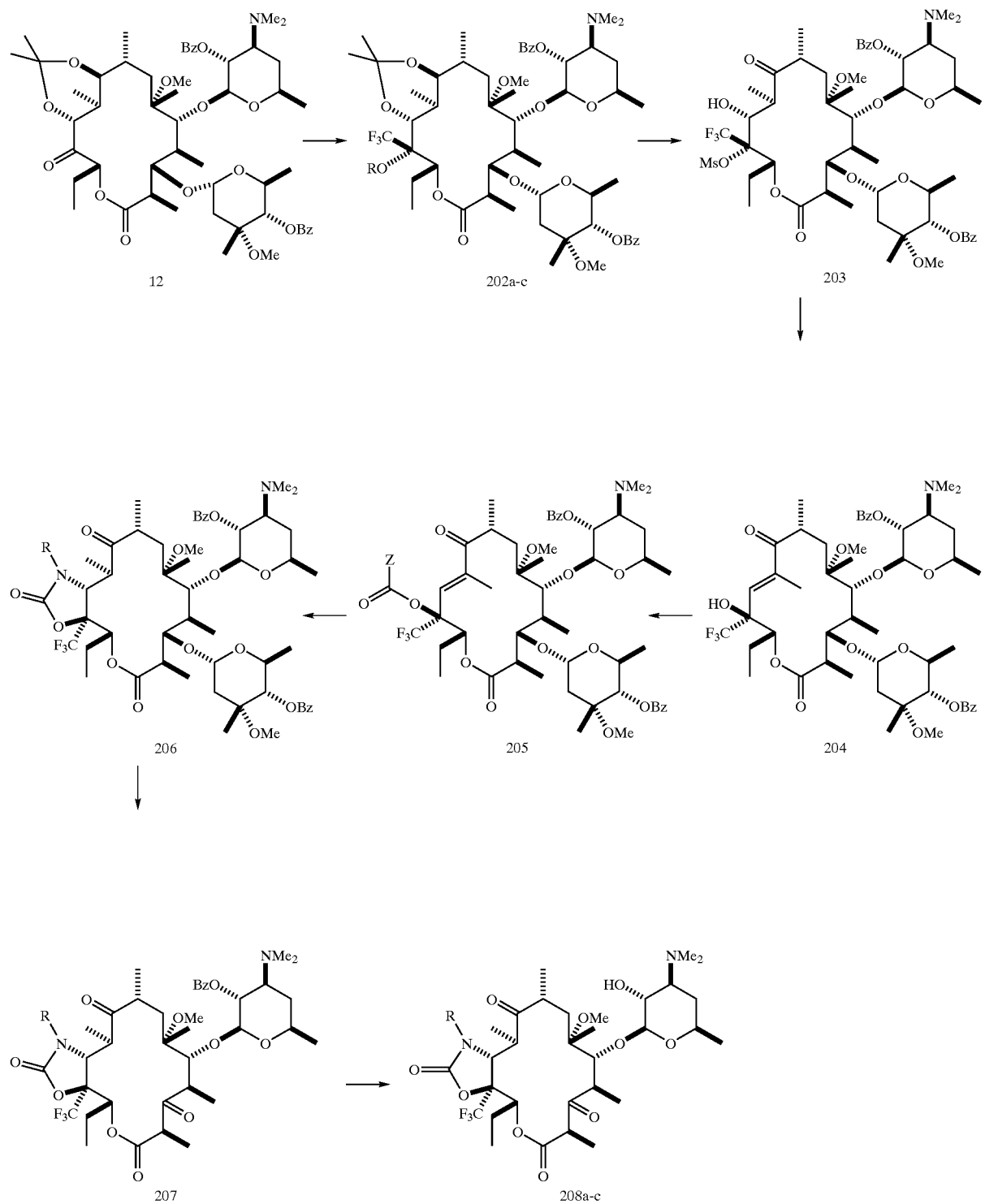

R = 
208a: X = CH
208b: X = N
R = 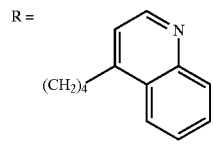
208c
Scheme 4.
Erythromycin C12 alkene formation
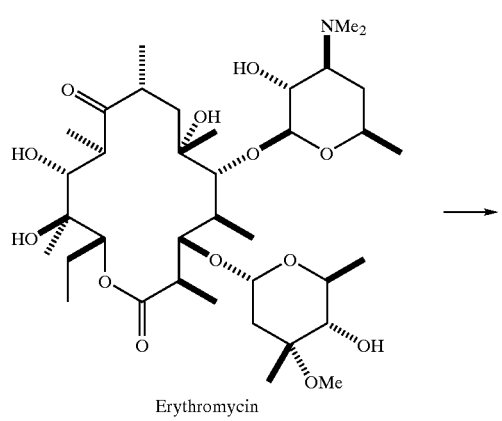
Erythromycin
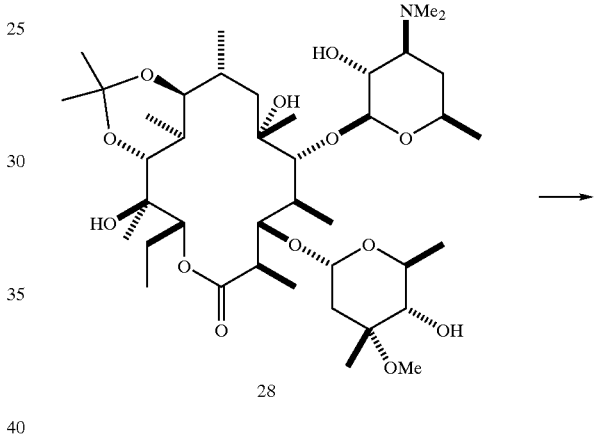
28
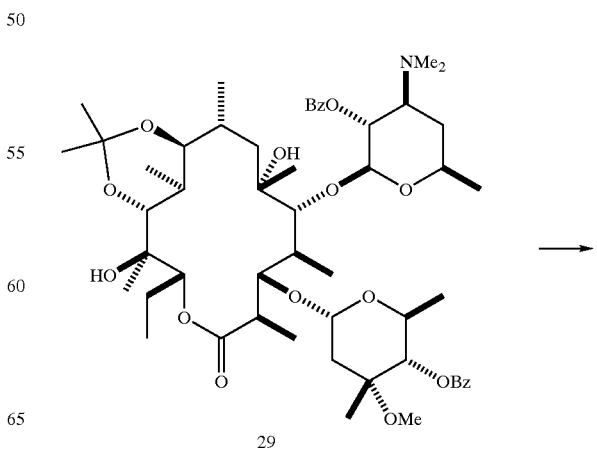
29
27

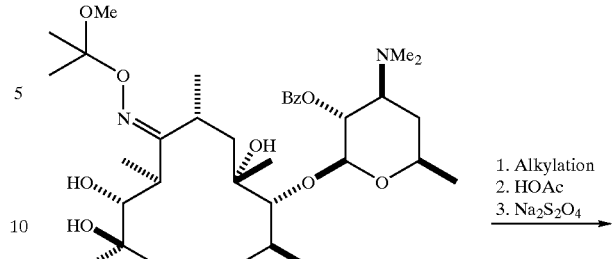

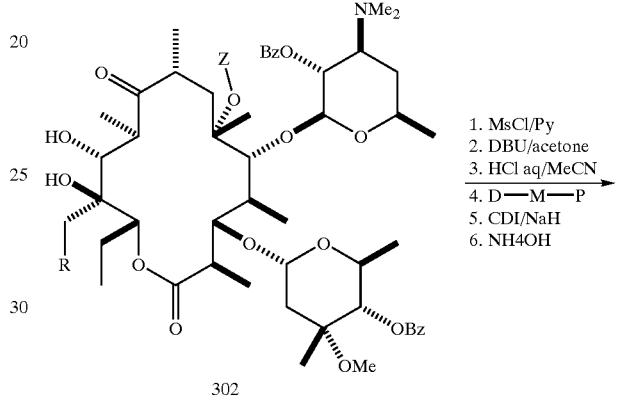

These manipulations may also be carried out on erythromycin as shown in Scheme 4 above. These transformations parallel those shown in the above example (Scheme 1, epoxide route) but are applied to a more demanding case wherein the intermediates contain a free C6 tertiary alcohol. Acetonide and carbonate protecting groups are useful in directing olefin formation at C12 over C6. Representative sugar protecting groups for this purpose include, for example, TMS and benzyl esters.

Scheme 5a.
Synthesis of novel C12 6-O-alkyl ketolide analogs

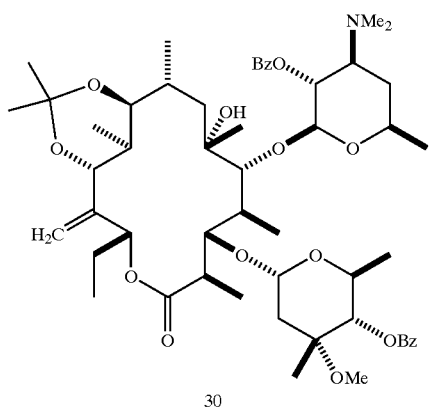

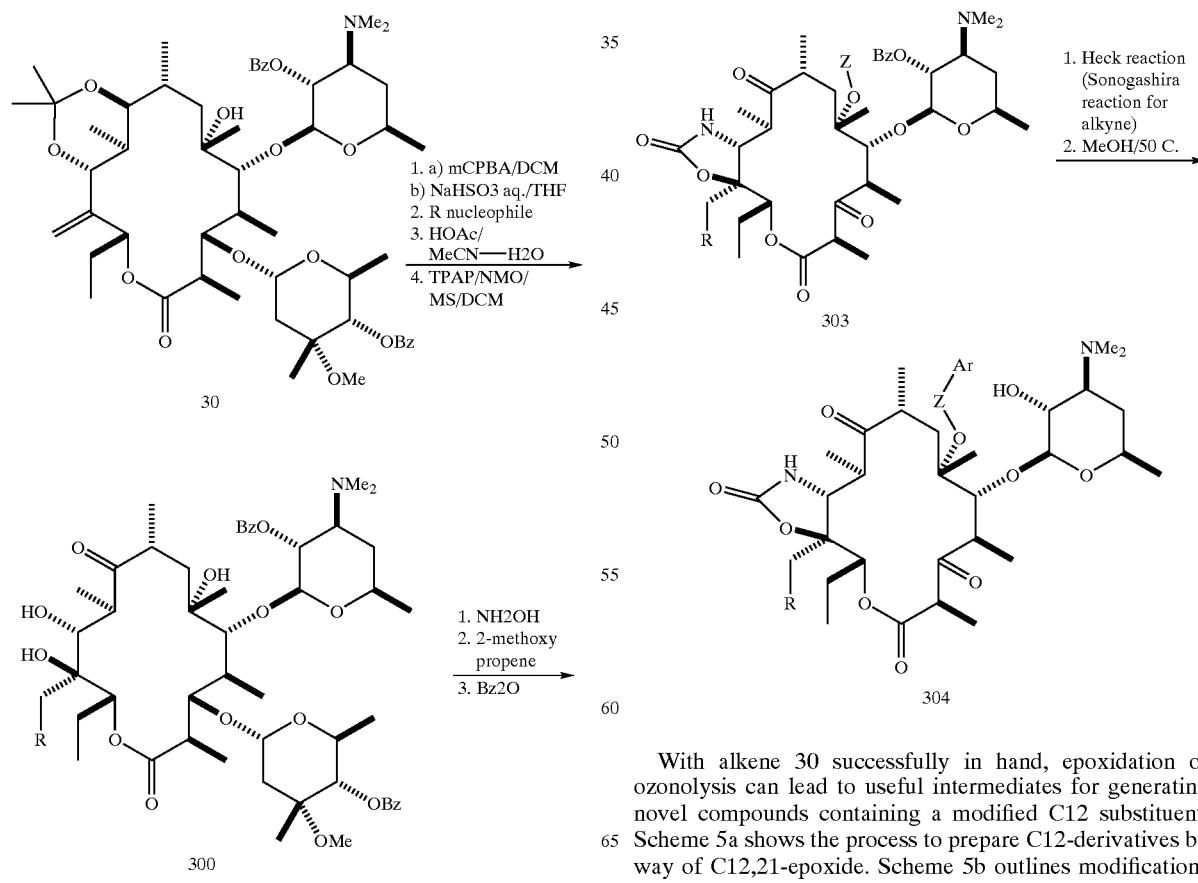

With alkene 30 successfully in hand, epoxidation or ozonolysis can lead to useful intermediates for generating novel compounds containing a modified C12 substituent. Scheme 5a shows the process to prepare C12-derivatives by way of C12,21-epoxide. Scheme 5b outlines modifications of C12-ketone.

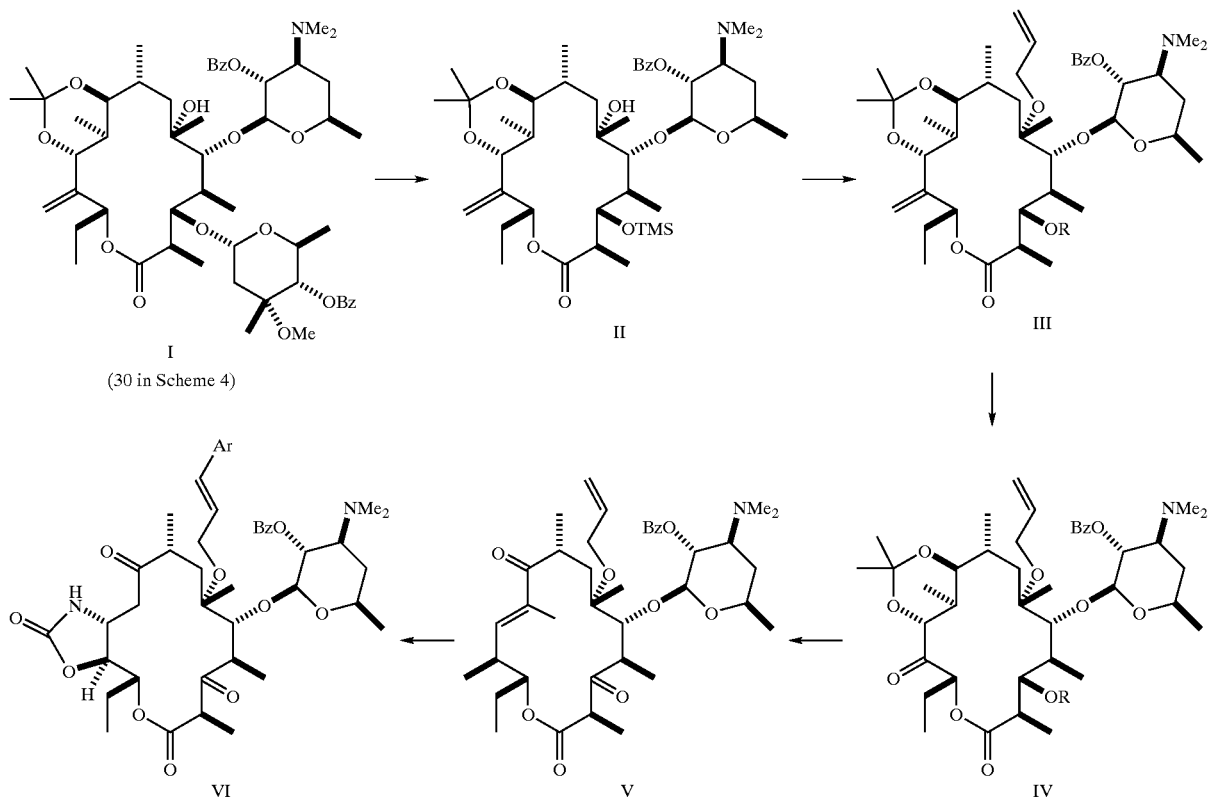
Scheme 5b.
Synthesis of novel 6-O-alkyl ketolide analogs via C12-ketone
Greater diversity at C12 can also be attained by conversion of the C12 ketone to an imine prior to the introduction of nucleophiles as shown in Scheme 6.
Scheme 6.
Synthesis of C11-C12 "reverse" carbamate
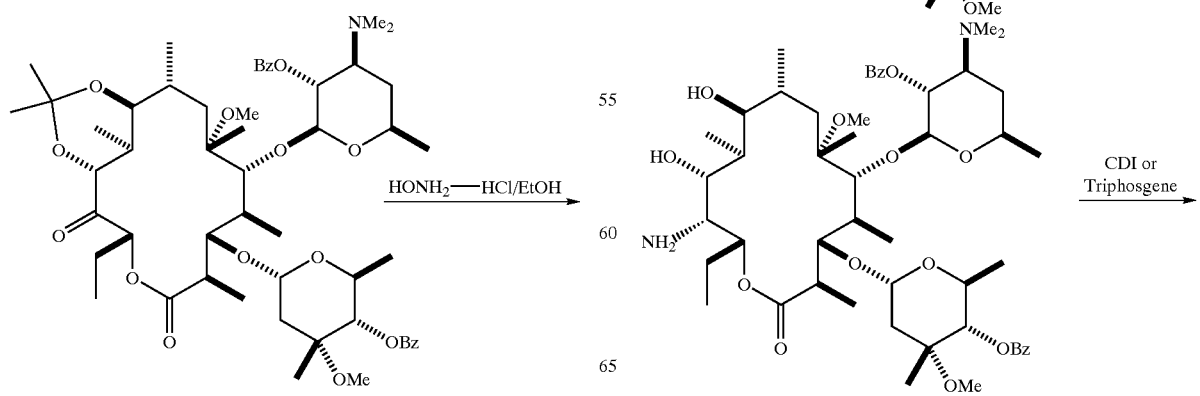
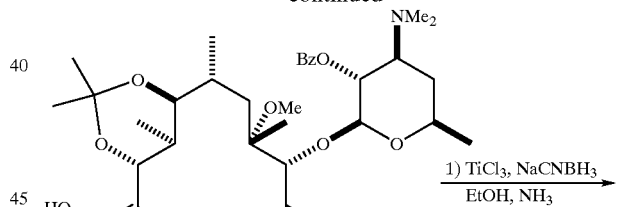

55

-continued

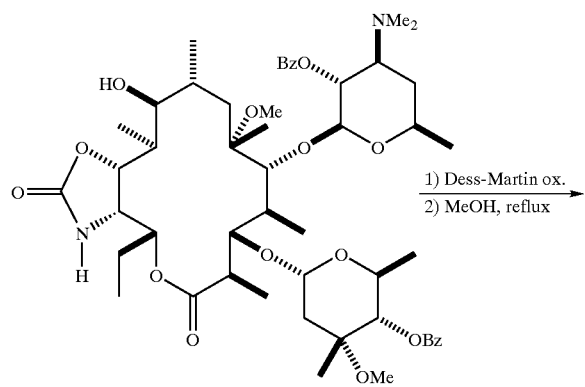

1) Dess-Martin ox.
2) MeOH, reflux

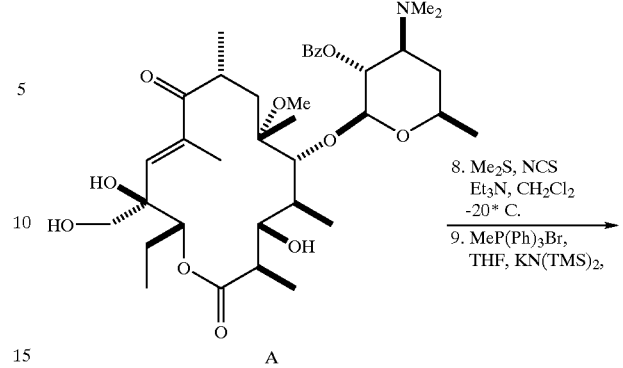

8. Me₂S, NCS
Et₃N, CH₂Cl₂
-20° C.
9. MeP(Ph)₃Br,
THF, KN(TMS)₂,

56

-continued

10. CDI, THF, NaH, 0° C.
11. amine, MeCN, H₂O,
60° C., 24 hrs
12. MeOH, 65° C., 8 hrs

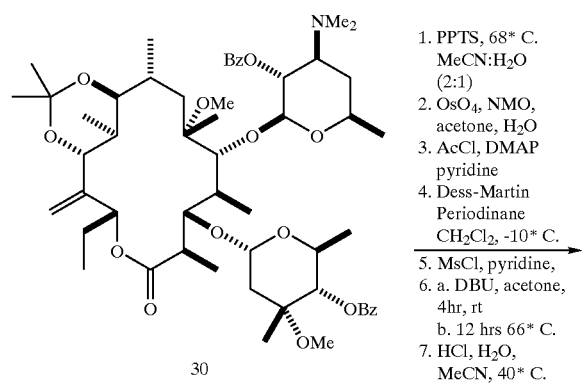

Scheme 7.
Synthesis of C12 vinyl macrolides

30

1. PPTS, 68° C.
MeCN:H₂O
(2:1)
2. OsO₄, NMO,
acetone, H₂O
3. AcCl, DMAP
pyridine
4. Dess-Martin
Periodinane
CH₂Cl₂, -10° C.
5. MsCl, pyridine,
6. a. DBU, acetone,
4hr, rt
b. 12 hrs 66° C.
7. HCl, H₂O,
MeCN, 40° C.

Dihydroxylation of alkene 30 can lead to useful intermediates for generating novel compounds containing modified C12 substituents as depicted in Scheme 7. Upon deprotection of the C9–C12 acetonide the C12 exocyclic olefin can be dihydroxylated yielding a tetraol that can be selectively protected at the primary C21 alcohol as the acetate. Selective oxidation of the C9 hydroxyl and mesylation of the C11 hydroxyl followed by elimination yields the C9–C11 enone. Removal of the cladinose and acetate yields a triol that can be bis oxidized to give a C12 formyl substituent. A Wittig reaction coverts this to the C12 vinyl substituent and then following in the manner described already the cyclic carbamate is installed.

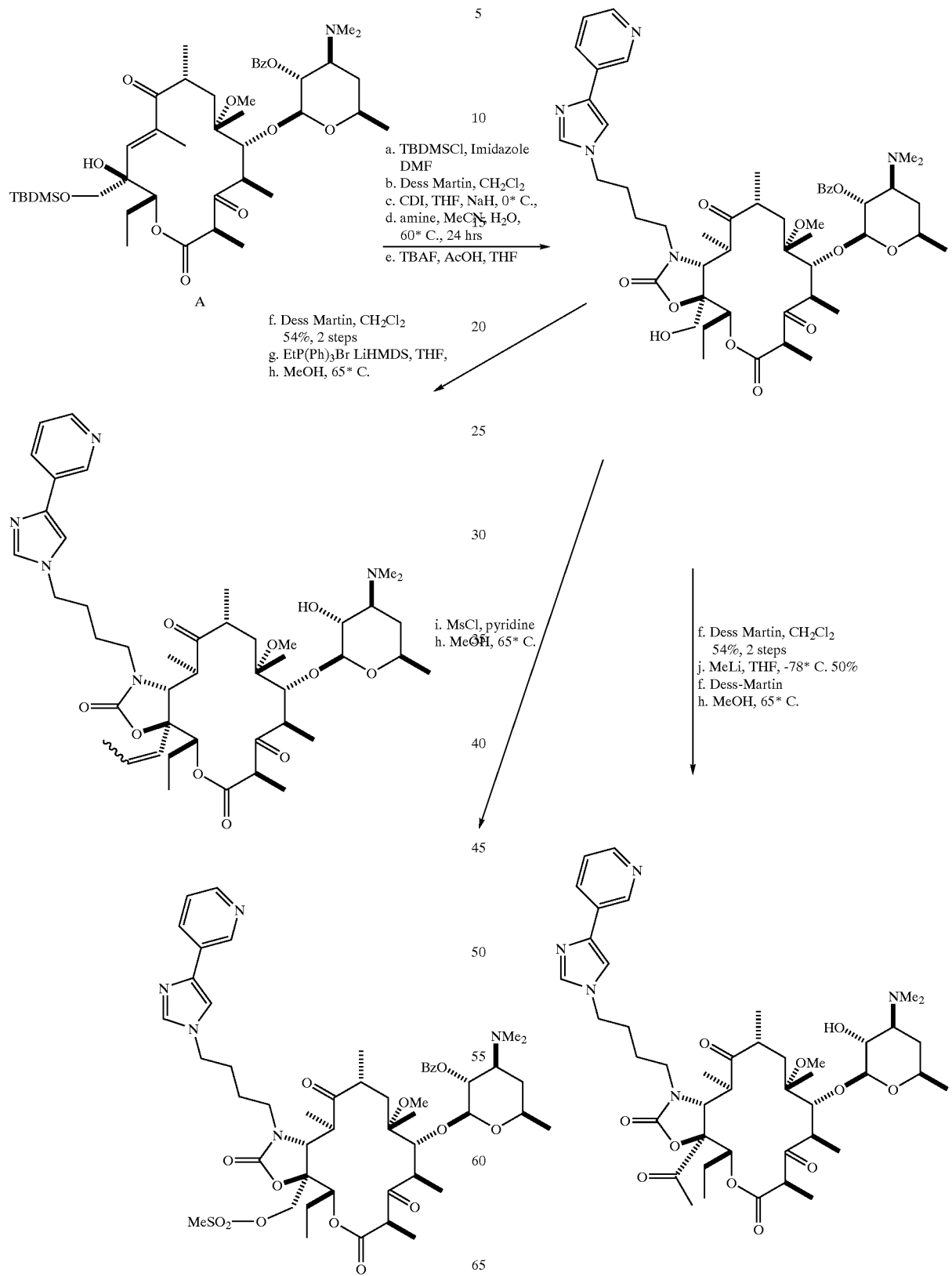

Further modification of dihydroxylated derived compound A can lead to further C12 modified macrolides, as described in Scheme 8. Selective silyl protection of the primary alcohol in A, followed by C3 oxidation, conversion to the cyclic carbamate in the usual fashion and disilylation yields the C12 hydroxymethyl macrolide. The C21 hydroxyl can be sulfonylated to form the C21 mesylate as depicted. The C12 hydroxymethyl can also be oxidized to form the C12 formyl macrolide. Wittig reaction on the C12 formyl, or reaction with organometallics, followed by oxidation yields the C12 alkenyl and C12 acteyl macrolides respectively as depicted.

Scheme 9 outlines the synthetic method to make novel C12 anhydrolides 308. Route 1 shows that novel C12 enone-ol 305 can be converted to 11,12-cyclic carbamate 306 in a similar manner as shown in Schene 2b. Further modifications include removal of cladinose under acidic condition, activating 3-hydroxy as mesylate and elimination under basic condition to give desired anhydrolide 308. Alternatively, C2, C3 double bond can be formed prior to the formation of C11, C12-cyclic carbamate as shown in Route 2.

Scheme 9.
Synthesis of anhydrolides-general scheme

Route 1

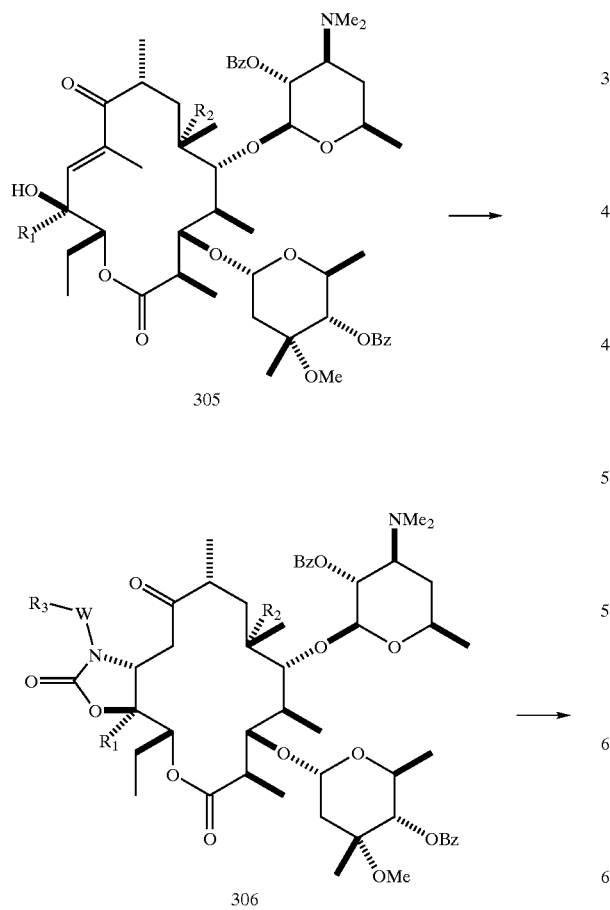

Route 2

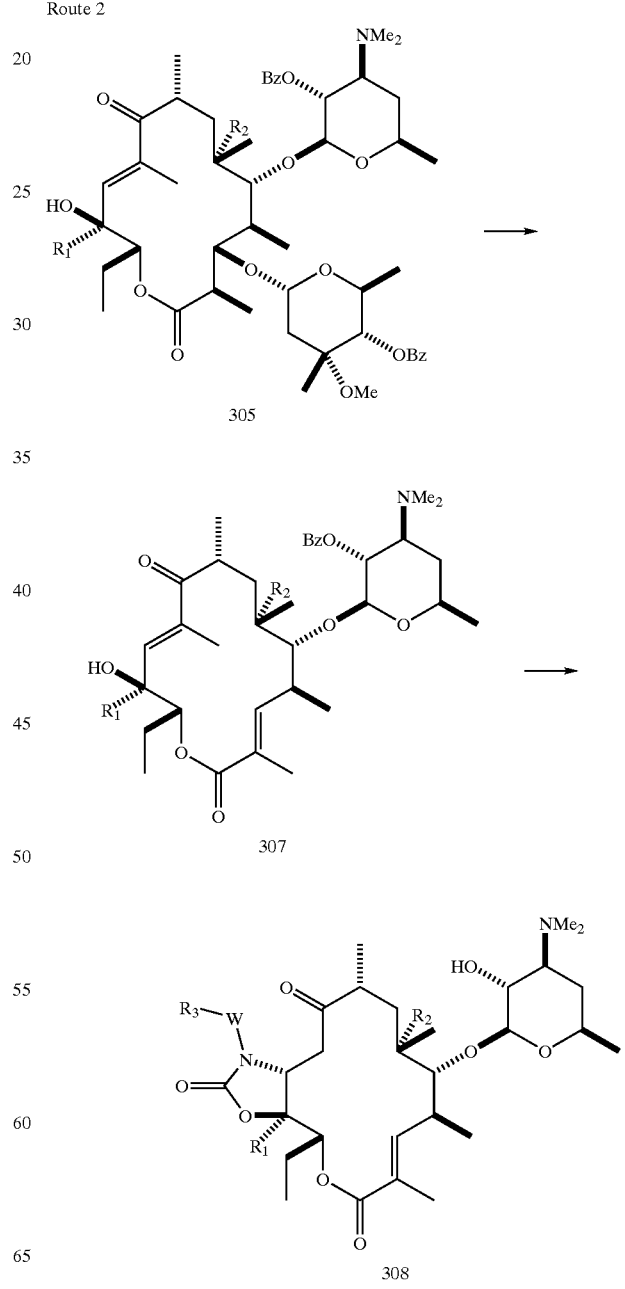

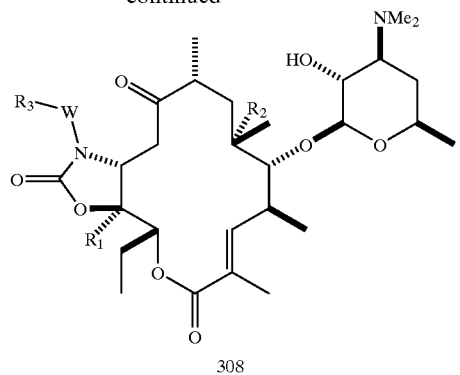

Scheme 10.
Synthesis of macrolide carbamate sidechains

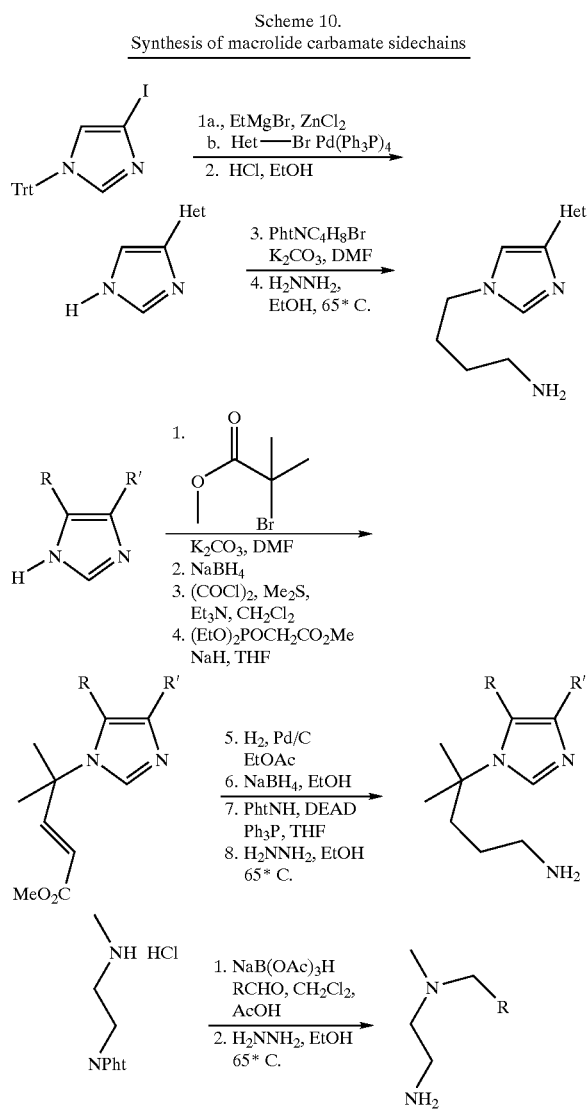

Scheme 10 depicts representative methods used construct side chains incorporated into the macrolides of the invention.

In the foregoing reaction schemes and other synthesis methods disclosed herein, diol protecting groups for the C9–C11 diol, wherein both alcohols are linked to form a 6–8 membered ring, may include, but are not limited to, those described in Greene and Wuts (1991), supra. Exemplary groups include cyclic acetals, such as methylene, ethylidene, 2,2,2-trichloroethylidene, benzylidene, p-methoxybenzylidene, 2,4-dimethoxybenzylidene, 3,4-dimthoxybenzylidene, 2-nitrobenzylidene; ketals such as 1-t-butylethylidene, 1-phenylethylidene, and (4-methoxyphenyl)ethylidene, acetonide, cyclopentylidene, cyclohexylidene, and cylcoheptylidene; cyclic ortho esters such as methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene, α-(N,N-dimethylamino)benzylidene, 2-oxacyclopentylidene; cyclic silyl ethers such as di-t-buylsilylene, 1,3-(1,1,3,3-tetraisopropyldisiloxanylidene), tetra-t-butoxydisilxane-1,2-diylidene; cyclic carbonates; and cyclic boronates such as ethyl, phenyl, their polymeric versions, and boronates linking two or more macrolides. Additionally, the diol as well as the sugar alcohols may be individually and independently protected with suitable alcohol blocking groups familiar to those skilled in the art. Exemplary protecting groups include but are not limited to silyl ethers such t-butyldimethyl-chlorosilyl, trimethylchlorosilyl, triisopropylchlorosilyl, triethylchlorosilyl, diphenylmethylsilyl, triphenylsilyl; optionally substituted ethers such as triphenylmethyl, methoxymethyl, methythiomethyl, benzyloxymethyl, t-butoxymethyl, 2-methoxyethoxymethyl, tetrahydropyranyl, 1-ethoxyethyl ether, allyl, benzyl, p-methoxybenzyl, nitrobenzyl; aryl and alkyl esters such as benzoylformate, formate, acetate, trichloroacetate, trifluoracetate, pivaloate; and carbonates such as methyl, 2,2,2-trichloroethyl, 2-(trimethylsilyl)ethyl, vinyl, allyl, p-nitrophenyl, benzyl, p-methoxybenzyl.

Pharmaceutical Compositions

Pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 $\mu$.

Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1–5µ. Predominantly in this application means that at least 70% but preferably more than 90% of all generated aerosol particles are within 1–5µ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic (DeVilbiss Medizinische Produkte (Deutschland) GmbH, Heiden, Germany) and UltraAire® (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Abbreviations

Abbreviations which have been used in the descriptions of the scheme and the examples that follow are: AcOH for acetic acid; AIBN for azobisisobutyronitrile; $Bu_3SnH$ for tributyltin hydride; CDI for carbonyldiimidazole; DBU for. 1,8-diazabicyclo[5.4.0]undec-7-ene; DCM for dichloromethane; DEAD for diethylazodicarboxylate; DMF for dimethylformamide; DMP for 2,2-dimethoxypropane DMSO for dimethylsulfoxide; DPPA for diphenylphosphoryl azide; $Et_3N$ for triethylamine; EtOAc for ethyl acetate; $Et_2O$ for diethyl ether; EtOH for ethanol; HOAc for acetic acid; LiHMDS or $LiN(TMS)_2$ for lithium bis(trimethylsilyl) amide; MCPBA for meta-chloroperbenzoic acid; MeOH for methanol; MsCl for methanesulfonyl chloride; NaHMDS or $NaN(TMS)_2$ for sodium bis(trimethylsilyl)amide; NMO for N-methylmorpholine N-oxide; $SOCl_2$ for thionyl chloride; PPTS for pyridium p-toluene sulfonate; Py for pyridine; TEA for triethylamine; THF for tetrahydrofuran; TMSCl for trimethylsilyl chloride; $TMSCF_3$ for trimethyl (trifluoromethyl)-silane; TPP for triphenylphosphine; TPAP for tetra-n-propylammonium perruthenate; DMAP for 4-dimethylamino pyridine, TsOH for p-toluene sulfonic acid.

Characterization and Purification Methods

Referring to the examples that follow, compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB–C18, 2.1×50 mm; Solvent system: 5–95% (or 35–95%, or 65–95% or 95–95%) acetonitrile in water with 0.05% TFA; Flow rate 0.8 mL/min; Molecular weight range 500–1500; Cone Voltage 20 V; Column temperature 40 C.) or a Hewlett Packard System (Series 1100 HPLC; Column: Eclipse XDB-C18, 2.1×50 mm; Solvent system: 1–95% acetonitrile in water with 0.05% TFA; Flow rate 0.4 mL/min; Molecular weight range 150–850; Cone Voltage 50 V; Column temperature 30 C.). All masses are reported as those of the protonated parent ions.

GCMS analysis was performed on a Hewlett Packard instrument (HP6890 Series gas chromatograph with a Mass Selective Detector 5973; Injector volume: 1 uL; Initial column temperature: 50 C.; Final column temperature: 250 C.; Ramp time: 20 minutes; Gas flow rate: 1 mL/min; Column: 5% Phenyl Methyl Siloxane, Model #HP 190915-443, Dimensions: 30.0 m×25 m×0.25 m).

Nuclear magnetic resonance (NMR) analysis was performed with a Varian 300 Mhz NMR (Palo Alto, Calif.). The spectral reference was either TMS or the known chemical shift of the solvent. Some compound samples were run at elevated temperatures (i.e. 75° C.) to promote increased sample solubility.

The purity of some of the invention compounds was assessed by elemental analysis (Desert Analytics, Tuscon, Ariz.)

Melting points were determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230–400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

The foregoing may be better understood by reference to the following examples which are presented for illustration and not to limit the scope of the inventive concepts.

EXAMPLE 1

Synthesis of 12, 21-anhydro-9-dihydro erythromycin A via his TMS 9, 11-carbonate

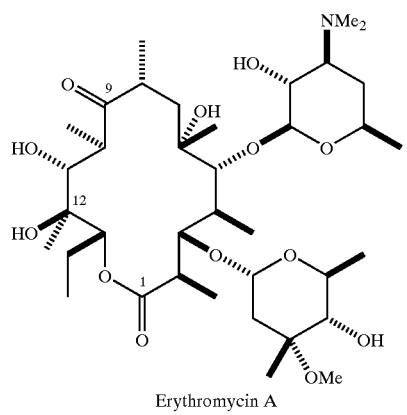

Erythromycin A

-continued

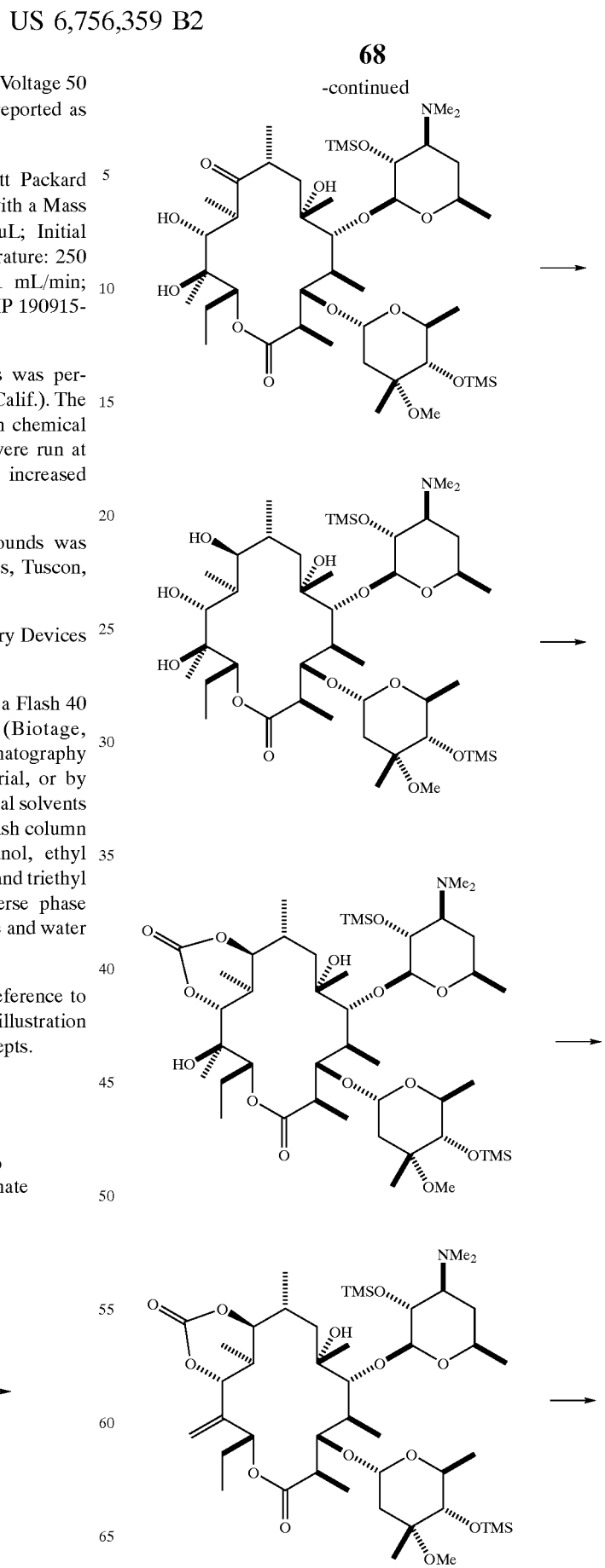

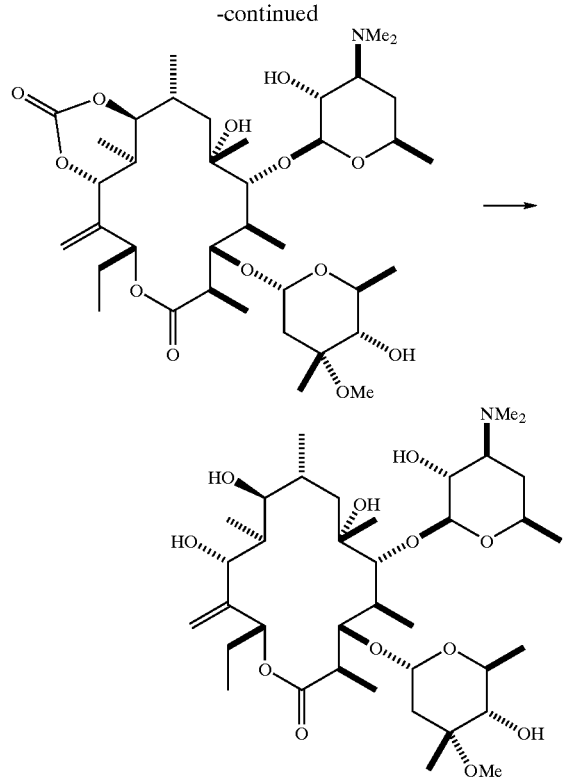

To a THF solution (0.15 M) of bis TMS 9-dihydro crythronolide A triol (prepared according to known procedures) was added CDI (1.1 eq) and $K_2CO_3$ (4.2 eq). After 3 h, EtOAc and sat. $NaHCO_3$ were added. The organic layer was washed with 5% $KH_2PO_4$, water and brine, dried over $Na_2SO_4$, filtered and concentrated. Purification by silica gel chromatography (25% to 50% EtOAc in Hx gradient) gave the desired carbonate as a white foam. MS m/z 906.9 (MH⁺).

To a 0° C. EtOAc solution (0.06 M) of the above carbonate was added $Et_3N$ (4.0 eq) followed by $SOCl_2$ (1.2 eq). After 1 h, the reaction was quenched with saturated $NaHCO_3$ and the organic layer was washed with 5% $KH_2PO_4$ (3×), water, and brine, dried over $Na_2SO_4$, and concentrated. Purification by silica gel chromatography (20% EtOAc in Hx with 2% $Et_3N$) gave the desired elimination product. MS m/z 888.9 (MH⁺).

The C12 alkene was combined with a 10% HCOOH in iPrOH to give a 0.35 M solution. After 1 h, 1M $K_2CO_3$ was added until the pH was approximately 8–9. The reaction was then diluted with EtOAc and the organic layer was washed with water and brine, dried over $Na_2SO_4$, filtered, and concentrated to give the crude product as a white foam. MS m/z 744.6 (MH⁺). The crude product was then suspended in MeOH (0.3 M) and to this was added 1M $K_2CO_3$ (1.5 eq). The reaction was be monitored by TLC and after 2.5 h, 5% $KH_2PO_4$ and EtOAc was added. The aqueous layer was extracted with more EtOAc (2×) and the combined organic layers were washed with brine, dried over $Na_2SO_4$, and concentrated. Purification by crystallization from MeCN gave the desired product. MS m/z 718.6 (MH⁺).

EXAMPLE 2

Synthesis of 12, 21-anhydro-9-dihydro erythromycin A via bis TMS 9, 11-acetonide

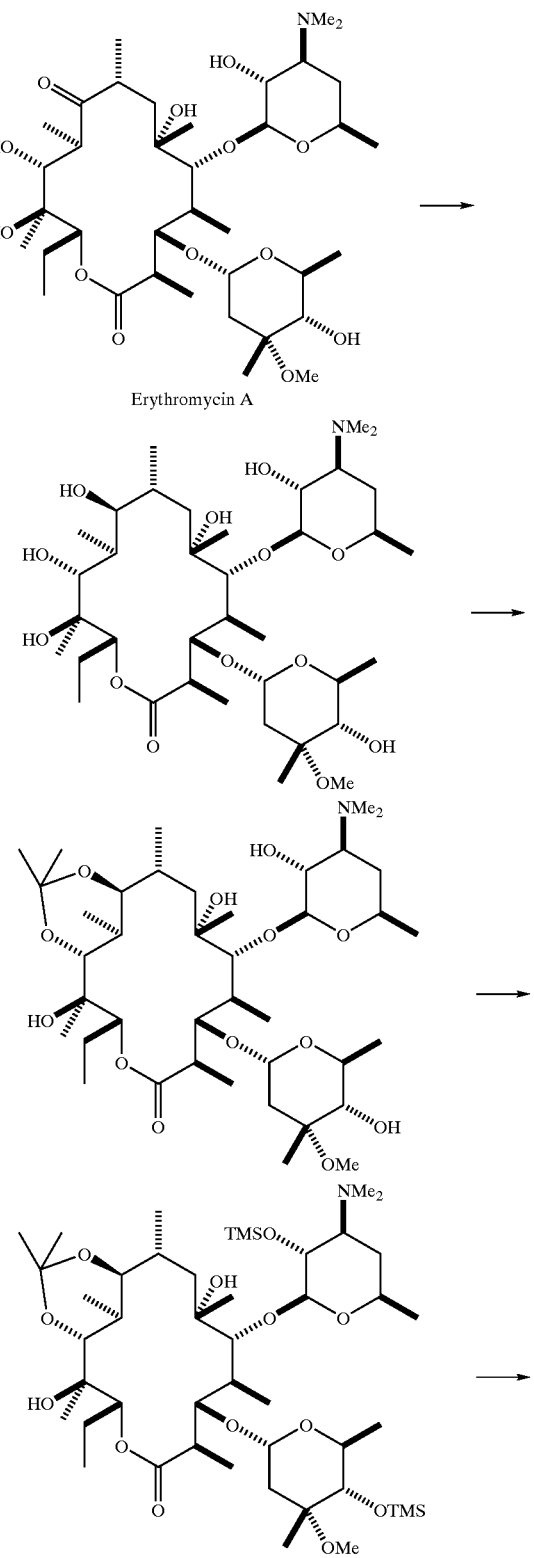

Erythromycin A

-continued

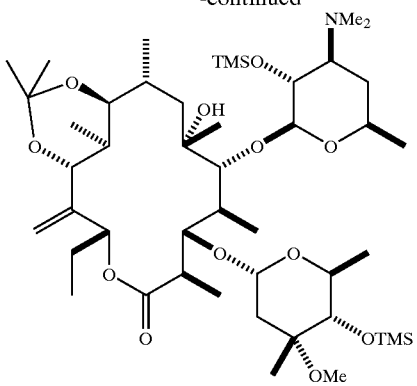

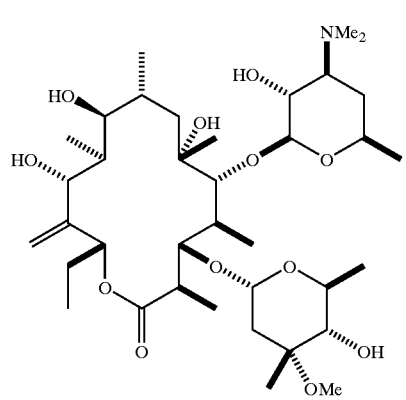

To a 1:1 acetone:2,2-dimethoxypropane solution (0.22 M) containing 9-dihydro erythronolide A was added PPTS (3 eq) and the resulting solution was refluxed. The reaction was monitored by TLC to watch for cleavage of the cladinose sugar. After approximately 1.5 h the reaction was cooled, quenched with Et$_3$N, and concentrated. The residue was suspended in CHCl$_3$, washed with 5% KH$_2$PO$_4$, 1N NH$_4$OH, and brine. The organic extracts were then dried over Na$_2$SO$_4$, and concentrated. Purification by silica gel chromatography (3% MeOH in CHCl$_3$ with 0.5% NHOH to 10% MeOH in CHCl$_3$ with 0.5% NH$_4$OH) gave the desired product. MS m/z 776 (MH$^+$).

To an EtOAc solution (0.13 M) of the acetonide was added dropwise via cannula an EtOAc (0.8 M) solution containing TMSCl (1.5 eq) and TMSIm (1.5 eq). After 2 hours, saturated NaHCO$_3$ was added and the organic layer was washed with water and brine, dried over Na$_2$SO$_4$, filtered, and concentrated. Purification by silica gel chromatography (25% to 50% EtOAc in Hx gradient) gave the desired bis TMS acetonide as a white foam.

To a 0° C. EtOAc solution (0.06 M) of the above acetonide was added Et$_3$N (4.0 eq) followed by SOCl$_2$ (1.2 eq). After 1.5 h, the reaction was quenched with saturated NaHCO$_3$ and the organic layer was washed with 5% KH$_2$PO$_4$ (3×), water, and brine, dried over Na$_2$SO$_4$, and concentrated to give the desired elimination product as a white foam.

To a 1:1 AcOH/MeOH solution (0.24 M) containing the alkene above was added H$_2$O (12 eq) and the solution was refluxed for 2 h. The reaction was then cooled and concentrated. The residue was suspended in CHCl$_3$ and washed with pH 10 NH$_4$OH solution (2×), water, and brine, dried over Na$_2$SO$_4$, and concentrated. Purification by silica gel chromatography chromatography (5% MeOH in CHCl$_3$ with 0.5% NH$_4$OH to 7.5% MeOH in CHCl$_3$ with 0.5% NH$_4$OH) followed by crystallization from MeCN gave the desired product. MS m/z 718.6 (MH$^+$).

EXAMPLE 3

C12 analogs via bis benzoate 9, 11 formates or 9, 11 acetonide

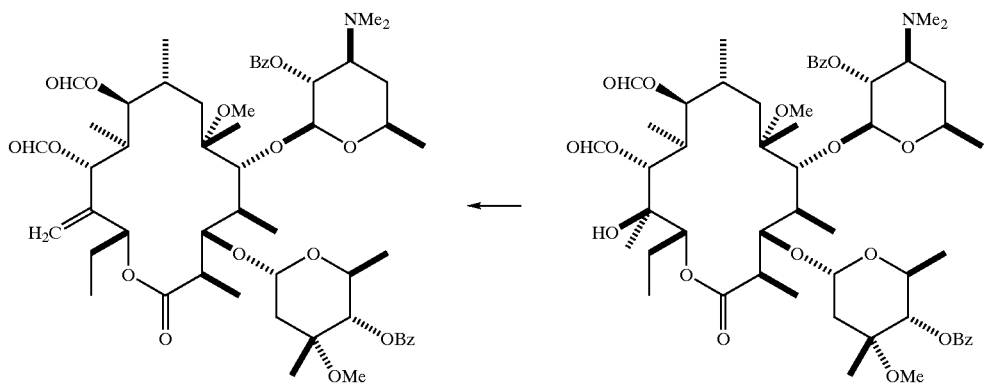

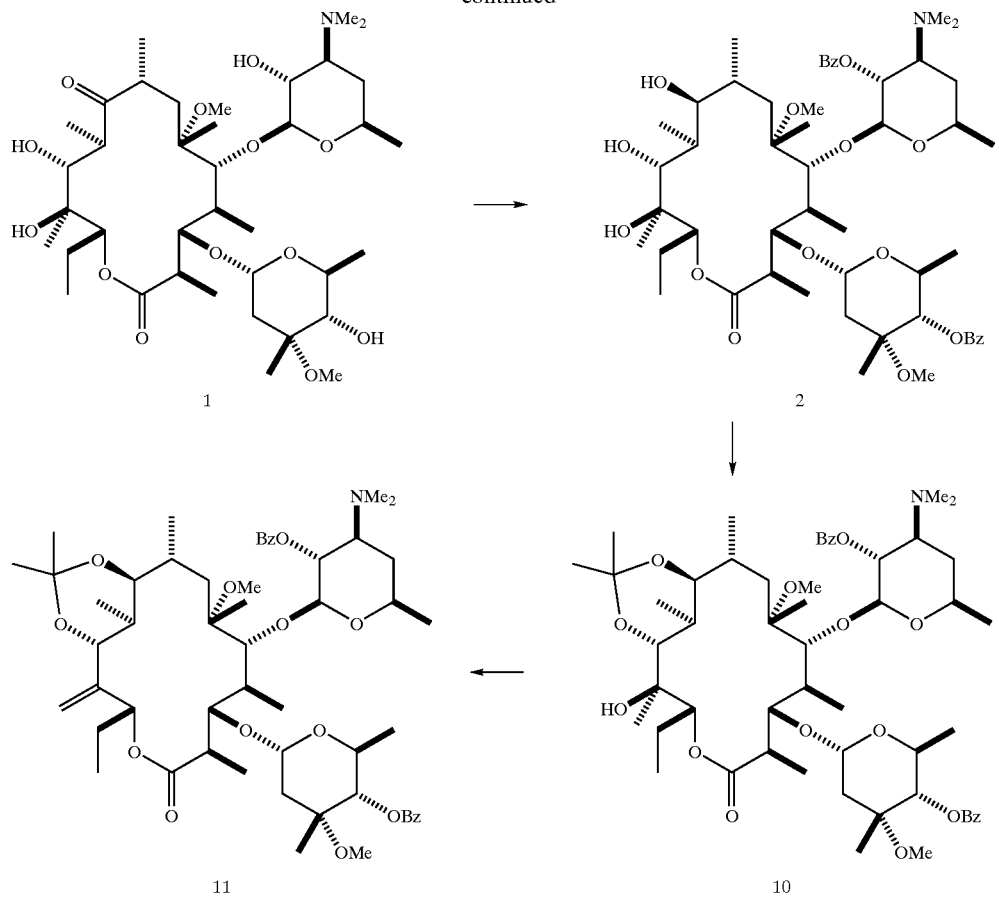

EXAMPLE 3(a)

Synthesis of Compound 2

To a solution of anhydrous methylene chloride (0.13 M) containing azeotropically dried compound 1 and DMAP (5 eq) was added anhydrous triethylamine (5 eq), and benzoic anhydride (5 eq). After stirring over night, the reaction was poured into ice-cold sat. sodium bicarbonate solution. The aqueous layer was extracted with methylene chloride (3×) and the combined organic layers were washed with 1 M $NaH_2PO_4$, brine, dried over $Na_2SO_4$, filtered, and concentrated. Purification by silica gel chromatography (8% MeOH/1% $NH_4OH$/91% DCM) followed by recrystallization from acetonitrile gave the desired dibenzoate product. ES/MS m/z 956.6 ($MH^+$).

To a THF solution of compound obtained from the above step was added ethanol (0.06 M 11:1 EtOH:THF) followed by fresh sodium borohydride (3.3 eq). The slightly cloudy mixture was monitored by LC/MS and stirred for 24 h at room temperature. Triethanolamine (7.8 eq) was added to the mixture and stirred for 8 h. The reaction mixture was then concentrated to a thick residue and to this was carefully added 10% aqueous $NaH_2PO_4$ followed by vigorous stirring for 20 min. The pH of the aqueous layer was corrected to ~9 with $K_2CO_3$ (if needed) and an equal volume of ethyl acetate was added. The organic layer was separated and the aqueous layer extracted ethyl acetate (3×). The combined organic layers were washed with brine, dried over $Na_2SO_4$, filtered, and concentrated. The crude material may be recrystallized from acetonitrile or purified by silica gel chromatography (4:1 hexane:acetone with 1% TEA). ES/MS 958.6 ($MH^+$).

EXAMPLE 3(b)

Synthesis of Compound 3

To a 0° C. $CH_2Cl_2$ solution (0.12 M) of compound 2 was added DMAP (2 eq) followed by dropwise addition of FAA (3 eq; for formyl acetic acid FAA synthesis, see reference: Krimen, L. I. Organic Synthesis, 1970, vol. 50, p.1.). The reaction was then warmed to rt and stirred for 18 h. Over the course of ~3 days additional DMAP (2 eq) and FAA (3 eq) were periodically added (about every 24 h) at 0° C. followed by warming to rt, until LC/MS showed >90% formation of the desired product. The reaction was quenched by pouring into cold $NaHCO_3$ (aq. layer has pH~9). The solution was next extracted with $CH_2Cl_2$ and concentrated in vacuo. The residue was re-dissolved in DCM, washed with 10% HCl aq., brine, and concentrated in vacuo to give a white foam (>90%) that can be used in the next step without further purification or may be recrystallized form $CH_3CN$. ES/MS 1014 ($MH^+$).

EXAMPLE 3(c)

Synthesis of Compound 4

To a 0° C. EtOAc solution of compound 3 was added anhydrous $Et_3N$ (4 eq) followed by rapid addition of thionyl chloride (1.7 eq). A pink precipitate forms immediately. The reaction was stirred for another 2 h at 0° C. then quenched with ice-cold saturated $NaHCO_3$. The aqueous layer was extracted with $CH_2Cl_2$ (3×) and the combined organic layers were washed with brine, dried over $Na_2SO_4$, and concentrated. Recrystallization from acetonitrile the pure product. ES/MS 996 (MH$^+$).

EXAMPLE 3(d)

Synthesis of Compound 10

To a 1.75:1 acetone: 2,2-dimethoxypropane (0.02M) solution containing azeotropically dried triol 2 was added pyridinium p-toluenesulfonate (PPTS, 3 eq) and the resulting solution was heated to reflux for 3.5 h. Reaction progress can be monitored by TLC (4:1, hexane:acetone, ~1% Et$_3$N, R$_f$=0.27) by quenching an aliquot from the reaction pot with CH$_2$Cl$_2$ containing Et$_3$N. Upon consumption of starting material, the reaction mixture was cooled to RT and Et$_3$N (5.8 eq) was added to quench the PPTS. The solvents were removed under reduced pressure and the resulting foam was redissolved in CH$_2$Cl$_2$ and washed with 5% aqueous NaH$_2$PO$_4$ (2×), water (2×), and brine. The organic layer was dried with Na$_2$SO$_4$, filtered, and concentrated in vacuo. Purification by silica gel chromatography (4:1 hexane:acetone, with 1% Et$_3$N) gave the desired acetonide. MS m/z 998.7 (MH$^+$).

EXAMPLE 3(e)

Synthesis of Compound 11

To a 0° C. solution of dry ethyl acetate (0.05M) containing acetonide 10 was added anhydrous triethylamine (4.3 eq) followed by slow addition of thionyl chloride (1.4 eq) over 15 minutes. A pink precipitate forms immediately. The reaction was monitored by LC/MS stirred for another 1.5 h at 0° C. The reaction mixture was then poured over ice and saturated NaHCO$_3$. The aqueous layer was extracted with CH$_2$Cl$_2$ (2×) and the combined organic layers were washed with brine, dried over Na$_2$SO$_4$, filtered, and concentrated. Purification by silica gel chromatography (15% acetone/hexane and 1% Et$_3$N) gave alkene 11. MS m/z 980.6 (MH$^+$).

EXAMPLE 4

C12 Analogs via Epoxide Ring Opening

EXAMPLE 4(a)

Synthesis of Scheme 1a Compound 5

Referring to Scheme 1a, above, Et$_3$N (4 eq.) was added to a 0.06M MeOH solution of 4 and the mixture was refluxed for 14 h. An additional Et$_3$N (1 eq) was then added and refluxing was continued for an additional 5 h. The solution was cooled to rt and concentrated in vacuo to give an approximately 1.2:1 ratio of 2'-OH:2"-OBz. The crude intermediate was next suspended in CH$_2$Cl$_2$ (0.14 M) and treated with Bz$_2$O (3 eq). After stirring overnight at rt, more Bz$_2$O (1 eq) and CH$_2$Cl$_2$ were added. After stirring for 23 h, CH$_2$Cl$_2$ was added and the reaction was quenched with sat. NaHCO$_3$ (aq.). The aqueous layer was extracted with CH$_2$Cl$_2$ (2×) and the combined organic layers were dried over MgSO$_4$, filtered, and concentrated. Purification by silica gel chromatography (5:1 hexanes:acetone with 1% Et$_3$N) gave the desired diol product 5. ES/MS m/z 941 (MH$^+$), C$_{52}$H$_{77}$NO$_{14}$=940 g/mol.

EXAMPLE 4(b)

Synthesis of Compound 6

To a 0.05 M CH$_2$Cl$_2$ solution of alkene 5 at 0° C. was added mCPBA (4 eq). The reaction was then warmed to rt and stirred for overnight. Additional mCPBA (1 eq) and CH$_2$Cl$_2$ were added and stirred for 5 h. The reaction was quenched by adding cyclohexene (3 eq) and stirring for 1 h. 3M NaHSO$_3$ (aq) was next added to reduce the desosamine N-oxide. After stirring overnight, the solution was extracted with NaHCO$_3$ and CH$_2$Cl$_2$. The organic extracts were washed with brine, dried over MgSO$_4$, filtered, and concentrated. Purification by silica gel chromatography (2:1 hexane/acetone with 1% Et$_3$N) gave the product 6. ES/MS m/z 957 (MH$^+$), C$_{52}$H$_{77}$NO$_{15}$=956 g/mol.

EXAMPLE 4(c)

Synthesis of Compound 7

To a solution of the epoxide 6 in 0.1 M CH$_2$Cl$_2$ at 0° C. was added the Dess Martin periodinane (1.2 eq). After 1 h, the reaction was warmed to rt, stirred for 6 h, diluted with CH$_2$Cl$_2$, filtered through celite, and concentrated. Purification by silica gel chromatography (6:1 to 4:1 hexanes:acetone gradient with 1% Et$_3$N) gave the ketone 7. ES/MS m/z 955 (MH$^+$), C$_{52}$H$_{75}$NO$_{15}$=954 g/mol.

EXAMPLE 4(d)

Synthesis of Compound 8

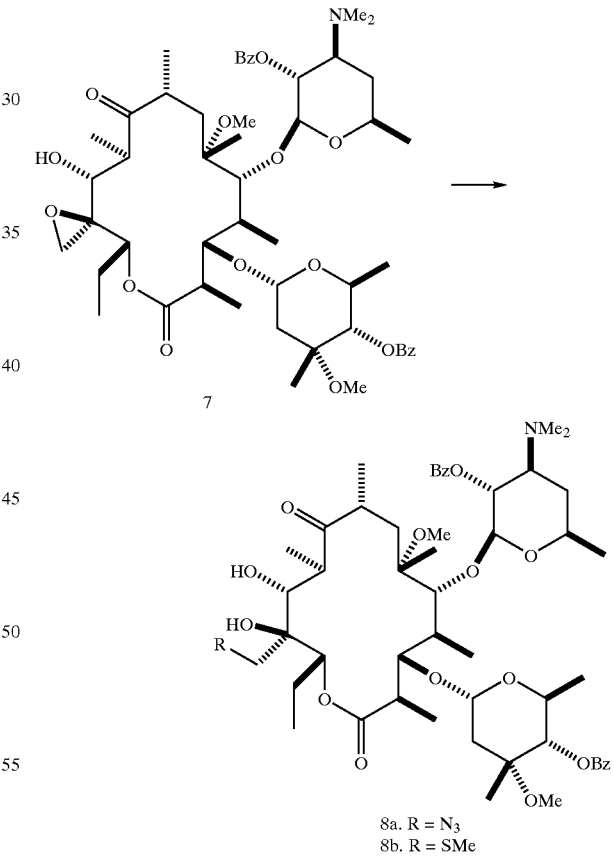

To 0.05M DMF solution of epoxide 7 was added LiClO$_4$ (2 eq) and NaN$_3$ (6 eq). After heating at 60 C. for 2 days, the reaction was quenched with NaHCO$_3$ (aq) and extracted with CH$_2$Cl$_2$. The organic extracts were washed with water, brine, dried over MgSO$_4$, filtered, concentrated, and purified by silica gel chromatography (7:1 to 5:1 hexanes:acetone with 1% Et$_3$N gradient) give the desired product 8a. ES/MS m/z 997.5 (MH+), $C_{52}H_{76}N_4O_{15}$=996.5 g/mol. Ring opening of the epoxide with NaSMe was performed in a similar matter (reaction stirred at rt for 2 h) to give the thiol ether 8b. ES/MS m/z 1002.5 (MH+), $C_{53}H_{79}NO_{15}S$=1001.5 g/mol.

EXAMPLE 4(e)

Synthesis of Compound 9

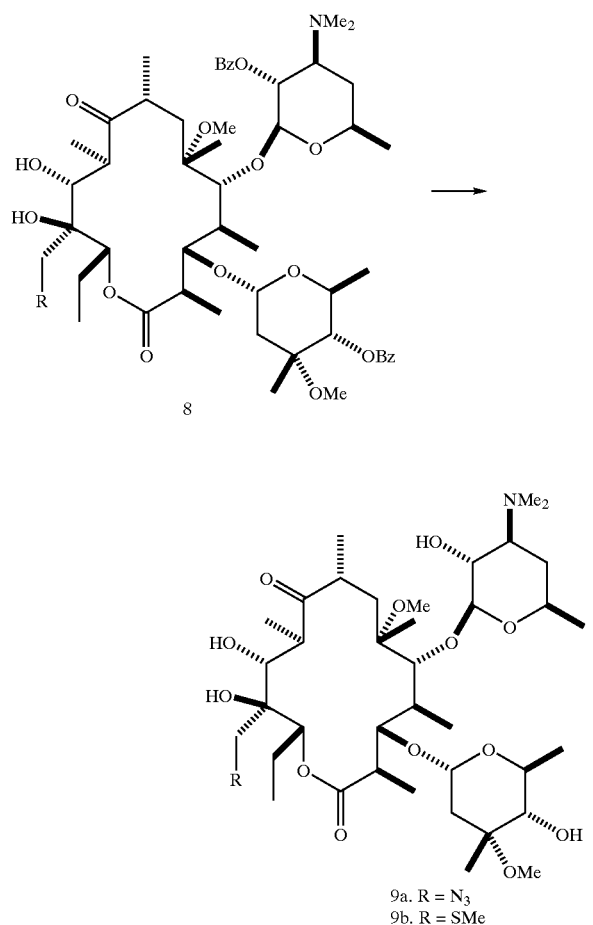

9a. R = N$_3$
9b. R = SMe

A 0.02M MeOH solution containing 8 was heated at 65° C. for 16 h and cooled to rt. K$_2$CO$_3$ was next added and heated to 40° C. for 46 h. The solution was diluted with CH$_2$Cl$_2$ and washed with aq. NaHCO$_3$. The aq layer was extracted with CH$_2$Cl$_2$ and the combined organic extracts were washed with brine, dried over MgSO$_4$, filtered, concentrated, and purified by silica gel chromatography (3:1 to 2:1 hexanes:acetone with 1% Et$_3$N gradient) to give the final product. 9a: ES/MS m/z 789 (MH+), $C_{38}H_{68}N_4O_{13}$= 788 g/mol. 9b: ES/MS m/z 794 (MH+), $C_{39}H_{71}NO_{13}S$=793 g/mol.

EXAMPLE 5

C12 Analogs via Epoxide (Scheme 1b)

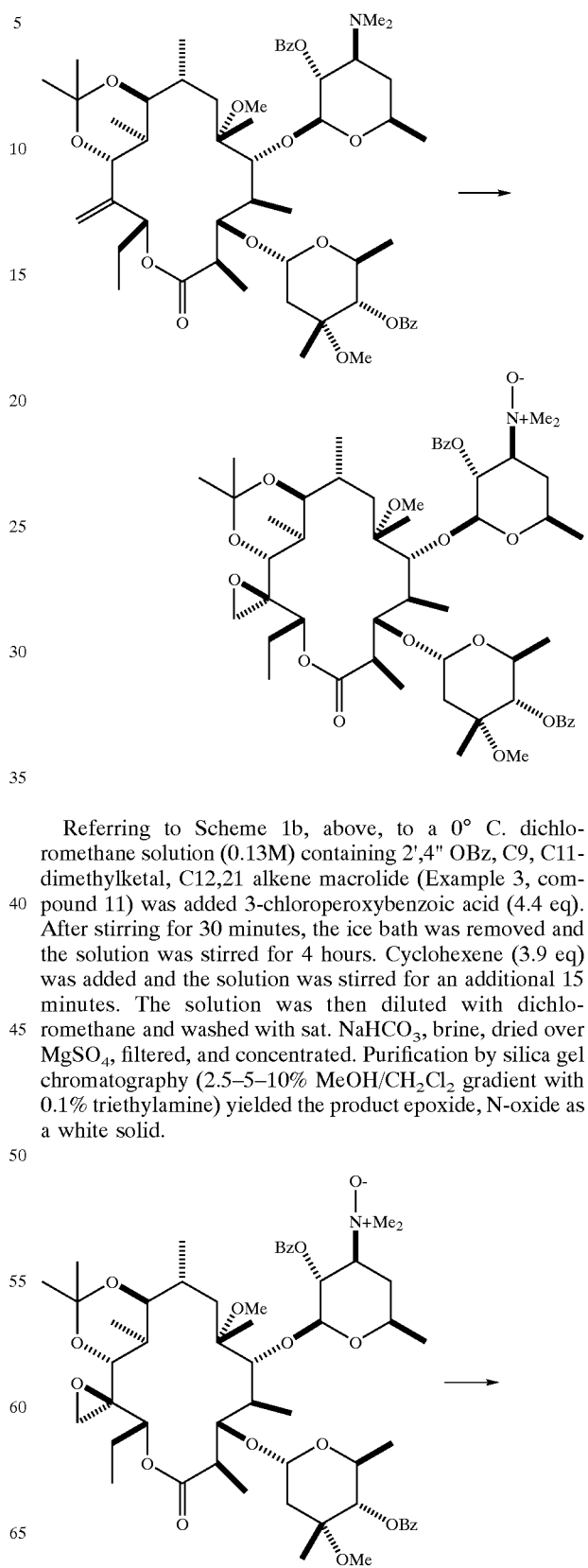

Referring to Scheme 1b, above, to a 0° C. dichloromethane solution (0.13M) containing 2',4" OBz, C9, C11-dimethylketal, C12,21 alkene macrolide (Example 3, compound 11) was added 3-chloroperoxybenzoic acid (4.4 eq). After stirring for 30 minutes, the ice bath was removed and the solution was stirred for 4 hours. Cyclohexene (3.9 eq) was added and the solution was stirred for an additional 15 minutes. The solution was then diluted with dichloromethane and washed with sat. NaHCO$_3$, brine, dried over MgSO$_4$, filtered, and concentrated. Purification by silica gel chromatography (2.5–5–10% MeOH/CH$_2$Cl$_2$ gradient with 0.1% triethylamine) yielded the product epoxide, N-oxide as a white solid.

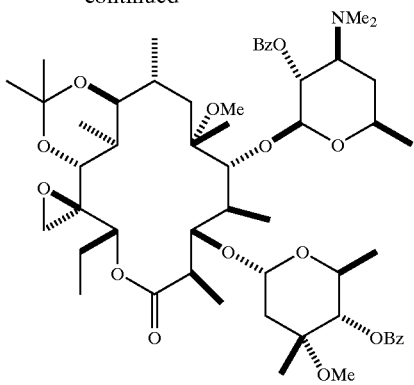

To a 0° C. dichloromethane solution (0.1 M) containing the epoxide was added 2-propanol (4 eq.), 4 A° powdered mol sieves and (tetrapropyl)ammonium perruthenate (0.05 eq). After stirring for 2 h, the ice bath was removed and the solution was stirred for an additional 2 hr. The reaction mixture was purified directly by column chromatography (15% acetone/$CH_2Cl_2$ with 0.1% triethylamine) yielding the product epoxide as a white solid. MS m/z 996.4 ($MH^+$).

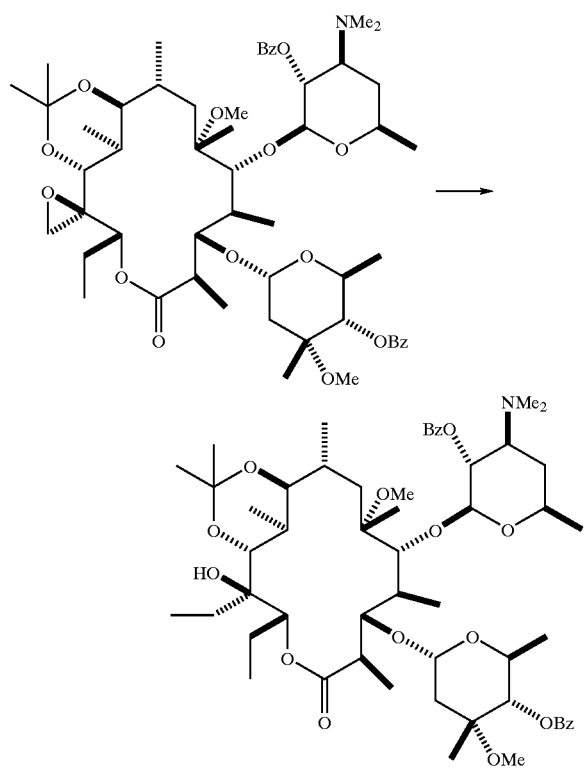

An oven dried 2-neck flask equipped with a 14/20 side arm connection to the manifold was cooled under Ar. An internal thermocouple was inserted and CuBr dimethyl sulfide complex (5 eq) was added. The system was evacuated under high vacuum and purged with Ar three times. Diethyl ether (0.05M in CuBr) was added and the heterogeneous solution was cooled in a −78° C. bath. Methyl lithium (10 eq) was added via syringe with the internal temperature ≦−60° C. The solution was held in the −78° C. bath for 10 minutes and then the bath was removed. Upon warming to −20° C., a homogeneous solution resulted. The solution was then held at −30° C. An oven dried 2-neck flask equipped with a 14/20 side arm connection to the manifold was cooled under Ar. C12, C21 epoxide was added and the system was evacuated under high vacuum and purged with Ar three times. Diethyl ether was added (0.07M) and the epoxide was stirred and heated gently to dissolve everything. Upon cooling, the epoxide solution was added via syringe to the cuprate solution (at −30° C.; a diethyl ether rinse was also included). The internal temperature during the addition was ≦−10° C. The resultant light yellow heterogeneous solution was held at 0° C. for 6 h with stirring. Sat. $NH_4Cl$ (40 mL) was added to stop the reaction, with the internal temp ≦10° C. The reaction was diluted with ethyl acetate and washed with sat. $NH_4Cl$ (2×), brine, dried over $MgSO_4$, filtered and concentrated. Purification by silica gel chromatography (15% acetone/hexanes with 0.1% triethylamine) yielded the C12 ethyl, hydroxy macrolide as a white solid. MS m/z 1012.4 ($MH^+$).

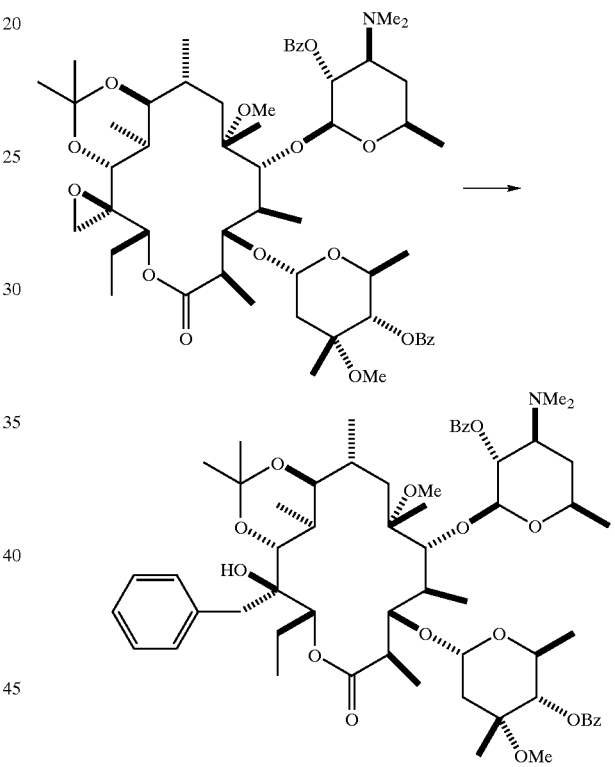

An oven dried 2-neck flask equipped with a 14/20 side arm connection to the manifold was cooled under Ar. An internal thermocouple was inserted and CuBr dimethyl sulfide complex (5 eq) was added. The system was evacuated under high vacuum and purged with Ar three times. Diethyl ether (0.05M in CuBr) was added and the heterogeneous solution was cooled in a −78° C. bath. Phenyl lithium (9.6 eq) was added via syringe with the internal temperature ≦5° C. The solution was then held in the 0° C. bath for 45 minutes. An oven dried 2-neck flask equipped with a 14/20 side arm connection to the manifold was cooled under Ar. C12, C21 epoxide was added and the system was evacuated under high vacuum and purged with Ar three times. Diethyl ether was added (0.07M) and the epoxide was stirred and heated gently to dissolve everything. Upon cooling, the epoxide solution was added via syringe to the cuprate solution (at 0° C.; 2× diethyl ether rinses were included). The internal temperature during the addition was ≦5° C. The resultant heterogeneous solution was stirred at 0° C. for 2.5 h and than at rt for 5 h. The solution was cooled to 0° C., and sat. NH₄Cl was added to stop the reaction, with the internal temp ≦10° C. The reaction was diluted with ethyl acetate and washed with sat. NH₄Cl, brine, dried over MgSO₄, filtered, and concentrated. Purification by silica gel chromatography (15% acetone/hexanes with 0.1% triethylamine). yielded the C12 phenyl, hydroxy macrolide as a white solid. MS m/z 1074.5 (MH⁺).

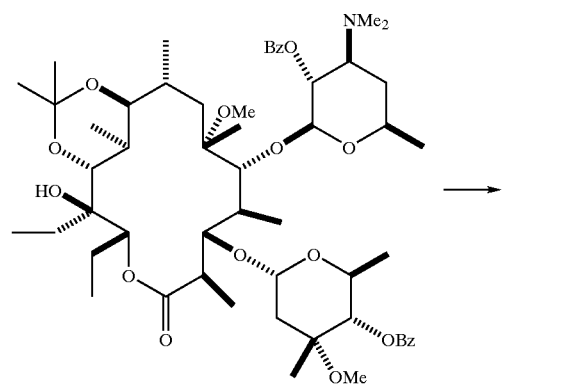

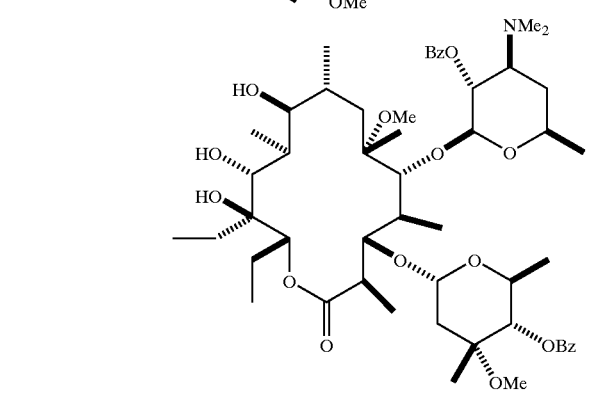

To C9, C11 ketal C12 ethyl, C12hydroxy macrolide in 2:1 acetonitrile/water (0.1M) was added pyridinium p-toluenesulfonate (5 eq). The solution was heated in a 68° C. oil bath for 46 hours. Upon cooling, the reaction was diluted with ethyl acetate, washed with sat. NaHCO₃, brine, dried over MgSO₄, filtered, and concentrated. Purification by flash chromatography (15% acetone/hexanes with 0.1% triethylamine) yielded the C12 ethyl, C9, C11, C12 triol macrolide as a white solid. MS m/z 972.4 (MH⁺).

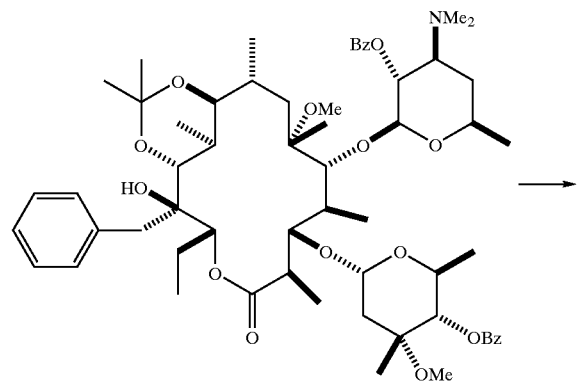

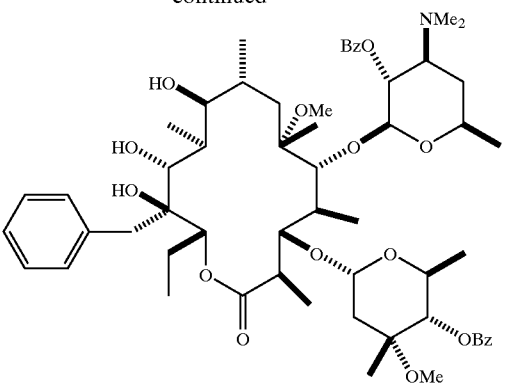

To C9, C11 ketal C12 phenyl, C12 hydroxy macrolide (obtained as described above) in 2:1 acetonitrile/water (0.09M) was added pyridinium p-toluenesulfonate (5 eq). The solution was heated in a 68° C. oil bath for 21 hours. Upon cooling, the reaction was diluted with ethyl acetate and washed with sat. NaHCO₃, brine, dried over MgSO₄, filtered, and concentrated. Purification by flash chromatography (20% acetone/hexanes with 0.1% triethylamine) yielded the C12 phenyl, C9, C11, C12 triol macrolide as a white solid. MS m/z 1034.4 (MH⁺).

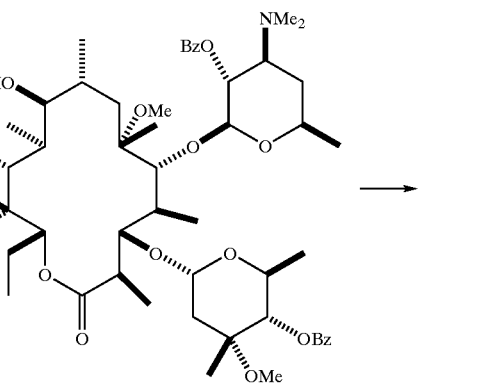

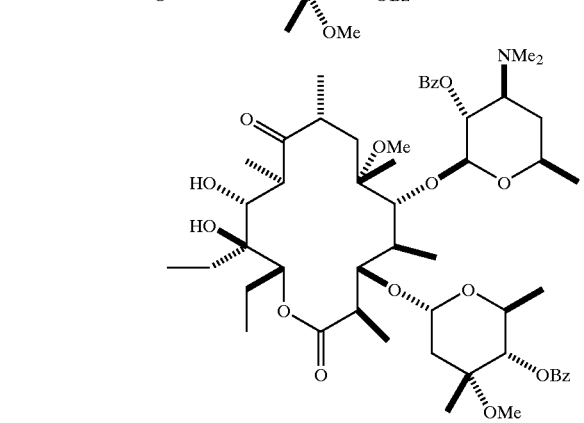

To C12 ethyl, C9, C11, C12 triol macrolide (obtained as described above) in dichloromethane (0.05M) at −5° C. was added Dess-Martin Periodinane (1.3 eq). The solution was stirred for 5 minutes and then was placed in a −10° C. refrigerator. After standing for 22 h, more Dess-Martin Periodinane (0.22 eq) was added and the solution stood in the −10° C. refrigerator for an additional 8 hours. The solution was diluted with ethyl acetate and washed with 1:1 10% Na$_2$S$_2$O$_3$/sat. NaHCO$_3$. The combined aqueous layers were back extracted with ethyl acetate and the combined organic layers were then washed with brine, dried over MgSO$_4$, filtered, and concentrated. Purification by flash chromatography (15% acetone/hexanes with 0.1% triethylamine) yielded the C12 ethyl C9 keto, C11, C12 diol macrolide as a white solid. MS m/z 970.5 (MH$^+$).

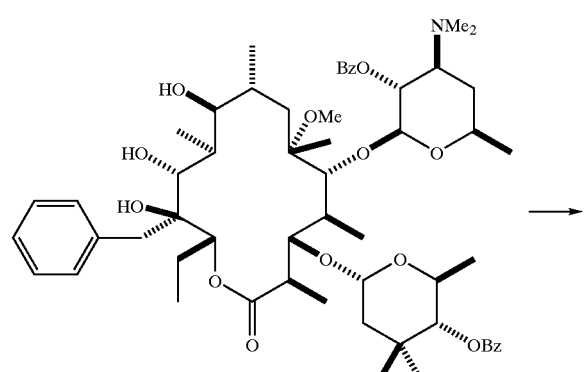

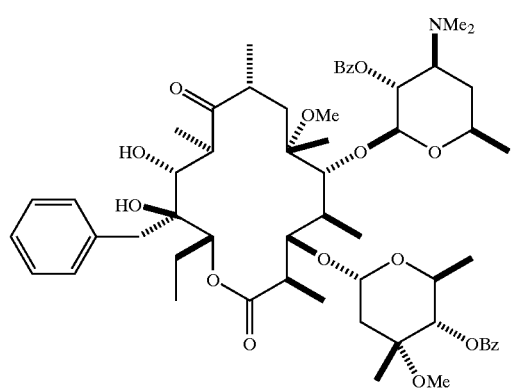

To C12 phenyl, C9, C11, C12 triol macrolide (obtained as described above) in dichloromethane (0.05M) at −5° C. was added Dess-Martin Periodinane (1.1 eq). The solution was stirred for 5 minutes and then was placed in a −10° C. refrigerator. After standing for 40 h, more Dess-Martin Periodinane (0.68 eq) was added and the solution stood in the −10° C. refrigerator for an additional 8 h. The solution was diluted with dichloromethane and washed with 1:1 10% Na$_2$S$_2$O$_3$/NaHCO$_3$, brine, dried over MgSO$_4$, filtered, and concentrated. Purification by flash chromatography (15% acetone/hexanes with 0.1% triethylamine) yielded the C12 phenyl C9 keto, C11, C12 diol macrolide as a white solid. MS m/z 1032.3 (MH$^+$).

C12 benzyl C9 Keto, C11 OMs, C12 OH macrolide

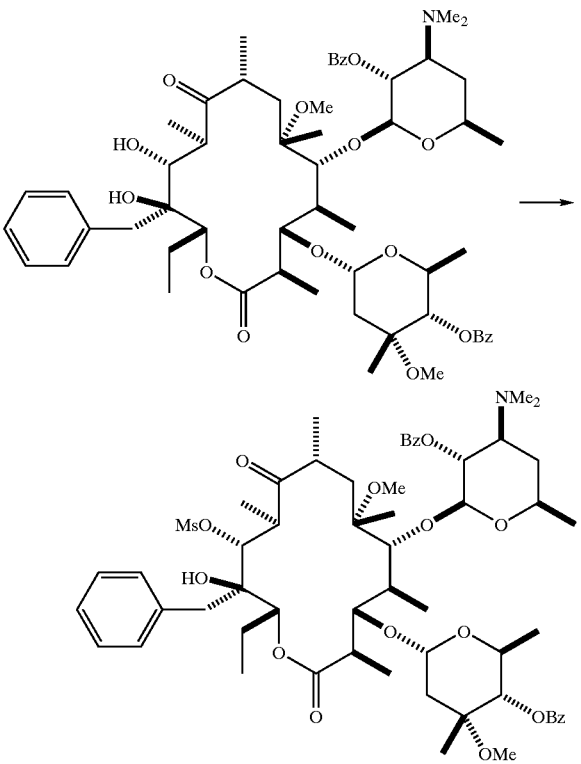

To C12 benzyl, C9 keto, C11, C12 diol macrolide (1 eq) in pyridine at 0° C. was added methanesulfonyl chloride (5 eq) via syringe over 5 minutes. The solution was stirred for 20 hours as the solution warmed to room temperature. Upon concentrating, the material was taken up in ethyl acetate and washed with NaHCO$_3$ $_{(sat)}$, with NaCl$_{(sat)}$, dried over MgSO$_4$, filtered and concentrated. Purification by flash chromatography (25% acetone/hexanes with 0.1% triethylamine) yielded the C12 benzyl C9 keto, C11 OMs, C12 hydroxy macrolide (90% yield) as a white solid. MH$^+$ (1110.5).

C12 benzyl C9, C10, C11 enone, C12 OH diol macrolide

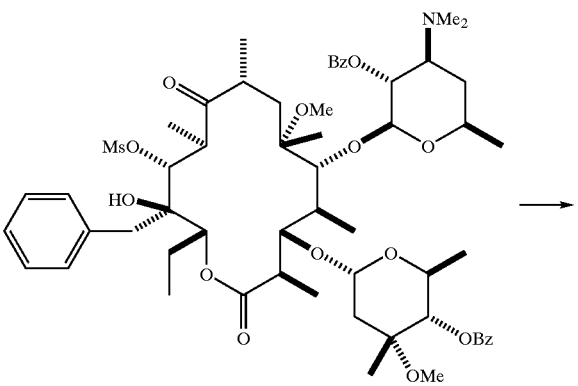

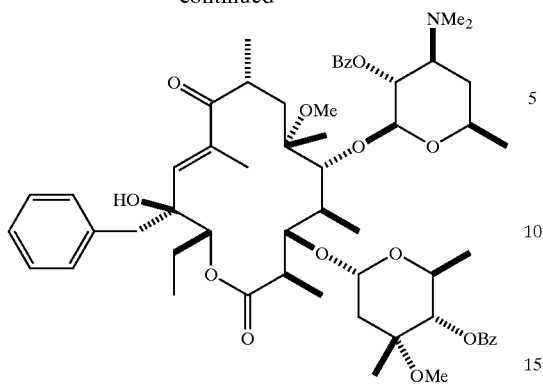

To C12 benzyl, C9, C11 OMs, C12 OH macrolide (1 eq) in acetone was added DBU (1.5 eq). The solution was stirred for 16 hours at rt and then for 26 hours at 60° C. The solution was diluted with ethyl acetate, washed with $H_2O$, with $NaCl_{(sat.)}$, dried over $MgSO_4$, filtered and concentrated yielding the C12 benzyl C9, C10, C11 enone, C12 OH macrolide (81% yield) as an off white solid. $MH^+$(1014.5).

C12 benzyl C9, C10, C11 enone, C3, C12 diol macrolide

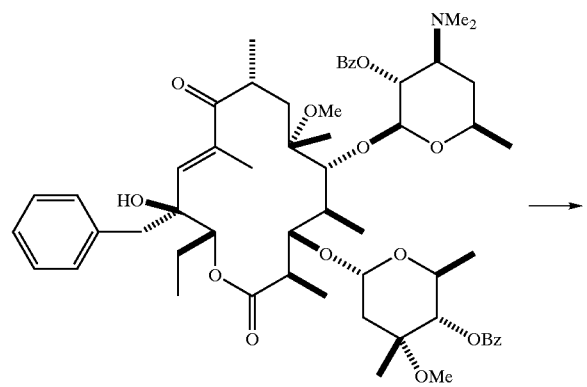

To C12 benzyl C9, C10, C11 enone C12 OH macrolide (1 eq) in acetonitrile was added 3MHCl(aq.) (10%). After standing for 22 hours the solution was diluted with ethyl acetate and washed with $NaHCO_{3\ (sat)}$, with $NaCl_{(sat.)}$, dried over $MgSO_4$, filtered and concentrated. Purification by flash chromatography (30% acetone/hexanes with 0.1% triethylamine) yielded the C12 benzyl C9, C10, C11 enone, C3, C12 diol macrolide (76% yield) as a white solid. $MH^+$(752.4).

C12 benzyl C9, C10, C11 enone, C3 oxo, C12 OH macrolide

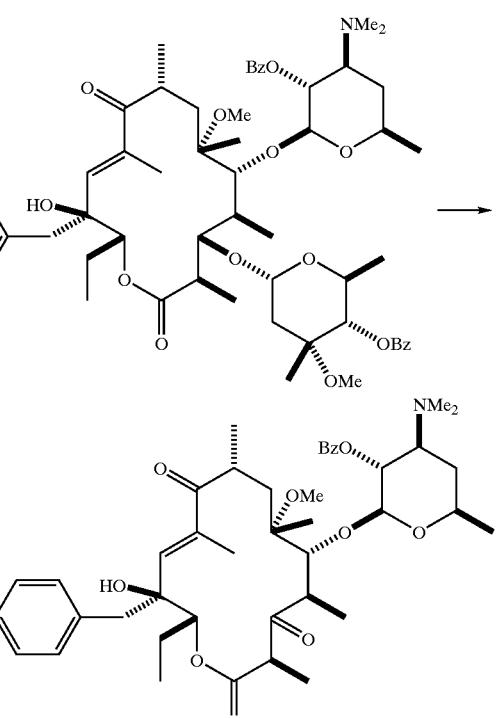

To C12 benzyl, C9, C10, C11 enone, C3, C12 diol macrolide (1 eq) in dichloromethane was added Dess-Martin Periodinane (1.3 eq). After stirring for 4 hours, the solution was diluted with ethyl acetate and washed with 1:1 10% $Na_2S_2O_3/NaHCO_{3\ (sat)}$, with $NaCl_{(sat.)}$, dried over $MgSO_4$, filtered and concentrated. Purification by flash chromatography (30% acetone/hexanes with 0.1% triethylamine) yielded the C12 benzyl C9, C10, C11 enone, C3 oxo, C12 OH macrolide (96% yield) as a white solid. $MH^+$(750.5).

C9, C10, C11 enone, C3 oxo, C12 benzyl, C12 OCOIm macrolide

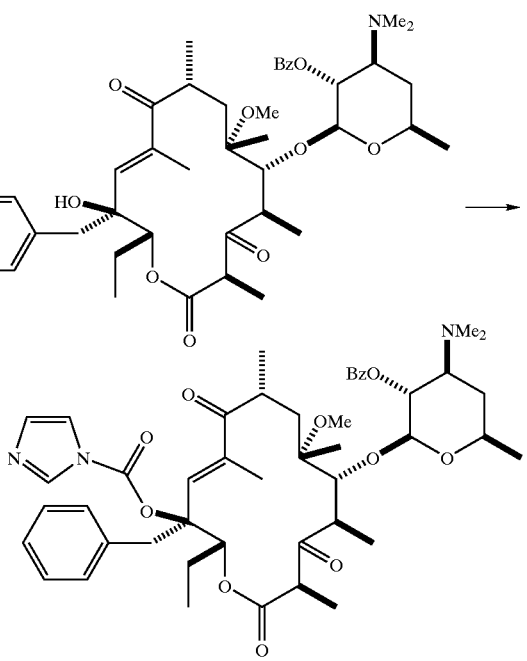

To a solution of C12 benzyl, C9, C10, C11 enone, C3 oxo, C12 OH macrolide (1 eq) and carbonyldiimidazole (3 eq) in tetrahydrofuran at 0° C. was added sodium hydride (2 eq). The solution was stirred at 0° C. for 4.5 hours, and than ethyl acetate was added. While still at 0° C., NaHCO$_3$ $_{(sat.)}$ was added. The mixture was then diluted with ethyl acetate and was washed with NaHCO$_3$ $_{(sat)}$, with NaCl $_{(sat.)}$, dried over MgSO$_4$, filtered, concentrated and pumped on yielding crude C12 benzyl C9, C10, C11 enone, C3 oxo, C12 OCOIm macrolide. The crude material was used in the next step without further purification.

EXAMPLE 6

Synthesis of (3aS,4R,7R,9R,10R,11S,13R,15R, 15aR)-3a-benzyl-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

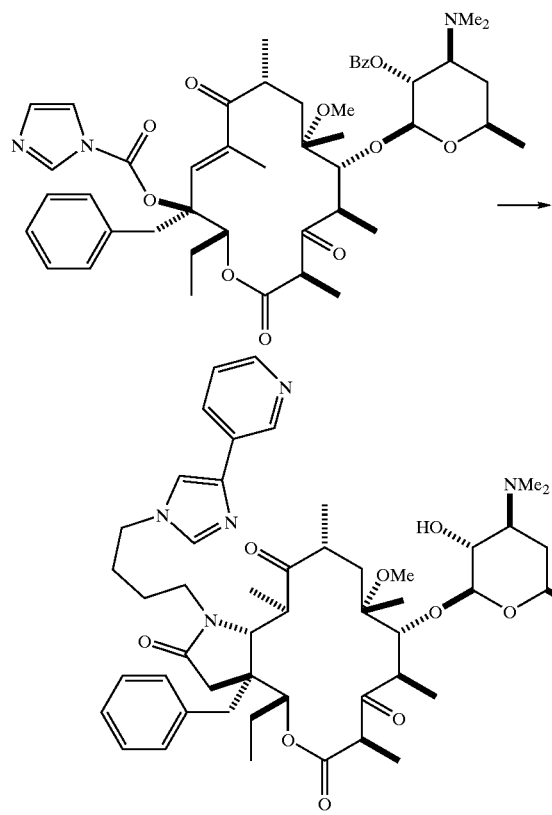

A solution of crude C12 phenyl, C9, C10, C11 enone, 3 oxo, C12 OCOIm macrolide (1 eq) in acetonitrile (1.5 mL) was added to 4-(4-(3-pyridyl)imidazolyl)butylamine (10 eq), and water (10%) was added. The solution was heated at 60° C. for 21 hours. Upon cooling the reaction was diluted with ethyl acetate and washed with NaHCO$_3$ $_{(sat)}$, NaCl$_{(sat.)}$, dried over MgSO$_4$, filtered and concentrated. To the crude material was added methanol (10 mL) and the solution was heated at reflux for 18 hours. Upon concentrating, the material was purified silica gel chromatography (0–3–5–10% methanol/dichloromethane with 0.1% triethylamine) and than by RP HPLC yielding (3aS,4R,7R, 9R,10R,11S,13R,15R,15aR)-3a-benzyl-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (35% yield) as a white solid. MH$^+$(888.5).

C12 Ethyl Analogs

EXAMPLE 7–EXAMPLE 43

EXAMPLE 7

Synthesis of C12 ethyl C9 keto, C11 OMs, C12 hydroxy macrolide

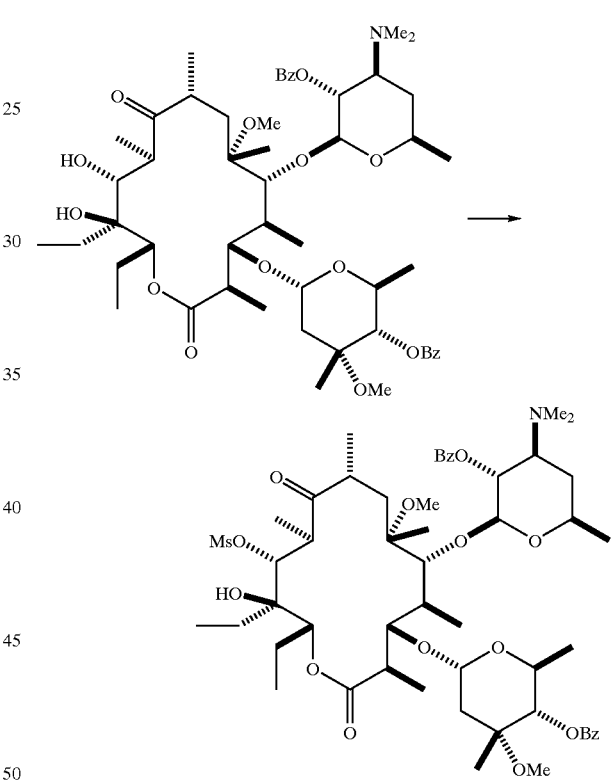

To 0° C. 0.2 M pyridine solution containing the C12 ethyl, C9 keto, C11, C12 diol macrolide of Example 5 (1 eq) was added methanesulfonyl chloride (5 eq) via syringe over 5 minutes. The solution was stirred for 18 hours as the solution warmed to rt. Upon concentrating, the material was taken up in ethyl acetate and washed with sat. NaHCO$_3$ (2×). The combined aqueous layers were back extracted with ethyl acetate and the combined organic layers were then washed with brine, dried over MgSO$_4$, filtered and concentrated. Purification by flash chromatography (20–25% acetone/hexanes with 0.1% triethylamine) yielded the C12 ethyl C9 keto, C11 OMs, C12 hydroxy macrolide as a white solid. MH$^+$(1048.5).

EXAMPLE 8

Synthesis of C12 ethyl C9, C10, C11 enone, C12 OH macrolide

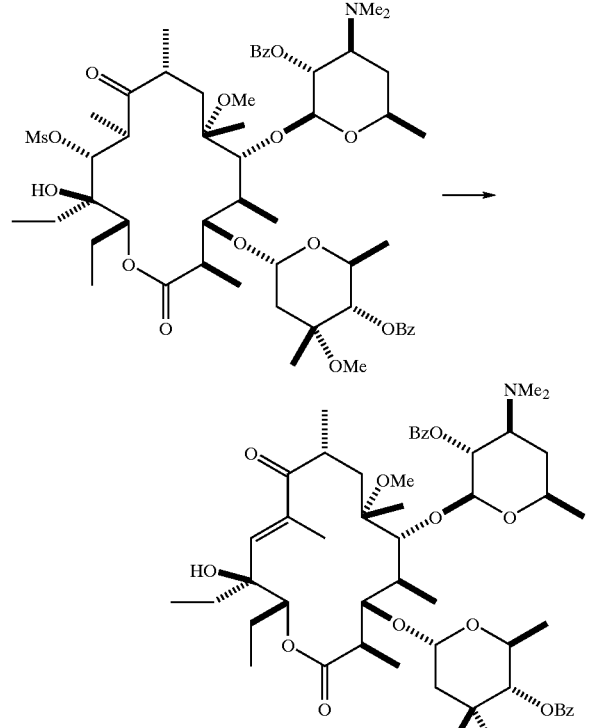

To C12 ethyl, C9, C11 OMs, C12 OH macrolide of Example 6 (1 eq) in acetone (0.07 M) was added DBU (1.2 eq). The solution was stirred for 6 hours at rt and then for 14 hours at 61° C. The solution was diluted with ethyl acetate, washed with H$_2$O, sat. NaHCO$_3$, brine, dried over MgSO$_4$, filtered, and concentrated to yield the C12 ethyl C9, C10, C11 enone, C12 OH-macrolide as an off white solid. MH$^+$ (952.5)

EXAMPLE 9

Synthesis of C12 ethyl C9, C10, C11 enone, C3, C12 diol macrolide

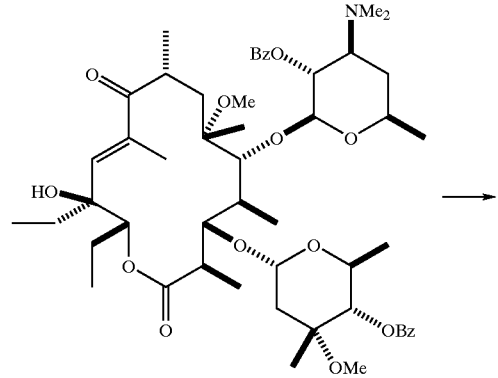

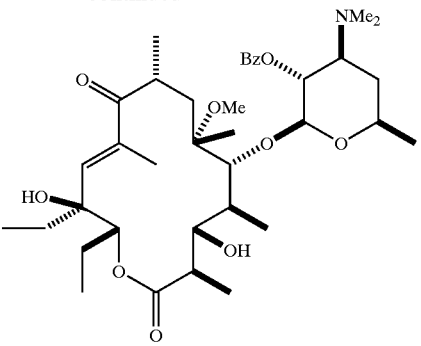

To C12 ethyl, C9, C10, C11 enone C12 OH macrolide of Example 7 (1 eq) in acetonitrile (0.08 M) was added 3M HCl(aq.) (19 eq). After standing for 22 hours the solution was diluted with ethyl acetate and washed with sat. NaHCO$_3$, brine, dried over MgSO$_4$, filtered, and concentrated. Purification by flash chromatography (30% acetone/hexanes with 0.1% triethylamine) yielded the C12 ethyl C9, C10, C11 enone, C3, C12 diol macrolide as a white solid. MH$^+$(690.4).

EXAMPLE 10

Synthesis of C12 ethyl C9, C10, C11 enone, C3 oxo, C12 OH macrolide

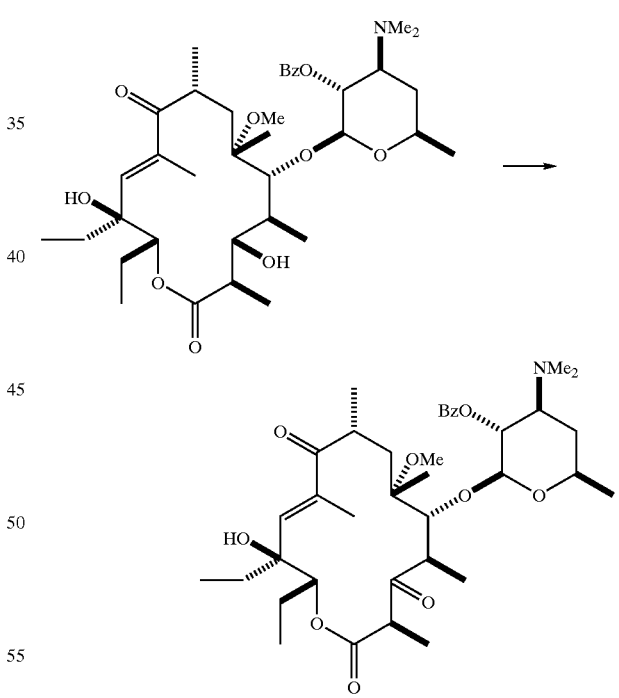

To C12 ethyl, C9, C10, C11 enone, C3, C12 diol, macrolide of Example 8 (1 eq) in dichloromethane (0.04 M) was added Dess-Martin Periodinane (1.5 eq). After stirring for 1 hour, the solution was diluted with ethyl acetate and washed with 1:1 10% Na$_2$S$_2$O$_3$/NaHCO$_3$, brine, dried over MgSO$_4$, filtered and concentrated. Purification by flash chromatography (30% acetone/hexanes with 0.1% triethylamine) yielded the C12 ethyl C9, C10, C11 enone, C3 oxo, C12 OH macrolide as a white solid. MH$^+$(688.5).

EXAMPLE 11

Synthesis of C12 ethyl C9, C10, C11 enone, C3 oxo, C12 OCOIm macrolide

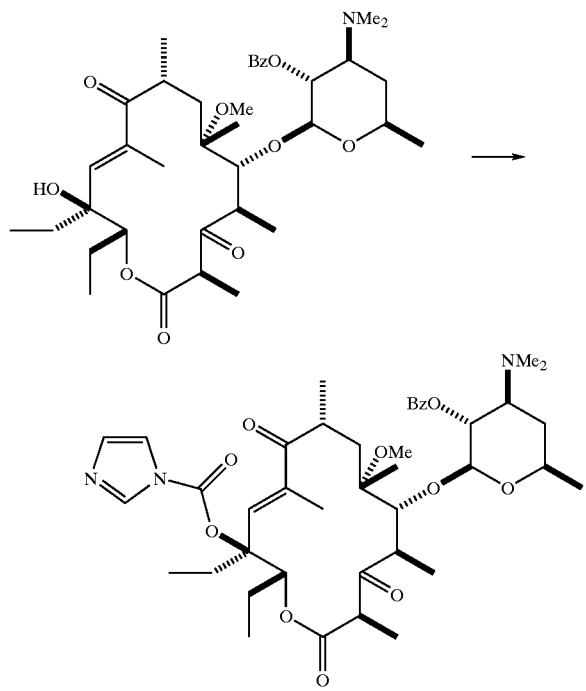

To a solution of C12 ethyl, C9, C10, C11 enone, C3 oxo, C12 OH macrolide of Example 10 (1 eq) and carbonyldiimidazole (3 eq) in tetrahydrofuran (0.1 M) at −15° C. was added sodium hydride (2 eq). The solution was stirred for 5 minutes at −15° C. and then was placed in a 0° C. ice bath. After stirring for 4 hours, ethyl acetate was added. While still at 0° C., NaHCO$_3$ $_{(sat.)}$ was added. The mixture was then diluted with ethyl acetate and was washed with sat. NaHCO$_3$ (2×), brine, dried over MgSO$_4$, filtered, concentrated, and dried under high vac. to yield the crude C12 ethyl C9, C10, C11 enone, C3 oxo, C12 OCOIm macrolide that was used in the next Example without further purification. MH$^+$(782.5).

EXAMPLE 12

Synthesis of (3aS,4R,7R,9R,10R,11S,13R,15R, 15aR)-3a,4-diethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

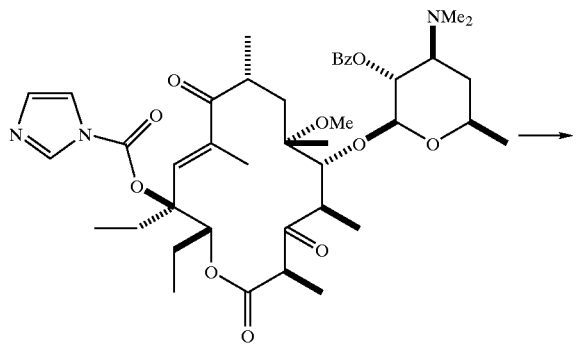

-continued

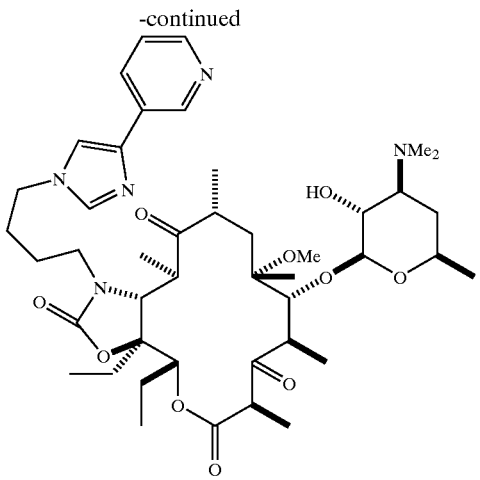

A solution of crude C12 ethyl, C9, C10, C11 enone, 3 oxo, C12 OCOIm macrolide of Example 11 (1 eq) in acetonitrile was added to 4-(4-(3-pyridyl)imidazolyl)butylamine (8 eq), and water was added. The solution was heated at 60° C. for 20 hours. Upon cooling the reaction was diluted with ethyl acetate and washed with NaHCO$_{3(sat)}$ NaCl(sat.), dried over MgSO$_4$, filtered and concentrated. To the crude material was added methanol and the solution was heated at reflux for 19 hours. Upon concentrating, the material was purified by RP HPLC. The combined product fractions coming off the HPLC were diluted with ethyl acetate and washed with NaHCO$_3$ $_{(sat)}$. The aqueous layer was back extracted with ethyl acetate and the combined organic layers were then washed with NaCl$_{(sat.)}$, dried over MgSO$_4$, filtered, concentrated, dissolved in acetonitrile/water and lyophilized yielding (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyridin-3-yl-1H-imidazol-1-yl)butyl] tetradecahydro-2H-oxacyclotetradecino[4,3-d][1,3]oxazol-10-yl 3,4,6-trideoxy-3-(dimethylamino)-D-xylo-hexopyranoside (44% yield) as a white solid. MH$^+$(826.5).

EXAMPLE 13

Synthesis of (3aS,4R,7R,9R,10R,11S,13R,15R, 15aR)-3a,4-diethyl-11-methoxy-7,9,11,13,15-pentamethyl-2,6,8,14-tetraoxo-1-[4-(4-phenyl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

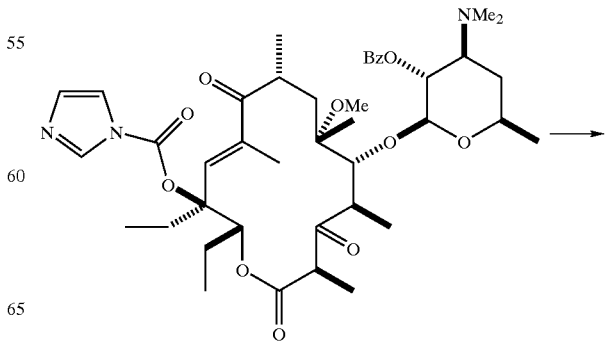

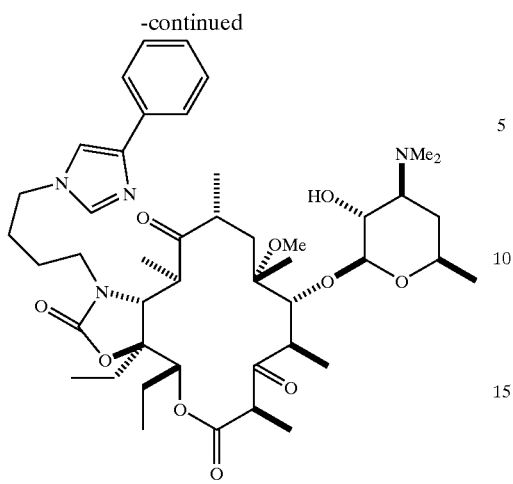

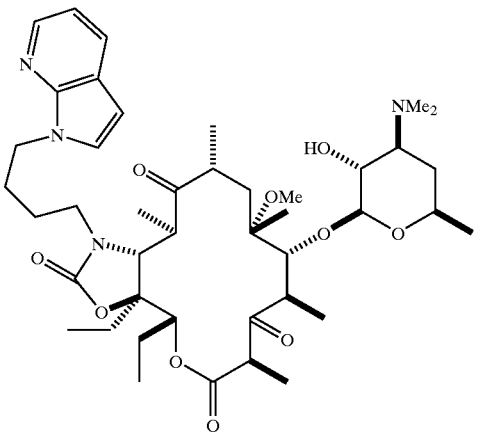

A solution of crude C12 ethyl, C9, C10, C11 enone, 3 oxo, C12 OCOIm macrolide of Example 11 (1 eq) in acetonitrile was added to 4-(4-phenyl)butylamine (4 eq), and water was added. The solution was heated at 60° C. for 60 hours. Upon cooling the reaction was diluted with ethyl acetate and washed with $NaHCO_3$ $_{(sat)}$, NaCl(sat.), dried over $MgSO_4$, filtered and concentrated. To the crude material was added methanol and the solution was heated at reflux for 19 hours. Upon concentrating, the material was purified by RP HPLC. The combined product fractions coming off the HPLC were diluted with ethyl acetate and washed with $NaHCO_{3(sat)}$. The aqueous layer was back extracted with ethyl acetate and the combined organic layers were then washed with NaCl $_{(sat.)}$, dried over $MgSO_4$, filtered, concentrated, dissolved in acetonitrile/water and lyophilized yielding (3aS,4R,7R,9R,10R,11S,13R,15R,15aR)-3a,4-diethyl-11-methoxy-7,9,11,13,15-pentamethyl-2,6,8,14-tetraoxo-1-[4-(4-phenyl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (42% yield) as a white solid. $MH^+$(825.5).

EXAMPLE 14

Synthesis of (3aS,4R,7R,9R,10R,11S,13R,15R,15aR)-3a,4-diethyl-1-[4-(3H-imidazo[4,5-b]pyridin-3-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside C12 ethyl, C9, C10, C11 enone, 3 oxo, C12 OCOIm macrolide of Example 11 (1 eq) was added to 4-Imidazo[4,5-b]pyridin-3-yl-butylamine (2.5 eq); acetonitrile and water were added. The solution was heated at 65° C. for 20 hours. Upon cooling the reaction was diluted with ethyl acetate and washed with $NaHCO_3$ $_{(sat)}$, NaCl(sat.), dried over $MgSO_4$, filtered and concentrated. To the crude material was added methanol and the solution was heated at 60° C. for 19 hours. Upon concentrating, the material was purified by RP HPLC. The combined product fractions coming off the HPLC were diluted with ethyl acetate and $NaHCO_3$ was added. The aqueous layer was separated and the organic layer was washed with $NaCl_{(sat.)}$, dried over $MgSO_4$, filtered, concentrated, dissolved in acetonitrile/water and lyophilized yielding (3aS,4R,7R,9R,10R,11S,13R,15R,15aR)-3a,4-diethyl-1-[4-(3H-imidazo[4,5b]pyridin-3-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside (38%) as a white solid. $MH^+$(800.00).

EXAMPLE 15

Synthesis of (3aS,4R,7R,9R,10R,11S,13R,15R,15aR)-3a,4-diethyl-11-methoxy-7,9,11,13,15-pentamethyl-2,6,8,14-tetraoxo-1-(4-quinolin-4-ylbutyl)tetradecahydro-2H-oxacyclotetradecino[4,3-1d][1,3]oxazol-10-yl 3,4,6-trideoxy-3-(dimethylamino)-D-xylo-hexopyranoside

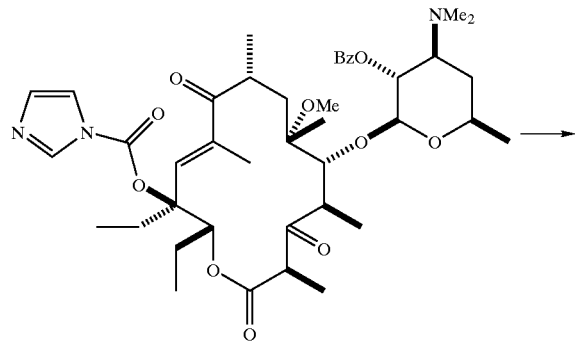

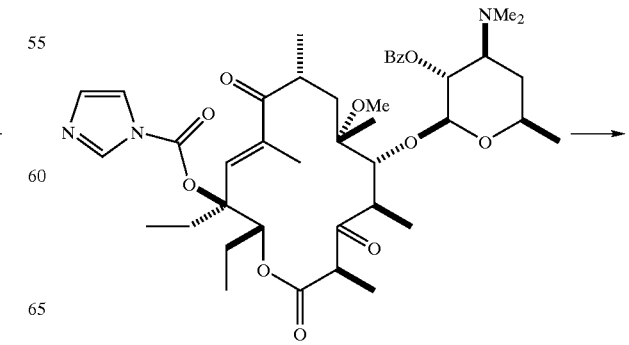

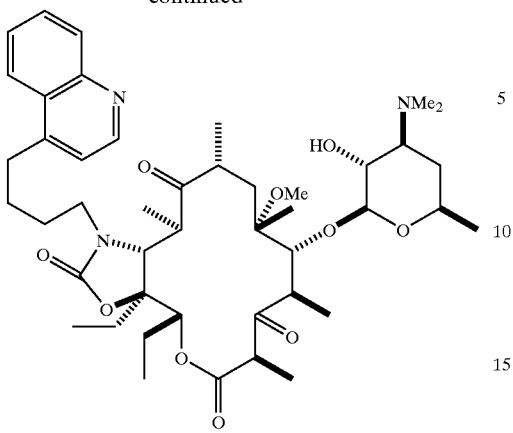

C12 ethyl, C9, C10, C11 enone, 3 oxo, C12 OCOIm macrolide of Example 11 (1 eq) was added to 4-Quinolin-4-yl-butylamine (4 eq); acetonitrile and water were added. The solution was heated at 65° C. for 20 hours. Upon cooling the reaction was diluted with ethyl acetate and washed with NaHCO$_3$ $_{(sat)}$, NaCl(sat.), dried over MgSO$_4$, filtered and concentrated. Purification by RP HPLC yielded the pure benzoylated ketolide and a mixture of benzoylated ketolide and (3aS,4R,7R,9R,10R,11S,13R,15R,15aR)-3a,4-diethyl-11-methoxy-7,9,11,13,15-pentamethyl-2,6,8,14-tetraoxo-1-(4-quinolin-4-ylbutyl)tetradecahydro-2H-oxacyclotetradecino[4,3-d][1,3]oxazol-10-yl 3,4,6-trideoxy-3-(dimethylamino)-D-xylo-hexopyranoside. To the mixture of benzoylated ketolide and product, was added methanol and the solution was heated at 60° C. for 19 hours. Upon concentrating, the material was purified by column chromatography (0–2–5–10% MeOH/CH2Cl2 with 0.1% triethylamine), and lyophilized from MeCN:H2O to provide (3aS,4R,7R,9R,10R,11S,13R,15R,15aR)-3a,4-diethyl-11-methoxy-7,9,11,13,15-pentamethyl-2,6,8,14-tetraoxo-1-(4-quinolin-4-ylbutyl)tetradecahydro-2H-oxacyclotetra-decino[4,3-d][1,3]oxazol-10-yl 3,4,6-trideoxy-3-(dimethylamino)-D-xylo-hexo-pyranoside (46% yield) as a white solid. MH$^+$ (810.05).

EXAMPLE 16
Synthesis of (3aS,4R,7S,9R,10R,11R,13R,15R,15aR)-3a,4-diethyl-7-fluoro-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

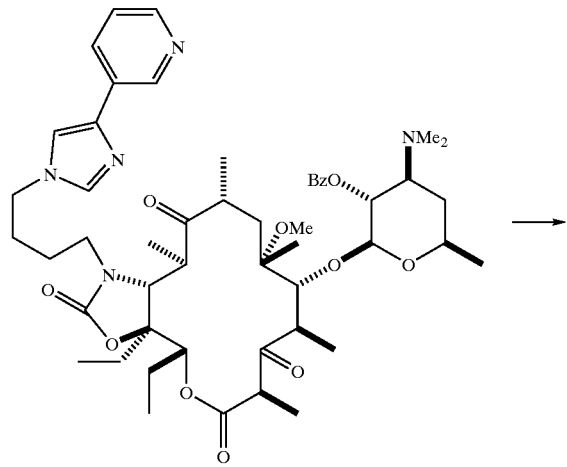

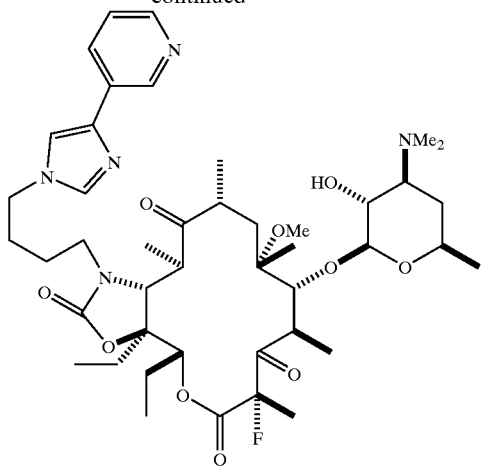

To 2' benzoylated (6S,1R,2R,4R,7R,8R,10R,13R)-7-[(4S,2R,3R,6R)-4-(dimethylamino)-3-hydroxy-6-methyl(2H-3,4,5,6-tetrahydropyran-2-yl)oxy]-17-aza-13,14-diethyl-6-methoxy-2,4,6,8,10-pentamethyl-12,15-dioxa-17-(4-(4-quinolyl)butyl)-bicyclo[12.3.0]heptadecane-3,9,11,16-tetraone in DMF at 0° C. was added 60% NaH (2 eq). After stirring for 1 hour at 0° C., N-fluorobenzenesulfonimide (1 eq) was added. After stirring for an additional hour at 0° C., the solution was diluted with ethyl acetate and NaHCO$_{3(sat.)}$ was added cautiously to quench. The reaction was then added to ethyl acetate and was washed with NaHCO$_3$ $_{(sat)}$, NaCl(sat.), dried over MgSO$_4$, filtered, concentrated and purified by RP HPLC. The combined product fractions coming off the HPLC were diluted with ethyl acetate and NaHCO$_3$ was added. The aqueous layer was separated and the organic layer was washed with NaCl$_{(sqt.)}$, dried over MgSO$_4$, filtered, and concentrated to provide the benzoylated 2-fluoroketolide. Methanol was added and the solution was heated at 60° C. for 19 hours. Upon concentrating, the material was purified by column chromatography (0–2–5–10% MeOH/CH2Cl2 with 0.1% triethylamine), and lyophilized from MeCN:H2O providing (3aS,4R,7S,9R,10R,11R,13R,15R,15aR)-3a,4-diethyl-7-fluoro-11-methoxy-7,9,11,13,15-pentamethyl-2,6,8,14-tetraoxo-1-[4-(4-pyridin-3-yl-1H-imidazol-1-yl)butyl]tetradeca-hydro-2H-oxacyclotetradecino[4,3-d][1,3]oxazol-10-yl 3,4,6-trideoxy-3-(dimethyl-amino)-D-xylo-hexopyranoside (62% yield) as a white solid. MH$^+$(844.50).

EXAMPLE 17
Synthesis of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclotetradecino[4,3-d][1,3]oxazol-10-yl 3,4,6-trideoxy-3-(dimethylamino)-D-xylo-hexopyranoside

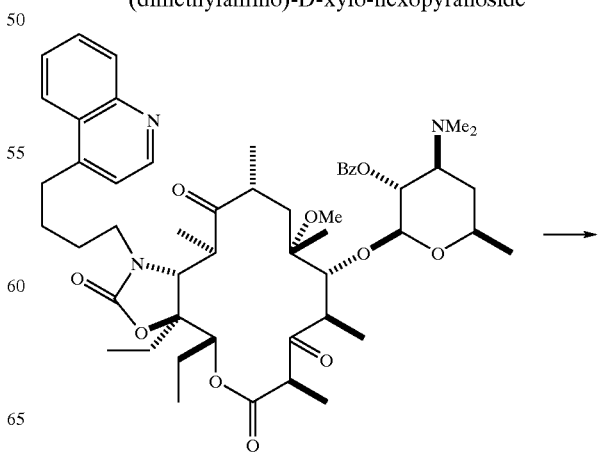

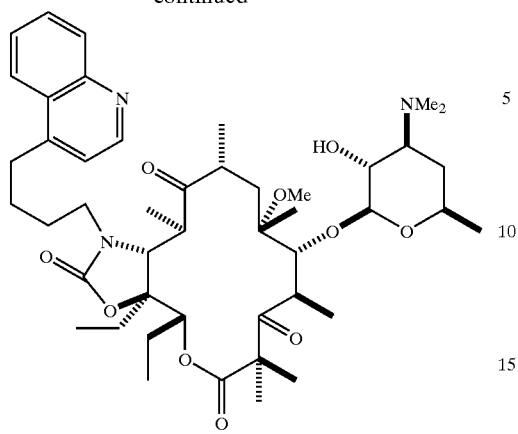

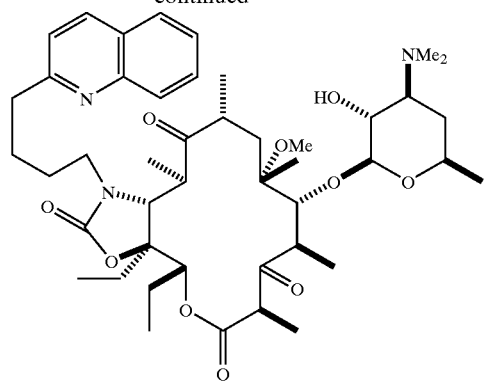

To 2' benzoylated (6S,1R,2R,4R,7R,8R,10R,13R)-7-[(4S, 2R,3R,6R)-4-(dimethylamino)-3-hydroxy-6-methyl(2H-3, 4,5,6-tetrahydropyran-2-yl)oxy]-17-aza-13,14-diethyl-6-methoxy-2,4,6,8,10-pentamethyl-12,15-dioxa-17-(4-(4-quinolyl)butyl)-bicyclo[12.3.0] heptadecane-3,9,11,16-tetraone (1 eq) in DMF at 0° C. was added 60% NaH (2 eq). After stirring for 1 hour at 0° C., N-fluorobenzenesulfonimide (1.1 eq) was added. After stirring for an additional hour at 0° C., the solution was diluted with ethyl acetate followed by addition of NaHCO$_{3(sat)}$ to quench the reaction. The reaction mixture was then added to ethyl acetate and was washed with NaHCO$_{3\,(sat)}$, NaCl(sat.), dried over MgSO$_4$, filtered, concentrated and purified by RP HPLC. The combined product fractions coming off the HPLC were diluted with ethyl acetate and NaHCO$_3$ was added. The aqueous layer was separated and the organic layer was washed with NaCl$_{(sat)}$, dried over MgSO$_4$, filtered, and concentrated yielding the benzoylated 2-fluoroketolide. Methanol was added and the solution was heated at 60° C. for 19 hours. Upon concentrating, the material was purified by column chromatography (0–2–5–10% MeOH/CH2Cl2 with 0.1% triethylamine), and lyophilized from MeCN:H$_2$O to give (3aS,4R,7S,9R,10R,11S,13R,15R,15aR)-3a,4-diethyl-7-fluoro-11-methoxy-7,9,11,13,15-pentamethyl-2,6, 8,14-tetraoxo-1-(4-quinolin-4-ylbutyl)tetradecahydro-2H-oxacyclotetradecino[4,3-d][1,3]oxazol-10-yl 3,4,6-trideoxy-3-(dimethylamino)-D-xylo-hexopyranoside (57% yield) as a white solid. MH$^+$(828.50).

EXAMPLE 18

Synthesis of (3aS,4R,7R,9R,10R,11S,13R,15R, 15aR)-3a,4-diethyl-11-methoxy-7,9,11,13,15-pentamethyl-2,6,8,14-tetraoxo-1-(4-quinolin-2-ylbutyl)tetradecahydro-2H-oxacyclotetradecino[4,3-d][1,3]oxazol-10-yl 3,4,6-trideoxy-3-(dimethylamino)-D-xylo-hexopyranoside C12 ethyl, C9, C10, C11 enone, 3 oxo, C12 OCOIm macrolide of Example 11 (1 eq) was added to 4-Quinolin-2-yl-butylamine (4 eq); acetonitrile and water was added. The solution was heated at 65° C. for 24 hours. Upon cooling the reaction was diluted with ethyl acetate and washed with NaHCO$_{3\,(sat)}$, NaCl(sat.), dried over MgSO$_4$, filtered and concentrated. Purification by RP HPLC yielded the benzoylated ketolide. To the benzoylated ketolide was added methanol and the solution was heated at 60° C. for 19 hours. Upon concentrating, the material was purified by column chromatography (0–2–5–10% MeOH/CH2Cl2 with 0.1% triethylamine), and lyophilized from MeCN:H2O providing (3aS,4R,7R,9R,10R,11S,13R,15R,15aR)-3a,4-diethyl-11-methoxy-7,9,11,13,15-pentamethyl-2,6,8,14-tetraoxo-1-(4-quinolin-2-ylbutyl)tetradecahydro-2H-oxacyclotetradecino[4,3-d][1,3]oxazol-10-yl 3,4,6-trideoxy-3-(dimethylamino)-D-xylo-hexopyranoside (40% yield) as a white solid. MH$^+$(810.50).

EXAMPLE 19

Synthesis of (3aS,4R,7S,9R,10R,11S,13R,15R, 15aR)-3a,4-diethyl-7-fluoro-11-methoxy-7,9,11,13, 15-pentamethyl-2,6,8,14-tetraoxo-1-(4-quinolin-2-ylbutyl)tetradecahydro-2H-oxacyclotetradecino[4,3-d][1,3]oxazol-10-yl 3,4,6-trideoxy-3-(dimethylamino)-D-xylo-hexopyranoside

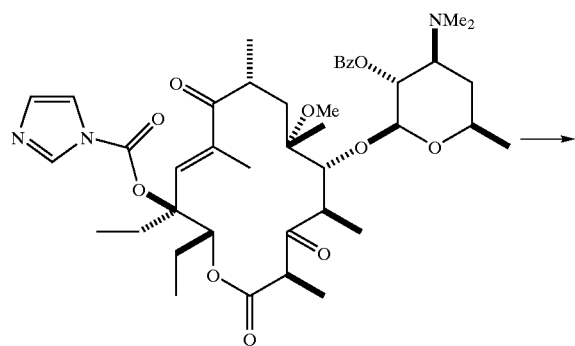

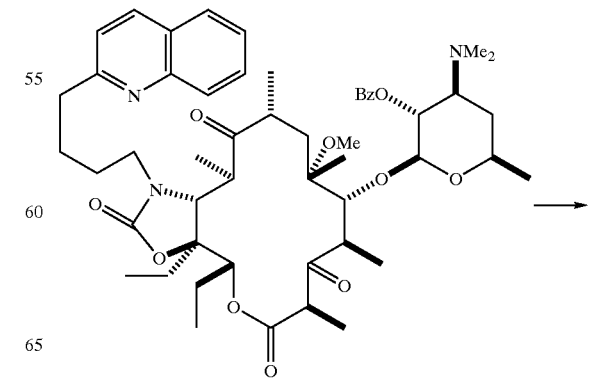

-continued

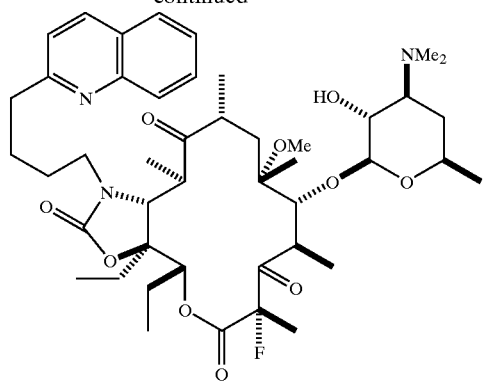

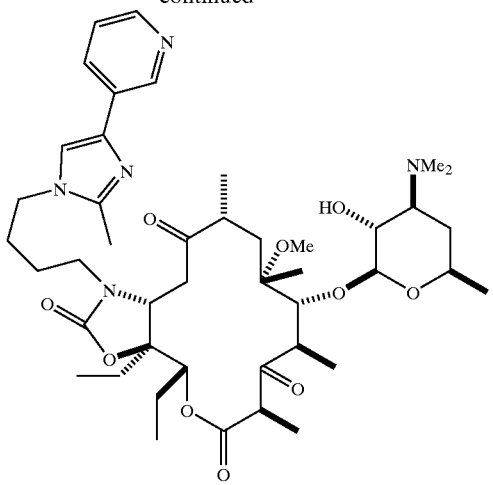

Using the procedure described above for the preparation of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclo-tetradecino[4,3-d][1,3]oxazol-10-yl 3,4,6-trideoxy-3-(dimethylamino)-D-xylo-hexo-pyranoside, utilizing 2' benzoylated (3aS,4R,7R,9R,10R,11S,13R,1SR,15aR)-3a,4-diethyl-11-methoxy-7,9,11,13,15-pentamethyl-2,6,8,14-tetraoxo-1-(4-quinolin-2-ylbutyl)tetradecahydro-2H-oxacyclotetradecino[4,3-d][1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-2-ylbutyl)tetradecahydro-2H-oxacyclo-tetradecino[4,3-d][1,3]oxazol-10-yl 3,4,6-trideoxy-3-(dimethylamino)-D-xylo-hexopyranoside was attained (52% yield) as a white solid. $MH^+(828.50)$.

EXAMPLE 20

Synthesis of (3aS,4R,7R,9R,10R,11S,13R,15R,15aR)-3a,4-diethyl-11-methoxy-7,9,11,13,15-pentamethyl-1-[4-(2-methyl-4-pyridin-3-yl-1H-imidazol-1-yl)butyl]-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside C12 ethyl, C9, C10, C11 enone, 3 oxo, C12 OCOIm macrolide of Example 11 (1 eq) was added to 4-(2-Methyl-4-pyridin-3-yl-imidazol-1-yl)-butylamine (4 eq), acetonitrile, and water. The solution was heated at 65° C. for 48 hours. Upon cooling the reaction was diluted with ethyl acetate and washed with $NaHCO_3$ $_{(sat)}$, NaCl(sat.), dried over $MgSO_4$, filtered and concentrated. To the crude material was added methanol and the solution was heated at 60° C. for 24 hours. Upon concentrating, the material was purified by column chromatography (0–5–10% MeOH/CH2Cl2 with 0.1% triethylamine) and than RP HPLC. The combined product fractions coming off the HPLC were diluted with ethyl acetate and $NaHCO_3$ was added. After mixing, the aqueous layer was separated and the organic layer was washed with $NaCl_{(sat.)}$, dried over $MgSO_4$, filtered, concentrated, dissolved in acetonitrile/water and lyophilized to provide (3aS,4R,7R,9R,10R,11S,13R,15R,15aR)-3a,4-diethyl-11-methoxy-7,9,11,13,15-pentamethyl-1-[4-(2-methyl-4-pyridin-3-yl-1H-imidazol-1-yl)butyl]-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside (28% yield) as a white solid product. $MH^+(840.50)$.

EXAMPLE 21

Synthesis of (3aS,4R,7R,9R,10R,11S,13R,15R,15aR)-3a,4-diethyl-11-methoxy-7,9,11,13,15-pentamethyl-1-[4-(5-methyl-4-pyridin-3-yl-1H-imidazol-1-yl)butyl]-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

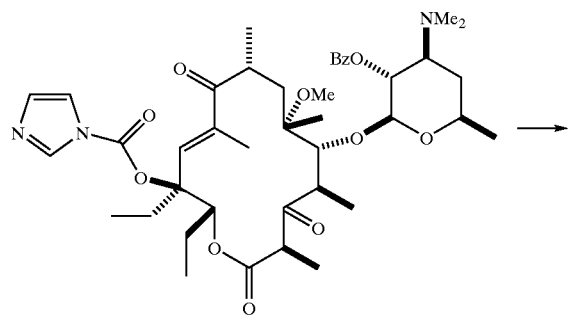

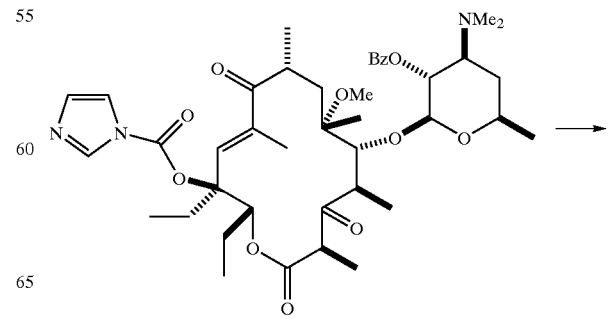

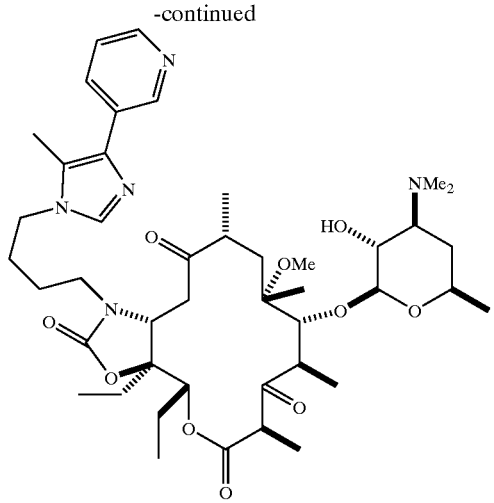

C12 ethyl, C9, C10, C11 enone, 3 oxo, C12 OCOIm macrolide of Example 11 (1 eq) was added to 4-(5-Methyl-4-pyridin-3-yl-imidazol-1-yl)-butylamine (4 eq), acetonitrile, and water. The solution was heated at 65° C. for 20 hours. Upon cooling the reaction was diluted with ethyl acetate and washed with NaHCO$_3$ $_{(sat)}$, NaCl(sat.), dried over MgSO$_4$, filtered and concentrated. To the crude material was added methanol and the solution was heated at 60° C. for 24 hours. Upon concentrating, the material was purified by column chromatography (0–5–10% MeOH/CH2Cl2 with 0.1% triethylamine) and than RP HPLC. The combined product fractions coming off the HPLC were diluted with ethyl acetate and NaHCO$_3$ was added. After mixing, the aqueous layer was separated and the organic layer was washed with NaCl$_{(sat.)}$, dried over MgSO$_4$, filtered, concentrated, dissolved in acetonitrile/water and lyophilized yielding (3aS,4R,7R,9R,10R,11S,13R,15R, 15aR)-3a,4-diethyl-11-methoxy-pentamethyl-1-[4-(5-methyl-4-pyridin-3-yl-1H-imidazol-1-yl)butyl]-2,6,8,14-tetraoxotetradecahydro-2H-oxacyclotetradecino[4,3-d][1,3] oxazol-10-yl 3,4,6-trideoxy-3-(dimethylamino)-D-xylo-hexopyranoside (37% yield) as a white solid. MH$^+$(840.50).

EXAMPLE 22

Synthesis of (3aS,4R,7R,9R,10R,11S,13R,15R, 15aR)-3a,4-diethyl-1-[4-(1H-imidazo[4,5-b]pyridin-1-yl)butyl]-11-methoxy-7,9,11,13,15-pentamethyl-2, 6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

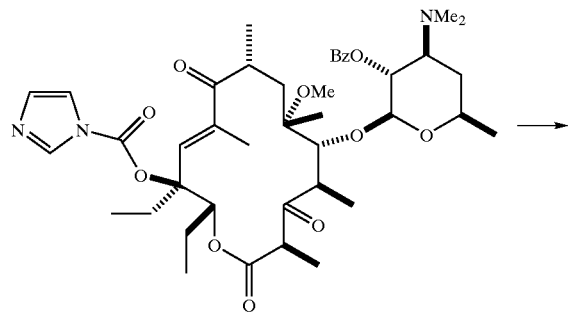

C12 ethyl, C9, C10, C11 enone, 3 oxo, C12 OCOIm macrolide of Example 11 (1 eq) was added to 4-Imidazo[4, 5-b]pyridin-1-yl-butylamine (6 eq), acetonitrile, and water. The solution was heated at 65° C. for 20 hours. Upon cooling the reaction was diluted with ethyl acetate (350 mL) and washed with NaHCO$_3$ $_{(sat)}$, NaCl(sat.), dried over MgSO$_4$, filtered and concentrated. To the crude material was added methanol and the solution was heated at 60° C. for 19 hours. Upon concentrating, the material was purified by RP HPLC. The combined product fractions coming off the HPLC were diluted with ethyl acetate and NaHCO$_3$ was added. The aqueous layer was separated and the organic layer was washed with NaCl$_{(sat.)}$, dried over MgSO$_4$, filtered, concentrated, dissolved in acetonitrile/water and lyophilized providing (3aS,4R,7R,9R,10R,11S,13R,15R, 15aR)-3a,4-diethyl-1-[4-(1H-imidazo[4,5-b]pyridin-1-yl) butyl]-11-methoxy-7,9,11,13,15-pentamethyl-2,6,8,14-tetraoxotetradecahydro-2H-oxacyclotetradecino[4,3-d][1,3] oxazol-10-yl 3,4,6-trideoxy-3-(dimethylamino)-D-xylo-hexopyranoside (31% yield) as a white solid. MH$^+$(800.00).

EXAMPLE 23

Synthesis of (3aS,4R,7R,9R,10R,11S,13R,15R, 15aR)-3a,4-diethyl-11-methoxy-7,9,11,13,15-pentamethyl-1-{2-[methyl(pyridin-3-ylmethyl) amino]ethyl}-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside

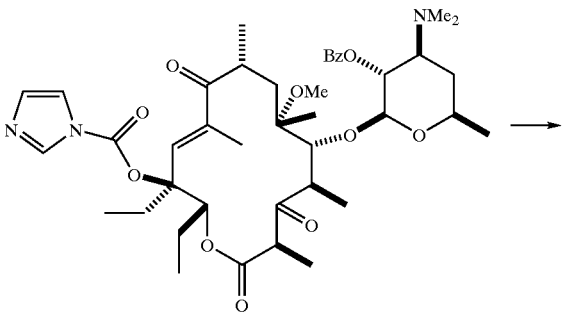

103

-continued

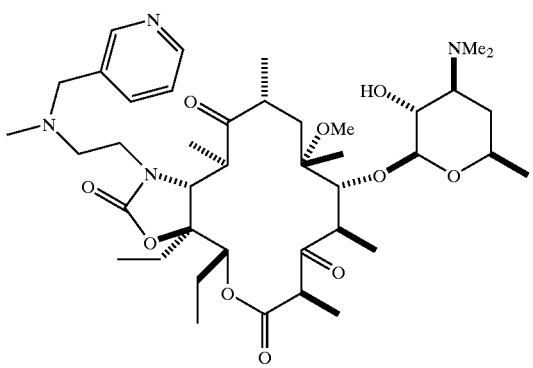

C12 ethyl, C9, C10, C11 enone, 3 oxo, C12 OCOIm macrolide of Example 11 (1 eq) was added to N1-Methyl-N1-pyridin-3-ylmethyl-ethane-1,2-diamine (6 e); acetonitrile (3 mL) and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-1-{2-[methyl(pyridin-3-ylmethyl)amino]ethyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (47% yield) as a white solid. MH$^+$(775.50).

EXAMPLE 24

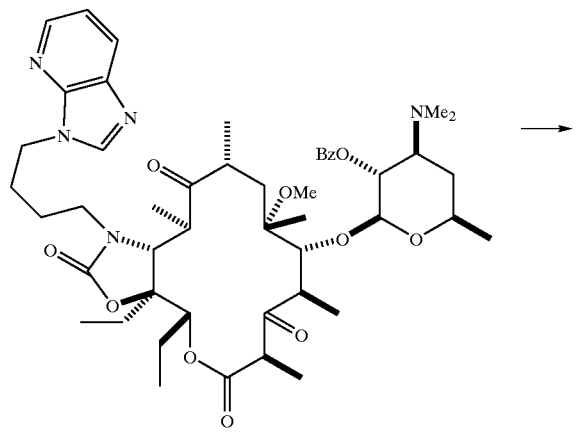

104

-continued

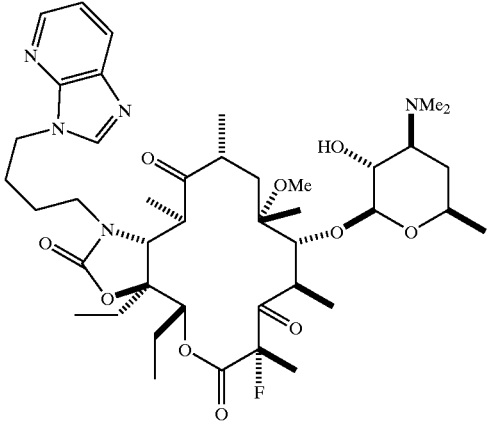

Using the procedure described above for the preparation of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclotetra-decino[4,3-d][1,3]oxazol-10-yl 3,4,6-trideoxy-3-(dimethylamino)-D-xylo-hexopyranoside, utilizing 2' benzoylated (3aS,4R,7R,9R,10R,11S,13R,15R,15aR)-3a,4-diethyl-1-[4-(3H-imidazo[4,5-b]pyridin-3-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-1-[4-(3H-imidazo[4,5-]pyridin-3-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was obtained (49% yield) as a white solid. MH$^+$(818.50).

EXAMPLE 25

Synthesis of (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyrimidin-5-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

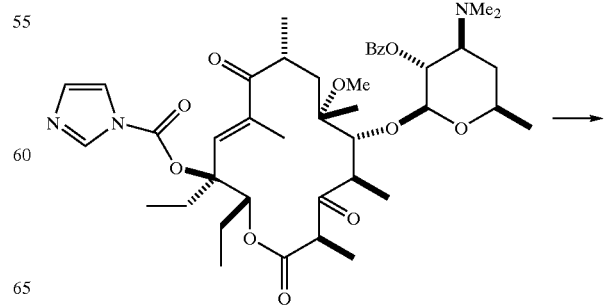

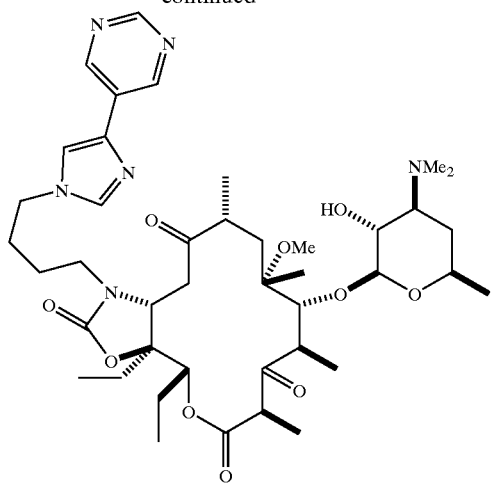

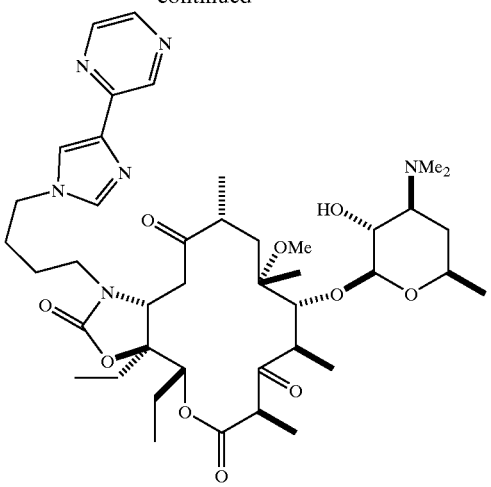

C12 ethyl, C9, C10, C11 enone, 3 oxo, C12 OCOIm macrolide of Example 11 (1 eq) was added to 4-(4-Pyrimidin-5-yl-imidazol-1-yl)-butylamine (4 eq), acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyrimidin-5-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside was attained (27% yield) as a white solid. MH$^+$(827.50).

C12 ethyl, C9, C10, C11 enone, 3 oxo, C12 OCOIm macrolide of Example 11 (1 eq) was added to 4-(4-Pyrazin-2-yl-imidazol-1-yl)-butylamine (6 eq), acetonitrile and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyrazin-2-yl-1H-imidazol-1-yl)butyl]tetradecahydro-2H-oxacyclotetradecino [4,3-d][1,3]oxazol-10-yl 3,4,6-trideoxy-3-(dimethylamino)-D-xylo-hexopyranoside was attained (29% yield) as a white solid. MH$^+$(827.50).

EXAMPLE 26

Synthesis of (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyrazin-2-yl-1H-imidazol-1-yl)butyl]tetradecahydro-2H-oxacyclotetradecino [4,3-d][1,3]oxazol-10-yl 3,4,6-tri-deoxy-3-(dimethylamino)-D-xylo-hexopyranoside

EXAMPLE 27

Synthesis of (3aS,4R,7S,9R,10R,11S,13R,15R,15aR)-3a,4-diethyl-7-fluro-1-[4-imidazo[4,5-b]pyridin-1-yl)butyl]-11-methoxy-7,9,11,13,15-pentamethyl-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside

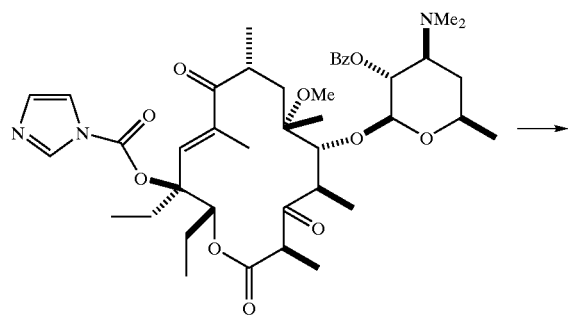

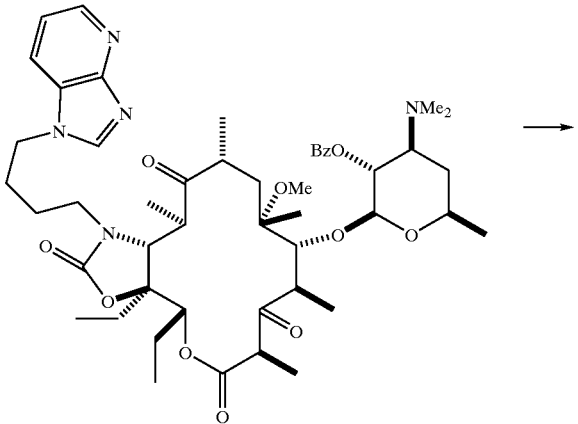

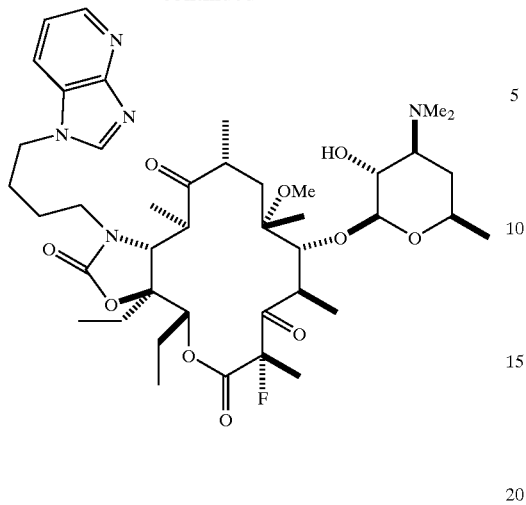
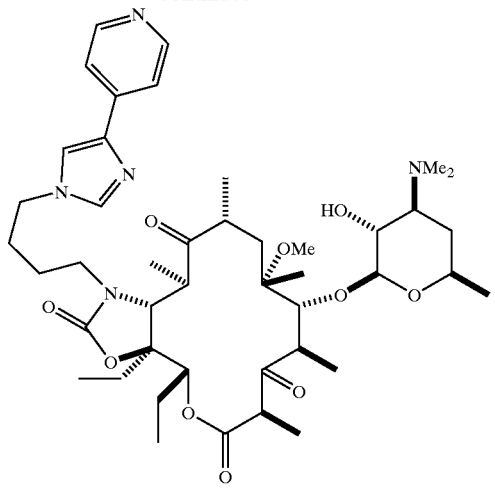

Using the procedure previously described for the preparation of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclo-tetradecino[4,3-d][1,3]oxazol-10-yl 3,4,6-trideoxy-3-(dimethylamino)-D-xylo-hexopyranoside, utilizing 2' benzoylated (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-1-[4-(1H-imidazo[4,5-b]pyridin-1-yl)butyl]-11-methoxy-7,9,11,13,15-pentamethyl-2,6,8,14-tetra-oxotetradecahydro-2H-oxacyclotetradecino[4,3-d][1,3]oxazol-10-yl 3,4,6-trideoxy-3-(dimethylamino)-D-xylo-hexopyranoside was attained (31% yield) as a white solid. MH$^+$(818.50).

12 ethyl, C9, C10, C11 enone, 3 oxo, C12 OCOIm macrolide of Example 11 (1 eq) was added to 4-(4-Pyridin-4-yl-imidazol-1-yl)-butylamine (5 eq); acetonitrile and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyridin-4-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside was attained (31% yield) as a white solid. MH$^+$(826.50).

EXAMPLE 28

Synthesis of (3aS,4R,7R,9R,10R,11S,13R,15R,15aR)-3a,4-diethyl-11-methoxy-7,9,11,13,15-pentamethyl-2,6,8,14-tetraoxo-1-[4-(4-pyridin-4-yl-1H-imidazol-1-yl)butyl]tetradecahydro-2H-oxacyclotetradecino [4,3-d][1,3]oxazol-10-yl 3,4,6-tri-deoxy-3-(dimethylamino)-D-xylo-hexopyranoside

EXAMPLE 29

Synthesis of (3aS,4R,7R,9R,10R,11S,13R,15R,15aR)-3a,4-diethyl-11-methoxy-7,9,11,13,15-pentamethyl-1-{4-[4-(6-methylpyridin-3-yl)-1H-imidazol-1-yl]butyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

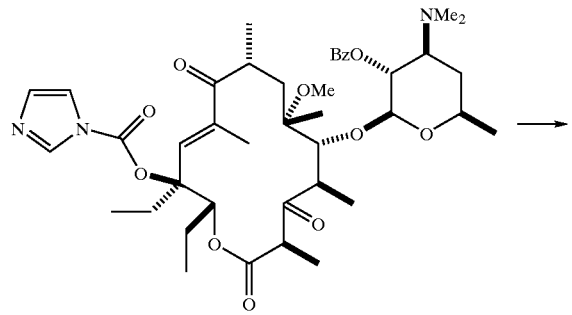
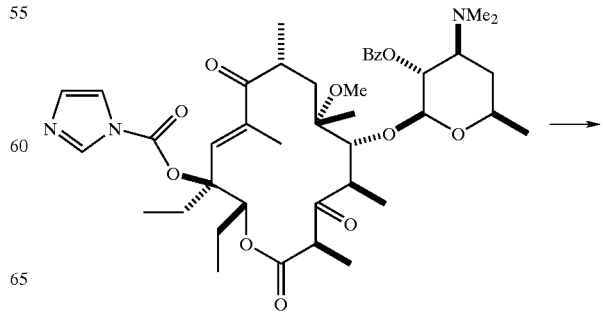

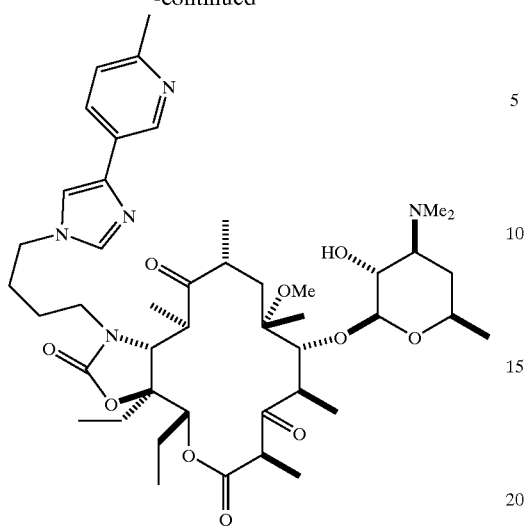

C12 ethyl, C9, C10, C11 enone, 3 oxo, C12 OCOIm macrolide of Example 11 (1 eq) was added to 4-[4-(6-Methyl-pyridin-3-yl)-imidazol-1-yl]-butylamine (3 eq), acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-1-{4-[4-(6-methylpyridin-3-yl)-1H-imidazol-1-yl]butyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (44% yield) as a white solid. MH⁺(840.50).

EXAMPLE 30

Synthesis of (3aS,4R,7S,9R,10R,11S,13R,15R,15aR)-3a,4-diethyl-7-fluoro-11-methoxy-7,9,11,13,15-pentamethyl-1-{4-[4-(6-methylpyridin-3-yl)-1H-imidazol-1-yl]butyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

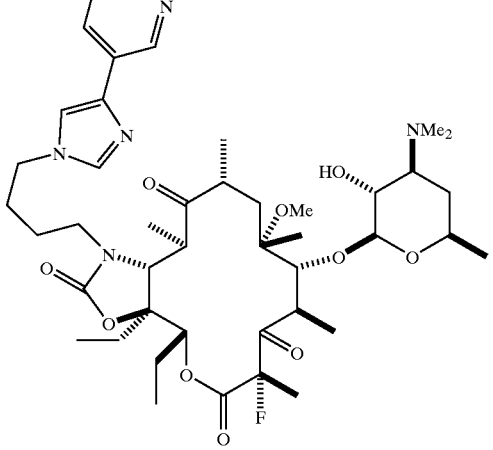

Using the procedure previously described for the preparation of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclotetra-decino[4,3-d][1,3]oxazol-10-yl 3,4,6-trideoxy-3-(dimethylamino)-D-xylo-hexo-pyranoside, utilizing 2' benzoylated (3aS,4R,7R,9R,10R,11S,13R,15R,15aR)-3a,4-diethyl-11-methoxy-7,9,11,13,15-pentamethyl-1-{4-[4-(6-methylpyridin-3-yl)-1H-imidazol-1-yl]butyl}-2,6,8,14-tetraoxotetradecahydro-2H-oxacyclotetradecino[4,3-d]-[1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-11-methoxy-7,9,11,13,15-pentamethyl-1-{4-[4-(6-methylpyridin-3-yl)-1H-imidazol-1-yl]butyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (61% yield) as a white solid. MH⁺(858.50).

EXAMPLE 31

Synthesis of (3aS,4R,7R,9R,10R,11S,13R,15R,15aR)-3a,4-diethyl-11-methoxy-7,9,11,13,15-pentamethyl-1-[4-methyl-4-(4-pyridin-3-yl-1H-imidazol-1-yl)pentyl]-2,6,8,14-tetraoxotetradecahydro-2H-oxacyclotetradecino [4,3-d][1,3] oxazol-10-yl 3,4,6-trideoxy-3-(dimethylamino)-D-xylo-hexopyranoside

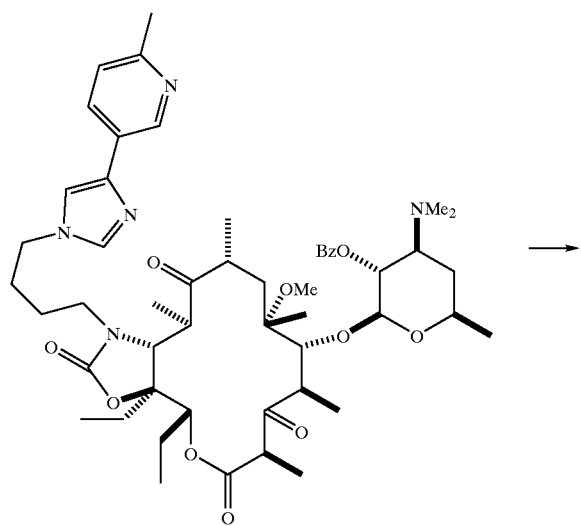

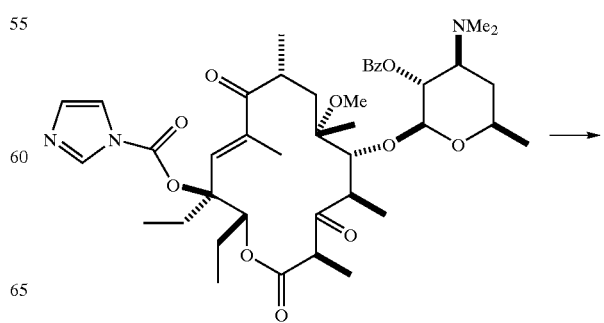

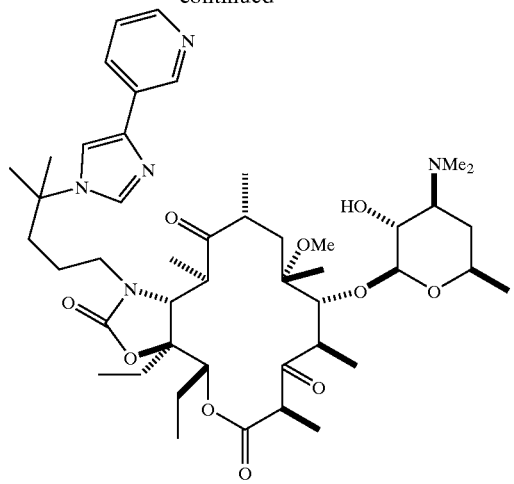

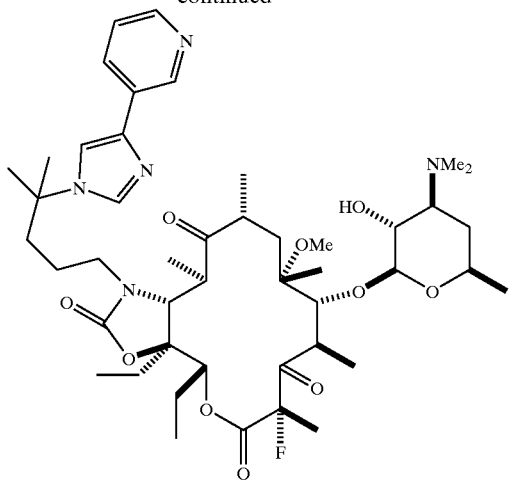

C12 ethyl, C9, C10, C11 enone, 3 oxo, C12 OCOIm macrolide of Example 11 (1 eq) was added to 4-Methyl-4-(4-pyridin-3-yl-imidazol-1-yl)-pentylamine (3 eq); acetonitrile and water. The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-1-[4-methyl-4-(4-pyridin-3-yl-1H-imidazol-1-yl)pentyl]-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (40% yield) as a white solid. MH⁺(958.50).

EXAMPLE 32

Synthesis of (3aS,4R,7S,9R,10R,11S,13R,15R,15aR)-3a,4-diethyl-7-fluoro-11-methoxy-7,9,11,13,15-pentamethyl-1-14-methyl-4-(4-pyridin-3-yl-1H-imidazo[-1-yl)pentyl]-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

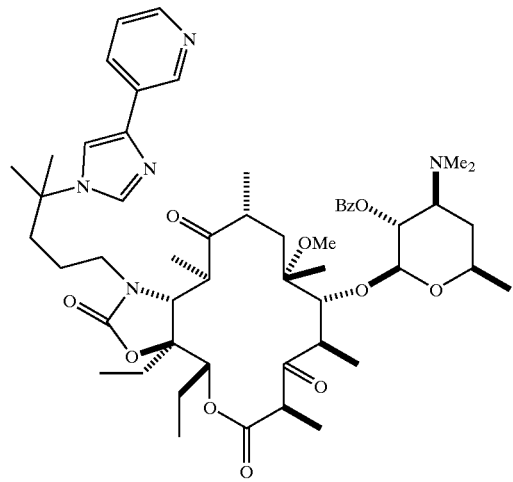

Using the procedure previously described for the preparation of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclotetra-decino[4,3-d][1,3]oxazol-10-yl 3,4,6-trideoxy-3-(dimethylamino)-D-xylo-hexo-pyranoside, utilizing 2' benzoylated (3aS,4R,7R,9R,10R,11S,13R,15R,15aR)-3a,4-diethyl-11-methoxy-7,9,11,13,15-pentamethyl-1-[4-methyl-4-(4-pyridin-3-yl-1H-imidazol-1H-yl)pentyl]-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-11-methoxy-7,9,11,13,15-pentamethyl-1-[4-methyl-4-(4-pyridin-3-yl-1H-imidazol-1-yl)pentyl]-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside was attained (42% yield) as a white solid. MH⁺(872.50).

EXAMPLE 33

Synthesis of (3aS,4R,7R,9R,10R,11S,13R,15R,15aR)-3a,4-diethyl-1-{4-[4-(6-fluoropyridin-3-yl)-1H-imidazol-1-yl]butyl}-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

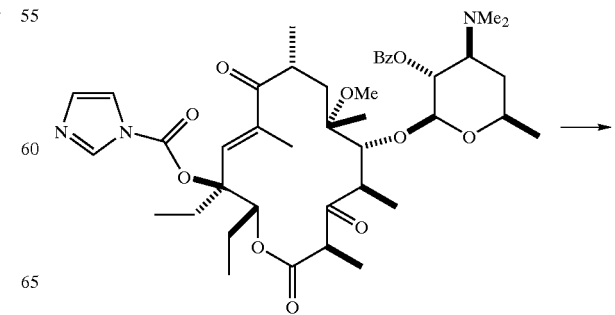

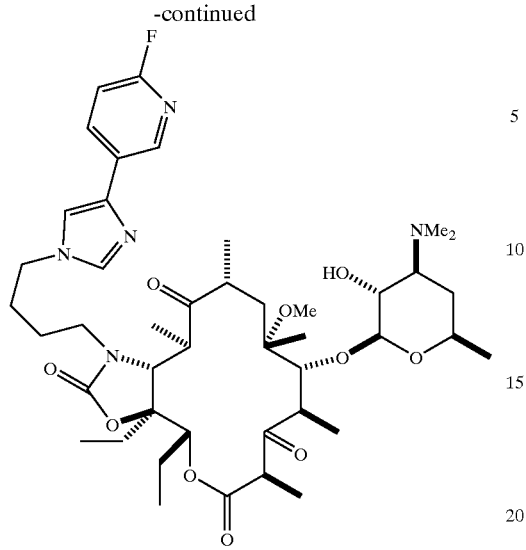

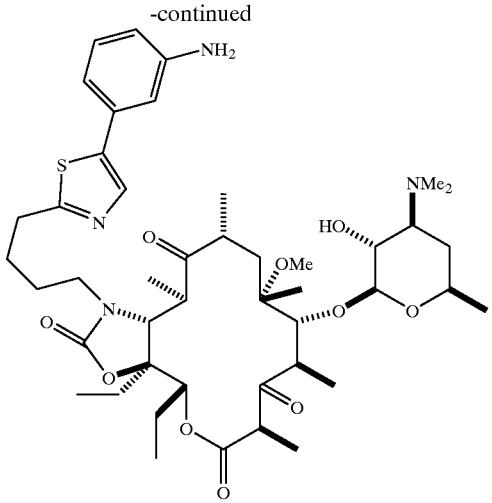

C12 ethyl, C9, C10, C11 enone, 3 oxo, C12 OCOIm macrolide of Example 11 (1 eq) was added to 4-[4-(6-Fluoro-pyridin-3-yl)-imidazol-1-yl]-butylamine (4 eq), acetonitrile and water (10%). The reaction conditions are the same as described previously for (3aS,4R,7R,9R,10R,11S, 13R,15R,15aR)-3a,4-diethyl-1-1-[4-(1H-imidazo[4,5-b] pyridin-1-yl)butyl]-11-methoxy-7,9,11,13,15-pentamethyl-2,6,8,14-tetraoxotetradecahydro-2H-oxacyclotetradecino[4, 3-d][1,3]oxazol-10-yl 3,4,6-trideoxy-3-(dimethylamino)-D-xylo-hexopyranoside. (3aS,4R,7R,9R,10R,11S,13R,15R, 15aR)-3a,4-diethyl-1-{4-[4-(6-fluoropyridin-3-yl)-1H-imidazol-1-yl]butyl}-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (79% yield) as a white solid. MH+(844.50).

C12 ethyl, C9, C10, C11 enone, 3 oxo, C12 OCOIm macrolide of Example 11 (1 eq) was added to 3-[2-(4-Amino-butyl)-thiazol-5-yl]-phenylamine (4 eq), acetonitrile, and water (10%). The reaction conditions are the same as described previously for (3aS,4R,7R,9R,10R, 11S,13R,15R,15aR)-3a,4-diethyl-1-[4-(1H-imidazo[4,5-b] pyridin-1-yl)butyl]-11-methoxy-7,9,11,13,15-pentamethyl-2,6,8,14-tetraoxotetradecahydro-2H-oxacyclotetradecino[4, 3-d][1,3]oxazol-10-yl 3,4,6-trideoxy-3-(dimethylamino)-D-xylo-hexopyranoside. (3aS,4R,7R,9R,10R,11S,13R,15R, 15aR)-1-{4-[5-(3-aminophenyl)-1,3-thiazol-2-yl]butyl}-3a, 4-diethyl-11-methoxy-7,9,11,13,15-pentamethyl-2,6,8,14-tetraoxotetradecahydro-2H-oxacyclotetradecino[4,3-d][1,3] oxazol-10-yl 3,4,6-trideoxy-3-(dimethylamino)-D-xylo-hexopyranoside was attained (12% yield) as a white solid. MH+(857.50).

EXAMPLE 34

Synthesis of (3aS,4R,7R,9R,10R,11S,13R,15R, 15aR)-1-{4-[5-(3-aminophenyl)-1,3-thiazol-2-yl] butyl}-3a,4-diethyl-11-methoxy-7,9,11,13,15-pentamethyl-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside

EXAMPLE 35

Synthesis of (3aS,4R,7R,9R,10R,11S,13R,15R, 15aR)-3a,4-diethyl-11-methoxy-7,9,11,13,15-pentamethyl-2,6,8,14-tetraoxo-1-[3-(3-pyridin-3-ylphenoxy)propyl]-tetradecahydro-2H-oxacyclotetradecino[4,3-d][1,3]oxazol-10-yl 3,4,6-trideoxy-3-(dimethylamino)-D-xylo-hexopyranoside

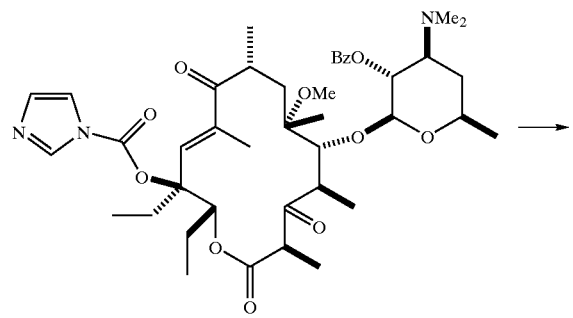

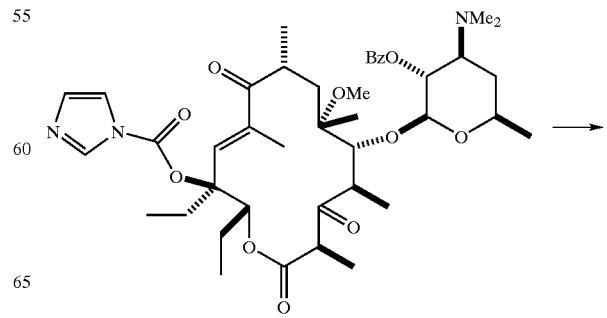

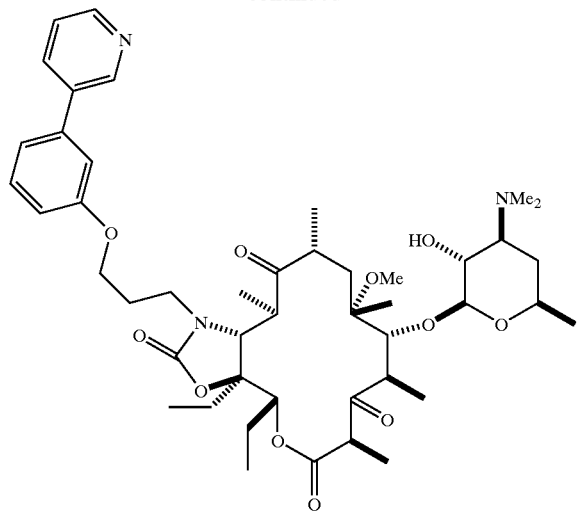

C12 ethyl, C9, C10, C11 enone, 3 oxo, C12 OCOIm macrolide of Example 11 (1 eq) was added to 3-(3-Pyridin-3-yl-phenoxy)-propylamine (3 eq), acetonitrile, and water. The reaction conditions are the same as described previously for (3aS,4R,7R,9R,-10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetra-decino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-2,6,8,14-tetraoxo-1-[3-(3-pyridin-3-ylphenoxy)propyl]-tetradecahydro-2H-oxacyclotetradecino[4,3-d][1,3]oxazol-10-yl 3,4,6-trideoxy-3-(dimethylamino)-D-xylo-hexopyranoside was attained (30% yield) as a white solid. MH⁺(838.50).

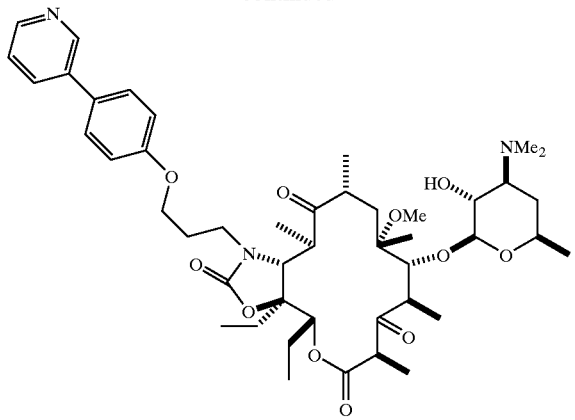

C12, ethyl, C9, C10, C11 enone, 3 oxo, C12 OCOIm macrolide of Example 11 (1 eq) was added to 3-(4-Pyridin-3-yl-phenoxy)-propylamine (3 eq), acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-2,6,8,14-tetraoxo-1-[3-(4-pyridin-3-ylphenoxy)propyl]-tetradecahydro-2H-oxacyclotetradecino[4,3-d][1,3]oxazol-10-yl 3,4,6-trideoxy-3-(dimethylamino)-D-xylo-hexopyranoside was attained (31% yield) as a white solid. MH⁺(838.50).

EXAMPLE 36

Synthesis of (3aS,4R,7R,9R,10R,11S,13R,15R,15aR)-3a,4-diethyl-11-methoxy-7,9,11,13,15-pentamethyl-2,6,8,14-tetraoxo-1-[3-(4-pyridin-3-ylphenoxy)propyl]-tetradecahydro-2H-oxacyclotetradecino[4,3-d][1,3]oxazol-10-yl 3,4,6-trideoxy-3-(dimethylamino)-D-xylo-hexopyranoside

EXAMPLE 37

Synthesis of (3aS,4R,7R,9R,10R,11S,13R,15R,15aR)-3a,4-diethyl-1-[4-(1H-imidazo[4,5-b]pyridin-1-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

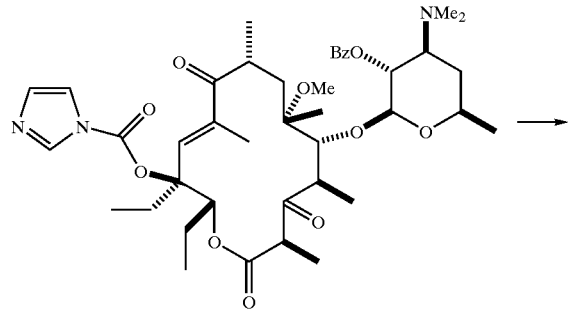

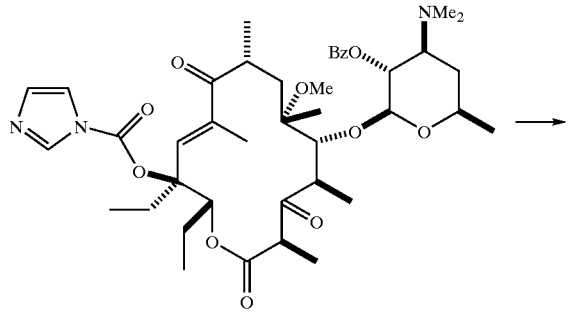

117

-continued

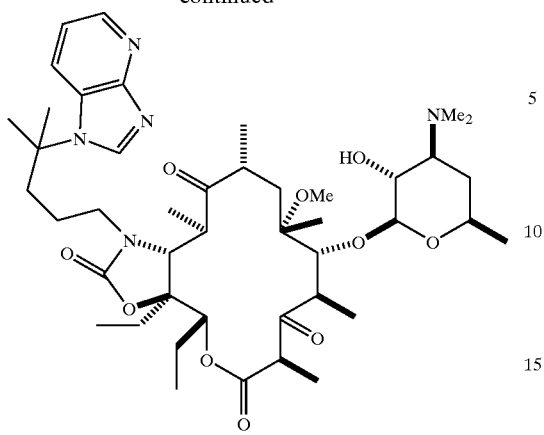

C12 ethyl, C9, C10, C11 enone, 3 oxo, C12 OCOIm macrolide of Example 11 (1 eq) was added to 4-Imidazo[4,5-b]pyridin-1-yl-4-methyl-pentylamine(4 eq), acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-1-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-1-[4-(1H-imidazo[4,5-b]pyridin-1-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (22% yield) as a white solid. MH+(828.50).

EXAMPLE 38

Synthesis of (3aS,4R,7R,9R,10R,11S,13R,15R,15aR)-3a,4-diethyl-1-[4-(3H-imidazol[4,5-b]pyridin-3-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

118

-continued

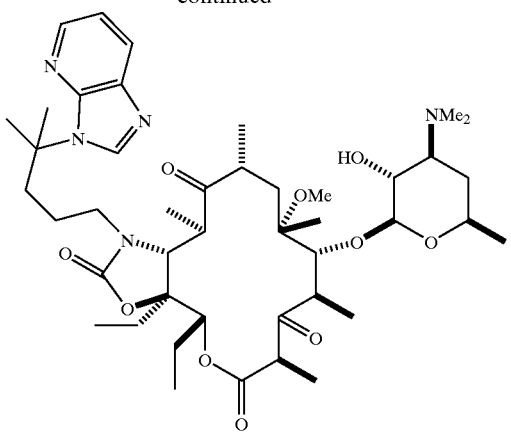

C12 ethyl, C9, C10, C11 enone, 3 oxo, C12 OCOIm macrolide of Example 11 (1 eq) was added to 4-Imidazo[4,5-b]pyridin-3-yl-4-methyl-pentylamine (3.8 eq), acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a, 4-diethyl-1-[4-(3 H-imidazo[4,5-b]pyridin-3-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (76% yield) as a white solid. MH+(828.50)

EXAMPLE 39

Synthesis of (3aS,4R,7S,9R,10R,11S,13R,15R,15aR)-3a,4-diethyl-7-fluoro-1-[4-(1H-imidazo[4,5-b]pyridin-1-yl)-4-methylpentyl]-11-methoxy-7,9,11,13,15-pentamethyl-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside

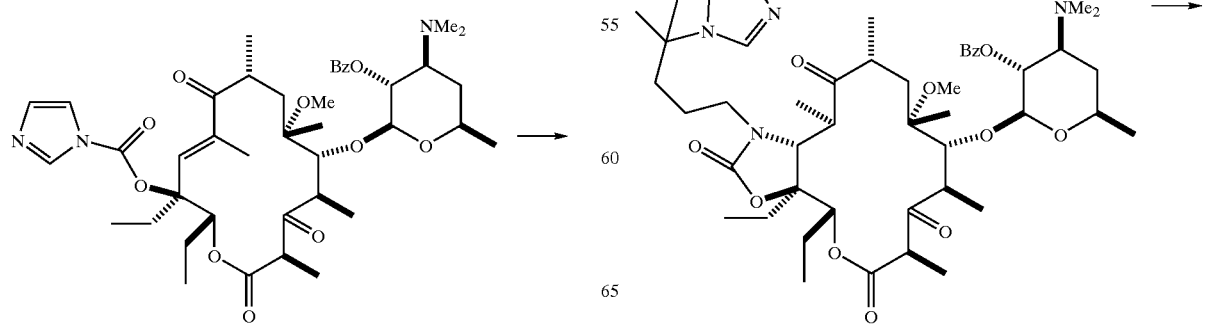

119

-continued

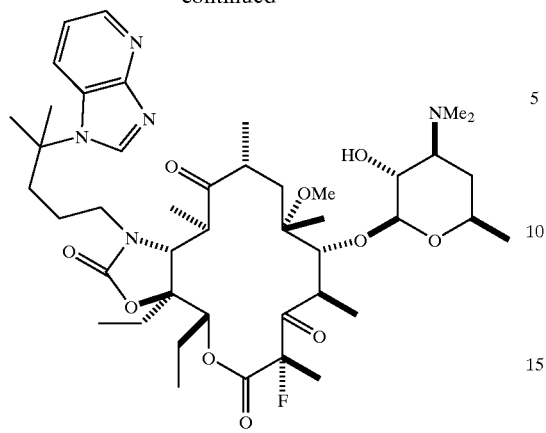

Using the procedure previously described for the preparation of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-4-ylbutyl)tetradecahydro-2H-oxacyclotetra-decino[4,3-d][1,3]oxazol-10-yl 3,4,6-trideoxy-3-(dimethylamino)-D-xylo-hexopyranoside, utilizing 2' benzoylated (3aS,4R,7R,9R,10R,11S,13R,15R,15aR)-3a,4-diethyl-1-[4-(1H-imidazo[4,5-b]pyridin-1-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-1-[4-(1H-imidazo[4,5-b]pyridin-1-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (58% yield) as a white solid. MH$^+$(846.50).

EXAMPLE 40

Synthesis of (3aS,4R,7S,9R,10R,11S,13R,15R,15aR)-3a,4-diethyl-7-fluoro-1-[4(3H-imidazo[4,5-b]pyridin-3-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

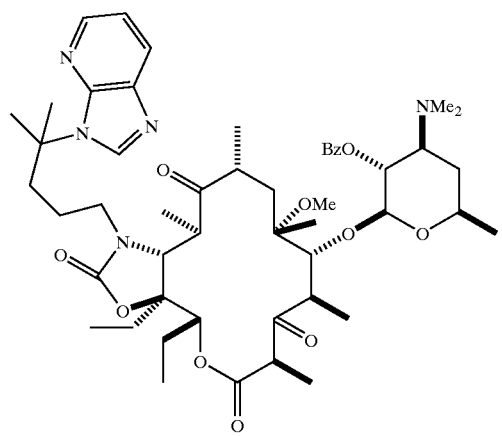

120

-continued

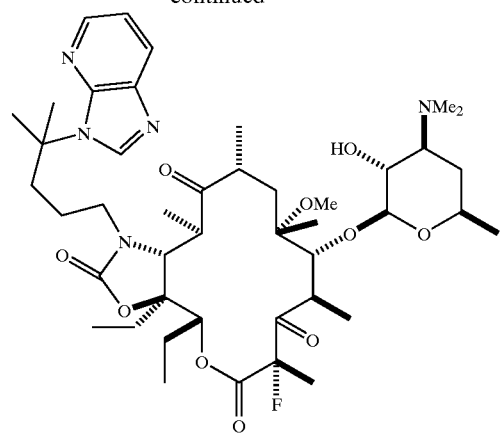

Using the procedure previously described for the preparation of (3aS,4R,7S,9R,10R,11S,13R,15R,15aR)-3a,4--diethyl-7-fluoro-11-methoxy-7,9,11,13,15-pentamethyl-2,6,8,14-tetraoxo-1-(4-quinolin-4-ylbutyl)tetradecahydro-2H-oxacyclotetra-decino[4,3-d][1,3]oxazol-10-yl 3,4,6-trideoxy-3-(dimethylamino)-D-xylo-hexopyranoside, utilizing 2' benzoylated (3aS,4R,7R,9R,10R,11S,13R,15R,15aR)-3a,4-diethyl-1-[4-(3H-imidazo[4,5-b]pyridin-3-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside as starting material, (3aS,4R,7S,9R,10R,11S,13R,15R,15aR)-3a,4-diethyl-7-fluoro-1-[4-(3H-imidazo[4,5-b]pyridin-3-yl)-4-methylpentyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was attained (63% yield) as a white solid. MH$^+$(846.50).

EXAMPLE 41

Synthesis of (3aS,4R,7R,9R,10R,11S,13R,15R,15aR)-3a,4-diethyl-11-methoxy-7,9,11,13,15-pentamethyl-1-{2-[methyl(quinolin-2-ylmethyl)amino]ethyl}-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside

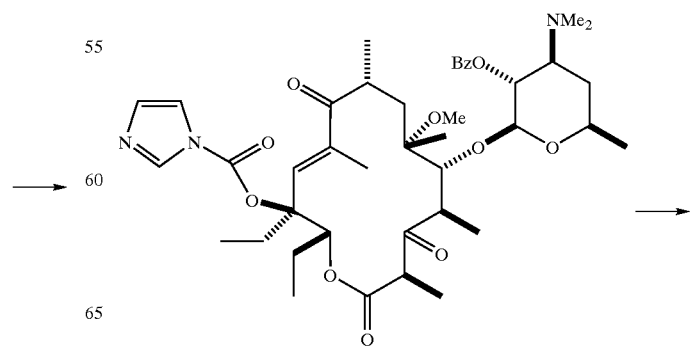

121
-continued

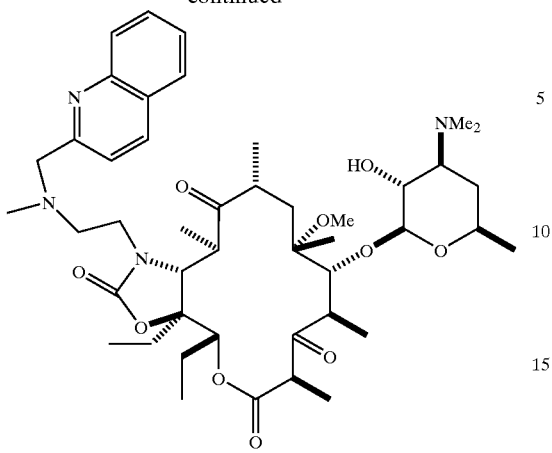

C12 ethyl, C9, C10, C11 enone, 3 oxo, C12 OCOIm macrolide of Example 11 (1 eq) was added to N1-Methyl-N1-quinolin-2-ylmethyl-ethane-1,2-diamine (6 eq); acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside. (3aS,4R,7R,9R,10R,11S,13R,15R,15aR)-3a,4-diethyl-11-methoxy-7,9,11,13,15-pentamethyl-1-{2-[methyl(quinolin-2-ylmethyl)amino]ethyl}-2,6,8,14-tetraoxotetradecahydro-2H-oxacyclotetradecino [4,3-d][1,3]oxazol-10-yl 3,4,6-trideoxy-3-(dimethylamino)-D-xylo-hexopyranoside was attained in a 13% yield. MH$^+$(825.50).

EXAMPLE 42

Synthesis of (3aS,4R,7R,9R,10R,11S,13R,15R,15aR)-3a,4-diethyl-11-methoxy-7,9,11,13,15-pentamethyl-1-{2-[methyl(quinolin-4-ylmethyl)amino]ethyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

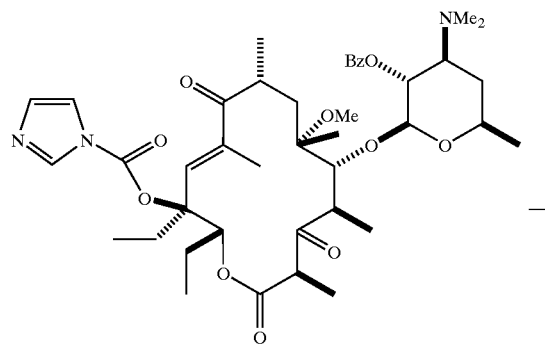

122
-continued

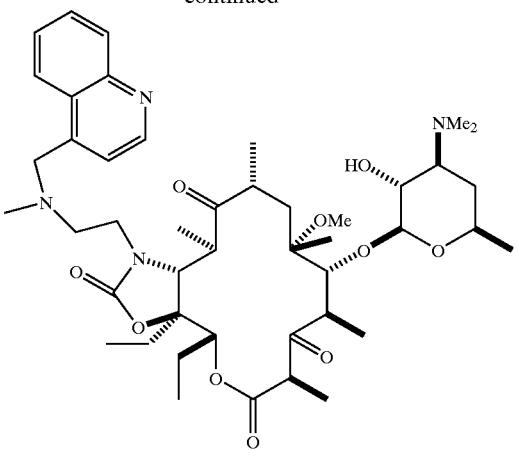

C12 ethyl, C9, C10, C11 enone, 3 oxo, C12 OCOIm macrolide of Example 11 (1 eq) was added to N1-Methyl-N1-quinolin-4-ylmethyl-ethane-1,2-diamine (6 eq), acetonitrile, and water (10%). The reaction conditions are the same as described previously for (3aS,4R,7R,9R,10R,11S,13R,15R,15aR)-3a,4-diethyl-1-[4-(1H-imidazo[4,5-b]pyridin-1-yl)butyl]-11-methoxy-7,9,11,13,15-pentamethyl-2,6,8,14-tetra-oxotetradecahydro-2H-oxacyclotetradecino [4,3-d][1,3]oxazol-10-yl 3,4,6-trideoxy-3-(dimethylamino)-D-xylo-hexopyranoside, yielding (3aS,4R,7R,9R,10R,11S,13R,15R,15aR)-3a,4-diethyl-11-methoxy-7,9,11,13,15-pentamethyl-1-{2-[methyl-(quinolin-4-ylmethyl)amino]ethyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside (18% yield) as an off white solid. MH$^+$(825.50).

EXAMPLE 43

Synthesis of (3aS,4R,7R,9R,10R,11S,13R,15R,15aR)-1-{2-[(3,3'-bipyridin-5-ylmethyl)(methyl)amino]ethyl}-3a,4-diethyl-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

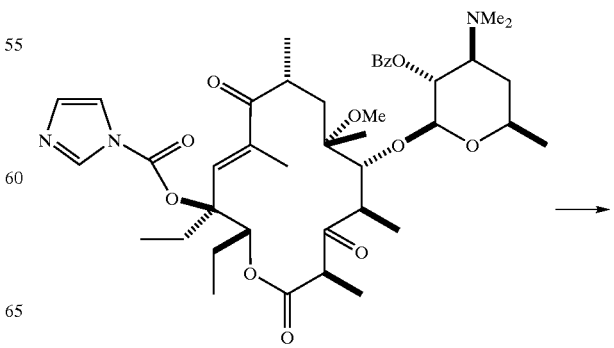

-continued

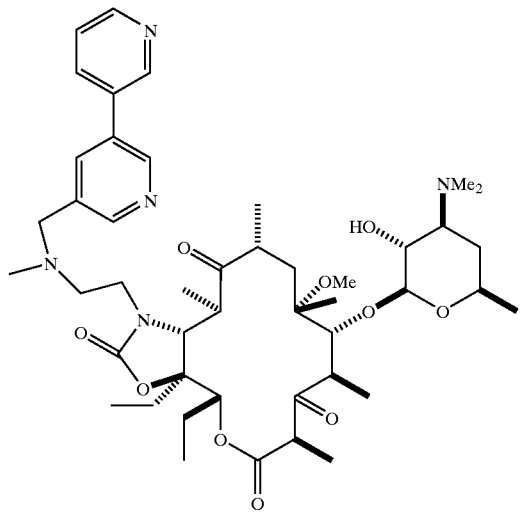

C12 ethyl, C9, C10, C11 enone, 3 oxo, C12 OCOIm macrolide of Example 11 (1 eq) was added to N1-[3,3'] Bipyridinyl-5-ylmethyl-N1-methyl-ethane-1,2-diamine (3 eq), acetonitrile, and water (10%). The reaction conditions are the same as described previously for (3aS,4R,7R,9R, 10R,11S,13R,15R,15aR)-3a,4-diethyl-1-[4-(1H-imidazo[4, 5-b]pyridin-1-yl)butyl]-11-methoxy-7,9,11,13,15-pentamethyl-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside, yielding (3aS,4R,7R,9R,10R,11S,13R,15R,15aR)-1-{2-[(3, 3'-bipyridin-5-ylmethyl)(methyl)amino]ethyl }-3a,4-diethyl-11-methoxy-7,9,11,13,15-pentamethyl-2,6,8,14-tetraoxotetradecahydro-2H-oxacyclotetradecino[4,3-d][1,3] oxazol-10-yl 3,4,6-trideoxy-3-(dimethylamino)-D-xylo-hexopyranoside (27% yield) as a white solid. MH$^+$(852.50).

EXAMPLE 44

Synthesis of (3aS,4R,7R,9R,10R,11S,13R,15R, 15aR)-3a,4-diethyl-11-methoxy-7,9,11,13,15-pentamethyl-1-{2-[methyl(quinolin-3-ylmethyl) amino]ethyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

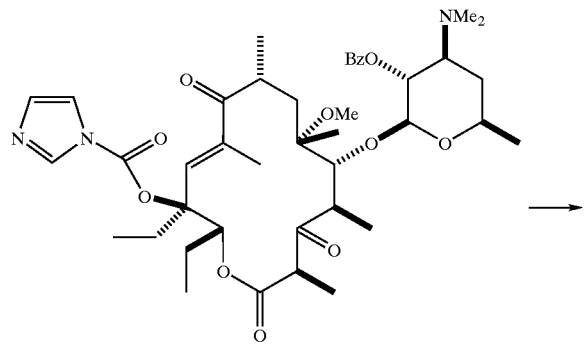

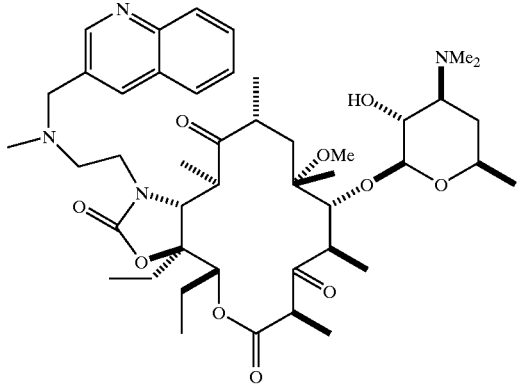

C12 ethyl, C9, C10, C11 enone, 3 oxo, C12 OCOIm macrolide of Example 11 (1 eq) was added to N1-Methyl-N1-quinolin-3-ylmethyl-ethane-1,2-diamine (6 eq); acetonitrile and water (10:1), respectively, were added. The solution was heated at 65° C. for 20 hours. Upon cooling the reaction was diluted with ethyl acetate and washed with NaHCO$_3$ $_{(sat)}$, NaCl(sat.), dried over MgSO$_4$, filtered and concentrated. To the crude material was added methanol and the solution was heated at 65° C. for 18 hours. Upon concentrating, the material was purified using flash chromatography (5% methanol/dichloromethane with 0.1% triethylamine), followed by further purification by RP HPLC. The combined product fractions coming off the HPLC were diluted with ethyl acetate and NaHCO$_3$ was added. The aqueous layer was separated and the organic layer was washed with NaCl$_{(sat)}$, dried over MgSO$_4$, filtered, concentrated, dissolved in acetonitrile/water and lyophilized yielding the product (3aS,4R,7R,9R,10R,11S,13R,15R, 15aR)-3a,4-diethyl-11-methoxy-7,9,11,13,15-pentamethyl-1-{2-[methyl(quinolin-3-ylmethyl)amino]ethyl}-2,6,8,14-tetraoxo-tetradecahydro-2H-oxacyclotetradecino [4,3-d][1, 3]oxazol-10-yl 3,4,6-trideoxy-3-(dimethylamino)-D-xylo-hexopyranoside (35% yield) as an off white solid. MH$^+$ (825.50).

EXAMPLE 45

Synthesis of (3aS,4R,7R,9R,10R,11S,13R,15R, 15aR)-3a,4-diethyl-11-methoxy-7,9,11,13,15-pentamethyl-2,6,8,14-tetraoxo-1-[4-(3-phenylisoxazol-5-yl)butyl]tetradecahydro-2H-oxacyclotetradecino [4,3-d][1,3]oxazol-10-yl 3,4,6-trideoxy-3-(dimethylamino)-D-xylo-hexopyranoside

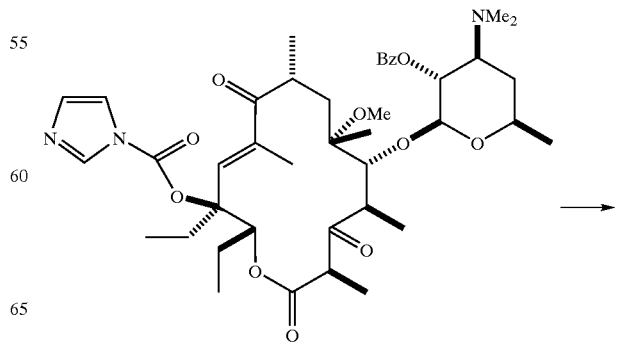

125
-continued

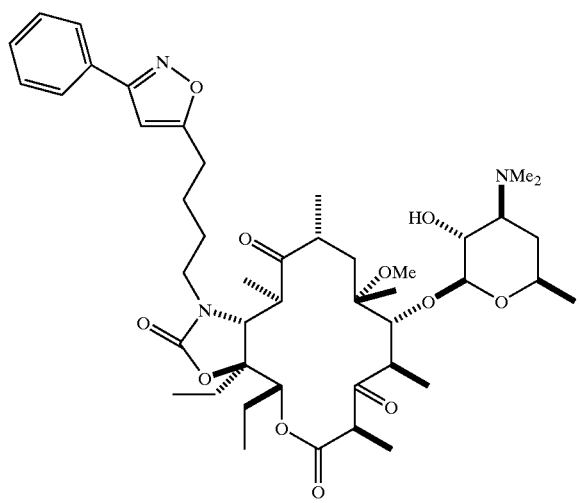

126
-continued

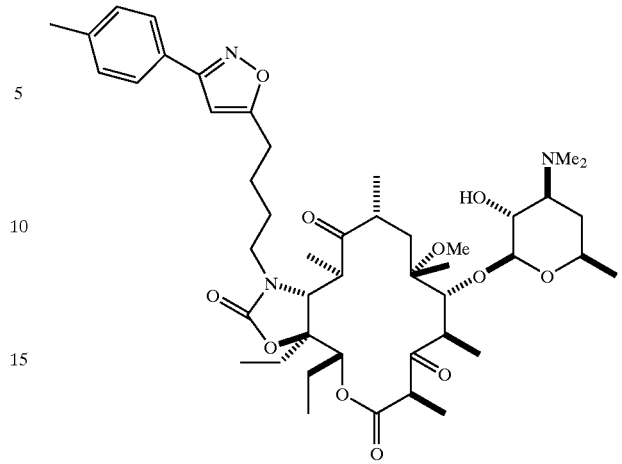

C12 ethyl, C9, C10, C11 enone, 3 oxo, C12 OCOIm macrolide of Example 11 (1 eq) was added to 4-(3-Phenyl-isoxazol-5-yl)-butylamine (6 eq). The reaction conditions are described in Example 44. (3aS,4R,7R,9R,10R,11S,13R,15R,15aR)-3a,4-diethyl-11-methoxy-7,9,11,13,15-pentamethyl-2,6,8,14-tetraoxo-1-[4-(3-phenylisoxazol-5-yl)butyl]tetradecahydro-2H-oxacyclotetradecino[4,3-d][1,3]oxazol-10-yl 3,4,6-trideoxy-3-(dimethylamino)-D-xylo-hexopyranoside was obtained as an off white solid in a 50% yield. MH⁺(826.50).

C12 ethyl, C9, C10, C11 enone, 3 oxo, C12 OCOIm macrolide of Example 11 (1 eq) was added to 4-(3-p-Tolyl-isoxazol-5-yl)-butylamine (6 eq). The reaction conditions were as described in Example 44. (3aS,4R,7R,9R,10R,11S,13R,15R,15aR)-3a,4-diethyl-11-methoxy-7,9,11,13,15-pentamethyl-1-{4-[3-(4-methylphenyl)isoxazol-5-yl]butyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside was obtained as an off white solid in a 73% yield. MH⁺(840.06).

Example 46

Synthesis of (3aS,4R,7R,9R,10R,11S,13R,15R,15aR)-3a,4-diethyl-11-methoxy-7,9,11,13,15-pentamethyl-1-{4-[3-(4-methylphenyl)isoxazol-5-yl]butyl}-2,6,8,14-tetraoxotetradecahydro-2H-oxacyclotetradecino[4,3-d][1,3]oxazol-10-yl 3,4,6-trideoxy-3-(dimethylamino)-D-xylo-hexopyranoside

EXAMPLE 47

Synthesis of C12 Vinyl Macrolides (Scheme 7)

EXAMPLE 47(a)

C12 alkene, C9, C11 diol macrolide

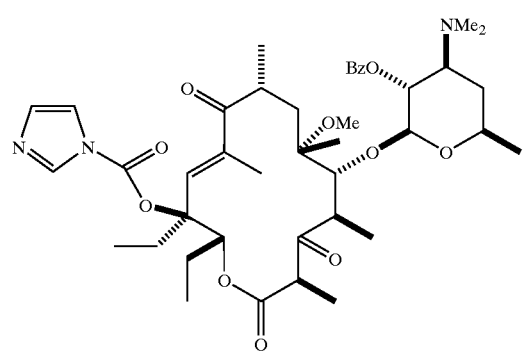

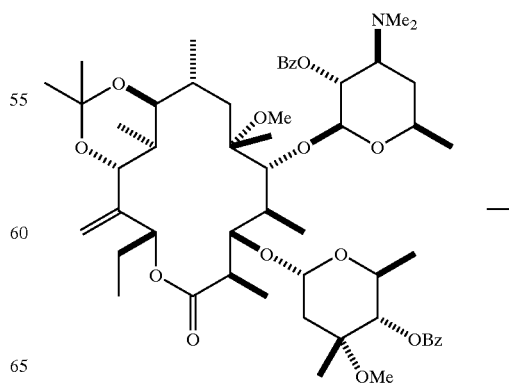

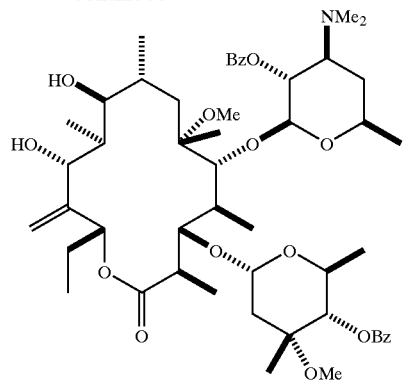

To 2', 4" Obz, C9, C11-dimethylketal C12, 21 alkene macrolide (1 eq) in 2:1 acetonitrile/water was added pyridinium p-toluenesulfonate (5 eq). The solution was heated in a 68° C. oil bath for 17 hours. Upon cooling, the solution was diluted with ethyl acetate, and solid NaHCO₃ was added (12 eq). The organic layer was then diluted with ethyl acetate, washed with NaHCO$_{3(sat)}$, and NaCl$_{(sat.)}$. The combined aqueous layers were back extracted with ethyl acetate, and the combined organic layers dried over MgSO₄, filtered and concentrated to yield C12 alkene, C9, C11 diol as a white solid (90% yield). The material is used as is for the next step. MH⁺(940.4).

EXAMPLE 47(b)

C12, C21, C11, C9 tetraol macrolide

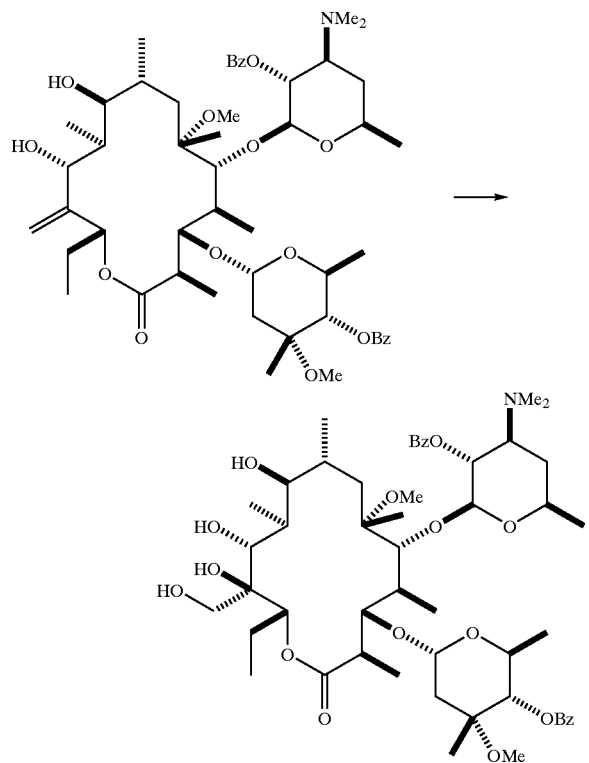

To C12 alkene, C9, C11 diol macrolide (1 eq) in 9:1 acetone/water was added N-methyl morpholine N-oxide mono-hydrate(2 eql), followed by 0.08M osmium tetroxide in tert-butanol. The solution was allowed to stir at room temperature for 4 hours. The solution was then diluted with ethyl acetate and cooled to 0° C. Upon cooling Na₂SO$_{3(sat)}$ was added and the solution was allowed to stir for 10 minutes. The reaction was then warmed to room temperature, diluted with ethyl acetate, and washed with NaHCO$_{3(sat)}$, and NaCl$_{(sat)}$. The combined aqueous layers were back extracted with ethyl acetate, and the combined organic layers were dried with MgSO₄, filtered and concentrated. Diethyl ether was added and the slurry was allowed to stir for 17 hours, then filered and rinsed with diethyl ether to yield the C9, C11, C12, C21 tetraol macrolide (82% yield) as an off-white solid. MH⁺(974.5).

EXAMPLE 47(c)

C21 acetate C9, C11, C12 triol macrolide

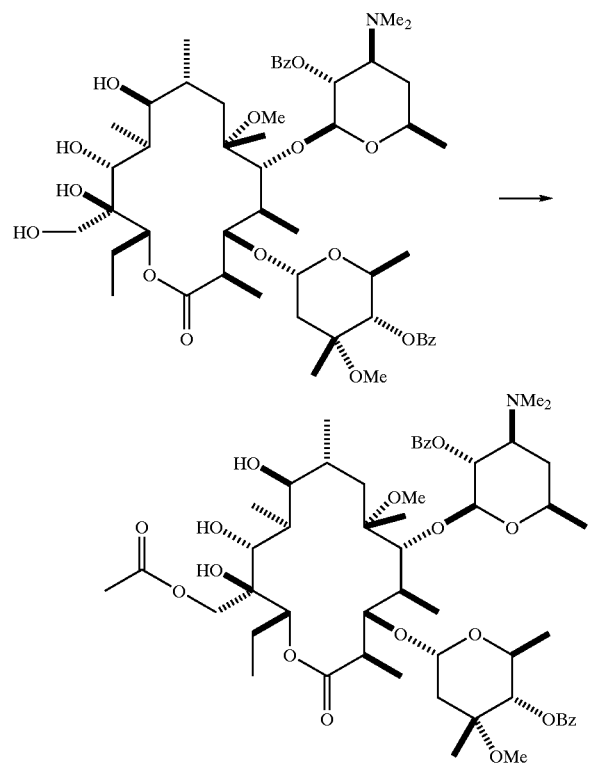

To C9, C11, C12, C21 tetraol macrolide (1 eq) in dichloromethane at 0° C. under argon was added acetic anhydride (1.1 eq), diisopropylethylamine (1.1 eq), and dimethylaminopyridine (0.1 eq). After stirring for 15 minutes, the solution was cooled at −10° for 17 hours. The solution was diluted with ethyl acetate, and washed with NaHCO$_{3(sat)}$, NaCl$_{(sat)}$, dried over MgSO₄, filtered and concentrated to yield the C21 acetate, C12, C11, C9 triol macrolide as an off white solid in quantitative yield. The material is used as is for the next step.

EXAMPLE 47(d)

C21 acetate C9 keto, C11, C12 diol macrolide

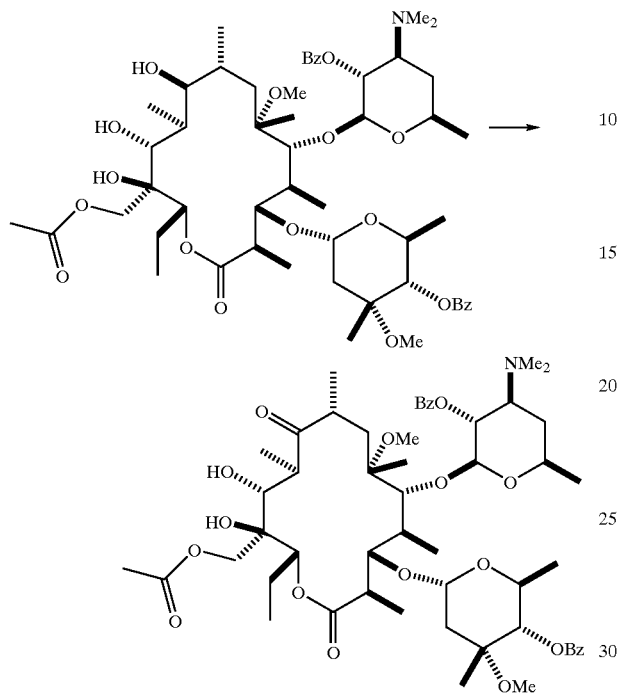

To C21 acetate, C9, C11, C12 triol macrolide (1 eq) in dichloromethane at 0° C. was added Dess-Martin Periodinane (1.2 eq). The solution was stirred at 0° C. for 14 hours. The reaction was diluted with ethyl acetate, and 1:1 10% Na$_2$S$_2$O$_3$/NaHCO$_{3(sat)}$ were added. The bilayer solution was stirred vigorously for 1 hour. The layers were separated and the organic layer was washed with NaCl$_{(sat)}$, dried over MgSO$_4$, filtered and concentrated yielding the C21 acetate, C9 keto, C11, C12 diol macrolide (99% yield) as an off white solid. The material is used as is for the next step. MH$^+$(1014.5).

EXAMPLE 47(e)

C21 acetate C9 keto, C11 OMs, C12 OH macrolide

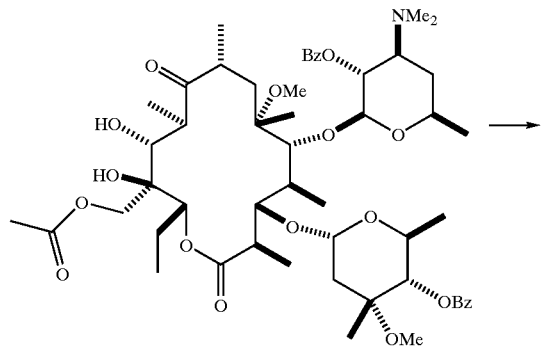

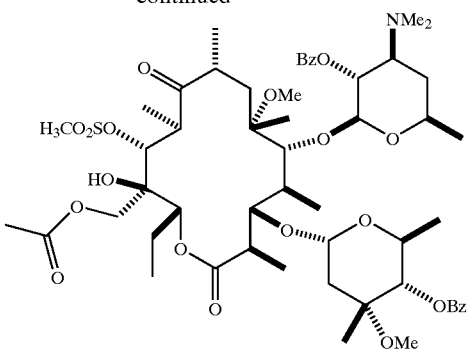

To C21 acetate, C9 keto, C11, C12 diol macrolide (1 eq) in pyridine at 0° C. was added methanesulfonyl chloride (5 eq) via syringe. The solution was stirred for 18 hours as the solution warmed to room temperature. After concentrating the reaction mixture, water was added and the slurry was stirred vigorously for 17 hours; the slurry was filtered and dried to afford the C21 acetate C9 keto, C11 OMs, C12 hydroxy macrolide (100% yield) as a yellow solid. MH$^+$ (1092.4).

EXAMPLE 47(f)

C21 acetate C9, C10, C11 enone, C12 OH diol macrolide

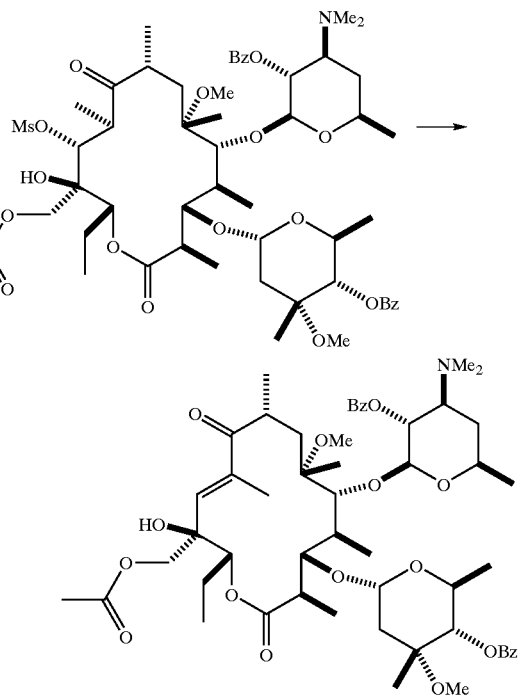

To C21 acetate, C9keto, C11 OMs, C12 OH macrolide (1 eq) in acetone was added DBU (2 eq). The solution was stirred for 5 hours at rt and then for 40 hours at 68° C. The solution was diluted with ethyl acetate, washed with H$_2$O, NaHCO$_{3(sat)}$, with NaCl$_{(sat)}$, dried over MgSO$_4$, filtered and concentrated yielding the C21 acetone C9, C10, C11 enone, C12 OH macrolide (90% yield) as an off white solid. MH$^+$(996.4).

EXAMPLE 47(g)

C9, C10, C11 enone, C3, C12, C21 triol macrolide

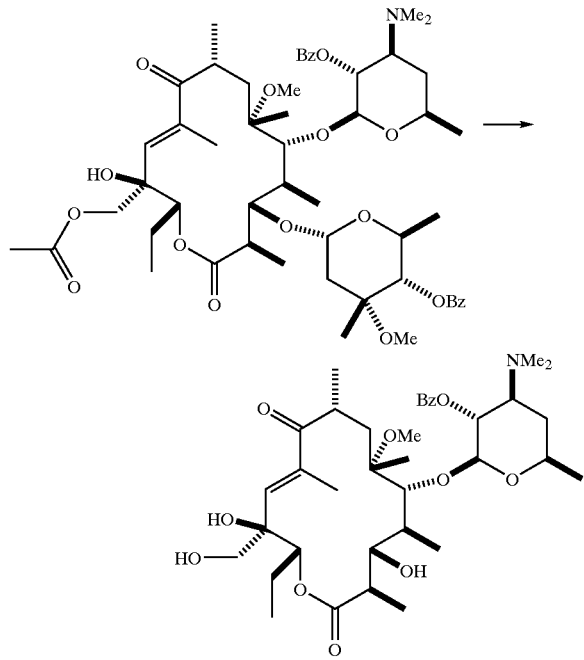

To C21 acetate, C9, C10, C11 enone C12 OH macrolide (1 eq) in acetonitrile was added 3$\underline{M}$ HCl(aq). The solution was heated at 40° C. for 22 hours; upon cooling, the solution was diluted with ethyl acetate and solid NaHCO$_3$ was added. The solution was washed with NaHCO$_{3(sat)}$, with NaCl$_{(sat.)}$, dried over MgSO$_4$, filtered and concentrated to yield an off white solid. Purification through flash chromatography (35% acetone/hexanes with 0.1% triethylamine) yielded crude product as a white solid. The material was further purified by triturating from diethyl ether/hexanes to yield C9, C10, C11 enone, C3, C12, C21 triol macrolide (24%). MH$^+$(690.4).

EXAMPLE 47(h)

C3, C21 oxo, C9, C10, C11 enone-12-ol macrolide

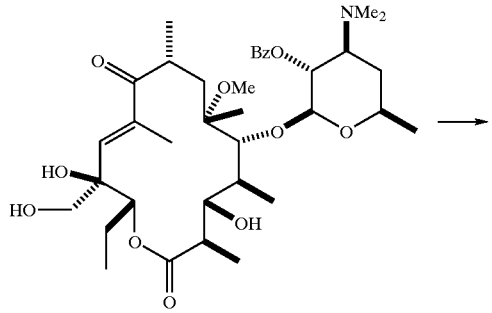

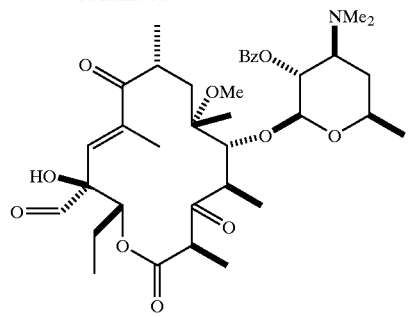

To N-Chlorosuccinimide (1 eq) in dichloromethane at 0° C. was added Methyl sulfide (1.2 eq). After stirring for 5 minutes, the solution was cooled to −20° C. To this solution was added C21, C3 hydroxy macrolide (0.4 eq) in dichloromethane. The resulting solution was stirred at −23° C. for 95 minutes at which time triethylamine (1 eq) was added dropwise. After stirring at −20° C. for 5 minutes, the solution was allowed to warm to room temperature. The solution was than added to ethyl acetate, washed with NaHCO$_{3(sat)}$, with NaCl$_{(sat.)}$, dried over MgSO$_4$, filtered and concentrated to yield an off white solid. Purification through flash chromatography (15–20% acetone/hexanes with 0.1% triethylamine) yielded the C3, C21 oxo, C9, C10, C11 enone-12-ol macrolide (75% yield) as a white solid. MH$^+$ (688.4).

EXAMPLE 47(i)

C12 vinyl, C3, oxo, C9, C10, C11 enone-12-ol macrolide

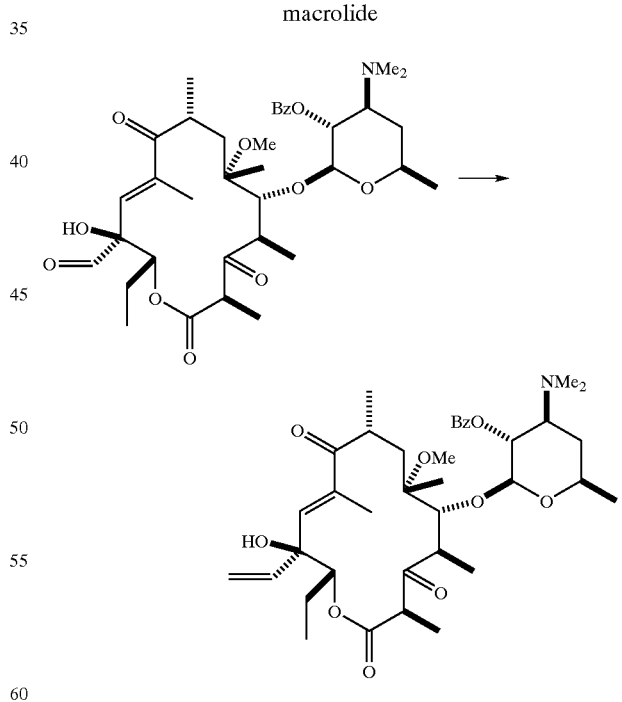

To methyl triphenylphosphonium bromide (1 eq) in tetrahydrofuran at −78° C. was added potassium bis(trimethylsilyl)amide/0.5$\underline{M}$ in toluene (1 eq). The cooling bath was removed and the anion solution was stirred for 1 hour. After cooling the anion solution back to −78° C., C21 aldehyde macrolide (0.5 eq) in tetrahydrofuran was added.

The cooling bath was removed and the anion solution was stirred for 4 hours at which time ethyl acetate and NH$_4$Cl$_{(sat.)}$ were added. After two layers formed, the reaction was added to ethyl acetate and NH$_4$Cl$_{(sat.)}$. Upon mixing and separating off the aqueos layer, the organic layer was washed with NaHCO$_{3(sat)}$, with NaCl$_{(sat.)}$, dried over MgSO$_4$, filtered and concentrated. Purification through flash chromatography (15–20% acetone/hexanes with 0.1% triethylamine) yielded the C12-vinyl, C3-oxo, C9, C10, C11 enone-12-ol macrolide (50% yield) as a white solid. MH$^+$(686.4).

EXAMPLE 47(j)

C12 vinyl C10, C11 enone, C3 oxo, C12 OCOIm macrolide

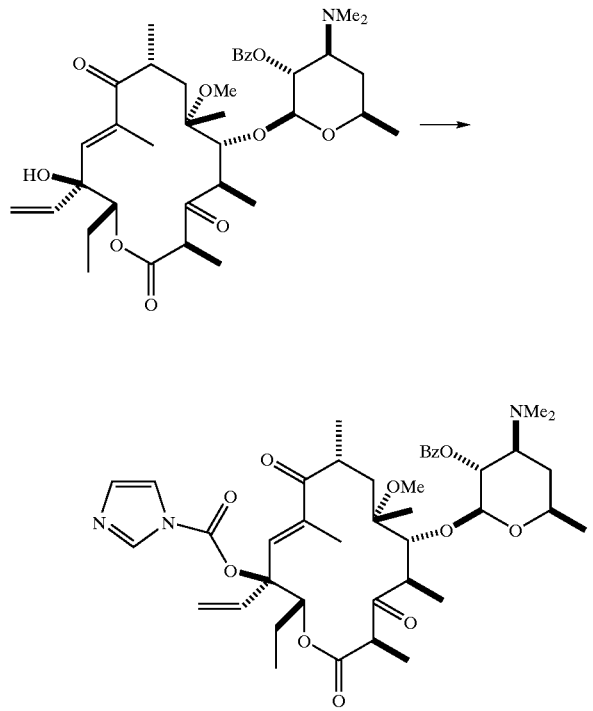

To a solution of C12 vinyl, C9, C10, C11 enone, C3 oxo, C12 OH macrolide (1 eq) and carbonyldiimidazole (3 eq) in tetrahydrofuran at 0° C. was added sodium hydride (2 eq). After stirring for 6 hours, ethyl acetate was added. While still at 0° C., NaHCO$_{3(sat.)}$ was added cautiously. The mixture was then diluted with ethyl acetate and was washed with NaHCO$_{3(sat.)}$, with NaCl$_{(sat.)}$, dried over MgSO$_4$, filtered, concentrated and pumped on yielding crude C12 vinyl C9, C10, C11 enone, C3 oxo, C12 OCOIm macrolide. The crude material was used in the next step without further purification. MH$^+$(780.5, and hydrolyzed 686.5).

EXAMPLE 48

Synthesis of (3aS,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside

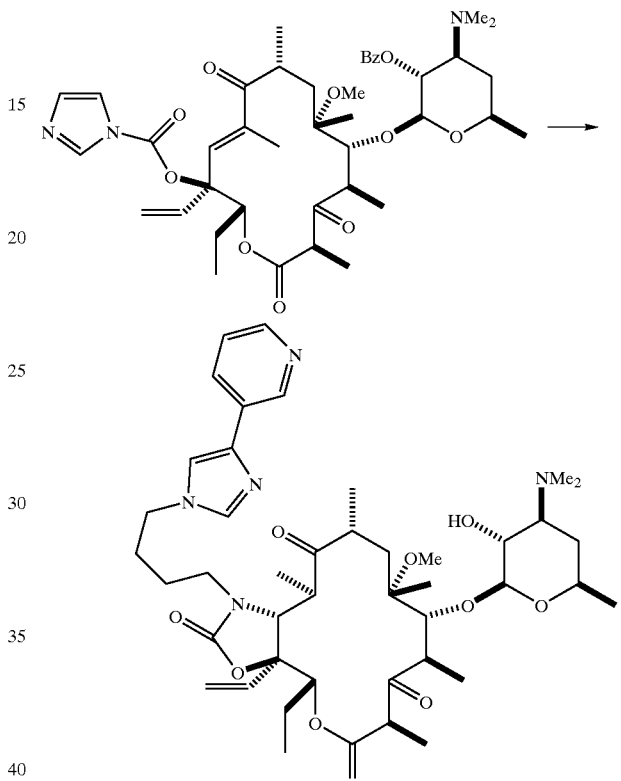

C12 vinyl, C9, C10, C11 enone, 3 oxo, C12 OCOIm macrolide (1 eq) was added to 4-(4-(3-pyridyl)imidazolyl) butylamine (4 eq); acetonitrile and water were added. The solution was heated at 65° C. for 14 hours. Upon cooling the reaction was diluted with ethyl acetate and washed with NaHCO$_{3(sat)}$, NaCl$_{(sat.)}$, dried over MgSO$_4$, filtered and concentrated. To the crude material was added dichloromethane, benzoic anhydride, triethylamine and dimethylaminopyridine. After standing for 12 hours the solution was concentrated and purified by RP HPLC. The combined product fractions coming off the HPLC were diluted with ethyl acetate and NaHCO$_3$ was added. After mixing, the aqueous layer was separated and the organic layer was washed with NaCl$_{(sat)}$, dried over MgSO$_4$, filtered, and concentrated, yielding benzoylated (3aS,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside (35% yield) as a white solid. To the benzoylated compound was added methanol and the solution was heated at 65° C. for 16 hours. Upon concentrating, the material was purified by RP HPLC. The combined product fractions coming off the HPLC were diluted with ethyl acetate and NaHCO₃ was added. After mixing, the aqueous layer was separated and the organic layer was washed with NaCl$_{(sat.)}$, dried over MgSO₄, filtered, concentrated, dissolved in acetonitrile/water and lyophilized yielding (3aS,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside (83% yield) as a white solid. MH⁺(824.50).

EXAMPLE 49

Synthesis of (3aS,4R,7S,9R,10R,11S,13R,15R,15aR)-4-ethyl-7-fluoro-11-methoxy-7,9,11,13,15-pentamethyl-2,6,8,14-tetraoxo-1-[4-(4-pyridin-3-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside

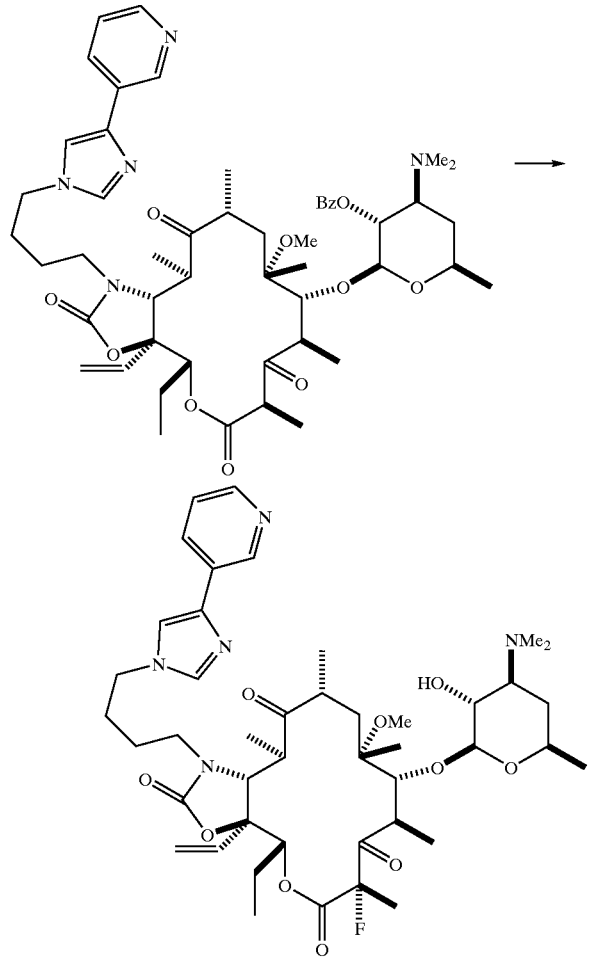

To benzoylated (3aS,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside (1 eq) in DMF (5.3 mL) at 0° C. was added 60% NaH (2 eq). After stirring for 1 hour at 0° C., N-fluorobenzenesulfonimide (1 eq) was added. After stirring for an additional hour at 0° C., the solution was diluted with ethyl acetate and NaHCO$_{3(sat.)}$ was added cautiously to quench. The reaction was then added to ethyl acetate and was washed with NaHCO$_{3(sat)}$, NaCl(sat.), dried over MgSO₄, filtered, concentrated and purified by RP HPLC. The combined product fractions coming off the HPLC were diluted with ethyl acetate and NaHCO₃ was added. The aqueous layer was separated and the organic layer was washed with NaCl$_{(sat.)}$, dried over MgSO₄, filtered and concentrated. Methanol was added and the solution was heated at 60° C. for 15 hours. Upon concentrating, the material was purified by RP HPLC. The combined product fractions coming off the HPLC were diluted with ethyl acetate and NaHCO₃ was added. The aqueous layer was separated and the organic layer was washed with NaCl$_{(sat.)}$, dried over MgSO₄, filtered, concentrated and lyophilized from MeCN:H2O yielding (3aS,4R,7S,9R,10R,11S,13R,15R,15aR)-4-ethyl-7-fluoro-11-methoxy-7,9,11,13,15-pentamethyl-2,6,8,14-tetraoxo-1-[4-(4-pyridin-3-yl-1H-imidazol-1-yl)-butyl]-3a-vinyltetradecahydro-2H-oxacyclotetradecino[4,3-d][1,3]oxazol-10-yl 3,4,6-trideoxy-3-(dimethylamino)-D-xylo-hexopyranoside (47% yield) as a white solid. MH⁺(842.50).

EXAMPLE 50

Synthesis of (3aS,4R,7R,9R,10R,11S,13R,15R,15aR)-4-ethyl-11-methoxy-7,9,11,13,15-pentamethyl-1-[4-methyl-4-(4-pyridin-3-yl-1H-imidazol-1-yl)pentyl]-2,6,8,14-tetraoxo-3a-vinyltetradecahydro-2H-oxacyclotetradecino [4,3-d][1,3]oxazol-10-yl 3,4,6-trideoxy-3-(dimethylamino)-D-xylo-hexopyranoside

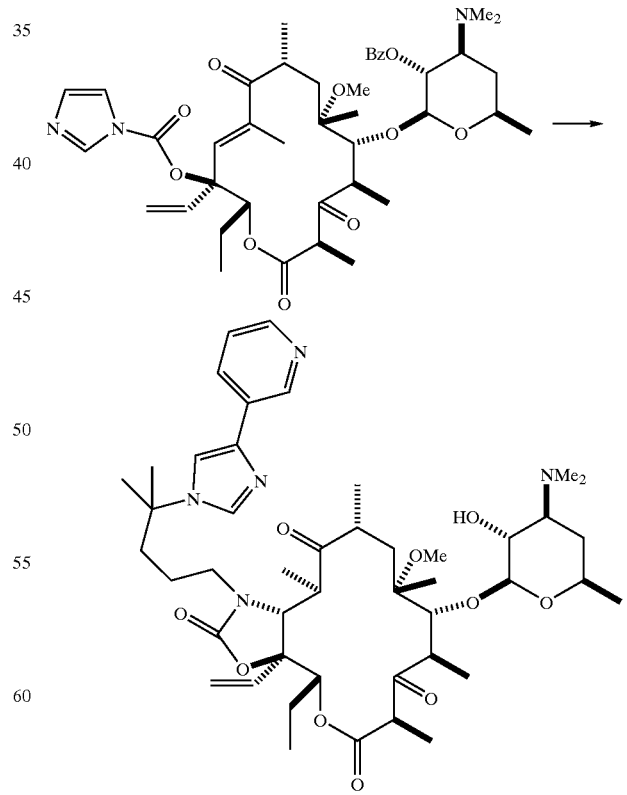

C12 vinyl, C9, C10, C11 enone, 3 oxo, C12 OCOIm macrolide (1 eq) was added to 4-Methyl-4-(4-pyridin-3-ylimidazol-1-yl)-pentylamine (3 eq); acetonitrile and water (10%). The solution was heated at 65° C. for 16 hours. Upon cooling the reaction was diluted with ethyl acetate and washed with NaHCO$_{3(sat)}$, NaCl$_{(sat.)}$, dried over MgSO$_4$, filtered and concentrated. To the crude material was added dichloromethane, benzoic anhydride, triethylamine (10%) and dimethylaminopyridine (2%). After standing for 17 hours the solution was concentrated and purified by RP HPLC. The combined product fractions coming off the HPLC were diluted with ethyl acetate and NaHCO$_3$ was added. After mixing, the aqueous layer was separated and the organic layer was washed with NaCl$_{(sat.)}$, dried over MgSO$_4$, filtered, and concentrated, affording the 2' benzoylated product (21% yield). Methanol was added, and the solution was heated at 65° C. for 16 hours. Upon concentrating, the material was purified by RP HPLC. The combined product fractions coming off the HPLC were diluted with ethyl acetate and NaHCO$_3$ was added. After mixing, the aqueous layer was separated and the organic layer was washed with NaCl$_{(sat.)}$, dried over MgSO$_4$, filtered, concentrated, dissolved in acetonitrile/water and lyophilized affording (3aS,4R,7R,9R,10R,11S,13R,15R,15aR)-4-ethyl-11-methoxy-7,9,11,13,15-pentamethyl-1-[4-methyl-4-(4-pyridin-3-yl-1H-imidazol-1-yl)pentyl]-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside (73% yield) as a white solid. MH$^+$(852.50).

EXAMPLE 51

Synthesis of C12 Vinyl Analogs (3aS,4R,7R,9R,10R,11S,13R,15R,15aR)-4-ethyl-1-[4-(3H-imidazo[4,5-b]pyridin-3-yl)butyl]-11-methoxy-7,9,11,13,15-pentamethyl-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside

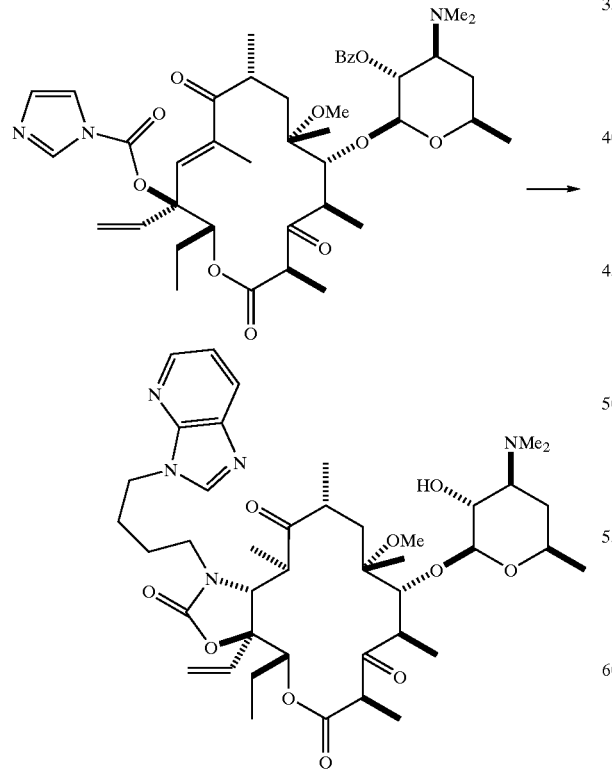

C12 vinyl, C9, C10, C11 enone, 3 oxo, C12 OCOIm macrolide of Example 47 (1 eq) was added to 4-Imidazo[4,5-b]pyridin-3-yl-butylamine (5 eq). The reaction conditions are described in Example 44. (3aS,4R,7R,9R,10R,11S,13R,15R,15aR)-4-ethyl-1-[4-(3H-imidazo[4,5-b]pyridin-3-yl)butyl]-11-methoxy-7,9,11,13,15-pentamethyl-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside was obtained as an off white solid in a 70% yield. MH$^+$(798.00).

EXAMPLE 52

Synthesis of (3aS,4R,7R,9R,10R,11S,13R,15R,15aR)-4-ethyl-1-[4-(1H-imidazo[4,5-b]pyridin-1-yl)butyl]-11-methoxy-7,9,11,13,15-pentamethyl-2,6,8,14-tetraoxo-3a-vinyltetradecahydro-2H-oxacyclotetradecino [4,3-d][1,3]oxazol-10-yl 3,4,6-trideoxy-3-(dimethylamino)-D-xylo-hexopyranoside

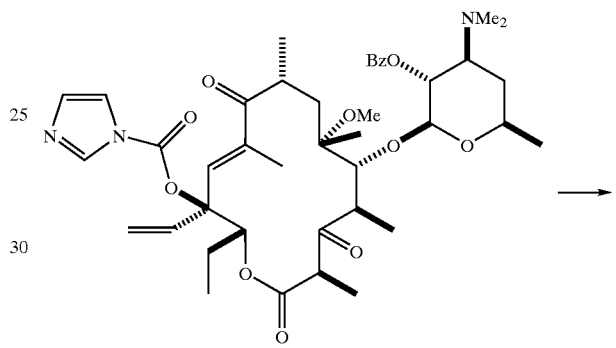

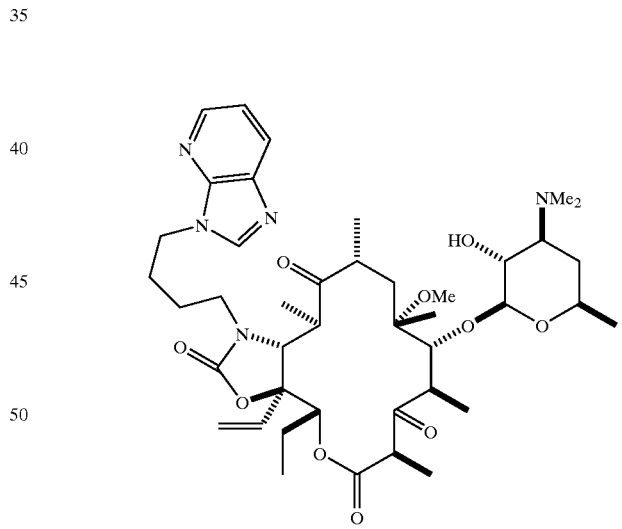

C12 vinyl, C9, C10, C11 enone, 3 oxo, C12 OCOIm macrolide of Example 47 (1 eq) was added to 4-Imidazo[4,5-b]pyridin-1-yl-butylamine (6 eq). The reaction conditions are described in Example 44. (3aS,4R,7R,9R,10R,11S,13R,15R,15aR)-4-ethyl-1-[4-(1H-imidazo[4,5-b]pyridin-1-yl)butyl]-11-methoxy-7,9,11,13,15-pentamethyl-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside was obtained as an off white solid in a 26% yield. MH$^+$(798.00).

EXAMPLE 53

Synthesis of (3aS,4R,7R,9R,10R,11S,13R,15R, 15aR)-4-ethyl-11-methoxy-7,9,11,13,15-pentamethyl-1-{4-[4-(6-methylpyridin-3-yl)-1H-imidazol-1-yl]butyl}-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside

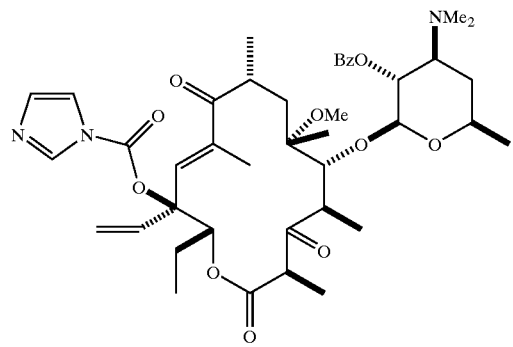

C12 vinyl, C9, C10, C11 enone, 3 oxo, C12 OCOIm macrolide of Example 47(1 eq) was added to 4-[4-(6-Methyl-pyridin-3-yl)-imidazol-1-yl]-butylamine (3 eq). The reaction conditions are described in Example 44. (3aS,4R, 7R,9R,10R,11S,13R,15R,15aR)-4-ethyl-11-methoxy-7,9, 11,13,15-pentamethyl-1-{4-[4-(6-methylpyridin-3-yl)-1H-imidazol-1-yl]butyl}-2,6,8,14-tetraoxo-3a-vinyltetradecahydro-2H-oxacyclotetradecino [4,3-d][1,3] oxazol-10-yl 3,4,6-trideoxy-3-(dimethylamino)-D-xylo-hexopyranoside was obtained as an off white solid in a 25% yield. MH⁺(838.05).

EXAMPLE 54

Synthesis of (3aS,4R,7R,9R,10R,11S,13R,15R, 15aR)-1-{2-[-(3,3'-bipyridin-5-ylmethyl)(methyl)amino]ethyl}-4-ethyl-11-methoxy-7,9,11,13,15-pentamethyl-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside

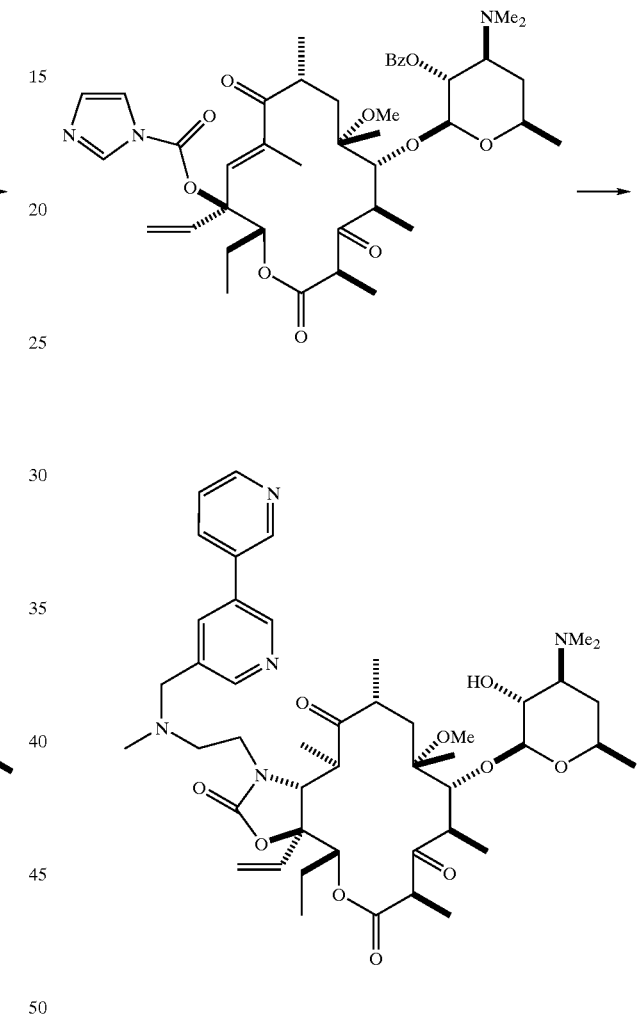

C12 vinyl, C9, C10, C11 enone, 3 oxo, C12 OCOIm macrolide of Example 47 (1 eq) was added to N1-[3,3'] Bipyridinyl-5-ylmethyl-N1-methyl-ethane-1,2-diamine (5 eq). The reaction conditions are described in Example 44. (3aS,4R,7R,9R,10R,11S,13R,15R,15aR)-1-{2-[(3,3'-bipyridin-5-ylmethyl)(methyl)-amino]ethyl}-4-ethyl-11-methoxy-7,9,11,13,15-pentamethyl-2,6,8,14-tetraoxo-3a-vinyl-tetradecahydro-2H-oxacyclotetradecino[4,3-d][1,3] oxazol-10-yl 3,4,6-trideoxy-3-(dimethylamino)-D-xylo-hexopyranoside was obtained as an off white solid ed in a 27% yield. MH⁺(850.50).

EXAMPLE 55

Synthesis of (3aS,4R,7R,9R,10R,11S,13R,15R, 15aR)-4-ethyl-11-methoxy-7,9,11,13,15-pentamethyl-2,6,8,14-tetraoxo-1-[4-(4-pyrazin-2-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside

EXAMPLE 56

Synthesis of (3aS,4R,7R,9R,10R,11S,13R,15R, 15aR)-4-ethyl-11-methoxy-7,9,11,13,15-pentamethyl-2,6,8,14-tetraoxo-1-[4-(4-pyrimidin-5-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside

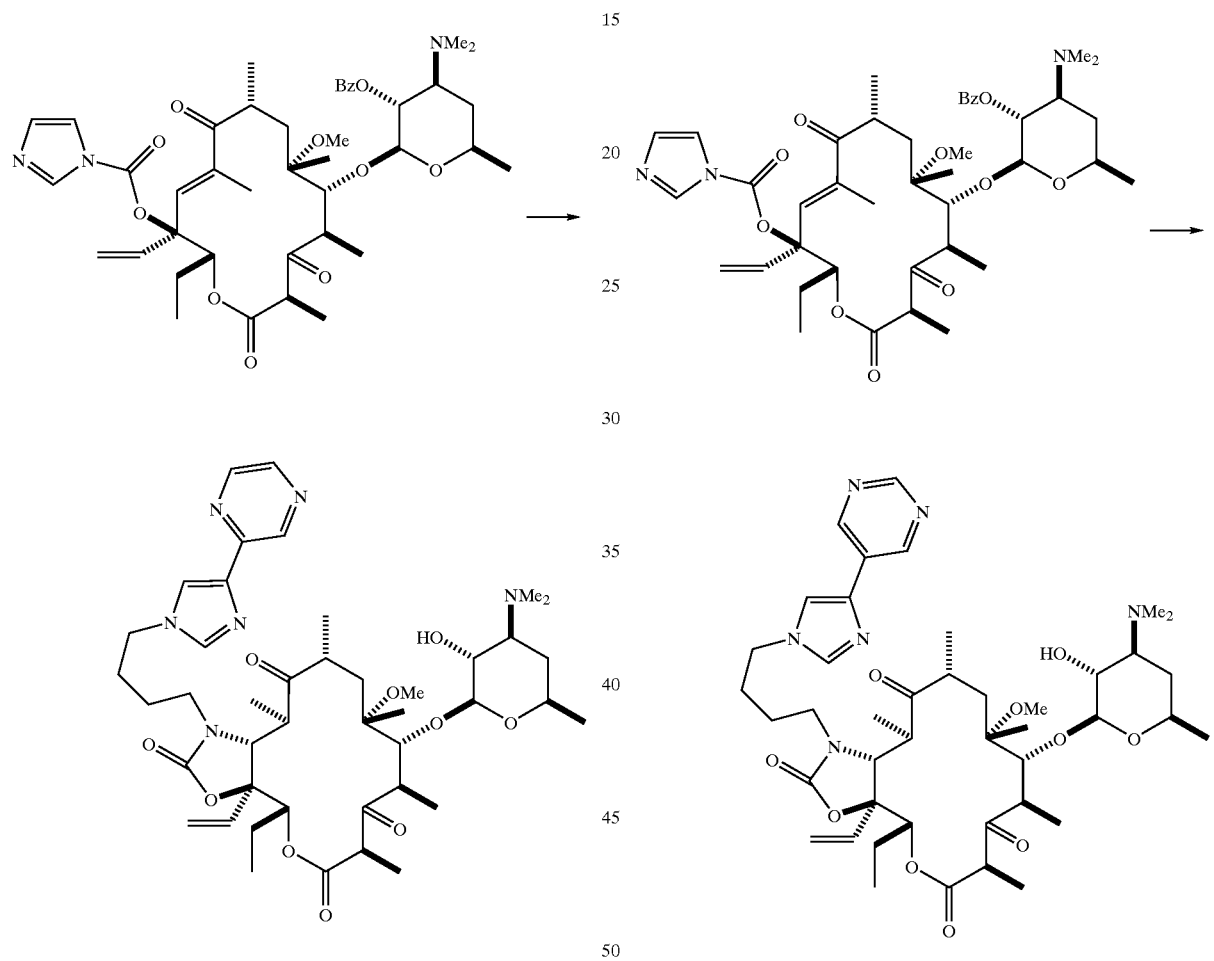

C12 vinyl, C9, C10, C11 enone, 3 oxo, C12 OCOIm macrolide of Example 47 (1 eq) was added to 4-(4-Pyrazin-2-yl-imidazol-1-yl)-butylamine (4 eq) The reaction conditions are described in Example 44. (3aS,4R,7R,9R,1R,11S, 13R,15R,15aR)-4-ethyl-11-methoxy-7,9,11,13,15-pentamethyl-2,6,8,14-tetraoxo-1-[4-(4-pyrazin-2-yl-1H-imidazol-1-yl)butyl]-3a-vinyltetradecahydro-2H-oxacyclotetradecino[4,3-d][1,3]oxazol-10-yl 3,4,6-trideoxy-3-(dimethylamino)-D-xylo-hexopyranoside was obtained as an off white solid in a 12% yield. MH$^+$(825.01).

C12 vinyl, C9, C10, C11 enone, 3 oxo, C12 OCOIm macrolide of Example 47 (1 eq) was added to 4-(4-Pyrimidin-5-yl-imidazol-1-yl)-butylamine (4 eq). The reaction conditions are described in Example 44. (3aS,4R,7R, 9R,10R,11S,13R,15R,15aR)-4-ethyl-11-methoxy-7,9,11,13, 15-pentamethyl-2,6,8,14-tetraoxo-1-[4-(4-pyrimidin-5-yl-1H-imidazol-1-yl)butyl]-3a-vinyltetradecahydro-2H-oxacyclotetradecino[4,3-d]-[1,3]oxazol-10-yl 3,4,6-trideoxy-3-(dimethylamino)-D-xylo-hexopyranoside was obtained as an off white solid in a 16% yield. MH$^+$(825.01).

EXAMPLE 57

Synthesis of (3aS,4R,7R,9R,10R,11S,13R,15R, 15aR)-4-ethyl-1-[4-(1H-imidazo[4,5-b]pyridin-1-yl)-4-methylpentyl]-11-methoxy-7,9,11,13,15-pentamethyl-2,6,8,14-tetraoxo-3a-vinyltetradecahydro-2H-oxacyclotetradecino[4,3-d][1,3]oxazol-10-yl 3,4,6-trideoxy-3-(dimethylamino)-D-xylo-hexopyranoside

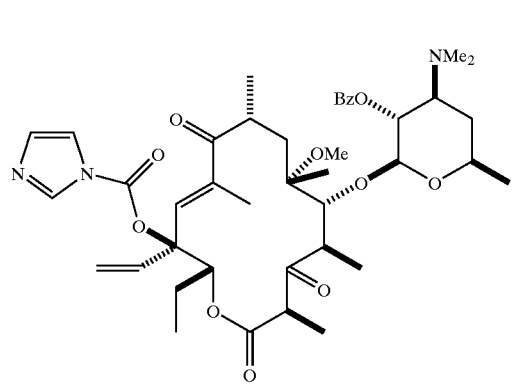

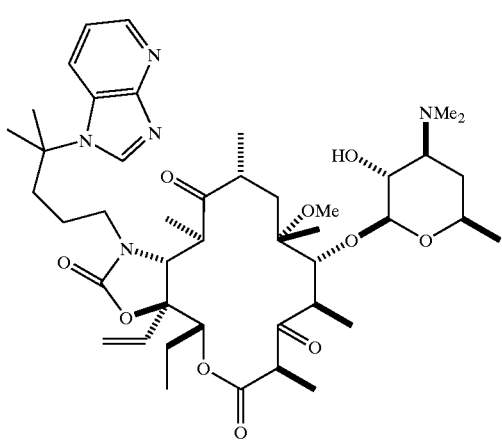

C12 vinyl, C9, C10, C11 enone, 3 oxo, C12 OCOIm macrolide of Example 47 (1 eq) was added to 4-Imidazo[4,5-b]pyridin-1-yl-4-methyl-pentylamine (4 eq). The reaction conditions are described in Example 44. (3aS,4R,7R,9R, 10R,11S,13R,15R,15aR)-4-ethyl-1-[4-(1H-imidazo[4,5-b]pyridin-1-yl)-4-methylpentyl]-11-methoxy-7,9,11,13,15-pentamethyl-2,6,8,14-tetraoxo-3a-vinyltetra-decahydro-2H-oxacyclotetradecino[4,3-d][1,3]oxazol-10-yl 3,4,6-trideoxy-3-(dimethyl-amino)-D-xylo-hexopyranoside was obtained as an off white solid in a 16% yield. MH$^+$(826.04).

EXAMPLE 58

Synthesis of (3aS,4R,7R,9R,10R,11S,13R,15R, 15aR)-4-ethyl-11-methoxy-7,9,11,13,15-pentamethyl-2,6,8,14-tetraoxo-1-(4-quinolin-4-ylbutyl)-3a-vinyltetradecahydro-2H-oxacyclotetradecino[4,3-d][1,3]oxazol-10-yl 3,4,6-trideoxy-3-(dimethylamino)-D-xylo-hexopyranoside

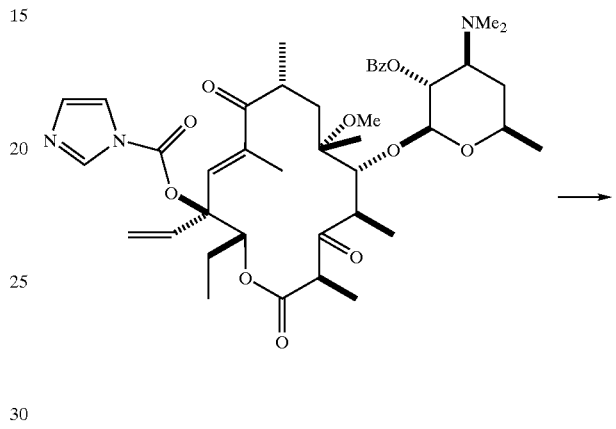

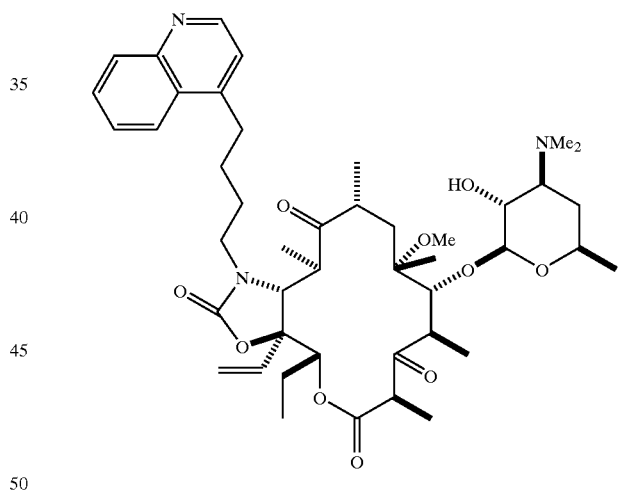

C12 vinyl, C9, C10, C11 enone, 3 oxo, C12 OCOIm macrolide of Example 47 (1 eq) was added to 4-Quinolin-4-yl-butylamine (20 eq). The reaction conditions are described in Example 44. (3aS,4R,7R,9R,10R,11S,13R, 15R,15aR)-4-ethyl-11-methoxy-7,9,11,13,15-pentamethyl-2,6,8,14-tetraoxo-1-(4-quinolin-4-ylbutyl)-3a-vinyltetradeca-hydro-2H-oxacyclotetradecino[4,3-d][1,3]oxazol-10-yl 3,4,6-trideoxy-3-(dimethyl-amino)-D-xylo-hexopyranoside was obtained as an off white solid in a 19% yield. MH$^+$(808.50).

EXAMPLE 59

Synthesis of C12 Substituted Macrolides (Scheme 8)

EXAMPLE 59(a)

C3 hydroxy, C21 OTBMDS, C9, C10, C11 enone-12-ol macrolide

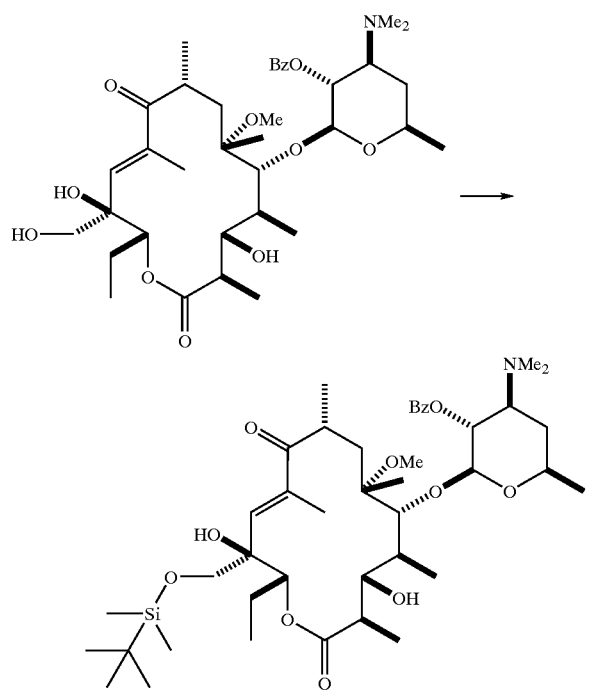

Referring to Scheme 8, to C21, C3 hydroxy macrolide (1 eq) in 10 mL of dimethylformamide was added imidazole (4 eq) and tert-butyldimethylsilyl chloride (1.3 eq). After stirring for 14 hours, more tert-butyldimethylsilyl chloride (1.3 eq) was added. After stirring for an additional 2 hours the reaction was added to ethyl acetate, was washed with NaHCO$_{3(sat)}$, with H2O, with NaCl$_{(sat)}$, dried over MgSO$_4$, filtered and concentrated. Purification by flash chromatography (30% acetone/hexanes with 0.1% triethylamine) afforded the C3 hydroxy, C21 OTBDMS, C9, C10, C11 enone-12-ol macrolide (77% yield) as a white solid. MH$^+$ (806.5).

EXAMPLE 59(b)

C21 OTBDMS, C9, C10, C11 enone, C3 oxo, C12 OH macrolide

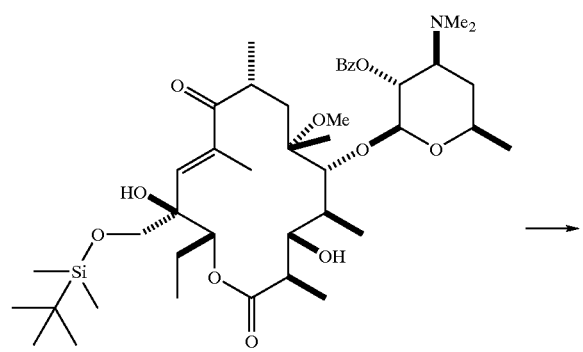

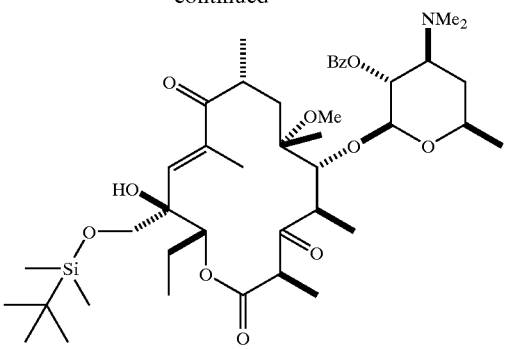

To C21 OTBDMS, C9, C10, C11 enone, C3, C12 diol macrolide (1 eq) in dichloromethane was added Dess-Martin Periodinane (2 eq). After stirring for 2 hours, the solution was diluted with ethyl acetate and washed with 1:1 10% Na$_2$S$_2$O$_3$/NaHCO$_{3(sat)}$, with NaCl$_{(sat.)}$, dried over MgSO$_4$, filtered and concentrated. Purification by flash chromatography (15–20% acetone/hexanes with 0.1% triethylamine) afforded the C21 OTBDMS, C9, C10, C11 enone, C3 oxo, C12 OH macrolide (59% yield) as a white solid. MH$^+$ (804.5).

EXAMPLE 59(c)

C21 OTBDMS, C10, C11 enone, C3 oxo, C12 OCOIm macrolide

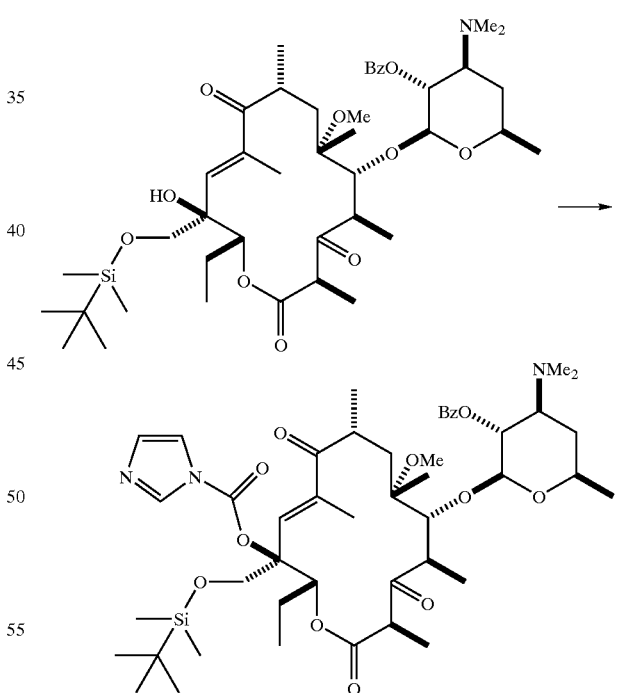

To a solution of C21 OTBDMS, C9, C10, C11 enone, C3 oxo, C12 OH macrolide (1 eq) and carbonyldiimidazole (3 eq) in tetrahydrofuran at 0° C. was added sodium hydride (2 eq). After stirring for 10 hours at 0° C., ethyl acetate was added. While still at 0° C., NaHCO$_{3(sat.)}$ was added cautiously. The mixture was then diluted with ethyl acetate and was washed with NaHCO$_{3(sat.)}$, with NaCl$_{(sat.)}$, dried over MgSO$_4$, filtered, concentrated and pumped on yielding crude C21 OTBDMS, C9, C10, C11 enone, C3 oxo, C12 OCOIm macrolide. The crude material was used in the next step without further purification. MH⁺(898.5).

EXAMPLE 60

Synthesis of (3aR,4R,7R,9R,10R,11R,13R,15R, 15aR)-3a-({[tert-butyl(dimethyl)silyl]oxy}methyl)-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

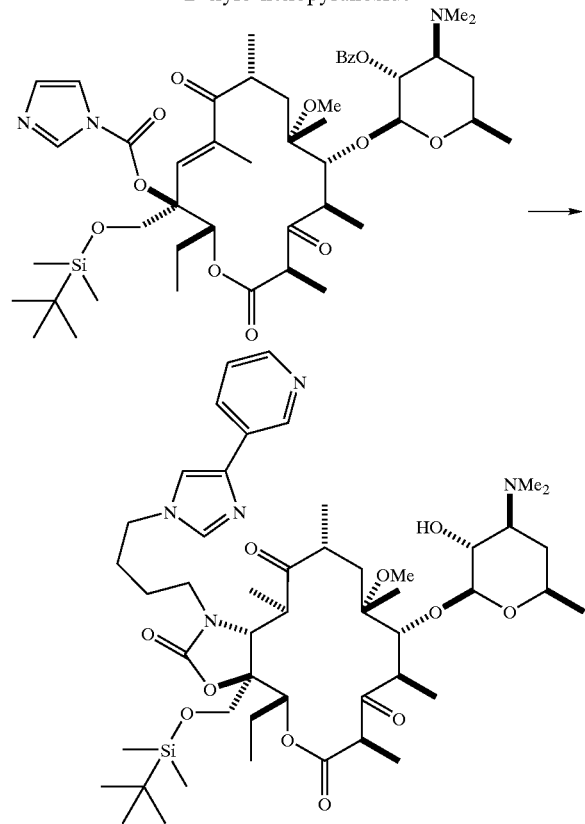

C21 OTBDMS, C9, C10, C11 enone, 3 oxo, C12 OCOIm macrolide (1 eq) was added to 4-(4-(3-pyridyl)imidazolyl)butylamine (6 eq); acetonitrile and water were added. The solution was heated at 60° C. for 3 days. Upon cooling the reaction was diluted with ethyl acetate and washed with NaHCO₃₍ₛₐₜ₎, NaCl₍ₛₐₜ₎, dried over MgSO₄, filtered and concentrated. To the crude material was added dichloromethane, benzoic anhydride, triethylamine, and dimethylaminopyridine, 1:20:3:1, respectively. After standing for 12 hours the solution was concentrated and purified by RP HPLC. The combined product fractions coming off the HPLC were diluted with ethyl acetate and NaHCO₃ was added. After mixing, the aqueous layer was separated and the organic layer was washed with NaCl₍ₛₐₜ₎, dried over MgSO₄, filtered, and concentrated, yielding benzoylated (3aR,4R,7R,9R,10R,11R,13R,15R,15aR)-3a-({[tert-butyl(dimethyl)silyl]oxy}methyl)-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (41% yield) as a white solid. To benzoylated (3aR,4R,7R,9R,10R,11R,13R,15R,15aR)-3a-({[tert-butyl(dimethyl)silyl]oxy}methyl)-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (1 eq) was added methanol and the solution was heated at 65° C. for 16 hours. Upon concentrating, the material was purified by RP HPLC. The combined product fractions coming off the HPLC were diluted with ethyl acetate and NaHCO₃ was added. After mixing, the aqueous layer was separated and the organic layer was washed with NaCl₍ₛₐₜ₎, dried over MgSO₄, filtered, concentrated, dissolved in acetonitrile/water and lyophilized yielding (3aR,4R,7R,9R,10R,11R,13R,15R,15aR)-3a-({[tert-butyl(dimethyl)silyl]oxy}methyl)-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (72% yield) as a white solid. MH⁺(942.60).

EXAMPLE 61

Synthesis of (3aR,4R,7R,9R,10R,11R,13R,15R, 15aR)-4-ethyl-3a-(hydroxymethyl)-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

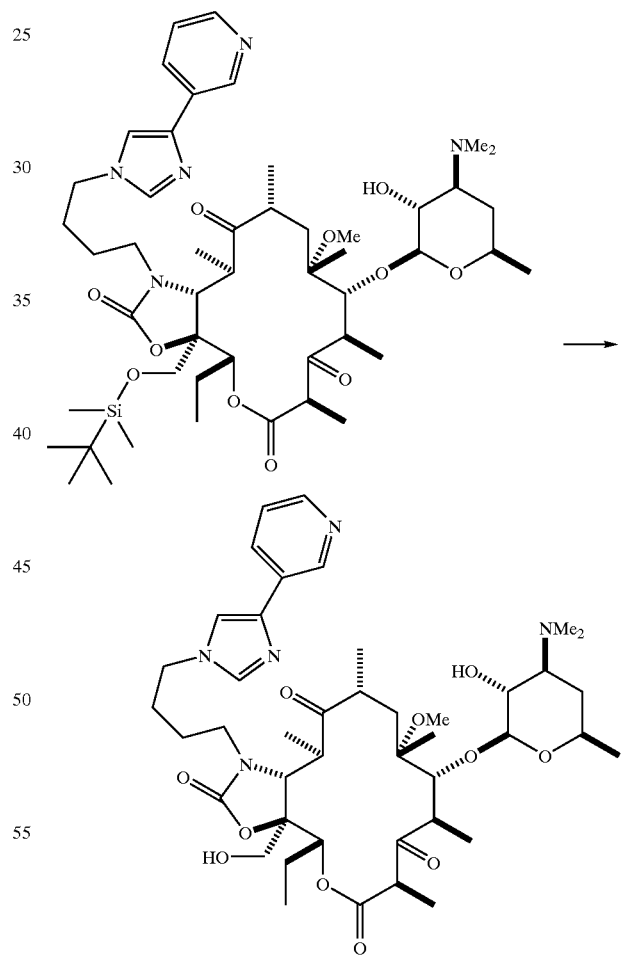

To (3aR,4R,7R,9R,10R,11R,13 R,15R,15aR)-3a-({[tert-butyl(dimethyl)silyl]-oxy}methyl)-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (1 eq)

in tetrahydrofuran was added acetic acid (2 eq) and tetrabutylammonium fluoride/1.0M in tetrahydrofuran (2 eq). After standing for 48 hours, ethyl acetate was added and the solution was washed with NaHCO$_{3(sat.)}$, NaCl$_{(sat.)}$, dried over MgSO$_4$, filtered, and concentrated. Purification by RP HPLC afforded (3aR,4R,7R,9R,10R,11R,13R,15R,15aR)-4-ethyl-3a-(hydroxymethyl)-11-methoxy-7,9,11,13,15-pentamethyl-2,6,8,14-tetraoxo-1-[4-(4-pyridin-3-yl-1H-imidazol-1-yl)-butyl]tetradecahydro-2H-oxacyclotetradecino[4,3-d][1,3]oxazol-10-yl 3,4,6-trideoxy-3-(dimethylamino)-D-xylo-hexopyranoside (48% yield) as a white solid. MH$^+$(828.50).

EXAMPLE 62

Synthesis of [(3aR,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-10-{[3,4,6-trideoxy-3-(dimethylamino)-D-xylo-hexopyranosyl]oxy}dodecahydro-2H-oxacyclotetradecino[4,3-d][1,3]oxazol-3a(4H)-yl]methyl methanesulfonate

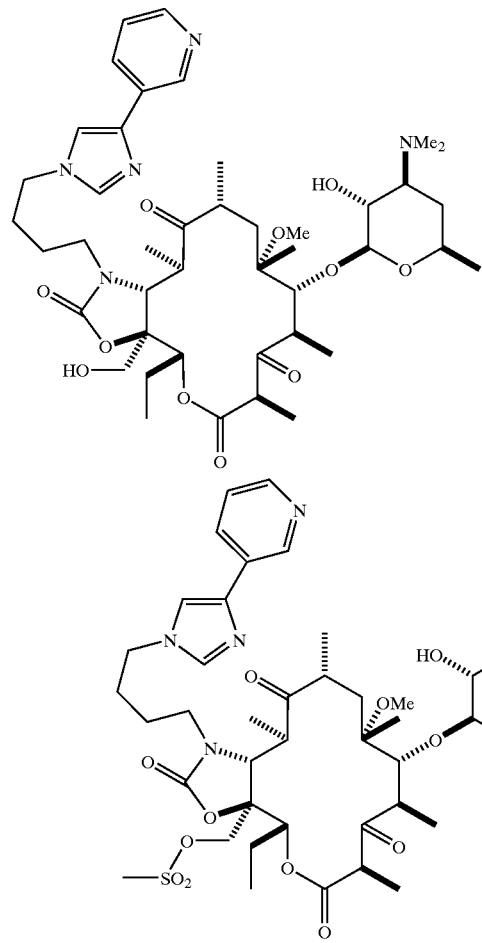

To benzoylated (3aR,4R,7R,9R,10R,11R,13R,15R,15aR)-4-ethyl-3a-(hydroxy-methyl)-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (1 eq) in pyridine was methanesulfonyl chloride (5 eq). After standing for 5 hours, the solution was concentrated, taken up in DMSO and purified by RP HPLC affording benzoylated [(3aR,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-10-{[3,4,6-trideoxy-3-(dimethylamino)-D-xylo-hexopyranosyl]oxy}dodecahydro-2H-oxacyclotetradecino[4,3-d][1,3]oxazol-3a(4H)-yl]methyl methanesulfonate (81% yield) as a white solid. To benzoylated [(3aR,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-10-{[3,4,6-trideoxy-3-(dimethylamino)-D-xylo-hexopyranosyl]-oxy}dodecahydro-2H-oxacyclotetradecino[4,3-d][1,3]oxazol-3a(4H)-yl]methyl methanesulfonate (0.03 mmoles) was added methanol and the solution was heated at 65° C. for 17 hours. Upon cooling the solution was concentrated and purified by RP HPLC yielding [(3aR,4R,7R,9R,10R,11R,13R,15R,15aR)-4-ethyl-11-methoxy-7,9,11,13,15-pentamethyl-2,6,8,14-tetraoxo-1-[4-(4-pyridin-3-yl-1H-imidazol-1-yl)butyl]-10-{[3,4,6-trideoxy-3-(dimethylamino)-D-xylo-hexopyranosyl]-oxy}dodecahydro-2H-oxacyclotetradecino[4,3-d][1,3]oxazol-3a(4H)-yl]methyl methanesulfonate (55% yield) as a white solid. MH$^+$(906.50).

EXAMPLE 63

Synthesis of (3aS,4R,7R,9R,10R,11R,13R,15R,15aR)-4-ethyl-3a-formyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

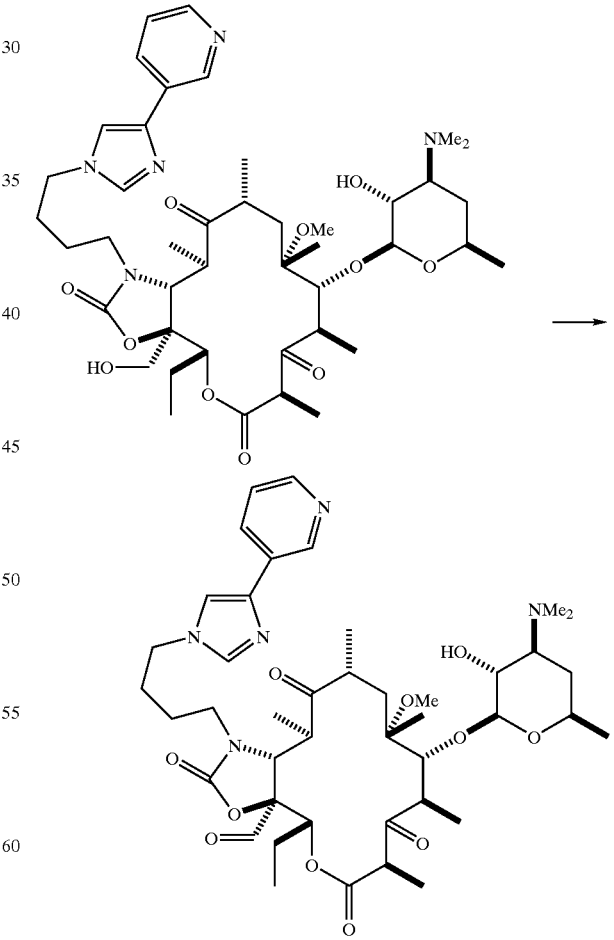

To (3aR,4R,7R,9R,10R,11R,13R,15R,15aR)-4-ethyl-3a-(hydroxymethyl)-11-methoxy-7,9,11,13,15-pentamethyl-2, 6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (1 eq) in dichloromethane was added Dess-Martin Periodinane (1.1 eq). After stirring for 3 hours, more Dess-Martin Periodinane (1 eq) was added. After stirring for an additional 15 hours, the solution was diluted with ethyl acetate and was washed with 1:1 10% Na$_2$S$_2$O$_3$/NaHCO$_3$ $_{(sat)}$, with NaCl$_{(sat.)}$, dried over MgSO$_4$, filtered and concentrated. Purification by RP HPLC yielded (3aS,4R,7R,9R,10R,11R,13R,15R,15aR)-4-ethyl-3a-formyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (19% yield) as a white solid. MH$^+$(826.5).

EXAMPLE 64

Synthesis of (3aS,4R,7R,9R,10R,11R,13R,15R,15aR)-3a-acetyl-4-ethyl-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

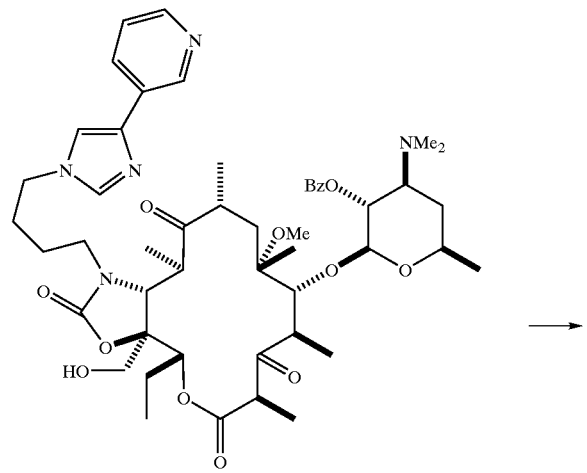

To benzoylated (3aR,4R,7R,9R,10R,11R,13R,15R,15aR)-4-ethyl-3a-(hydroxymethyl)-11-methoxy-7,9,11,13,15-pentamethyl-2,6,8,14-tetraoxo-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (1 eq) in dichloromethane was added Dess-Martin Periodinane (2 eq). After stirring for 2.5 hours the solution was diluted with ethyl acetate and was washed with 1:1 10% Na$_2$S$_2$O$_3$/NaHCO$_3$$_{(sat)}$, with NaCl$_{(sat.)}$, dried over MgSO$_4$, filtered and concentrated yielding C21 aldehyde (94%). To the aldehyde (1 eq) in tetrahydrofuran (2 mL) at −78° C. was added methyl lithium (0.5 eq). After stirring for 30 minutes at −78° C., acetone was added. The cooling bath was removed, NaHCO$_3$$_{(sat.)}$ was added and upon warming to room temperature the solution was diluted with ethyl acetate, washed with NaHCO$_3$$_{(sat)}$, with NaCl$_{(sat.)}$, dried over MgSO$_4$, filtered and concentrated. Purification by RP HPLC yielded C12 hydroxyethyl macrolide (50%). To this material in dichloromethane was added Dess-Martin Periodinane (1 eq). After stirring for 2 hours, the solution was diluted with ethyl acetate and was washed with 1:1 10% Na$_2$S$_2$O$_3$/NaHCO$_3$ $_{(sat)}$, with NaCl$_{(sat.)}$, dried over MgSO$_4$, filtered and concentrated yielding C12 acetyl macrolide (99%). Methanol was added and the solution was heated at 65° C. for 19 hours. Upon cooling the solution was concentrated and purified by RP HPLC yielding (3aS,4R,7R,9R,10R,11R,13R,15R,15aR)-3a-acetyl-4-ethyl-11-methoxy-7,9,11,13,15-pentamethyl-2,6,8,14-tetraoxo-1-[4-(4-pyridin-3-yl-1H-imidazol-1-yl)butyl]-tetradecahydro-2H-oxacyclotetradecino[4,3-d][1,3]oxazol-10-yl 3,4,6-trideoxy-3-(dimethylamino)-D-xylo-hexopyranoside (16.4 mg, 51% yield) as a white solid. MH$^+$(840.5).

EXAMPLE 65

Synthesis of (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-2-ylbutyl)tetradecahydro-2H-oxacyclotetradecino[4,3-d][1,3]oxazol-10-yl 3,4,6-trideoxy-3-(dimethylamino)-D-xylo-hexopyranoside and (3aS,4R,7R,9R,10R,11S,13R,15R,15aR)-4-ethyl-11-methoxy-7,9,11,13,15-pentamethyl-2,6,8,14-tetraoxo-3a-[(1E)-prop-1-enyl]-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside

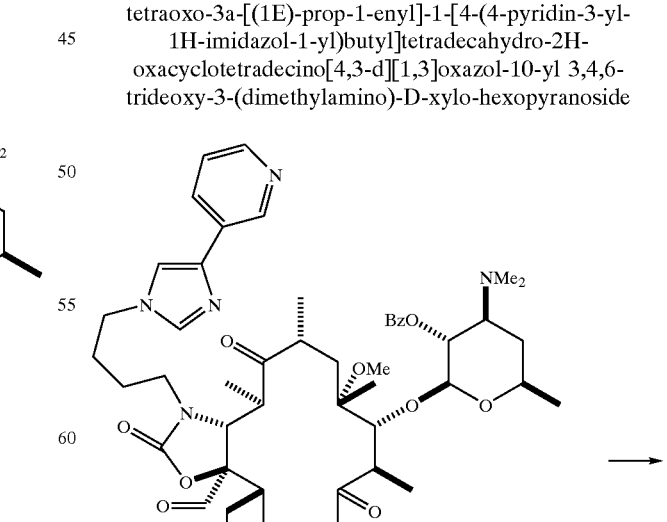

153
-continued

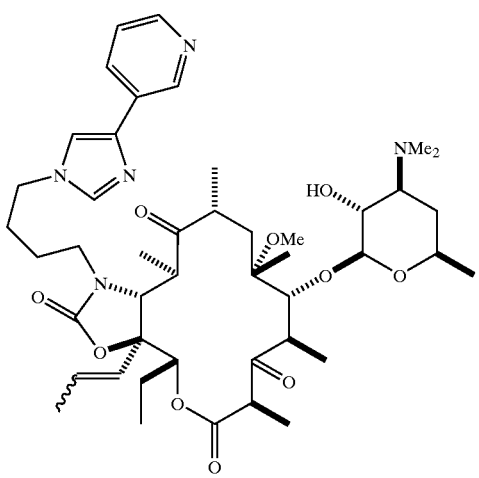

To ethyl triphenylphosphonium bromide (1 eq) in tetrahydrofuran at −78° C. was added lithium bis(trimethylsilyl) amide/1.0M in tetrahydrofuran (1 eq). The cooling bath was removed and the solution was stirred for 1 hour. After cooling the solution back to −78° C., C21 aldehyde macrolide (3 eq) in tetrahydrofuran was added. The cooling bath was removed and the solution was stirred for 64 hours at which time ethyl acetate was added. The solution was washed with NaHCO$_{3(sat)}$, with NaCl$_{(sat)}$, dried over MgSO$_4$, filtered and concentrated. Purification through flash chromatography (0–3–5–10% methanol/dichloromethane with 0.1% triethylamine) and subsequently by preparatory RP HPLC, yielded the Z-C12-prenyl macrolide (smaller retention time, 23% yield) as a white solid and E-C12 prenyl macrolide (larger retention time, 10% yield) as a white solid. To the benzoylated isomers (1 eq) was added methanol and the solution was heated at 65° C. for 14 hours. Upon concentrating, the material was purified by RP HPLC. The combined product fractions coming off the HPLC were diluted with ethyl acetate and NaHCO$_3$ was added. After mixing, the aqueous layer was separated and the organic layer was washed with NaCl$_{(sat)}$, dried over MgSO$_4$, filtered, concentrated, dissolved in acetonitrile/water and lyophilized yielding the products (3aS,4R,7S,9R,10R,11S,13R,15R, 15aR)-3a,4-diethyl-7-fluoro-11-methoxy-7,9,11,13,15-pentamethyl-2,6,8,14-tetraoxo-1-(4-quinolin-2-ylbutyl) tetradecahydro-2H-oxacyclotetradecino [4,3-d][1,3]oxazol-10-yl 3,4,6-trideoxy-3-(dimethylamino)-D-xylo-hexopyranoside and (3aS,4R,7R,9R,10R,11S,13R,15R, 15aR)-4-ethyl-11-methoxy-7,9,11,13,15-pentamethyl-2,6,8,14-tetraoxo-3a-[(1E)-prop-1-enyl]-1-[4-(4-pyridin-3-yl-1H-imidazol-1-yl)butyl]tetradecahydro-2H-oxacyclotetradecino[4,3-d][1,3]oxazol-10-yl 3,4,6-trideoxy-3-(dimethylamino)-D-xylo-hexopyranoside (71% yield) as white solids. MH$^+$(838.04).

154
EXAMPLE 66

Synthesis of (3aS,4R,7S,9R,10R,11S,13R,15R, 15aR)-4-ethyl-7-fluoro-11-methoxy-7,9,11,13,15-pentamethyl-2,6,8,14-tetraoxo-3a-[(1Z)-prop-1-enyl]-1-[4-(4-pyridin-3-yl-1H-imidazol-1-yl)butyl] tetradecahydro-2H-oxacyclotetradecino[4,3-d][1,3] oxazol-10-yl 3,4,6-trideoxy-3-(dimethylamino)-D-xylo-hexopyranoside

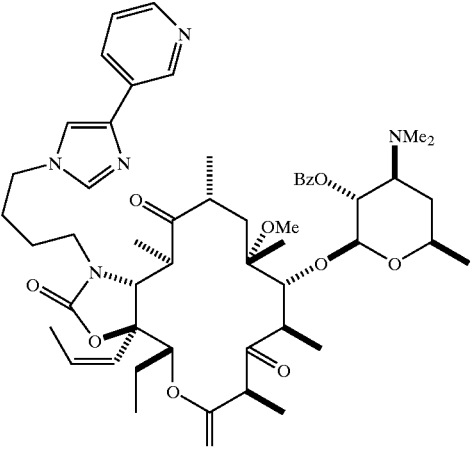

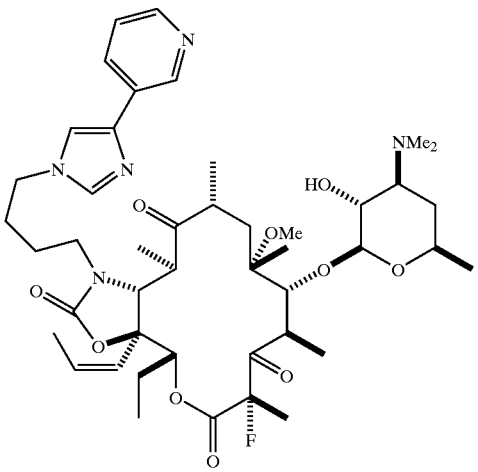

To benzoylated (3aS,4R,7S,9R,10R,11S,13R,15R,15aR)-3a,4-diethyl-7-fluoro-11-methoxy-7,9,11,13,15-pentamethyl-2,6,8,14-tetraoxo-1-(4-quinolin-2-ylbutyl)-tetradecahydro-2H-oxacyclotetradecino[4,3-d][1,3]oxazol-10-yl 3,4,6-trideoxy-3-(dimethylamino)-D-xylo-hexopyranoside (1 eq) in DMF at 0° C. was added 60% NaH (2 eq). After stirring for 1 hour at 0° C., N-fluorobenzenesulfonimide (1.1 eq) was added. After stirring for an additional hour at 0° C., the solution was diluted with ethyl acetate and NaHCO$_{3(sat.)}$ was added cautiously to quench. The reaction was then added to ethyl acetate and was washed with NaHCO$_{3(sat)}$, NaCl(sat.), dried over MgSO$_4$, filtered, and concentrated. Methanol was added and the solution was heated at 60° C. for 15 hours. Upon concentrating, the material was purified by silica gel chromatographly (0–5–10% methanol/dichloromethane with 0.1% triethylamine) and than by RP HPLC. The combined product fractions coming off the HPLC were diluted with ethyl acetate and NaHCO$_3$ was added. The aqueous layer was separated and the organic layer was washed with NaCl$_{(sat.)}$, dried over MgSO$_4$, filtered, concentrated and lyophilized from MeCN:H2O yielding (3aS,4R,7S,9R,10R,11S,13R,15R,15aR)-4-ethyl-7-fluoro-11-methoxy-7,9,11,13,15-pentamethyl-2,6,8,14-tetraoxo-3a-[(1Z)-prop-1-enyl]-1-[4-(4-pyridin-3-yl-1H-imidazol-1-yl)butyl] tetradecahydro-2H-oxacyclotetradecino[4,3-d][1,3]oxazol-10-yl 3,4,6-trideoxy-3-(dimethylamino)-D-xylo-hexopyranoside (40% yield) as a white solid. MH$^+$(856.50).

EXAMPLE 67

C12 Modification via Ketone Intermediate to Generate Ketolides (Scheme 2a, R=H)

EXAMPLE 67(a)

Synthesis of Compound 12

Referring to Scheme 2a, to a −78° C. 0.02M CH$_2$Cl$_2$:MeOH (19:1 v/v) solution containing the alkene 11 (Example 3) and 1.2 eq TsOH H$_2$O (both azeotropically dried with benzene before use) was bubbled in O$_3$ until a medium blue color appeared. The reaction was stirred for an additional 10 min. and then sparged with N$_2$ until the solution became colorless. After adding dimethyl sulfide (3.0 eq), the solution was stirred for 10 min., treated with Et$_3$N (5 eq), warmed to rt, and concentrated. Purification by silica gel chromatography (7:1 hexane:acetone with 1% Et$_3$N) gave the ketone product 12. ES/MS m/z 982.5 (MH$^+$), C$_{54}$H$_{79}$NO$_{15}$=981.5 g/mol.

EXAMPLE 67(b)

Synthesis of Compound 13

NaBH$_4$ (4 eq) was added to a 0.2M EtOH solution of ketone 12. After stirring at rt for 20 h, the reaction was poured into 4:1 CH$_2$Cl$_2$:NaHCO$_3$ (aq.) and stirred vigorously for 1 h. The aq. layer was washed with brine, dried over MgSO$_4$, filtered, concentrated. The residue was the resuspended in MeOH and stirred overnight. After removing the MeOH in vacuo, the residue was dissolved in EtOAc. The resulting solution was washed with NaHCO$_3$ (aq.), water, and brine, dried over MgSO$_4$, filtered, and concentrated to give the crude product 13. ES/MS m/z 985 (MH$^+$), C$_{54}$H$_{81}$NO$_{15}$=984 g/mol.

EXAMPLE 67(c)

Synthesis of Compound 14

To a 0° C. 0.2M CH$_2$Cl$_2$ solution containing alcohol 13 and DMAP (0.5 eq) was added Et$_3$N (3 eq) followed by addition of MsCl (1.5 eq) over a 0.5 h period. After 15 min., the reaction was quenched with sat. NaHCO$_3$ (aq.) and poured into EtOAc. The organic layer was washed with water and brine, dried, filtered, and concentrated to give the crude product 14. ES/MS m/z 1063 (MH$^+$), C$_{55}$H$_{83}$NO$_{17}$S= 1062 g/mol.

EXAMPLE 67(d)

Synthesis of Compound 15

To a 0.08M MeCN solution of acetonide 14 was added 10% HCl (aq) to give a 2:1 (v/v) MeCN:H$_2$O mixture. After stirring for 14 h, 1N NaOH was added until a pH~9 solution persisted. The organic solvent was then removed in vacuo and the remaining solution was extracted with CH$_2$Cl$_2$ (2×). The organic extracts were washed with brine, dried, filtered, concentrated, and purified by silica gel chromatography (3:1 to 2:1 hexanes:acetone with 1% Et$_3$N gradient) to give the triol 15. ES/MS m/z 760 (MH$^+$), C$_{37}$H$_{61}$NO$_{13}$S=759 g/mol.

EXAMPLE 67(e)

Synthesis of Compound 16

To a 0.1M CH$_2$Cl$_2$ solution of triol 6 at 0° C. was added the Dess Martin periodinane (2.1 eq). After 26 h, the reaction was quenched with sat. NaHCO$_3$ (aq.) diluted with CH$_2$Cl$_2$, filtered through celite, washed with brine, dried over MgSO$_4$, filtered, and concentrated. Purification by silica gel chromatography (4:1 hexanes:acetone with 1% Et$_3$N) gave the diketone 16. ES/MS m/z 756 (MH$^+$), C$_{37}$H$_{57}$NO$_{13}$S=755 g/mol.

EXAMPLE 67(f)

Synthesis of Compound 17

DBU (2 eq) was quickly added to a 0.1M acetone solution of alcohol 16 and stirred overnight at rt. The mixture was then concentrated and the residue was purified by silica gel chromatography (4:1 hexanes:acetone with 1% Et$_3$N) to give enone 17. ES/MS m/z 660 (MH$^+$), C$_{36}$H$_{53}$NO$_{10}$=659 g/mol.

EXAMPLE 67(g)

Synthesis of Compound 18

To a −15° C. 0.2M THF solution of alcohol 17 and carbonyl diimidazole (2 eq) was added NaH (1.2 eq). After stirring for 15 min., the solution was warmed to 0° C., diluted with EtOAc, and quenched with sat. NaHCO$_3$ (aq.). The aq. layer was extracted with EtOAc (2×) and the extracts were washed with water and brine, dried over MgSO$_4$, filtered, and concentrated to give the crude carbamate 18.

EXAMPLE 67(h)

Synthesis of Compound 19

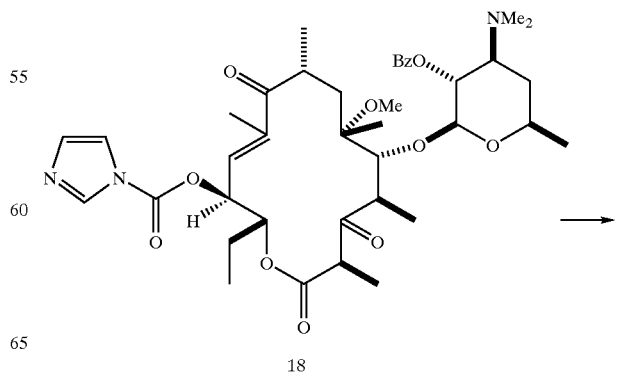

18

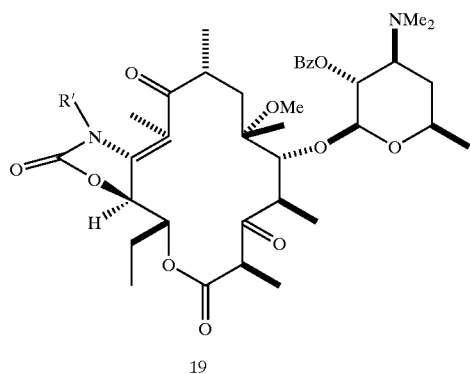

19

A 0.2M MeCN:$H_2O$ (9:1 v/v) solution containing carbamate 18 and ammonia (4 eq) was heated at 70° C. for 23 h. The reaction was then poured into EtOAc and washed with NaHCO$_3$, water, and brine, dried over MgSO$_4$, filtered, and concentrated. Purification by silica gel chromatography (1:1 to 1:2 hexanes:acetone with 1% Et$_3$N gradient) gave the cyclic carbamate 19. 19a: R'=H, ES/MS m/z 703 (MH$^+$), $C_{37}H_{54}N_2O_{11}$=702 g/mol.

Compounds with variations in the R' were obtained by following the procedure for the synthesis of 19a and substituting the appropriate amine in place of ammonia. The requisite amine starting materials are set forth below to give the following analogs:

| ID | Amine | R' | ES/MS (MH+) |
|---|---|---|---|
| 19b | 4-(4-Phenyl-imidazol-1-yl)-butylamine | 4-(4-Phenyl-imidazol-1-yl)-butyl | 901 |
| 19c | 4-Quinolin-4-yl-butylamine | 4-Quinolin-4-yl-butyl | 886 |
| 19d | 4-Imidazo[4,5-b]pyridin-3-yl-butylamine | 4-Imidazo[4,5-b]pyridin-3-yl-butyl | 876 |
| 19e | 4-Imidazo[4,5-b]pyridin-1-yl-butylamine | 4-Imidazo[4,5-b]pyridin-1-yl-butyl | 876 |
| 19f | 4-(4-Phenyl-imidazol-1-yl)-propylamine | 4-(4-Phenyl-imidazol-1-yl)-propyl | 887 |
| 19g | 4-Imidazo[4,5-b]pyridin-1-yl-propylamine | 4-Imidazo[4,5-b]pyridin-1-yl-propyl | 862 |
| 19h | 4-Imidazo[4,5-b]pyridin-3-yl-propylamine | 4-Imidazo[4,5-b]pyridin-3-yl-propyl | 862 |
| 19i | 4-Indol-1-yl-butylamine | 4-Indol-1-yl-butyl | 874 |
| 19j | 4-(2-quinolyl)butylamine | 4-(2-quinolyl)butyl | 887 |
| 19k | 4-(4-(3-pyridyl)imidazolyl)butylamine | 4-(4-(3-pyridyl)imidazolyl)butyl | 903 |
| 19l | 4-(4-(4-pyridyl)imidazolyl)butylamine | 4-(4-(4-pyridyl)imidazolyl)butyl | 903 |
| 19m | 4-pyrrolo[3,2-b]pyridinylbutylamine | 4-pyrrolo[3,2-b]pyridinylbutyl | 876 |
| 19n | 4-(3-quinolyl)butylamine | 4-(3-quinolyl)butyl | 887 |
| 19o | 4-(2-methyl-4-quinolyl)butylamine | 4-(2-methyl-4-quinolyl)butyl | 901 |
| 19p | 4-[2-(trifluoromethyl)-4-quinolyl]butylamine | 4-[2-(trifluoromethyl)-4-quinolyl]butyl | 955 |
| 19q | 4-[8-(trifluoromethyl)-4-quinolyl]butylamine | 4-[8-(trifluoromethyl)-4-quinolyl]butyl | 955 |
| 19r | 3-(4-(3-pyridyl)phenoxy)propylamine | 3-(4-(3-pyridyl)phenoxy)propyl | 915 |
| 19s | 3-(3-(3-pyridyl)phenoxy)propylamine | 3-(3-(3-pyridyl)phenoxy)propyl | 915 |
| 19t | 4-(5-phenyl-1,3-thiazol-2-yl)butylamine | 4-(5-phenyl-1,3-thiazol-2-yl)butyl | 919 |
| 19u | 4-[5-(2,4-difluorophenyl)-1,3-thiazol-2-y1]butylamine | 4-[5-(2,4-difluorophenyl)-1,3-thiazol-2-yl]butyl | 955 |
| 19v | 4-[5-(3-aminophenyl)-1,3-thiazol-2-yl]butylamine | 4-[5-(3-aminophenyl)-1,3-thiazol-2-yl]butyl | 934 |
| 19w | oxy(2-phenoxyethyl)amine | R'NH2 = oxy(2-phenoxyethyl)amine | 840 |

EXAMPLE 67(i)

Synthesis of Compound 20

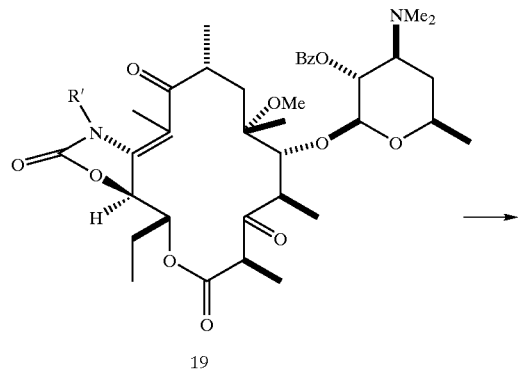

19

20

A 0.06M MeOH solution of each of 19a–19w was heated at 70° C. for 23 h. The solvent was the removed in vacuo the residue was purified by silica gel chromatography (2:3 hexanes:acetone with 2% Et$_3$N) to give the desired product 20a–20w as shown in the following table:

EXAMPLE 68

C12 Modification via Ketone Intermediate to Generate Analogs with a C3 Sugar (Scheme 2b)

EXAMPLE 68(a)

Synthesis of Compound 21

Referring to Scheme 2b, an aqueous solution of acetic acid (84 eq) was added to acetonide 14 (Example 67(c)) in MeCN to give a 0.08M MeCN:H$_2$O solution (2:1 v/v). The reaction was stirred for 16 h at 65–70° C. and then concentrated from toluene/iPrOH (2×) and toluene (1×). Purification by silica gel chromatography (4:1 hexanes:acetone with 1% Et$_3$N gradient) gave diol 21. ES/MS m/z 1022.5 (MH$^+$), C$_{52}$H$_{79}$NO$_{17}$S=1021.5 g/mol.

EXAMPLE 68(b)

Synthesis of Compound 22

To a 0.1M CH$_2$Cl$_2$ solution of diol 21 at 0° C. was added the Dess Martin periodinane (1.05 eq) and the resulting mixture was warmed to rt over 1.5 h. After 3 h an additional periodinane (0.1 eq) was added and stirring was continued for 2 h. The reaction was quenched with sat. NaHCO$_3$ (aq.) followed with EtOAc. After vigorously stirring for 15 min., the solution was filtered through celite with additional EtOAc. The organic layer was washed with NaHCO$_3$ (aq) and brine, dried over MgSO$_4$, filtered, and concentrated. Purification by silica gel chromatography (6:1 hexanes:acetone with 1% Et$_3$N) gave the ketone 22. ES/MS m/z 1020 (MH$^+$), C$_{52}$H$_{77}$NO$_{17}$S=1019 g/mol.

EXAMPLE 68(c)

Synthesis of Compound 23

DBU (3.3 eq) was quickly added to a 0.08M acetone solution of alcohol 22, stirred for 23 h, and then concen-

| Compound ID | R' | ES/MS (MH+) | Formula | MS (g/mol) |
|---|---|---|---|---|
| 20a | H | 599 | C$_{30}$H$_{50}$N$_2$O$_{10}$ | 598 |
| 20b | 4-(4-Phenyl-imidazol-1-yl)-butyl | 797 | C$_{43}$H$_{64}$N$_4$O$_{10}$ | 796 |
| 20c | 4-Quinolin-4-yl-butyl | 782 | C$_{43}$H$_{63}$N$_3$O$_{10}$ | 781 |
| 20d | 4-Imidazo[4,5-b]pyridin-3-yl-butyl | 772 | C$_{40}$H$_{61}$N$_5$O$_{10}$ | 771 |
| 20e | 4-Imidazo[4,5-b]pyridin-1-yl-butyl | 772 | C$_{40}$H$_{61}$N$_5$O$_{10}$ | 771 |
| 20f | 4-(4-Phenyl-imidazol-1-yl)propyl | 783 | C$_{42}$H$_{62}$N$_4$O$_{10}$ | 782 |
| 20g | 4-Imidazo[4,5-b]pyridin-1-yl-propyl | 758 | C$_{39}$H$_{56}$N$_5$O$_{10}$ | 757 |
| 20h | 4-Imidazo[4,5-b]pyridin-3-yl-propyl | 758 | C$_{39}$H$_{56}$N$_5$O$_{10}$ | 757 |
| 20i | 4-Indol-1-yl-butyl | 770 | C$_{42}$H$_{63}$N$_3$O$_{10}$ | 769 |
| 20j | 4-(2-quinolyl)butyl | 783 | C$_{43}$H$_{63}$N$_3$O$_{10}$ | 782 |
| 20k | 4-(4-(3-pyridyl)imidazolyl)butyl | 799 | C$_{42}$H$_{63}$N$_5$O$_{10}$ | 798 |
| 20l | 4-(4-(4-pyridyl)imidazolyl)butyl | 799 | C$_{42}$H$_{63}$N$_5$O$_{10}$ | 798 |
| 20m | 4-pyrrolo[3,2-b]pyridinylbutyl, | 772 | C$_{41}$H$_{62}$N$_4$O$_{10}$ | 771 |
| 20n | 4-(3-quinolyl)butyl, | 783 | C$_{43}$H$_{63}$N$_3$O$_{10}$ | 782 |
| 20o | 4-(2-methyl-4-quinolyl)butyl | 797 | C$_{44}$H$_{65}$N$_3$O$_{10}$ | 796 |
| 20p | 4-[2-(trifluoromethyl)-4-quinolyl]butyl | 851 | C$_{44}$H$_{62}$F$_3$N$_3$O$_{10}$ | 850 |
| 20q | 4-[8-(trifluoromethyl)-4-quinolyl]butyl | 851 | C$_{44}$H$_{62}$F$_3$N$_3$O$_{10}$ | 850 |
| 20r | 3-(4-(3-pyridyl)phenoxy)propyl | 811 | C$_{44}$H$_{63}$N$_3$O$_{11}$ | 810 |
| 20s | 3-(3-(3-pyridyl)phenoxy)propyl | 811 | C$_{44}$H$_{63}$N$_3$O$_{11}$ | 810 |
| 20t | 4-(5-phenyl-1,3-thiazol-2-yl)butyl | 815 | C$_{43}$H$_{63}$N$_3$O$_{10}$S | 814 |
| 20u | 4-[5-(2,4-difluorophenyl)-1,3-thiazol-2-yl]butyl | 851 | C$_{43}$H$_{61}$F$_2$N$_3$O$_{10}$S | 850 |
| 20v | 4-[5-(3-aminophenyl)-1,3-thiazol-2-yl]butyl | 830 | C$_{43}$H$_{64}$N$_4$O$_{10}$S | 829 |
| 20w | R'NH2 = oxy(2-phenoxyethyl)amine | 736 | C$_{38}$H$_{58}$N$_2$O$_{12}$ | 735 | trated. The residue was suspended in EtOAc, washed with NaHCO$_3$ (aq.) and brine, dried over MgSO$_4$, filtered, and concentrated again. Purification by silica gel chromatography (4:1 hexanes:acetone with 1% Et$_3$N) gave the enone 23. ES/MS m/z 924 (MH$^+$), C$_{51}$H$_{73}$NO$_{14}$=923 g/mol.

EXAMPLE 68(d)

Synthesis of Compound 24

To a −15° C. 0.2M THF solution of alcohol 23 and carbonyl diimidazole (2 eq) was added NaH (1.2 eq). After stirring for 0.5 h, the solution was warmed to 0° C. and stirred for an additional 2 h. The reaction was next diluted with EtOAc and quenched with sat. NaHCO$_3$ (aq.). The organic layer was washed with brine, dried over MgSO$_4$, filtered, and concentrated to give the crude carbamate 24.

EXAMPLE 68(e)

Synthesis of Compound 25

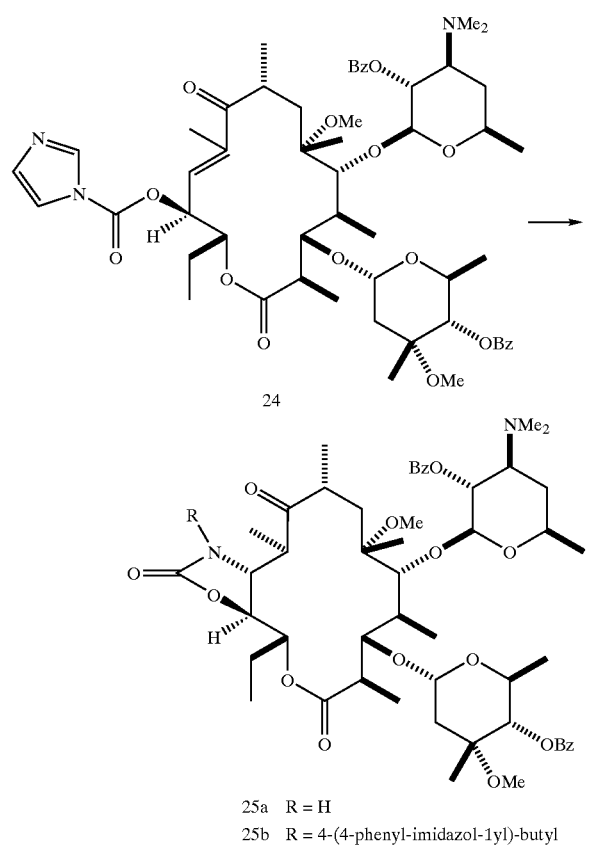

25a  R = H
25b  R = 4-(4-phenyl-imidazol-1yl)-butyl

To a 0.1 M MeCN:THF (5:1) solution of carbamate 24 was added NH$_4$OH (20 eq) and heated at 50° C. for 23 h. The reaction was then poured into CH$_2$Cl$_2$ and washed with brine, dried over MgSO$_4$, filtered, and concentrated. Purification by silica gel chromatography (7:2 hexanes:acetone with 1% Et$_3$N) gave the cyclic carbamate 25a. ES/MS m/z 967.5 (MH$^+$), C$_{52}$H$_{74}$N$_2$O$_{15}$=966.5 g/mol. Cyclic carbamate formation using 4-(4-phenyl-imidazol-1-yl)-butylamine was performed in a similar fashion to give compound 25b. ES/MS m/z 1166 (MH$^+$), C$_{65}$H$_{88}$N$_4$O$_{15}$=1165 g/mol.

EXAMPLE 68(f)

Synthesis of Compound 26

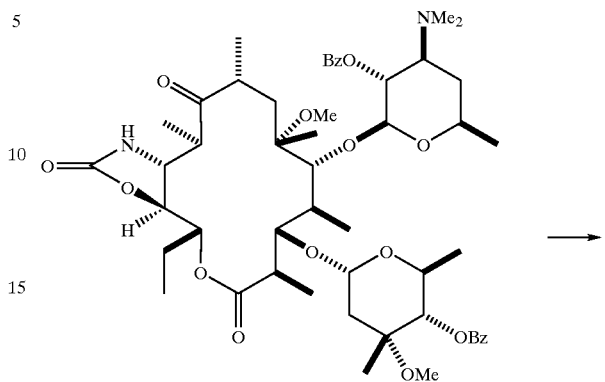

A 0.05M MeOH solution of 25a was heated at 75° C. for 24 h. The solvent was the removed in vacuo and the residue was purified by silica gel chromatography (3:1 hexanes:acetone with 1% Et$_3$N) to give the desired product 26. ES/MS m/z 863 (MH$^+$), C$_{45}$H$_{70}$N$_2$O$_{14}$=862 g/mol.

EXAMPLE 69

Erythromycin C12 Alkene Formation (Scheme 4)

EXAMPLE 69(a)

Synthesis of Compound 28

Referring to Scheme 4, 0.07M CH$_2$Cl$_2$:dimethoxypropane (2:1) solution containing 9-dihydroerythromycin A 27 and PPTS (2 eq) was heated at 50–55° C. for 2.5 h. The reaction was cooled to rt, quenched with Et$_3$N (2.1 eq), and diluted with CH$_2$Cl$_2$. The solution was next washed with sat. NaHCO$_3$ (aq), water, and brine, dried over MgSO$_4$, filtered, and concentrated. Purification by silica gel chromatography (2:1 hexanes:acetone with 1% Et$_3$N) gave the desired acetonide 28. ES/MS m/z 776 (MH$^+$), C$_{40}$H$_{73}$NO$_{13}$=775 g/mol.

EXAMPLE 68(b)

Synthesis of Compound 29

A 0.15M EtOAc solution containing compound 28 (azeotropically dried with benzene), DMAP (4 eq, azeotropically dried with benzene), Bz$_2$O (4 eq), and Et$_3$N (4 eq) was stirred for 20 h, after which time the solution was diluted with EtOAc and quenched with sat. NaHCO$_3$ (aq). The organic layer was then washed with brine, dried, filtered, and concentrated. Purification by silica gel chromatography (8:1 hexanes:acetone with 1% Et$_3$N) gave the benzoate 29. ES/MS m/z 985 (MH$^+$), C$_{54}$H$_{81}$NO$_{15}$=984 g/mol.

EXAMPLE 68(c)

Synthesis of Compound 30

To a 0° C. 0.1M EtOAc solution of compound 29 was quickly added Et$_3$N (4 eq.) followed by SOCl$_2$ (1.1 eq). The reaction was stirred for 80 min., then quenched with sat. NaHCO$_3$ (aq) and poured into EtOAc. The organic layer was washed with brine, dried over MgSO$_4$, filtered, and concentrated. Purification by silica gel chromatography (3:2 hexanes:ethyl actetate with 1% Et$_3$N) gave the alkene product 30. ES/MS m/z 967 (MH$^+$), C$_{54}$H$_{79}$NO$_{14}$=966 g/mol.

EXAMPLE 70

Synthesis of 6-O-alkyl Ketolide Analogs (Scheme 5a)

EXAMPLE 70(a)

Synthesis of Compound 300 (R=Me)
Step 1
Referring to Scheme 5a, to a 0° C. 0.1 M CH$_2$Cl$_2$ solution containing 30 was added mCPBA (5 eq). Warmed the reaction to rt and stirred for 16 h. Added cyclohexene (4 eq) and continued stirring for another 16 h. Poured into cold NaHCO$_3$ aq. and extracted with CH$_2$Cl$_2$ (3×). The organic extracts were washed with saturated NaHCO$_3$ aq. (6×) and brine (2×), dried with Na$_2$SO$_4$ and concentrated in vacuo to give N-oxide epoxide intermediate. This intermediate was dissolved in CH$_2$Cl$_2$ (0.1 M). To this solution at 0° C. was added sequentially isoproponol (2 eq) and tetra-n-propylammonium perruthenate (5 mol %). Warmed to rt and stirred for 16 h. Concentrated in vacuo to give a black residue. Purification by silica gel chromatography (5:1 hexane:acetone with 1% Et$_3$N) gave the epoxide product. ES/MS m/z 982.5 (MH$^+$), C$_{54}$H$_{79}$NO$_{15}$=981.5 g/mol.
Step 2
A solution (0.1 M in anhydrous diethyl ether) of compound obtained from step 1 was added to dimethyl lithium cuprate (LiMe$_2$Cu) solution (0.1 M in anhydrous diethyl ether, 5 eq) at −78° C. The mixture was warmed to 0° C. and stirred under this temperature for 8 h. Poured into cold NH$_4$Cl aq. and the pH of aqueous was ~7. Extracted with ether and CH$_2$Cl$_2$. The organic extracts were combined, washed with brine, dried over Na$_2$SO$_4$ and concentrated in vacuo. The resulting residue was purified by silica gel chromatography (5:1 hexane:acetone with 1% Et$_3$N) to give the C12-ethyl intermediate. ES/MS m/z 999 (MH$^+$), C$_{55}$H$_{83}$NO$_{15}$=998 g/mol.
Step 3
An aqueous solution of acetic acid (100 eq) was added to acetonide from step 2 in MeCN to give a 0.08M MeCN:H$_2$O solution (2:1 v/v). The reaction was stirred for 70 h at 65–70° C. and neutralized with saturated NaHCO$_3$ aq. The reaction was extracted with CH$_2$Cl$_2$, and the organic layer was washed with brine, dried over Na$_2$SO$_4$, filtered, concentrated, and purified by silica gel chromatography (4:1 hexanes:acetone with 1% Et$_3$N) to afford 9,11-diol. ES/MS m/z 959 (MH$^+$), C$_{52}$H$_{79}$NO$_{15}$=958 g/mol.

Step 4
To a 0° C. CH$_2$Cl$_2$ solution (0.2 M) of product obtained from step 3 was added tetra-n-propylammonium perruthenate (5 mol %), N-methylmorpholine N-oxide (1.2 equiv.) and 3 A molecular sieves (100 wt. %). The reaction was stirred under argon at 0° C. for 16 hrs. Diluted with EtOAc and filtered through a celite pad. The filtrate was concentrated in vacuo to give a residue which was purified by flash column chromatography (2:1 hexane/EtOAc+1% Et3N). Compound 300 (R=Me) was obtained as white foam. ES/MS m/z 956 (MH$^+$), C$_{52}$H$_{77}$NO$_{15}$=955 g/mol.

EXAMPLE 70(b)

Synthesis of 301 (R=Me)
Step 1
A 50% (w/w) aqueous solution of hydroxylamine (13 eq) was added to a 0.5M solution of Compound 300 in 2-propanol. Glacial acetic acid (4.2 eq) was added. The mixture was stirred at 50 C. for 18 h and then returned to ambient temperature. The reaction mixture was poured into dichloromethane and saturated aqueous sodium bicarbonate. The pH of the aqueous layer was adjusted to 9 with 6N sodium hydroxide, and the layers were separated. The organic phase was washed with brine, dried over magnesium sulfate, filtered, and concentrated. The crude material was purified by flash chromatography over silica gel (2:1 hexanes:acetone+2% triethylamine) to give the desired product. ES/MS m/z 868 (M+H$^+$, C$_{45}$H$_{74}$N$_2$O$_{14}$=867 g/mol.
Step 2
A 0.3M solution of the compound from step 1, in dichloromethane was cooled to 0 C. 2,2-dimethoxypropane (10 eq) and pyridinium p-toluenesulfonate (2 eq) were added. After 0.5 h, the reaction was brought to ambient temperature. The mixture was stirred for 48 h and poured into dichloromethane and saturated aqueous sodium bicarbonate. The layers were separated. The organic phase was washed with water then brine, dried over magnesium sulfate, filtered, and concentrated. The crude material was re-dissolved in toluene and concentrated. The material was used without further purification. ES/MS m/z 940 (M+H$^+$), C$_{49}$H$_{82}$N$_2$O$_{15}$=939 g/mol.
Step 3
Benzoic anhydride (1.5 eq) was added to a 0.2M solution of the compound from step 2 in EtOAc. The mixture was stirred at ambient temperature for 6 h and then poured into EtOAc and saturated sodium bicarbonate. The layers were separated. The organic layer was washed with water and brine, dried over magnesium sulfate, filtered, and concentrated. The crude material was purified by flash chromatography over silica gel (eluting with 6:1 hexanes:acetone+1% TEA) to give compound 301. ES/MS m/z 1044 (M+H$^+$), C$_{56}$H$_{86}$N$_2$O$_{16}$=1043 g/mol.

EXAMPLE 70(c)

Synthesis of 302 (R=Me)
Step 1. 6-O-alkylation
A. Allylation (O—Z=O-allyl)
A 0.1M solution of compound 301 in 1:1 THF:DMSO was cooled to 5 C. Freshly distilled allyl bromide (4 eq) was added. A 0.5M solution of potassium tert-butoxide in 1:1 THF:DMSO (3 eq) was added over 2 h while keeping the reaction mixture at 5–7 C. The mixture was poured into EtOAc and saturated sodium bicarbonate. The layers were separated. The organic layer was washed with water and brine, dried over magnesium sulfate, filtered, and concentrated. The crude material was used without further purification. ES/MS m/z 1084 (M+H$^+$), C$_{59}$H$_{90}$N$_2$O$_{16}$=1083 g/mol.

B. Propargylation (O—Z=O-propargyl)

A 0.15M solution of compound 301 in 2:1THF:DMSO was cooled to 10 C. 3-Bromo-1-(trimethylsilyl)propyne (6 eq) was added. A 0.67M solution of potassium tert-butoxide in 2:1 THF:DMSO (5 eq) was added over 2 h while keeping the reaction mixture at 12–15 C. The mixture was poured into EtOAc and saturated sodium bicarbonate. The layers were separated. The organic layer was washed sequentially with water and brine, dried over magnesium sulfate, filtered, and concentrated. The crude material was used without further purification. ES/MS m/z 1140 (M+H$^+$), $C_{61}H_{94}N_2O_{16}Si$=1139 g/mol.

Step 2

A. 0.1M solution of compound from step 1 in 2:1:1 acetonitrile:water:HOAc was stirred overnight at ambient temperature. Toluene and 2-propanol were added, and the mixture was concentrated under reduced pressure. The residue was re-dissolved in toluene and concentrated under reduced pressure. The crude material was used without further purification. ES/MS m/z 1012 (M+H$^+$), $C_{55}H_{82}N_2O_{15}$=1011 g/mol.

B. For Propargyl Compound Only

Potassium carbonate (2 eq) was added to a 0.05M solution of the compound from Step 2. The mixture was stirred at ambient temperature for 2 h and then poured into ethyl acetate and saturated sodium bicarbonate. The layers were separated. The organic layer was washed sequentially with water and brine, dried over magnesium sulfate, filtered, and concentrated. The crude material was used without further purification. ES/MS m/z 1010 (M+H$^+$), $C_{59}H_{80}N_2O_{15}$=1009 g/mol.

Step 3

A 0.1M solution of compound from step 2 in 1:1 EtOH:water was treated with sodium hydrosulfite (5.5 eq) and formic acid (4.7 eq). The mixture was stirred at 80 C. for 6 h and then returned to ambient temperature. The reaction was quenched by addition of sodium bicarbonate and extracted with EtOAc. The combined extracts were washed sequentially with sodium bicarbonate, water, and brine. The organic layer was dried over magnesium sulfate, filtered, and concentrated. The crude material was purified by flash chromatography over silica gel to give compound 302 (O—Z=O-allyl). ES/MS m/z 997 (M+H$^+$), $C_{55}H_{81}NO_{15}$=996 g/mol.

EXAMPLE 70(d)

Synthesis of 303 (R=Me, O—Z=O-allyl)

Step 1

A 0.3M solution of the compound 302 in pyridine was cooled to 0 C. and treated with methanesulfonyl chloride (6 eq). The reaction was brought to ambient temperature and stirred overnight. The reaction mixture was poured into EtOAc and saturated sodium bicarbonate. The layers were separated. The organic layer was washed sequentially with water and brine, dried over magnesium sulfate, filtered, and concentrated. The crude material was used without further purification. ES/MS m/z 1075 (M+H$^+$), $C_{56}H_{83}NO_{17}S$=1074 g/mol.

Step 2

A 0.2M solution of the compound from step 1 in acetone was treated with 1,8-diazabicyclo[5.4.0]undec-7-ene (5.0 eq). The reaction was brought to ambient temperature and stirred overnight. The reaction mixture was poured into EtOAc and saturated sodium bicarbonate. The layers were separated. The organic layer was washed with water and brine, dried over magnesium sulfate, filtered, and concentrated. The crude material was purified by flash chromatography over silica gel to give the desired compound. ES/MS m/z 979 (M+H$^+$), $C_{55}H_{79}NO_{14}$=978 g/mol.

Step 3

A 0.05M solution of the compound from step 2 in 2:1 acetonitrile:3N aqueous HCl was stirred overnight at ambient temperature. The mixture was cooled to 0 C. and neutralized with 6N aqueous sodium hydroxide. Volatiles were removed under reduced pressure, and the resulting syrup was extracted with EtOAc. The combined extracts were washed sequentially with sodium bicarbonate, water, and brine. The organic layer was dried over magnesium sulfate, filtered, and concentrated. The crude material was purified by flash chromatography over silica gel to give the desired compound. ES/MS m/z 717 (M+H$^+$), $C_{40}H_{61}NO_{10}$=716 g/mol.

Step 4

A 0.1 M solution of the compound from step 3 was cooled to 0 C. and treated with Dess-Martin periodinane (1.5 eq). The solution was stirred for 3 h and poured into EtOAc and saturated sodium bicarbonate. The layers were separated. The organic layer was washed with water and brine, dried over magnesium sulfate, filtered, and concentrated. The crude material was purified by flash chromatography over silica gel to give the desired compound. ES/MS m/z 715 (M+H$^+$), $C_{40}H_{59}NO_{10}$=714 g/mol.

Step 5

A 0.1M solution of the compound from step 4 and 1,1-carbonyldiimidazole (3.0 eq) in tetrahydrofuran was cooled to −15 C. Sodium hydride (60% dispersion in mineral oil, 2 eq) was added. The mixture was stirred at −15 C. for 20 min. The solution was stirred at ambient temperature for an additional 1 h and poured into EtOAc and saturated sodium bicarbonate. The layers were separated. The organic layer was washed with water and brine, dried over magnesium sulfate, filtered, and concentrated. The crude material was used without further purification. ES/MS m/z 809 (M+H$^+$), $C_{44}H_{61}N_3O_{11}$=808 g/mol.

Step 6

Ammonium hydroxide (90 eq) was added to a 0.15M solution of the compound from step 5 in 10:1 acetonitrile::tetrahydrofuran. The mixture was stirred at ambient temperature for 4 days. The reaction mixture was poured into EtOAc and saturated sodium bicarbonate. The layers were separated. The organic layer is washed with water and brine, dried over magnesium sulfate, filtered, and concentrated. The crude material was purified by flash chromatography over silica gel (4:1 hexanes:acetone+1% TEA) to give compound 303. ES/MS m/z 757 (M+H$^+$), $C_{41}H_{60}N_2O_{11}$=756 g/mol.

EXAMPLE 70(e)

Synthesis of 304 (R=Me)

Step 1. Coupling of Heterocycle

A. Heck Coupling

Tris(dibenzylideneacetone)dipalladium(0) chloroform adduct (0.25 eq) and tri-O-tolylphosphine (1.0 eq) were added to a degassed 0.1M solution of compound V (1.0 eq), 3-bromoquinoline (10 eq), and triethylamine (2.0 eq) in acetonitrile. The mixture was stirred at 75 C. for 42 h and returned to ambient temperature. The reaction mixture was poured into EtOAc and saturated sodium bicarbonate. The layers were separated. The organic layer was washed with water and brine, dried over magnesium sulfate, filtered through Celite, and concentrated. The crude material was purified by flash chromatography over silica gel (3:1 hexanes:acetone+2% TEA) to give the desired compound. ES/MS m/z 884 (M+H$^+$), $C_{50}H_{65}N_3O_{11}$=883 g/mol.

O—Z—Ar=

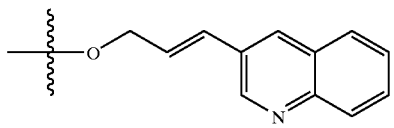

B. Sonogashira

Tetrakis(triphenylphosphine)palladium(0) (0.25 eq) and copper(I) iodide (0.25 eq) are added to a degassed 0.1M solution of compound V, 3-bromoquinoline (10 eq), and triethylamine (2.0 eq) in N,N-dimethylformamide. The mixture is stirred at 80 C. for 16 h and returned to ambient temperature. The reaction mixture is poured into EtOAc and saturated sodium bicarbonate. The layers are separated. The organic layer is washed with water and brine, dried over magnesium sulfate, filtered through Celite, and concentrated. The crude material is purified-by flash chromatography over silica gel to give the desired compound.

O—Z—Ar=

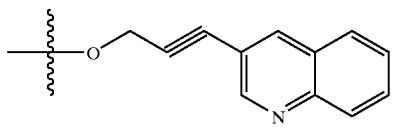

Step 2

A 0.05M solution of the compound from step 1A was refluxed in methanol for 20 h. The mixture was returned to ambient temperature, and volatiles were removed under reduced pressure. Purification by flash chromatography over silica gel (1:1 hexanes:acetone+2% TEA) gave compound 304. ES/MS m/z 780 (M+H$^+$), $C_{43}H_{61}N_3O_{10}$=779 g/mol.

O—Z—Ar=

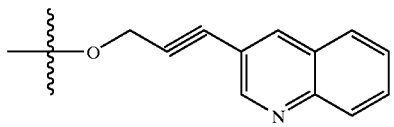

Compounds having general structure 304a, below, are made following the above scheme. ArX (where X is I, Br or Cl) are used in the step of Heck reaction. Compounds having general structure 304b are made following the above scheme. ArX (where X is I, Br or Cl) are used in the step of Sonogashira reaction.

General Structure:

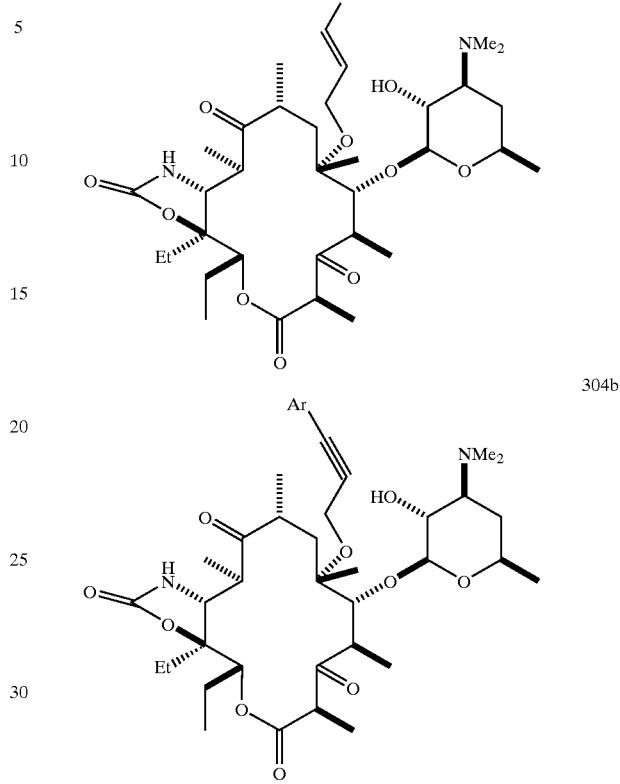

where Ar is 2-quinolyl, 3-quinolyl, 4-quinolyl, 5-quinolyl, 6-quinolyl, 7-quinolyl, 8-quinolyl, 1-naphthyl, 2-naphthyl,

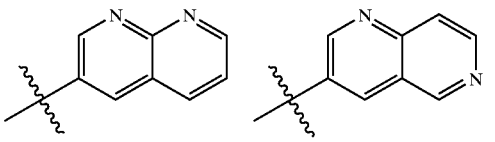

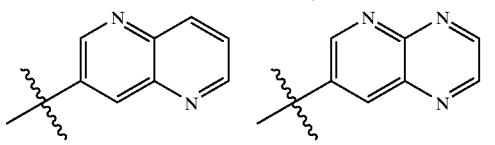

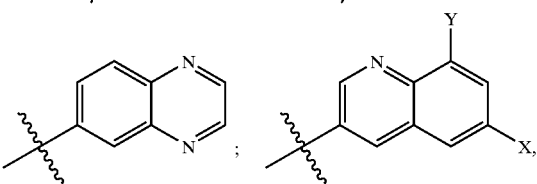

where Y is H, and X is F, Cl, OH, CN, $NO_2$, $NH_2$, pyridyl, OR, or Ac; or X is H, and Y is $NO_2$, $NH_2$, $CH_3$, or $CF_3$;

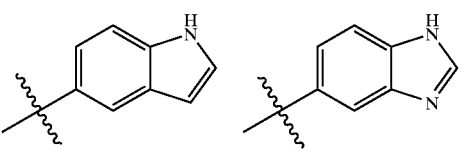

-continued

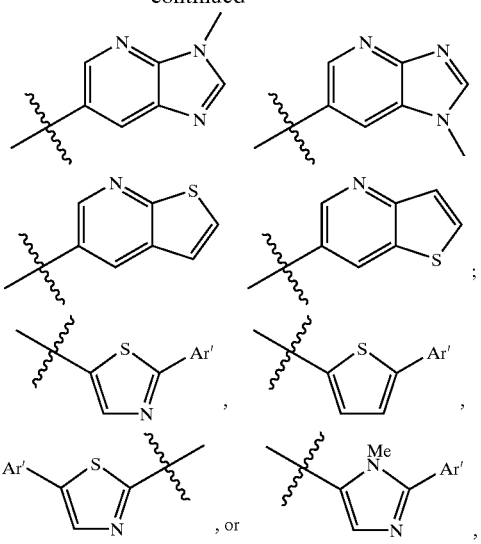

, or where Ar' is pyridyl, substituted-pyridyl, phenyl, substituted phenyl, thiophene, substituted thiophene, furanyl, substituted furanyl, thiazole, substituted thiazole, imidazole, substituted imidazole, pyrimidinyl, pyrazinyl or pyridazinyl.

EXAMPLE 71

Synthesis of 6O-alkylated, 12-H Derivatives (Scheme 5b)

EXAMPLE 71(a)

Synthesis of Compound II, Scheme 5b
Step 1. Removal of the C3-cladinose

Referring to Scheme 5b, above, 2',4"-OBz-9,11-dimethylketal-12,21-ene macrolide (I) (1 eq) was dissolved in 1:1 $CH_3CN/HCl$ (6M) and the reaction mixture was stirred at RT for 24 hours. The reaction was diluted with CH2Cl2 and poured into $NaHCO_3$ (sat), neutralized with $K_2CO_3$ (s) until a pH of ~8 was obtained. The product was separated, and the aqueous layer was extracted with $CH_2Cl_2$. The combined organic layers were washed with brine and dried over $Na_2SO_4$, filtered, and concentrated in vacuo. The crude foam was taken on to the subsequent step without further purification. ES/MS m/z found 664.9(M+H)+, exact mass for $C_{36}H_{58}NO_{10}(M+H)+$=664.85.

Step 2. Reinstallation of the 9,11-acetonide

To the crude product from step 1 (above) in $CH_2Cl_2$ (0.02M) was added PPTS (4 equivs) and DMP (23 equivs). The reaction mixture was heated to reflux for 4 hours. After cooling to room temperature, the reaction mixture was washed with $NaHCO_3$ (sat) and brine. The organic layer was dried over $Na_2SO_4$, filtered, and concentrated under reduced pressure. The foam was chromatographed over silica gel (4:1, hexane/acetone, with 0.1% triethylamine) to yield the desired product, as a white solid. ES/MS m/z found 705.0 $(M+H)^+$, exact mass for $C_{39}H_{62}NO_{10}$ $(M+H)^+$=704.91.

Step 3. C3-Silylether Formation.

The alcohol obtained in step 2 (above) was dissolved in $CH_2Cl_2$ (0.1M) and imidiazole (5 equivs) was added in one portion, followed by TMSCl (1.8 equivs) via syringe, at 0° C. The reaction mixture was stirred for 1 hour after which time $NaHCO_3$ (sat) was added, the layers separated, and the organic layer was washed with brine. The product was dried over $Na_2SO_4$, filtered and concentrated in vacuo. The crude material was chromatographed over silica gel (5:1, hexane/acetone, with 0.2% triethylamine) to yield the Compound II as a white foam (98%). ES/MS m/z found 705.0(M+H)+, exact mass for $C_{39}H_{62}NO_{10}(M+H)^+$=704.91.

EXAMPLE 71(b)

Synthesis of III, Scheme 5b
6O-Allylation of Compound II.

To Compound II in dry THF (0.1M) was added allyl methyl carbonate (1.6 equivs) and the solution was degassed with a steady flow of argon for 10 minutes. $Pd(OAc)_2$ (0.05 mol equiv) and $PPh_3$ (0.1 mol equiv) were placed in a bomb, suspended in THF and subsequently degassed with argon for 10 minutes. The solution containing the carbonate and Compound I was transferred to the bomb via syringe and the reaction mixture was heated to 90° C. overnight. After work-up with sat. $NaHCO_3$, the organic layer was separated, and washed with brine, and dried over $Na_2SO_4$. Upon concentration, the product was purified over silica gel (4:1, hexane/acetone with 0.1% TEA) to afford the desired allylated product, Compound III. Removal of the TMS group was accomplished with prolonged stirring upon aqueous work-up. For R=TMS: ES/MS m/z found 816.8(M+H+), exact mass for $C_{45}H_{74}NO_{10}Si$ $(M+H)^+$=817.16. For R=H: ES/MS m/z found 744.9 $(M+H^+)$, exact mass for $C_{42}H_{66}NO_{10}(M+H)^+$=744.97.

EXAMPLE 71(c)

Synthesis of IV, Scheme 5b
Step 1. Ozonolytic Cleavage of Compound III:

Compound III and TsOH (1.2 equivs) is dissolved in EtOAc (0.04M) and cooled to −78° C. Ozone is bubbled through the solution until a blue color persists. The excess ozone is displaced with nitrogen. and the reaction quenched with DMS (3 equivs), followed by the addition of TEA (4 equivs). The reaction mixture is washed with $NaHCO_3$ (sat) and brine, dried over $Na_2SO_4$, and upon concentration, is purified via column chromatography.

Step 2. Olefination of Aldehyde

To a solution of methyl triphenylphosphonium bromide (2 equivs) in THF (0.45M) is added $KN(TMS)_2$ (1.9 equivs of 0.5M solution in toluene) at −78° C. After ylide formation is complete, the aldehyde from step 1 is added to the ylide as a solution in THF (0.2M) at −78° C. The reaction mixture is allowed to stir for 4 hours, warming to room temperature over this time. To the solution is added $NH_4Cl$ and diluted with EtOAc. The two layers are separated, and the organic layer is washed with $NaHCO_3$ (sat) and brine. The organic layer is dried with $Na_2SO_4$, concentrated under reduced pressure, and chromatographed over silica gel to obtain the title compound IV.

EXAMPLE 71(d)

Synthesis of V, Scheme 5b
Step 1. Reduction of 12-Keto

Compound IV is dissolved in absolute ethanol (0.2M) followed by the addition of $NaBH_4$ (3 equivs). The reaction mixture is stirred under argon for 16 hours at ambient temperature. The solution is then diluted with EtOAc and neutralized with $NaHCO_3$ (sat) with vigorous stirring for 2 hours. The two phases were separated and the organic layer is washed with water, and then brine. The organic phase is dried over $Na_2SO_4$, filtered, and concentrated under reduced pressure. The crude product is then subjected to mesylation without further purification.

Step 2. Mesylation 12-Hydroxy

A 0.3M solution of the compound from step 1 in pyridine is cooled to 0 C. and treated with methanesulfonyl chloride (7 eq). The reaction is brought to ambient temperature and stirred overnight. The reaction mixture is poured into EtOAc and saturated sodium bicarbonate. The layers are separated. The organic layer is washed with water and brine, dried over sodium sulfate, filtered, and concentrated. The crude material is purified by flash chromatography over silica gel to give the desired compound.

Step 3. Removal of Acetonide and 30-Protecting Group

A 0.02M solution of the compound from step 2 in 1:1 acetonitrile:3N aqueous HCl is stirred for two hours at ambient temperature. The mixture is cooled to 0° C. and neutralized with $NaHCO_3$ (sat). Volatiles are removed under reduced pressure, and the resulting syrup is extracted with EtOAc. The combined extracts are washed sequentially with sodium bicarbonate, water, and brine. The organic layer is dried over sodium sulfate, filtered, and concentrated. The crude material is purified by flash chromatography over silica gel to give the desired compound.

Step 4. Corey-Kim Oxidation

Methyl sulfide (3.5 eq) is added to a 0.1M solution of N-chlorosuccinimide (3.0 eq) in dichloromethane at −10 C. The mixture is stirred for 15 min. A 0.1M solution of the compound from step 3 (1.0 eq) in dichloromethane is added dropwise over 10 min. The mixture is stirred an additional 30 min and then quenched with triethylamine (2.0 eq). The reaction is brought to 0° C. over 30 min and then poured into EtOAc and saturated sodium bicarbonate. The layers are separated. The organic layer is washed with water and brine, dried over magnesium sulfate, filtered, and concentrated. The crude material is purified by flash chromatography over silica gel to give the desired compound.

Step 5. Elimination

A 0.3M solution of the compound from step 3 in acetone is cooled to 0 C. and treated with 1,8-diazabicyclo[5.4.0]undec-7-ene (5.0 eq). The reaction is brought to ambient temperature and stirred for 5 h. The reaction mixture is poured into EtOAc and saturated sodium bicarbonate. The layers are separated. The organic layer is washed with water and brine, dried over magnesium sulfate, filtered, and concentrated. The crude material is purified by flash chromatography over silica gel to give compound V.

EXAMPLE 71(e)

Synthesis of VI, Scheme 5b

Step 1. Imidazole Carbamate

A 0.2M solution of the compound from step 4 and 1,1-carbonyldiimidazole (2.0 eq) in tetrahydrofuran is cooled to −15 C. Sodium hydride (60% dispersion in mineral oil, 1.2 eq) is added. The mixture is stirred at −15 C. for 15 min and at 0 C. for an additional 10 min. The reaction is diluted with ethyl acetate and quenched with saturated aqueous sodium bicarbonate. The layers are separated. The organic layer is washed with water and brine, dried over magnesium sulfate, filtered, and concentrated. The crude material is used without further purification.

Step 2. Cyclic Carbamate

Ammonium hydroxide (90 eq) is added to a 0.15M solution of the compound from step 5 in 10:1 acetonitrile::tetrahydrofuran. The mixture is stirred at 50 C. for 16 h and then returned to ambient temperature. The reaction mixture is poured into EtOAc and saturated sodium bicarbonate. The layers are separated. The organic layer is washed with water and brine, dried over magnesium sulfate, filtered, and concentrated. The crude material is purified by flash chromatography over silica gel to give compound V.

Step 3. Coupling of Heterocycle: Heck Coupling

Tris(dibenzylideneacetone)dipalladium(0) chloroform adduct (0.25 eq) is added to a degassed 0.1M solution of compound V, tri-O-tolylphosphine (1.0 eq), 3-bromoquinoline (10 eq), and triethylamine (2.0 eq) in acetonitrile. The mixture is stirred at 70 C. for 30 h and returned to ambient temperature. The reaction mixture is poured into EtOAc and saturated sodium bicarbonate. The layers are separated. The organic layer is washed with water and brine, dried over magnesium sulfate, filtered through Celite, and concentrated. The crude material is purified by flash chromatography over silica gel to give the desired compound.

Step 4. Deprotection

A 0.05M solution of the compound from step 1 is stirred in methanol at 70 C. for 16 h. The mixture is returned to ambient temperature, and volatiles are removed under reduced pressure. Purification by flash chromatography over silica gel gives compound VI.

Compounds having following structure VIa are made following the above scheme. ArX (X=I, Br, Cl) are used in the step of Heck reaction.

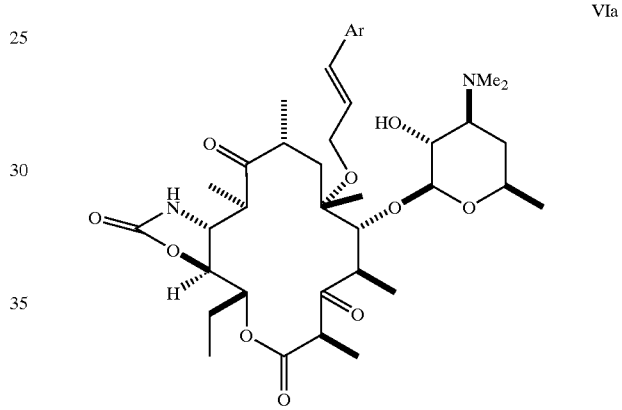

VIa

Where Ar is as described in Example 70(e) for C12-ethyl, O6-allyl/propargy derivatives (above).

EXAMPLE 72

Synthesis of C12-trifluoromethyl Derivatives 208a–c, Scheme 3

EXAMPLE 72(a)

Synthesis of 202a–c, Scheme 3

Step 1. $CF_3$ Addition, R=TMS

Referring to synthesis Scheme 3, above, to ketone 12, (1 equiv) in dry THF (0.4 M) at 0° C. was added dry KF (0.25 equiv) and $TMSCF_3$ (2 equiv). After stirring for 10 minutes at 0° C., several drops of potassium t-butoxide (1.0 M solution in THF) was slowly added. An exotherm was observed and the solution turned from colorless to golden-yellow. The ice bath was removed and after 15 min. the reaction was complete by both TLC and LCMS. The reaction was quenched with $NaHCO_3$ (sat) and the product extracted with dichloromethane (3×) and the combined organic layers were dried over $Na_2SO_4$, filtered and concentrated in vacuo. Purification by column chromatography (5:1, hexane/acetone, with 0.5% triethylamine) yielded the product 12-trifluoroemethyl-12-trimethylsilylether 202a as a white solid. LCMS (ES) (M+H)=1125.3; exact mass for $C_{58}H_{89}F_3NO_{15}Si$ (M+H)=1124.60.

Step 2. Desilylation, R=H

The trifluoromethyl-silylether (202a) from step 1, above, (1 equiv) was dissolved in THF (0.14 M) and TBAF (2 to 3 equiv) was added at 0° C. The ice bath was removed and the reaction mixture stirred for 1.5 hours. Complete deprotection of the silylether was observed by analysis of the LCMS and TLC data. Brine was added to reaction vessel, and diluted with methylene chloride. The layers were separated and the aqueous layer back extracted with methylene chloride (2x). The combined organic layers were dried over $Na_2SO_4$, filtered, and concentrated under reduced pressure. The resulting residue was purified over silica gel (4:1, hexane/acetone, with 0.2% triethylamine) to yield the product, 12-trifluoroemethyl-12-OH-clarithromycin derivative 202b, as a white solid. LCMS (ES) (M+H)=1052.9; exact mass for $C_{55}H_{81}F_3NO_{15}$ (M+H)=1052.56.

Step 3. Mesylation, R=Ms

The alcohol obtained in Step 2 (202b) was dissolved (1 equiv) in dry THF (0.4 M), cooled to 0° C., and lithium bis(trimethylsilyl)amide (3–4 equiv of 1M LiHMDS in THF) was added via syringe. After stirring for 20 minutes at 0° C., methanesulfonyl chloride was added (2 equiv) dropwise. A temperature of 0° C. was maintained for 1 hour after which time the reaction was complete. Excess base was quenched with $NaHCO_3$ (sat) and the product extracted with dichloromethane (4×30 mL) and the combined organic layers were dried over $Na_2SO_4$, filtered and concentrated in vacuo. Purification by column chromatography (4:1, hexane/acetone, with 0.5% triethylamine) yielded the product 12-trifluoroemethyl-12-mesylate clarithromycin derivative 202c as a white solid. LCMS (ES) (M+H)=1130.9; exact mass for $C_{38}H_{61}F_3NO_{13}S$ (M+H)=1130.53.

EXAMPLE 72(b)

Synthesis of 203, Scheme 3

Step 1. Deprotection of Acetonide

To C12-trifluoromethyl-C12-mesylate clarithromycin 202c (1 equiv) in acetonitrile (0.02 M) was added 3N hydrochloric acid$_{(aq)}$, (to make a 3:1 $CH_3CN$ to 3N HCl) and the reaction mixture was stirred at room. temperature for 1 hour. The reaction mixture was poured over ice and $NaHCO_3$ (sat), the product was extracted with ethyl acetate, dried over $Na_2SO_4$, filtered and concentrated in vacuo. The titled compound 203 was obtained as a white foam which was taken on crude, without purification. LCMS (ES): Mass found (M+H)=1091.2; exact mass for $C_{53}H_{79}F_3NO_{17}S$ (M+H)=1090.50.

Step 2. Oxidation of C9

To the crude product obtained in step 1, above (1 equiv) in methylene chloride (0.02 M) was added Dess-Martin periodinane (1.5 equiv) at 0° C. The reaction mixture was stirred at 0° C. for 1 hour. The reaction was quenched with $NaHCO_3$ (sat), the layers separated, the organic layer was then washed with $Na_2S_2O_3$ (aq), and followed by brine. The organic layer was dried over $Na_2SO_4$, filtered and concentrated in vacuo. The crude foam was purified over silica gel (3:1, hexane/acetone, with 0.5% TEA) to give the titled C9-ketone, compound 203.

EXAMPLE 72(c)

Synthesis of 204, Scheme 3

Inverision of C12: Enone Formaton

To compound 203 in acetone (0.1 M) was added DBU (3 equiv) at room temperature. The reaction mixture was heated to 60° C. for 48 hours. A single product was observed by TLC and LCMS, no starting material remained after this time. The solvent was removed under reduced pressure and the residue was dissolved in methylene chloride, washed with $NaHCO_3$ (sat), followed by a brine wash. The organic layer was dried over $Na_2SO_4$, filtered and concentrated in vacuo. The crude foam was purified over silica gel (3:1, hexane/acetone, with 0.5% TEA) to give the desired enone, compound 204. LCMS (ES): Mass found (M+H)=992.9; Exact mass for $C_{52}H_{73}F_3NO_{14}^+$(M+H)=992.50. $^{13}C$ NMR: the C9 signal appears at 205 ppm, and new vinyl signal for C10 at 143 ppm.

EXAMPLE 72(d)

Synthesis of 205, Scheme 3

C12-carbonate Formation

To compound 204 in THF (0.08 M) was added LiHMDS (5 equiv) at 0° C. The reaction mixture was stirred for 1 hour, followed by the addition of (4-ntirophenyl)-chloroformate (4 equiv). Stirring was continued for another 1 hour, allowing reaction vessel to slowly warm from 0° C. to room temperature. The reaction was quenched with $NaHCO_3$ (sat), diluted with EtOAc, separated, and the organic layer was washed with water (5x) and brine. The product was dried over $Na_2SO_4$, filtered and concentrated in vacuo and the crude foam, compound 205, was used immediately in the following step. LCMS (ES): Mass found (M+H)=1157.8; Exact mass for $C_{59}H_{76}F_3N_2O_{18}^+$(M+H)=1157.50.

EXAMPLE 72(e)

Synthesis of 206, Scheme 3

11,12-cyclic Carbamate: General Procedure

To a solution of compound 205 (from above) in a 4:1, acetonitrile/water was added the alkyl-aryl amine (5–10 equiv) as described for specific examples. The reaction was heated to 60° C. for 2 hours, after which time conversion to the carbamate was complete according to both TLC and LCMS data. The reaction was quenched with $NaHCO_3$ (sat), diluted with EtOAc, separated, and the organic layer was washed with water (8x) and brine. The product was dried over $Na_2SO_4$, filtered and concentrated in vacuo and the crude foam was chromatographed over silica gel (5:4, hexane/acetone, and 1% TEA) to give the desired products, 206a–c. All products were observed as the (M+2H)/2 ion as opposed to the usual M+H in the LCMS data.

Compound 206a: Alkyl is Butyl, and Aryl is Imidazole-3-phenyl

LCMS (ES); Mass found [(M+2H)/2]=617.7 Exact mass for $C_{66}H_{89}F_3N_4O_{15}^{2+}$[(M+2H)/2]=617.32.

Compound 206b: alkyl is butyl, and aryl is imidazole-3-pyridyl

LCMS (ES); Mass found [(M+2H)/2]=618.3 Exact mass for $C_{65}H_{88}F_3N_5O_{15}^{2+}$[(M+2H)/2]=617.81.

Compound 206c: alkyl is butyl, and aryl is 4-quinolyl

LCMS (ES); Mass found [(M+2H)/2]=610.1 Exact mass for $C_{66}H_{88}F_3N_3O_{15}^{2+}$[(M+2H)/2]=609.81.

EXAMPLE 72(f)

Synthesis of 207, Scheme 3

C3-ketolides

Compound 206 in $CH_3CN$ and 6N HCl (3:1, $CH_3CN$/6N HCl) was stirred for 3 hours at room temperature, after which time hydrolysis was complete. With vigorous stirring, the reaction mixture was poured over $NaHCO_3$ (sat), diluted with EtOAc, and $K_2CO_3$(s) was added until a pH=8 had been attained. The layers were separated and the organic layer was washed with brine, dried over $Na_2SO_4$, filtered and concentrated in vacuo. The crude foam was dissolved in $CH_2Cl_2$ (3.0 mL) followed by the addition of Dess-Martin periodinane (2.5 equiv) at 0° C. and allowed to warm to room temperature over 1.5 hours. Complete conversion to the 3-keto product was determined by both TLC and LCMS. The reaction was quenched with 1:1 $NaHCO_3(aq)/Na_2S_2O_3$ (aq) and stirred for 10 minutes. The layers were separated, washed with brine, and dried over $Na_2SO_4$. Upon concentration, the foam was purified over silica gel (3:2, hexand/acetone, with 0.5% TEA) to give the desired 3-keto products 207a–c.

Compound 207a: alkyl is butyl, and aryl is imidazole-3-phenyl

LCMS (ES); Mass found [(M+2H)/2]=486.4; exact mass for $C_{51}H_{69}F_3N_4O_{11}{}^{2+}[(M+2H)/2]=485.25$.

Compound 207b: alkyl is butyl, and aryl is imidazole-3-pyridyl

LCMS (ES); Mass found [(M+2H)/2]=486.1; exact mass for $C_{43}H_{64}F_3N_5O_{10}{}^{2+}[(M+2H)/2]=485.75$.

Compound 207c: alkyl is butyl, and aryl is 4-quinolyl

LCMS (ES); Mass found [(M+2H)/2]=478.0; exact mass for $C_{51}H_{68}F_3N_3O_{11}{}^{2+}[(M+2H)/2]=477.74$.

EXAMPLE 72(g)

Synthesis of 208, Scheme 3

Compound 207 was dissolved in MeOH (0.01 M) and the reaction mixture was refluxed over night. The MeOH was removed under reduced pressure and the crude foam was then purified over silica gel (1:1, hexane/acetone, with 0.5% TEA) to give the titled compounds, 208a–c.

Compound 208a: alkyl is butyl, and aryl is imidazole-3-phenyl

LCMS (ES); Mass found (M+H)=865.8; Exact mass for $C_{44}H_{64}F_3N_4O_{10}{}^{+}(M+H)=865.46$.

Compound 208b: alkyl is butyl, and aryl is imidazole-3-pyridyl

LCMS (ES); Mass found (M+H)=434.3; Exact mass for $C_{43}H_{64}F_3N_4O_{10}{}^{+2}[(M+H)/2]=434.00$.

Compound 208c: alkyl is butyl, and aryl is 4-quinolyl

LCMS (ES); Mass found (M+H)=426.1; Exact mass for $C_{44}H_{64}F_3N_3O_{10}{}^{+2}[(M+H)/2]=425.50$.

EXAMPLE 73

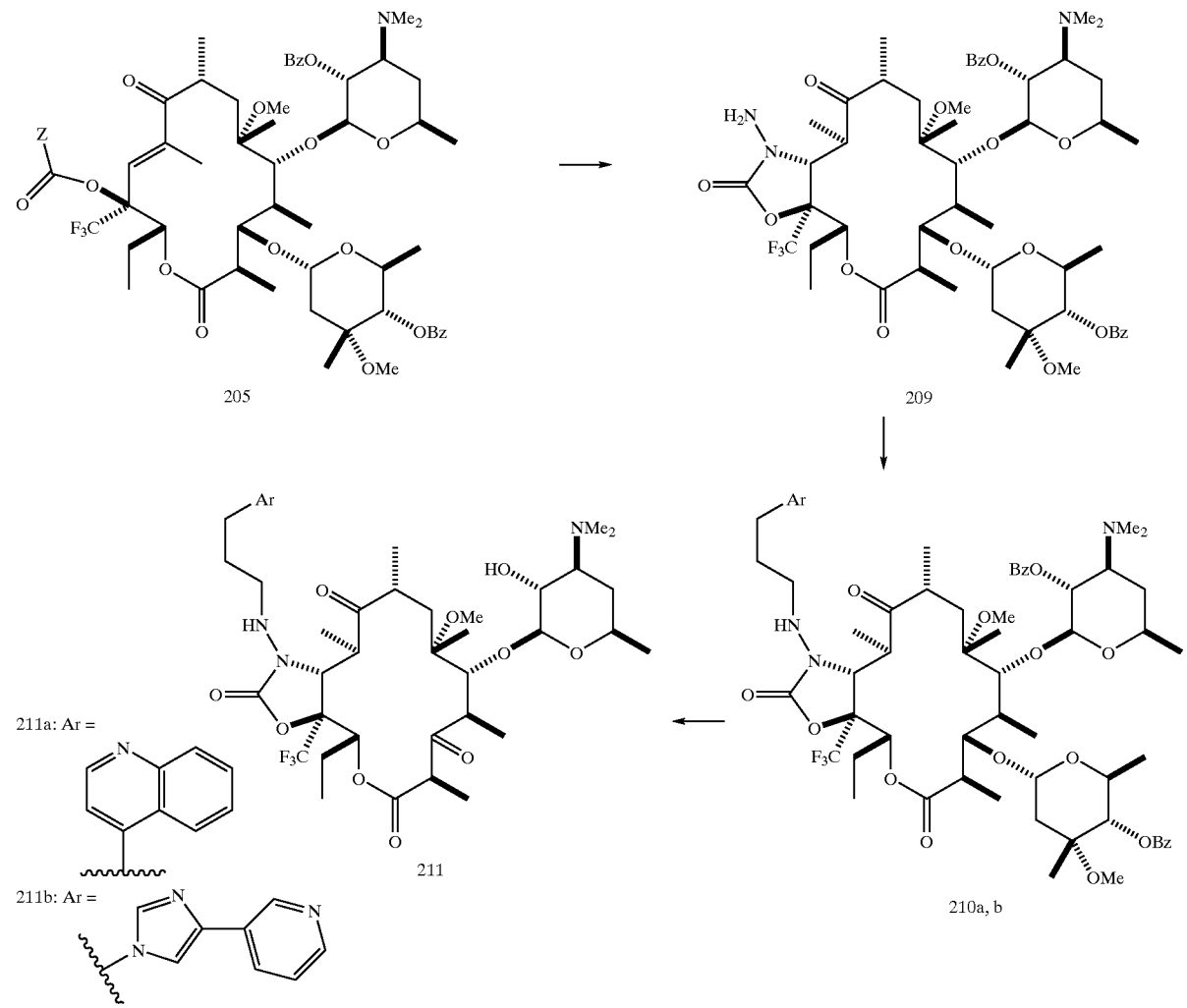

General Scheme to 12-CF3 11,12-Carbazate Ketolides

EXAMPLE 73(a)

Synthesis of 209, Carbazate Formation

The carbazate is formed directly from the nitrophenyl carbonate 205 (obtained from Example 72(a)), by addition of hydrazine (~10 equiv) to the same reaction pot following the formation of the carbonate, and prior to work-up. The reaction mixture was then warmed to room temperature and stirred for 2.5 hours. Both TLC and LCMS indicated that carbonate had been consumed and formation of the carbazate was complete. The reaction was quenched with NaHCO$_3$ (sat), diluted with EtOAc, separated, and the organic layer was washed with water, and then with brine. The product was dried over Na$_2$SO$_4$, filtered, concentrated in vacuo, and the crude foam was chromatographed over silica gel (4:1, hexane/acetone, and 0.1% TEA) to give the titled compound, 209. LCMS (ES); Mass found (M+H)= 1051.1; Exact mass for $C_{53}H_{75}F_3N_3O_{15}{}^+$(M+H)=1050.52.

Synthesis of 210a, Scheme 2d

To compound 209 in methanol (0.1 M) was added 4-(3-propanal)-quinoline (2 equiv), and glacial acetic acid (4 equiv) at room temperature. After 4 hours, NaCNBH$_3$ (5.3 equiv) was added to the reaction vessel and the reaction mixture was stirred overnight at room temperature. The reaction was quenched with NaHCO$_3$ (sat), diluted with EtOAc, separated, and the organic layer was washed with brine. The product was dried over Na$_2$SO$_4$, filtered, concentrated in vacuo, and the crude foam was chromatographed over silica gel (4:1, hexane/acetone, and 0.1% TEA) to give 210a.

LCMS (ES); Mass found [(M+2H)/2]=610.1;
Exact mass for $C_{65}H_{87}F_3N_4O_{15}{}^{2+}$[(M+2H)/2]=610.31.

EXAMPLE 73(b)

Synthesis of 210b

To carbazate 209 in glacial acetic acid (0.05 M) was added 4-(3-pyridyl)-imidazole (8 equiv) and acrolein (1.2 equiv) at room temperature. After 2 hours the reaction was quenched with NaHCO$_3$ (sat), the imine extracted with EtOAc, and concentrated under reduced pressure. The crude intermediate was dissolved in MeOH (0.02 M), 2 drops of HOAc was added, followed by NaCNBH$_3$ (10 equiv), and the reaction mixture was stirred for 8 hours at room temperature. The reaction was quenched with NaHCO$_3$ (sat), diluted with EtOAc, separated, and the organic layer was washed with brine. The crude carbazate product 210b was taken on to the next step without further purification. LCMS (ES); Mass found [(M+2H)/2]=618.6; Exact mass for $C_{64}H_{87}F_3N_6O_{15}{}^{2+}$ [(M+2H)/2]=6 18.70.

EXAMPLE 73(c)

Synthesis of 211a–b

Step 1. Removal of C3-sugar, General Procedure

The carbazate 210 was dissolved in CH$_3$CN/HCl (6N) (1.5:1) at room temperature. After 2 hours, TLC indicated that hydrolysis of the cladinose sugar was complete. The reaction was quenched with NaHCO$_3$ (sat), diluted with EtOAc, and the pH was adjusted to ~8 with K$_2$CO$_3$(s). The layers were separated, and the aqueous layer was extracted with EtOAC (3x), the combined organic layers were washed with brine. The product was dried over Na$_2$SO$_4$, filtered, concentrated in vacuo, and the crude foam was carried on to the next step without further purification.

Step 2. Oxidation of the C3-OH, General Procedure

To the crude 11,12-carbazate from step 1 (above), in CH$_2$Cl$_2$ (0.01 M) was added Dess-Martin periodinane (2 equiv) at 0° C. The reaction mixture was warmed to room temperature over 2 hours, after which time oxidation was complete. The reaction was quenched with a 1:1 solution of NaHCO$_3$(sat) and Na$_2$S$_2$O$_3$ (1M). The layers were separated, and the aqueous layer extracted with additional CH$_2$Cl$_2$ (2x). The combined organic layers were then washed with brine and dried over Na$_2$SO$_4$, filtered, concentrated in vacuo, and the crude foam was purified over silica gel (4:1, hexane/acetone with 0.1% TEA) to give the pure ketolide.

Step 3. Deprotection of 2'Benzoate, General Procedure

The ketolide, from Step 2 (above), was dissolved in MeOH (0.01 M) and refluxed overnight. The methanol was removed under reduced pressure and the crude foam was chromatographed over silica gel (3:1 to 1:1, hexane/acetone with 0.1% TEA), to give the final carbazate derivatives, 211a–b.

Compound 211a: aryl is 4-quinolyl
LCMS (ES); Mass found [(M+2H)/2]=426.8; Exact mass for $C_{43}H_{63}F_3N_4O_{10}{}^{2+}$[(M+2H)/2]=426.49.

Compound 211b: aryl is imidazole-3-pyridyl
LCMS (ES); Mass found [(M+2H)/2]=434.6; Exact mass for $C_{49}H_{67}F_3N_6O_{11}{}^{2+}$[(M+2H)/2]=434.49.

EXAMPLE 74

Synthesis of C11-C12 "Reverse" Carbamate
(Synthesis Scheme 6)

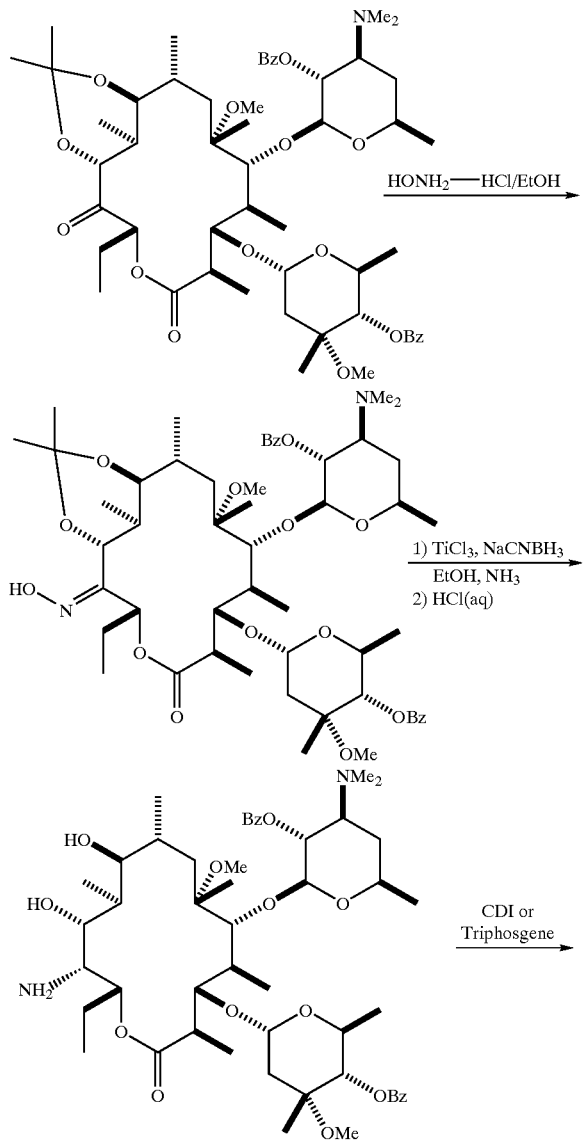

-continued

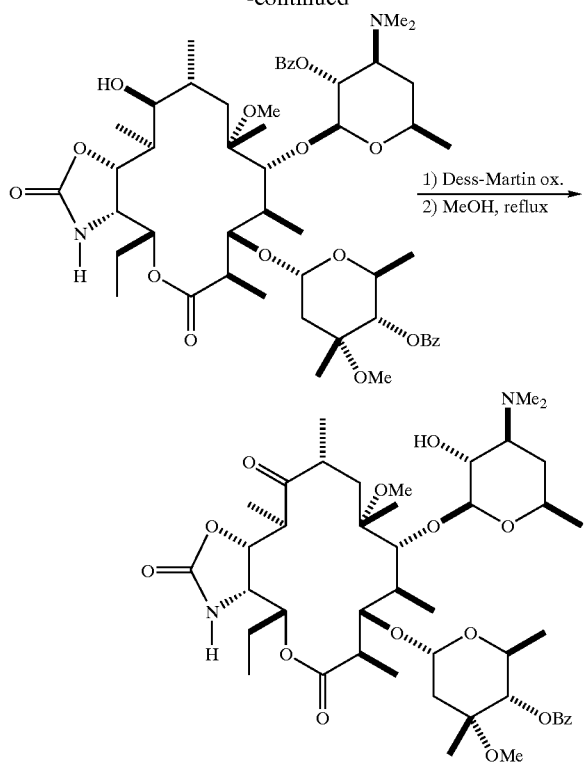

To 2',4"-OBz-9,11-dimethylketal-12-keto-macrolide in EtOH (0.04M) was added Et$_3$N (9.5 eq), followed by hydroxylamine hydrochloride (4.7 eq). The reaction mixture was stirred at room temperature overnight after which time complete conversion to the oxime was observed. The solvent was removed under reduced pressure and the residue taken up in CH$_2$Cl$_2$ and washed with NaHCO$_3$ (sat). The organic layer was dried over Na$_2$SO$_4$, filtered, and concentrated in vacuo. The 12-oxime-derivative was purified by column chromatography over silica gel (2:1, hexane/acetone, with 0.5% triethylamine) to give the desired 12-oxime-9,11-acetonide as a white solid. The crude product may be taken on to the reduction step directly. ES/MS 997.6 (MH$^+$).

To 2',4"-OBz-9,11-dimethylketal-12-oxime-macrolide in EtOH (0.02M) was added NH$_3$ (2M in ethanol; 33 eq), followed by the addition of NaCNBH$_3$ (7.9 eq). The reaction mixture was cooled to 0° C. and TiCl$_3$ (5 eq) was added dropwise over 5 minutes. The ice bath was removed and stirring continued at room temperature. Reaction progress was monitored by TLC and LCMS; both indicated that the reduction to the amine had reached completion after 30 minutes. At this point, the acetonide at the 9 and 11 positions was still intact. Deprotection was accomplished by the slow addition of HCl (6M; 70 eq) at 0° C. The blue slurry was poured over ice and the pH was adjusted to ~10 with dry NaHCO$_3$. The grey slury was diluted with water to decrease the emulsion during the extraction process. The product was extract from the aqueous layer with CHCl$_3$ (5×) and the combined organic layers were dried over Na$_2$SO$_4$. Concentration in vacuo followed by purification over silica gel (2% MeOH/97% CH$_2$Cl$_2$ and 1% triethylamine) gave the single isomer 12-amino-9,11-diol as a white solid. The structure and stereochemistry at C-12 was confirmed by X-ray analysis. ES/MS 943.2 (MH$^+$). The intermediate acetonide can also be isolated if the deprotection step is omitted. ES/MS 983.5 (MH$^+$).

To 2',4"-OBz-9,11-hydroxy-12-amino-macrolide in CH$_2$Cl$_2$ (0.05M) was added TEA (2.2 eq) and triphosgene (1.1 eq) at 0° C. The reaction vessel was warmed to room temperature and stirred for 15 minutes after which time no starting material remained. Aqueous NaHCO$_3$ (sat) was added to reaction mixture, and the layers were separated. The product was further extracted from the aqueous layer with additional CH$_2$Cl$_2$ (3×). The combined organic layers then dried over Na$_2$SO$_4$, filtered, and concentrated in vacuo. Purification over silica gel (5:1, hexane/acetone and 0.5% triethylamine) gave the 9-hydroxy-11,12-oxazolidonone derivative as a white solid. Structure confirmed by X-ray analysis. ES/MS 969.5 (MH$^+$).

To 2',4"-OBz-9-hydroxy-11,12-oxazolidinone-macrolide in CH$_2$Cl$_2$ (0.1 M) was added Dess-Martin periodinane (1.2 eq) at 0° C. The reaction vessel was warmed to room temperature and stirred for 30 minutes after which time no starting material remained. Aqueous NaHCO$_3$ (sat) was added to reaction mixture, and the layers separated. The aqueous layer was extracted with CH$_2$Cl$_2$ (3×). The combined organic layers then dried over Na$_2$SO$_4$, filtered, and concentrated in vacuo. Purification over silica gel (5:1, hexane/acetone and 0.5% triethylamine) gave the 9-keto-11,12-oxazolidonone derivative as a white solid. ES/MS 967.4 (MH$^+$).

The 2',4"-OBz-9-Keto-11,12-oxazolidinone-macrolide was dissolved in MeOH (0.01 M) and heated to reflux for 3 days. The solvent removed in vacuo, followed by purification over silica gel (3:1, hexane/acetone and 0.5% triethylamine) to give the 9-keto-11,12-oxazolidonone derivative as a white solid. ES/MS 863.6 (MH$^+$).

EXAMPLE 75

2-Fluoro analogs

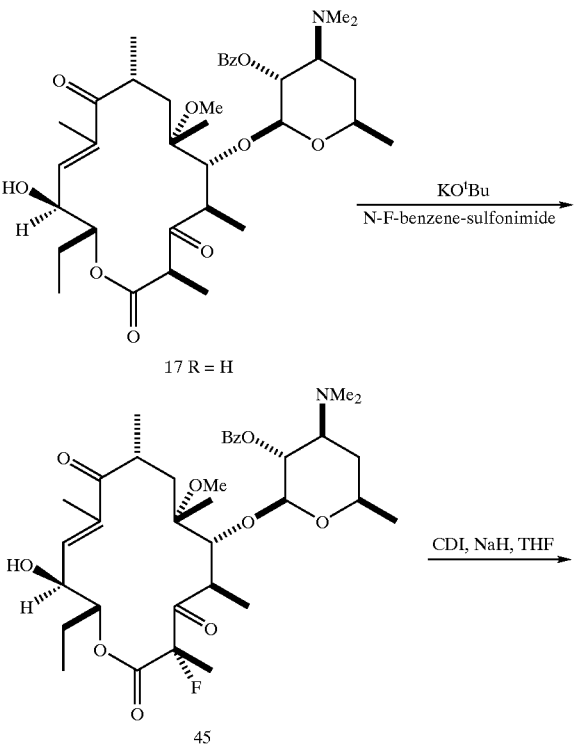

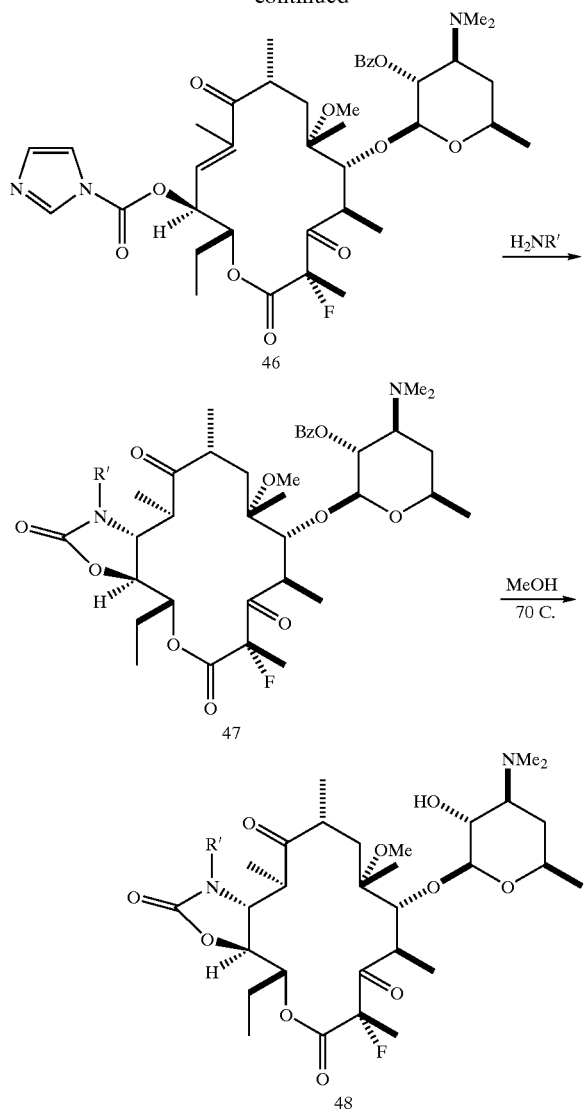

To a −15° C. (MeOH/ice bath) 0.15 M THF solution containing the 10, 11 anhydroketolide (17, Example 67) was added KO'Bu (1.15 eq, 1.0 M in THF). After 5 min., N-fluorobenzenesulfonimide (1.2 eq) was added and the solution was stirred for 10 min. before being warmed to 0° C. over 0.5 h. The reaction was next diluted with EtOAc and quenched with sat. NaHCO$_3$. The organic layer was washed with water and brine, dried over MgSO$_4$, filtered, and concentrated. Purification by silica gel chromatography 10 (4:1 hexanes : acetone with 1% Et$_3$N) gave the desired halo product 45. ESMS m/z 678 (MH$^+$), C$_{36}$H$_{52}$FNO$_{10}$=677 g/mol.

To a −15° C. (MeOH/ice bath) 0.18 M THF solution containing the C2 fluorine 45 and CDI (2 eq) was added NaH (60%, 1.2 eq). After stirring for 10 min., the solution was warmed to −5° C. over 10 min. The reaction was next diluted with EtOAc and quenched with sat. NaHCO$_3$. The organic layer was washed with water and brine, dried over Na$_2$SO$_4$, filtered, and concentrated. The product 46 was used without further purification.

The crude carbamate product 46 was added to a 0.25 M MeCN solution containing the appropriate amine R'NH$_2$ (4 equiv.) and stirred at rt for 2 h before being heated to 70° C. for 16 h. The reaction was next diluted with EtOAc and quenched with sat. NaHCO$_3$. The organic layer was washed with water and brine, dried over Na$_2$SO$_4$, filtered and concentrated. Purification by silica gel chromatography (5:2 hexanes:acetone with 2% Et$_3$N) gave the desired cyclic carbamate product. 47a: R'=4-quinolin-4-yl-butyl, ESMS m/z 904 (MH$^+$), C$_{50}$H$_{66}$FN$_3$O$_{11}$=903 g/mol. 47b: R'=4-(4-phenyl-imidazol-1-yl)-butyl, ESMS m/z 919 (MH$^+$), C$_{50}$H$_{67}$FN$_4$O$_{11}$=918 g/mol. 47c: R'=4-quinolin-4-yl-butyl, ESMS m/z 904 (MH$^+$). 47d: R'=4-(4-(3-pyridyl)imidazolyl)butyl, ESMS m/z 920.5.

A 0.05 M MeOH solution containing the benzoate was heated to 70° C. for 3 h and then concentrated. Purification by silica gel chromatography (1:1 hexane/acetone with 2% Et$_3$N) gave the desired products. 48a: R'=4-quinolin-4-yl-butyl, ESMS m/z 800 (MH$^+$), C$_{43}$H$_{62}$FN$_3$O$_{10}$=799 g/mol. 48b: R'=4-(4-phenyl-imidazol-1-yl)-butyl, ESMS m/z 815 (MH$^+$), C$_{43}$H$_{63}$FN$_4$O$_{10}$=814 g/mol. 48c: R'=4-(2-quinolyl) butyl, ESMS m/z 800 (MH$^+$). 48d: R'=4-(4-(3-pyridyl) imidazolyl)butyl, ESMS m/z 816.5.

EXAMPLE 76

Synthesis of 2-F acrolein pyridyl-imidazole carbazate

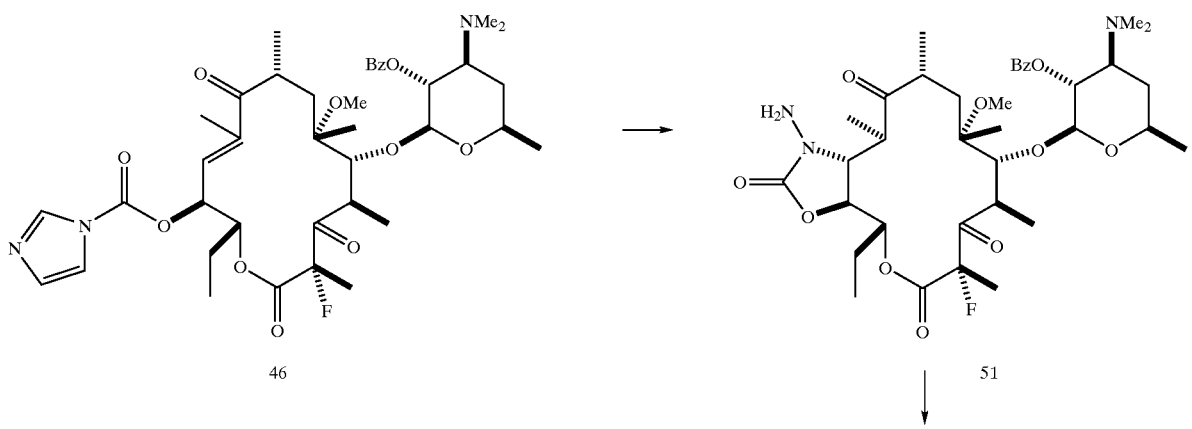

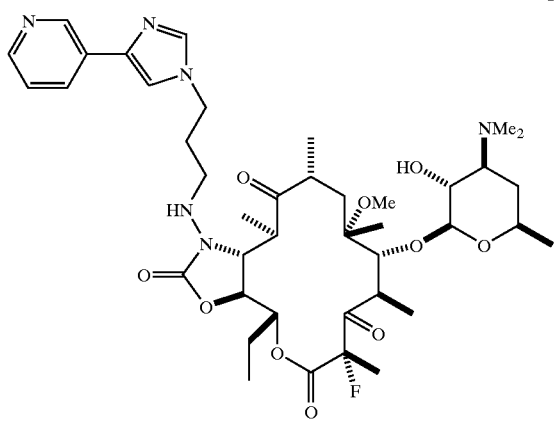

53

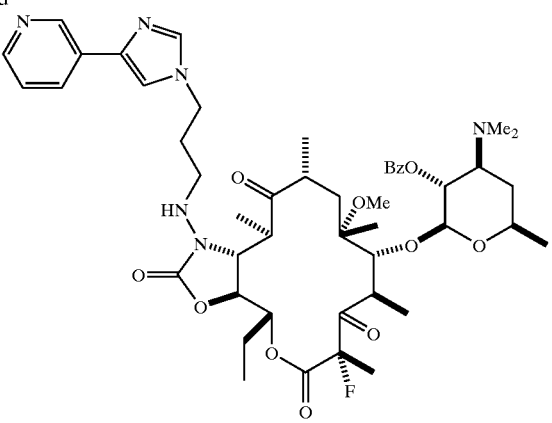

52

Compound 51 was prepared as described in Example 80 for the analogous 2-H compound except using compound 46 (Example 75) as the starting material. ES/MS m/z 369 [(M+2H$^+$)/2], $C_{37}H_{54}FN_3O_{11}$=736 g/mol.

Compound 52 was prepared from 51 as described in Example 80 for the analogous 2-H compound. ES/MS m/z 461 [(M+2H$^+$)/2], $C_{48}H_{65}FN_6O_{11}$=921 g/mol.

Compound 53 was prepared from 52 as described in Example 80 for the analogous 2-H compound. ES/MS m/z 409 [(M+2H$^+$)/2], $C_{41}H_{61}FN_6O_{10}$=817 g/mol.

EXAMPLE 77

Synthesis of 2-F quinolyl carbazate

51 ⟶

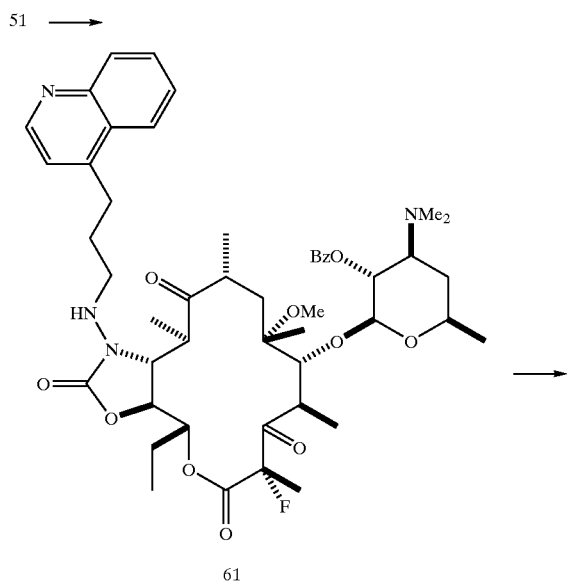

61

-continued

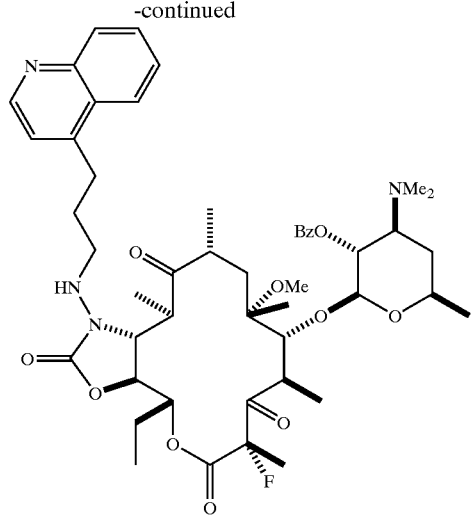

62

Starting material 51 (Example 76, 1.0 eq) and 4-quinolinecarboxaldehyde (1.2 eq) were dissolved in methanol. Glacial acetic acid (4.0 eq) was added. The solution was stirred at ambient temperature for 5.5 h. Sodium cyanoborohydride (2.0 eq) was added. The mixture was stirred overnight. The reaction was quenched by the addition of saturated aqueous sodium bicarbonate and then poured into EtOAc. The phases were separated. The organic layer was washed with brine and then dried over Na$_2$SO$_4$, filtered, and concentrated. Column chromatography (1:1 hexanes:EtOAc+2% Et$_3$N) gave the desired product 61. ES/MS m/z 906 (MH$^+$), $C_{49}H_{65}FN_4O_{11}$=905 g/mol.

A 0.05M solution of starting material 61 in methanol was refluxed for 15 h. The mixture was brought to ambient temperature and concentrated. Column chromatography (2:3 hexanes:EtOAc+2% Et$_3$N) gave the desired product 62. ES/MS m/z 401 [(M+2H$^+$)/2], $C_{48}H_{67}N_5O_{11}$=801 g/mol.

EXAMPLE 78

Synthesis of 2-F crotonaldehyde pyridyl-imidazole carbazate

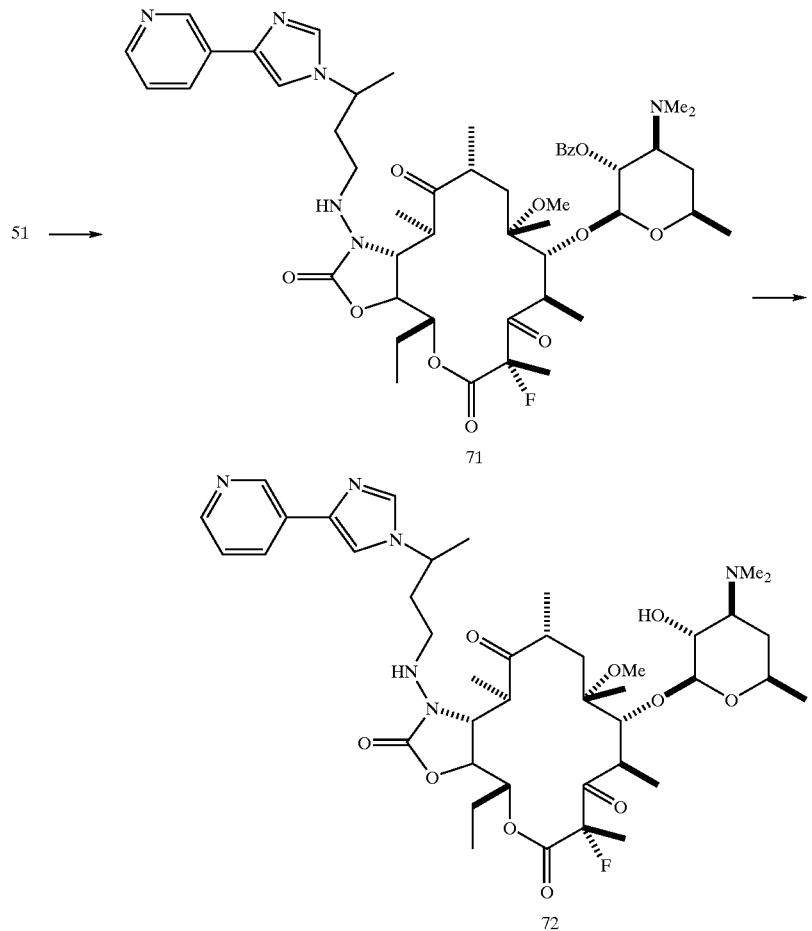

Compound 71 was obtained as described in Step 1 of Example 82 for the analogous 2-H compound except using comound 51 (Example 76) as the starting material. ES/MS m/z 468 [(M+2H$^+$)/2], $C_{49}H_{67}FN_6O_{11}$=935 g/mol.

Compound 72 was obtained as described in Step 2 of Example 82 for the analogous 2-H compound except using comound 71 as the starting material. ES/MS m/z 416 [(M+2H$^+$)/2], $C_{42}H_{63}FN_6O_{10}$=831 g/mol.

EXAMPLE 79

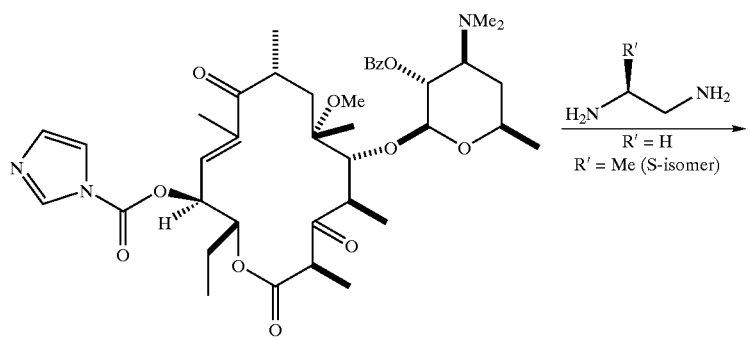

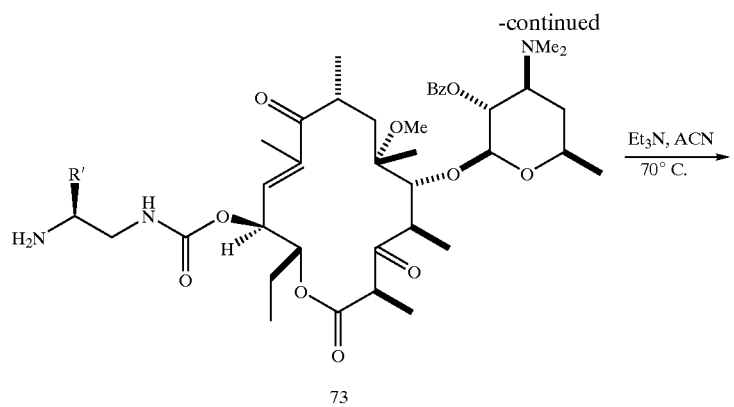

73

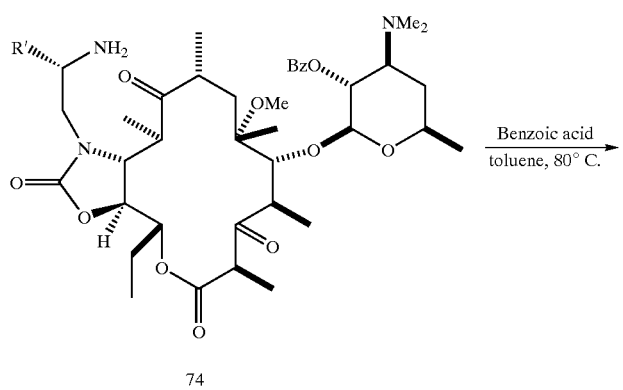

74

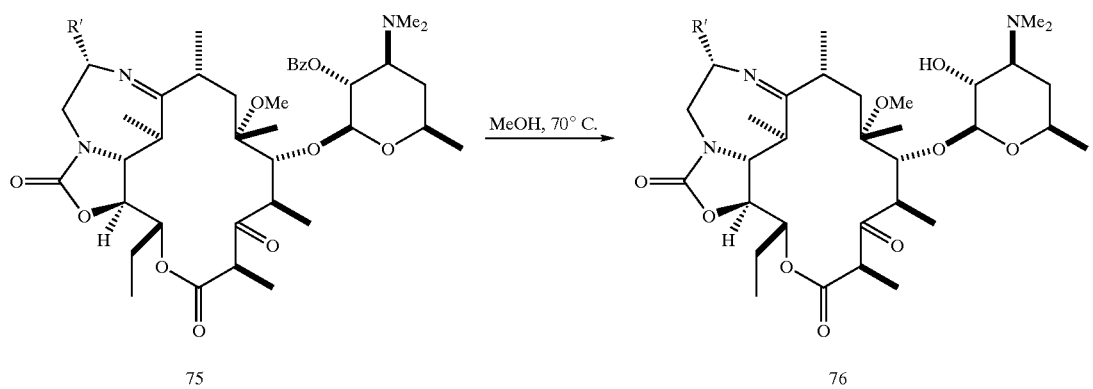

75 76

The previously described crude carbamate intermediate 18 (Example 67) was added to a 0.22 M MeCN solution containing the appropriate amine (2 eq. [ethylene diamine; (S)-(−)-1,2-diamonopropane-.2HCl]) and stirred at rt for 2 h to overnight. The reaction was next diluted with EtOAc and quenched with water (2×), brine, dried over $Na_2SO_4$, filtered, and concentrated. The products were purified by silica gel chromatography where necessary and redissolved in 0.2M MeCN containing $Et_3N$ (10 eq) and heated at 55–60° C. for 15–39 h before being concentrated and chromatographed (silica gel, 1:1 hexane/acetone with 2% $Et_3N$). 74a: R'=H, ESMS m/z 746 ($MH^+$), $C_{39}H_{59}N_3O_{11}$= 745 g/mol. 74b: R'=Me, ESMS m/z 760 ($MH^+$), $C_{40}H_{61}N_3O_{11}$=759 g/mol.

To a 0.05 M toluene solution containing the carbamate 74 and benzoic acid or pivalic acid (2 eq) was stirred at 70° C. for 3 days then at to 80° C. for an additional 2 days. Purification by silica gel chromatography (2:1 hexanes:acetone with 2% $Et_3N$) gave the cyclic imine product. 75a: R'=H, ESMS m/z 728 ($MH^+$), $C_{39}H_{57}N_3O_{10}$=727 g/mol. 727 g/mol. 75b: R'=Me, ESMS m/z 742 ($MH^+$), $C_{40}H_{59}N_3O_{10}$=741 g/mol.

A 0.05 M MeOH solution containing the benzoate 75 was heated to 70° C. for 3 h and then concentrated. Purification by silica gel chromatography (1:2 hexanes:acetone with 2% $Et_3N$) gave the desired product. 76a: R'=H, ESMS m/z 624 ($MH^+$), $C_{32}H_{53}N_3O_9$=623 g/mol. 76b: R'=Me, ESMS m/z 638 ($MH^+$), $C_{33}H_{55}N_3O_9$=637 g/mol.

EXAMPLE 80

Synthesis of 2-H acrolein pyridyl-imidazole carbazate analog

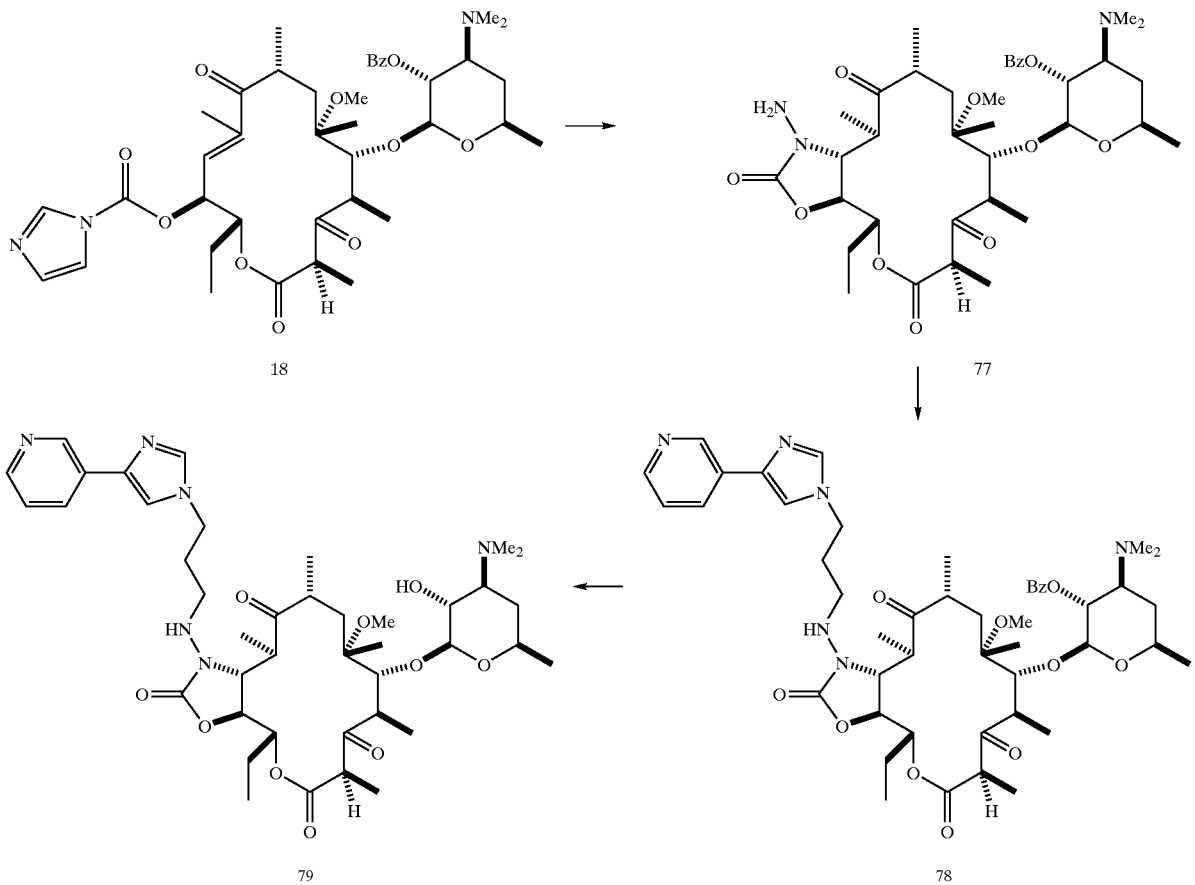

Compound 18 of Example 67 (1.00 eq) was dissolved in DMF. Hydrazine hydrate (4.0 eq) was added. The solution was stirred at ambient temperature for 3 h. The reaction mixture was poured into EtOAc and washed sequentially with water and brine. The organic layer was dried over Na2SO4, filtered, and concentrated. Column chromatography (5:2 hexanes:EtOAc+2% Et3N) gave the cyclic carbazide 77, ES/MS m/z 360 [(M+2H+)/2], $C_{37}H_{55}N_3O_{11}$=718 g/mol.

The cyclic carbazate 77 (1.0 eq) and 4-(3-pyridyl)-imidazole (3.0 eq) was dissolved in HOAc. Freshly distilled acrolein (1.2 eq) was added. The solution was stirred at ambient temperature for 16 h; and sodium triacetoxyborohydride (8.0 eq) was added. The solution was stirred for an additional 8.5 h. The reaction mixture was poured into EtOAc and quenched by the addition of 6N aqueous sodium hydroxide and saturated aqueous sodium bicarbonate. The layers were separated; and the organic layer was washed with brine then dried over $Na_2SO_4$, filtered, and concentrated. Column chromatography (2:1 hexanes:acetone+2% $Et_3N$ to 1:2 hexanes:acetone+2% $Et_3N$) gave 78. ES/MS m/z 452 [(M+2H+)/2], $C_{48}H_{66}N_6O_{11}$=903 g/mol.

A 0.05M solution of 78 in methanol was refluxed for 15 h. The mixture was brought to ambient temperature and concentrated. Column chromatography (94:5:1 $CHCl_3$:MeOH:$NH_4OH$) gave 79. ES/MS m/z 400 [(M+2H+)/2], $C_{41}H_{62}N_6O_{10}$=799 g/mol.

EXAMPLE 81

Synthesis of 2-H quinolyl carbazate

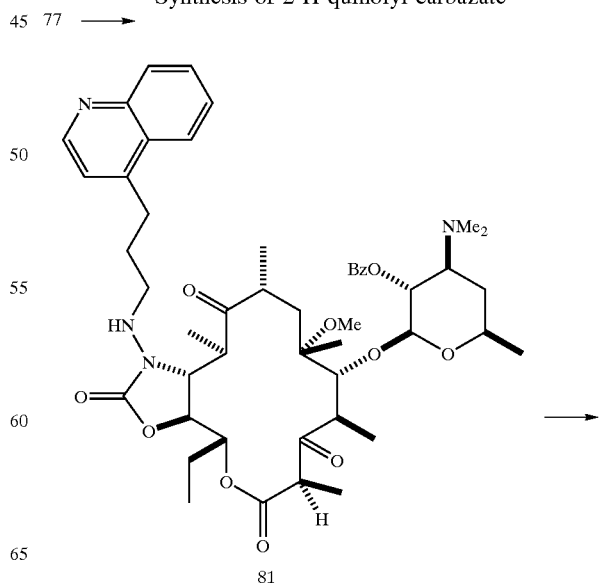

-continued

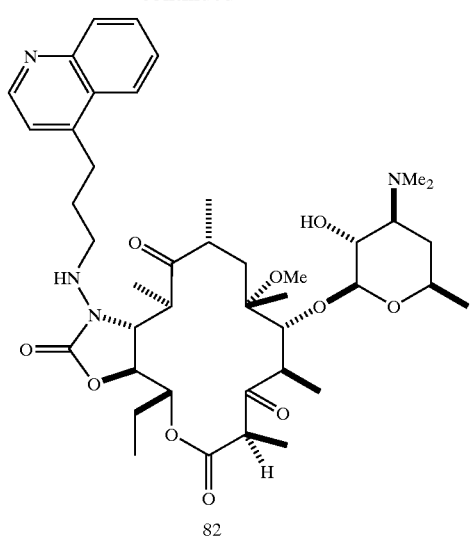

82

The cyclic carbazate 77 (Example 80, 1.0 eq) and 4-quinolinecarboxaldehyde (1.2 eq) were dissolved in methanol. Glacial acetic acid (4.0 eq) was added. The solution was stirred at ambient temperature for 5 h. Sodium cyanoborohydride (2.0 eq) was added. The mixture was stirred overnight. The reaction was quenched by the addition of saturated aqueous sodium bicarbonate and then poured into EtOAc. The phases were separated. The organic layer was washed with brine and then dried over $Na_2SO_4$, filtered, and concentrated. Column chromatography (1:1 hexanes:EtOAc+2% $Et_3N$) gave the desired product 81 (78.3%). ES/MS m/z 888 (MH$^+$), $C_{49}H_{66}N_4O_{11}$=887 g/mol.

A 0.05M solution of 81 in methanol was refluxed for 15 h. The mixture was brought to ambient temperature and concentrated. Column chromatography (2:3 hexanes:EtOAc+2% $Et_3N$) gave the desired 2-H quinolyl carbazate 82. ES/MS m/z 392 [(M+2H$^+$)/2], $C_{48}H_{67}N_5O_{11}$= 783 g/mol.

EXAMPLE 82

Synthesis of 2-H crotonaldehyde pyridyl-imidazole carbazate

77 ⟶

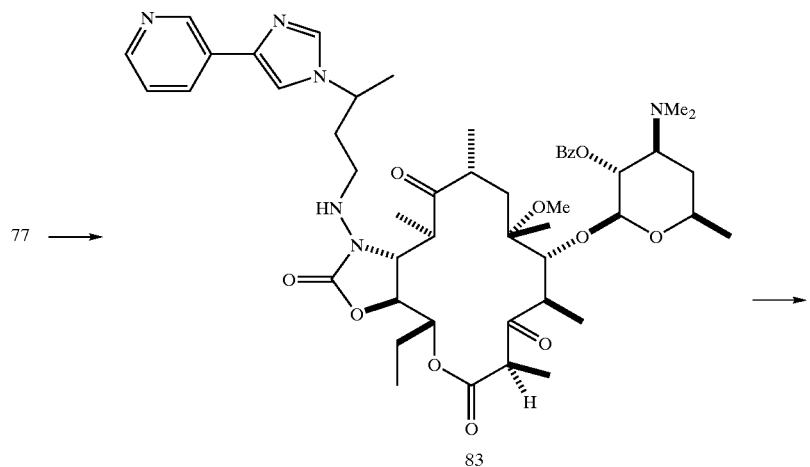

83

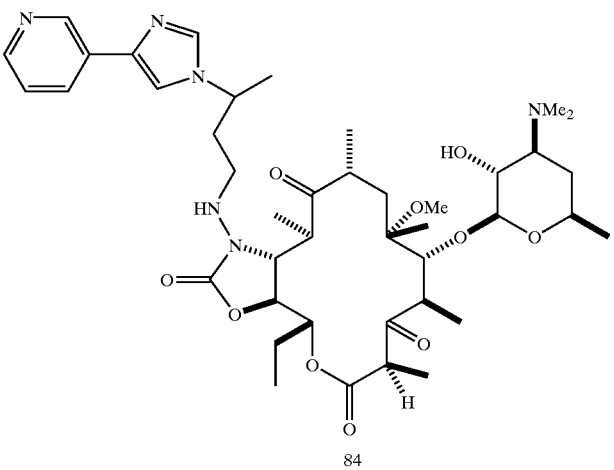

84

Compound 77 (Example 80) was converted to compound 83 as described in Example 80 for the analogous acrolein-derived compound except using crotonaldehyde in place of acrolein. ES/MS m/z 459 [(M+2H$^+$)/2], $C_{49}H_{68}N_6O_{11}$=917.

Compound 83 was converted to compound 84 as described in Example 80 for the analogous acrolein-derived compound. ES/MS m/z 407 [(M+2H$^+$)/2], $C_{41}H_{62}N_6O_{10}$=813 g/mol.

EXAMPLE 83

Synthesis of 2-gem-dimethyl carbamate water, and brine. The organic layer was dried over $Na_2SO_4$, filtered, and concentrated. Column chromatography (3:2 hexanes:EtOAc+2% $Et_3N$) gave the product 86. ES/MS m/z 446 [(M+2H$^+$)/2], $C_{48}H_{67}N_5O_{11}$=890 g/mol.

A 0.05M solution of 86 in methanol was refluxed for 15 h. The mixture was brought to ambient temperature and concentrated. Column chromatography (2:3 hexanes:EtOAc+2% $Et_3N$) gave the desired 2-gem-dimethyl carbamate 87. ES/MS m/z 394 [(M+2H$^+$)/2], $C_{48}H_{67}N_5O_{11}$=786 g/mol.

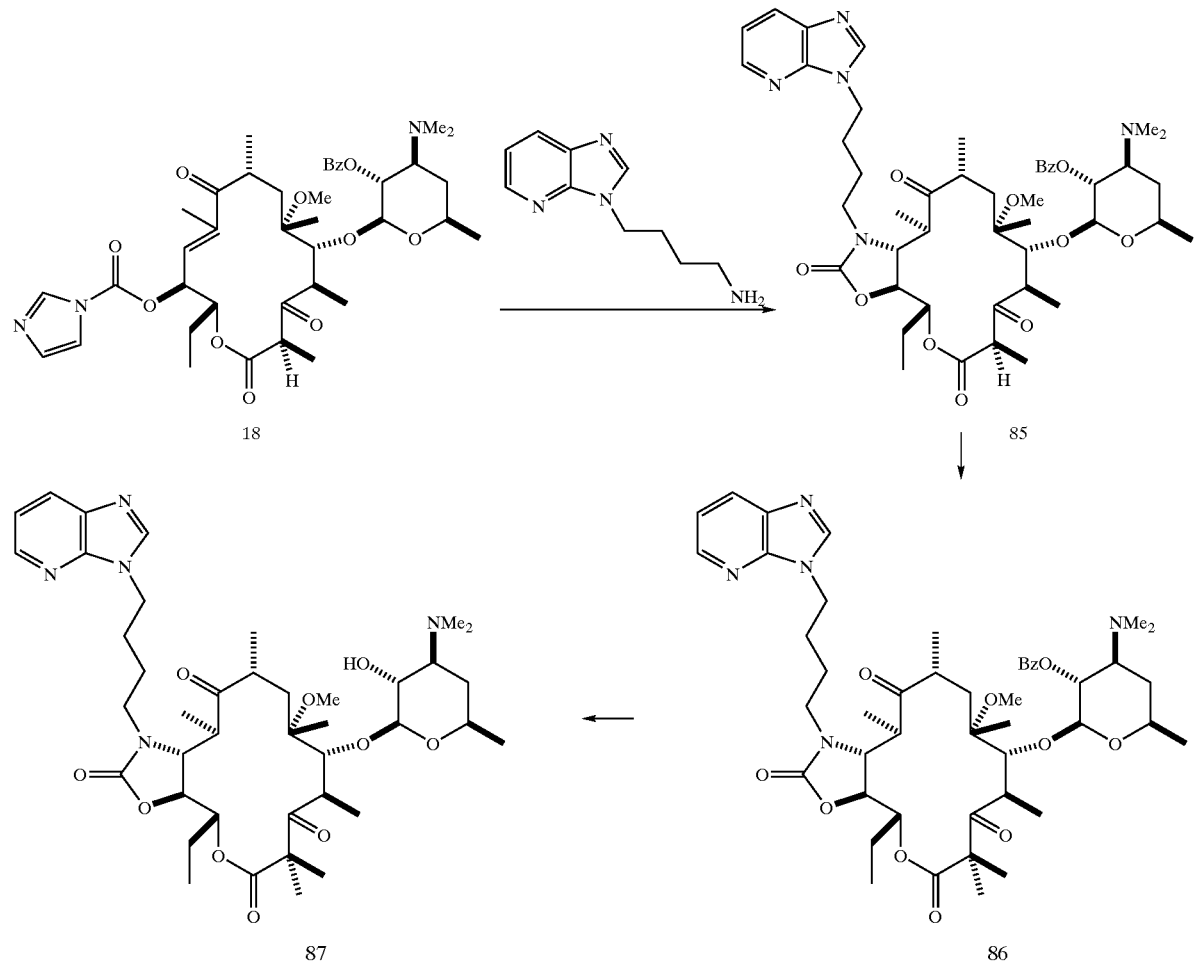

Compound 18 from Example 67 (1.0 eq) and the appropriate butanamine were dissolved in acetonitrile. The reaction was stirred at 70° C. for 14 h. The mixture was brought to ambient temperature, diluted with EtOAc, and washed sequentially with water and brine. The organic layer was dried over $Na_2SO_4$, filtered, and concentrated. Column chromatography (3:2 hexanes:EtOAc+2% $Et_3N$) gave 85. ES/MS m/z 439 [(M+2H$^+$)/2], $C_{47}H_{65}N_5O_{11}$=876 g/mol.

Compound 85 (1.0 eq) was dissolved in 1:1 THF:DMSO and cooled to 0° C. A solution of MeBr in ether (3.0 eq) was added. A solution of potassium tert-butoxide in THF was added dropwise over 20 min. The reaction was stirred at 0° C. for 2.5 h. The mixture was diluted with EtOAc, and washed sequentially with saturated sodium bicarbonate,

EXAMPLE 84

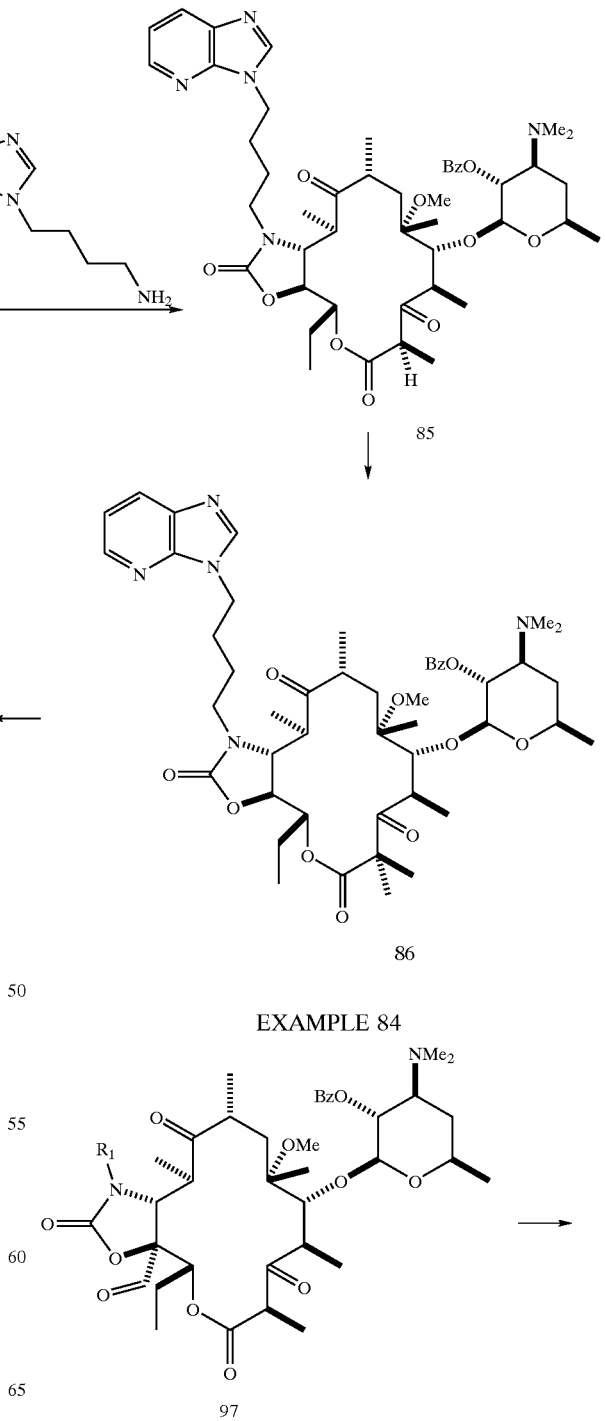

195

-continued

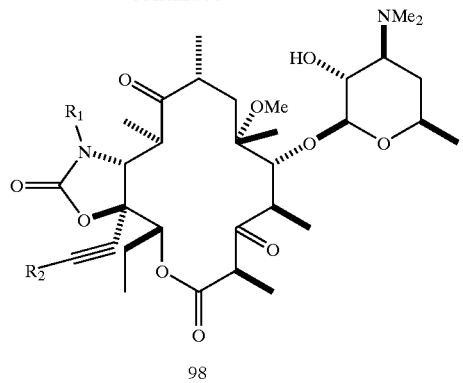

98

Step 1

To a stirred solution of aldehyde 97 ($R_1$=4-(4-(3-pyridyl)imidazolyl)butyl, synthesized using the product of Example 63 as the starting material: To a solution of the starting material in methylene chloride (0.2 M) is added benzoic anhydride (2 equiv.). The mixture is stirred under argon at room temperature until the starting material disappears, poured into sat. NaHCO3 aq and extracted with EtOAc. The organic portions are combined, washed with brine, dried with MgSO4 and concentrated in vacuo. The crude material is purified by flash column chromatography (silica gel, hexane/acetone to give compound 97) in $CH_2Cl_2$ (0.1 M) at 0 C. under argon is added triphenylphosphine (2.3 equiv.). The mixture is stirred for 10 min. and carbon tetra-bromide (1.15 equiv.) is added. The mixture is kept at 0 C. with stirring until complete conversion of the starting material, diluted with water and extracted with $CH_2Cl_2$. The combined extracts are dried with $MgSO_4$ and concentrated under reduced pressure. The resulting residue is purified by flash column chromatography (silica gel) to give 1,1-dibromo-olefin intermediate.

Step 2

To a stirred solution of material obtained from step 1 in anhydrous THF (0.1 M) at −78 C. under argon is added n-BuLi solution (1.6 M in hexane, 2.1 equiv.). The mixture is kept at −78 C. until complete conversion of the starting material, quenched with ammonium chloride aqueous solution and extracted with $CH_2Cl_2$. The combined extracts are dried with $MgSO_4$ and concentrated under reduced pressure. The resulting residue is purified by flash column chromatography (silica gel) to give 12-alkyne ($R_2$=H) intermediate.

Step 3

A 0.05M solution of the compound from step 2 is stirred in methanol at 70 C. for 16 h. The mixture is returned to ambient temperature, and volatiles are removed under reduced pressure. Purification by flash chromatography over silica gel gives compound 98.

The following compounds are made according to the procedure described above. 98b: $R_1$=4-(4-Phenyl-imidazol-1-yl)-butyl; 98c: $R_1$=4-Quinolin-4-yl-butyl; 98d: $R_1$=4-Imidazo[4,5-b]pyridin-3-yl-butyl; 98e: $R_1$=4-Imidazo[4,5-b]pyridin-1-yl-butyl; and 98f: $R_1$=4-(2-quinolyl)butyl.

196

EXAMPLE 85

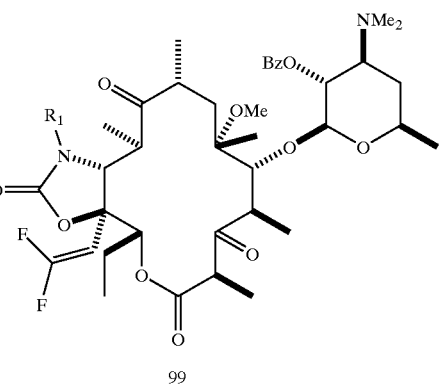

99

Step 1

A solution of aldehyde 97 ($R_1$=4-(4-(3-pyridyl)imidazolyl)butyl, 0.1 M, Example 84), powdered activated Zn (16 equiv.) and bromodifluoromethyl[tris(dimethylamino)]phosphonium bromide (8 equiv., made from dibromodifluoromethane and hexamethylphosphorous triamide according to procedure by Houlton, S. J. et al, *Tetrahedron* 1993, 8087) in anhydrous THF is heated to 50 C. under argon until complete conversion of the starting material. The reaction is cooled to room temperature. The solid is filtered off and the filtrate is partitioned between $CHCl_3$ and $NaHCO_3$ aq. The organic layer is separated, washed with brine, dried with $MgSO_4$ and concentrated under reduced pressure. The resulting residue is purified by flash column chromatography (silica gel) to give 1,1-difluoro-olefin intermediate.

Step 2

A 0.05M solution of the compound from step 1 is stirred in methanol at 70 C. for 16 h. The mixture is returned to ambient temperature, and volatiles are removed under reduced pressure. Purification by flash chromatography over silica gel gives compound 99.

The following compounds are made according to the procedure described above. 99b: $R_1$=4-(4-Phenyl-imidazol-1-yl)-butyl; 99c: $R_1$=4-Quinolin-4-yl-butyl; 99d: $R_1$=4-Imidazo[4,5-b]pyridin-3-yl-butyl; 99e: $R_1$=4-Imidazo[4,5-b]pyridin-1-yl-butyl; and 99f: $R_1$=4-(2-quinolyl)butyl.

EXAMPLE 86

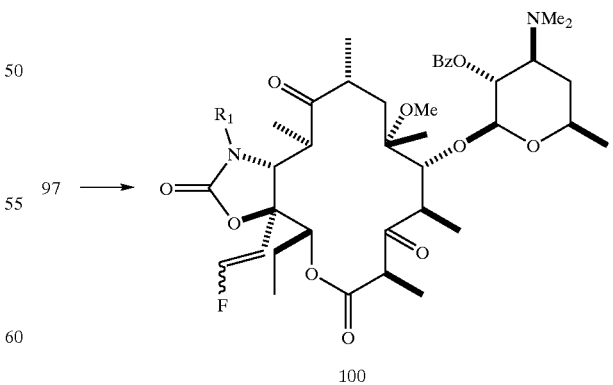

100

Step 1

To a solution of aldehyde 97 ($R_1$=4-(4-(3-pyridyl)imidazolyl)butyl, 0.1 M, Example 84) and fluoroiodomethyltriphenylphosphonium iodide (1.2 equiv., synthesized using commercially available materials according to the procedure by Burton and Greenlimb, *J. Org. Chem.*, 1975, 40, 2796) in anhydrous DMF at 0 C. is added zinc-copper couple (1.5 equiv.) under argon. The mixture is stirred at 0 C., then at elevated temperature (5~25 C.) until complete conversion of the starting material. The solid is filtered off and the filtrate is partitioned between $CHCl_3$ and $NaHCO_3$ aq. The organic layer is separated, washed with brine, dried with $MgSO_4$ and concentrated under reduced pressure. The resulting residue is purified by flash column chromatography (silica gel) to give fluoro-olefin intermediate as a mixture of E/Z isomers.

Step 2

A 0.05M solution of the compound from step 1 is stirred in methanol at 70 C. for 16 h. The mixture is returned to ambient temperature, and volatiles are removed under reduced pressure. Purification by flash chromatography over silica gel gives compound 100.

The following compounds are made according to the procedure described above. 100b: $R_1$=4-(4-Phenyl-imidazol-1-yl)-butyl; 100c: $R_1$=4-Quinolin-4-yl-butyl; 100d: $R_1$=4-Imidazo[4,5-b]pyridin-3-yl-butyl; 100e: $R_1$=4-Imidazo[4,5-b]pyridin-1-yl-butyl; and 100f: $R_1$=4-(2-quinolyl)butyl.

EXAMPLE 87

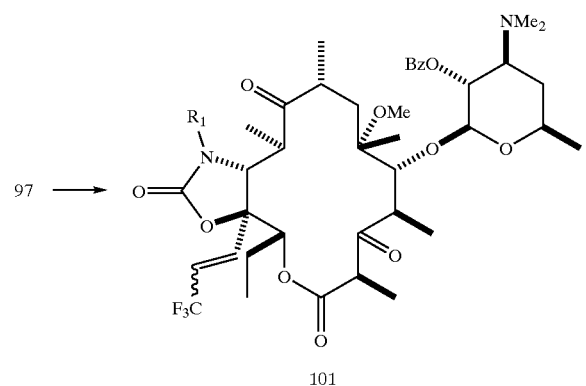

Step 1

Molecular sieves (4A, powder) is added to a 1 M solution of tetrabutylammonium fluoride in THF (10 equiv.), and the mixture is stirred at room-temperature overnight under argon. To the mixture is added a solution of aldehyde 97 ($R_1$=4-(4-(3-pyridyl)imidazolyl)butyl, 0.2 M, Example 84) and 2,2,2-trifluoroethyl-diphenylphosphine oxide (2 equiv., synthesized using commercially available materials according to the procedure by Ishibashi, H. et al, *J. Org. Chem.*, 2002, 67, 3156) in THF. After the mixture is stirred for 1 h, molecular sieves is removed by filtration. Water is added to the filtrate, and the whole is extracted with EtOAc. The organic extract is washed with brine, dried with $MgSO_4$ and concentrated under reduced pressure. The resulting residue is purified by flash column chromatography (silica gel) to give trifluoromethyl-olefin intermediate as a mixture of E/Z isomers.

Step 2

A 0.05M solution of the compound from step 1 is stirred in methanol at 70 C. for 16 h. The mixture is returned to ambient temperature, and volatiles are removed under reduced pressure. Purification by flash chromatography over silica gel gives compound 101.

The following compounds are made according to the procedure described above. 101b: $R_1$=4-(4-Phenyl-imidazol-1-yl)-butyl; 101c: $R_1$=4-Quinolin-4-yl-butyl; 101d: $R_1$=4-Imidazo[4,5-b]pyridin-3-yl-butyl; 101e: $R_1$=4-Imidazo[4,5-b]pyridin-1-yl-butyl; and 101f: $R_1$=4-(2-quinolyl)butyl.

EXAMPLE 88

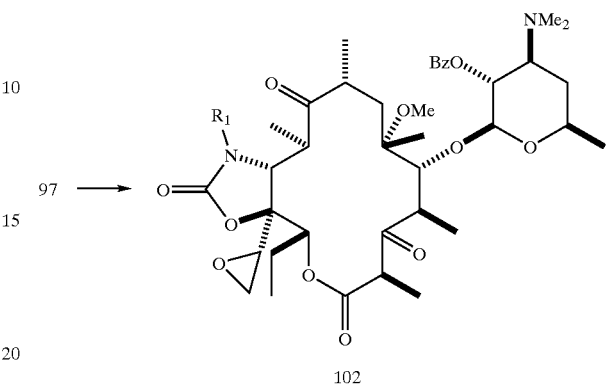

Step 1

To a stirred suspension of NaH (60% dispersion in oil, 1.2 equiv.) in dry DMSO (0.3 M) at 0 C. is added trimethylsulfoxonium iodide (1.2 equiv.). After 15 min., compound 97 ($R_1$=4-(4-(3-pyridyl)imidazolyl)butyl, 1 equiv., Example 84) in DMSO (0.2 M) is introduced. The reaction is stirred for 30 min (or until complete conversion of the starting material) at room temperature, diluted with water, and extracted with EtOAc. The organic layer is washed with brine, dried with $MgSO_4$ and concentrated under reduced pressure. The resulting residue is purified by flash column chromatography (silica gel) to give 12-epoxy intermediate.

Step 2

A 0.05M solution of the compound from step 1 is stirred in methanol at 70 C. for 16 h. The mixture is returned to ambient temperature, and volatiles are removed under reduced pressure. Purification by flash chromatography over silica gel gives compound 102.

The following compounds are made according to the procedure described above. 102b: $R_1$=4-(4-Phenyl-imidazol-1-yl)-butyl; 102c: $R_1$=4-Quinolin-4-yl-butyl; 102d: $R_1$=4-Imidazo[4,5-b]pyridin-3-yl-butyl; 102e: $R_1$=4-Imidazo[4,5-b]pyridin-1-yl-butyl; and 102f: $R_1$=4-(2-quinolyl)butyl.

EXAMPLE 89

Synthesis of Anhydrolide Derivatives (Scheme 9)

EXAMPLE 89(a)

Preparation of Compound 305

R1=H, R2=OMe, compound 23 in Example 68(c).
R1=CF3, R2=OMe, compound 204 in example 72(c).
R1=Et, R2=OMe, product of Example 8.
R1=Et, R2=O-allyl, see compound obtained from step 4 for making 303 in Example 70(d).

EXAMPLE 89(b)

Preparation of Compound 306

R1=H,R2=OMe

Step 1

Same as synthesis of 24 in Example 68(d).

Step 2

R3-W=4-(4-phenyl-imidazol-1-yl)-butyl. Same as synthesis of 25b in Example 68(e).

EXAMPLE 89(c)

Preparation of Compound 307

R1=Et, R2=O-allyl or O-propargyl

Step 1

Compound 305 is dissolved in a mixture of acetonitrile/3 N HCl aqueous (2:1) (0.1 M). The mixture is stirred under argon until the starting material disappears, poured into sat. NaHCO3 aq and extracted with EtOAc. The organic portions are combined, washed with brine, dried with MgSO4 and concentrated in vacuo. The crude material is purified by flash column chromatography (silica gel, hexane/acetone).

Step 2

To material obtained from step 1 in dichloromethane (0.1 M) at 0 C. is added triethylamine (2 equiv) and methanesulfonyl chloride (1.1 equiv). The mixture is stirred at 25 C. until complete conversion of the starting material (monitored by TLC and LC/MS), poured into sat. NaHCO3 aq and extracted with EtOAc. The organic portions are combined, washed with brine, dried with MgSO4 and concentrated in vacuo. The crude material is purified by flash column chromatography (silica gel, hexane/acetone).

Step 3

To material obtained from step 2 in THF (0.1 M) at 0 C. is added sodium hydride (2.2 equiv.). The mixture is stirred at rt until complete conversion of the starting material (monitored by TLC and LC/MS), poured into sat. NaHCO3 aq and extracted with EtOAc. The organic portions are combined, washed with brine, dried with MgSO4 and concentrated in vacuo. The crude material is purified by flash column chromatography (silica gel, hexane/acetone) to give compound 307.

EXAMPLE 89(d)

Preparation of Compound 308 (Route 1)

R1=H, R2=OMe, R3-W=4-(4-phenyl-imidazol-1-yl)-butyl

Step 1

Compound 306 is dissolved in a mixture of acetonitrile/3 N HCl aqueous (2:1). The mixture is stirred under argon until the starting material disappears, poured into sat. NaHCO3 aq and extracted with EtOAc. The organic portions are combined, washed with brine, dried with MgSO4 and concentrated in vacuo. The crude material is purified by flash column chromatography (silica gel, hexane/acetone).

Step 2

To material obtained from step 1 in dichloromethane at 0 C. was added triethylamine (2 equiv) and methanesulfonyl chloride (1.1 equiv). The mixture is stirred at rt until complete conversion of the starting material (monitored by TLC and LC/MS), poured into sat. NaHCO3 aq and extracted with EtOAc. The organic portions are combined, washed with brine, dried with MgSO4 and concentrated in vacuo. The crude material is purified by flash column chromatography (silica gel, hexane/acetone).

Step 3

To material obtained from step 2 in THF at 0 C. is added sodium hydride (1.2 equiv.). The mixture is stirred at rt until complete conversion of the starting material (monitored by TLC and LC/MS), poured into sat. NaHCO3 aq and extracted with EtOAc. The organic portions are combined, washed with brine, dried with MgSO4 and concentrated in vacuo. The crude material is purified by flash column chromatography (silica gel, hexane/acetone).

Step 4

The solution of material obtained from step 3 in MeOH (0.05 M) is heated to 60 C. until the starting material disappears. The solvent is removed under reduced pressure. Purification using flash chromatography (silica gel, hexane/acetone) then gives the desired material 308.

EXAMPLE 89(e)

Preparation of Compound 308 (Route 2)

R1=Et,R3-W=H

Step 1

A 0.2M solution of the compound 307 and 1,1-carbonyldiimidazole (2.0 eq) in tetrahydrofuran is cooled to −15 C. Sodium hydride (60% dispersion in mineral oil, 1.2 eq) is added. The mixture is stirred at −15 C. for 15 min and at 0 C. for an additional 10 min. The reaction is diluted with ethyl acetate and quenched with saturated aqueous sodium bicarbonate. The layers are separated. The organic layer is washed with water and brine, dried over magnesium sulfate, filtered, and concentrated. The crude material is used without further purification.

Step 2

Ammonium hydroxide (90 eq) is added to a 0.15M solution of the compound from step 1 in 10:1 acetonitrile-:tetrahydrofuran. The mixture is stirred at 50 C. for 16 h and then returned to ambient temperature. The reaction mixture is poured into EtOAc and saturated sodium bicarbonate. The layers are separated. The organic layer is washed with water and brine, dried over magnesium sulfate, filtered, and concentrated. The crude material is purified by flash chromatography over silica gel.

Step 3. Heck Reaction

R2=(2E)-3-(3-quinolyl)prop-2-en-1-oxy

Tris(dibenzylideneacetone)dipalladium(0) chloroform adduct (0.25 eq) is added to a degassed 0.1M solution of compound obtained from step 2, tri-O-tolylphosphine (1.0 eq), 3-bromoquinoline (10 eq), and triethylamine (2.0 eq) in acetonitrile. The mixture is stirred at 70 C. for 30 h and returned to ambient temperature. The reaction mixture is poured into EtOAc and saturated sodium bicarbonate. The layers are separated. The organic layer is washed with water and brine, dried over magnesium sulfate, filtered through Celite, and concentrated. The crude material is purified by flash chromatography over silica gel to give the desired compound.

Step 3. Sonogashira Reaction

R2=3-(5-(2-pyridyl)-2-thienyl)prop-2-yn-1-oxy

Tetrakis(triphenylphosphine)palladium(0) (0.25 eq) and copper(I) iodide (0.25 eq) are added to a degassed 0.1M solution of compound obtained from step 2, 5-bromo-2-(2-pyridyl)thiophene (10 eq), and triethylamine (2.0 eq) in N,N-dimethylformamide. The mixture is stirred at 80 C. for 16 h and returned to ambient temperature. The reaction mixture is poured into EtOAc and saturated sodium bicarbonate. The layers are separated. The organic layer is washed with water and brine, dried over magnesium sulfate, filtered through Celite, and concentrated. The crude material is purified by flash chromatography over silica gel to give the desired compound.

Step 4

A 0.05M solution of the compound from step 3 is stirred in methanol at 70 C. for 16 h. The mixture is returned to ambient temperature, and volatiles are removed under reduced pressure. Purification by flash chromatography over silica gel gives compound 308.

Compounds having general structure 308a are made following the above scheme. ArX (X=I, Br, Cl) are used in the step of Heck reaction. Compounds having general structure 308b are made following the above scheme. ArX (X=I, Br, Cl) are used in the step of Sonogashira reaction.

General Structure

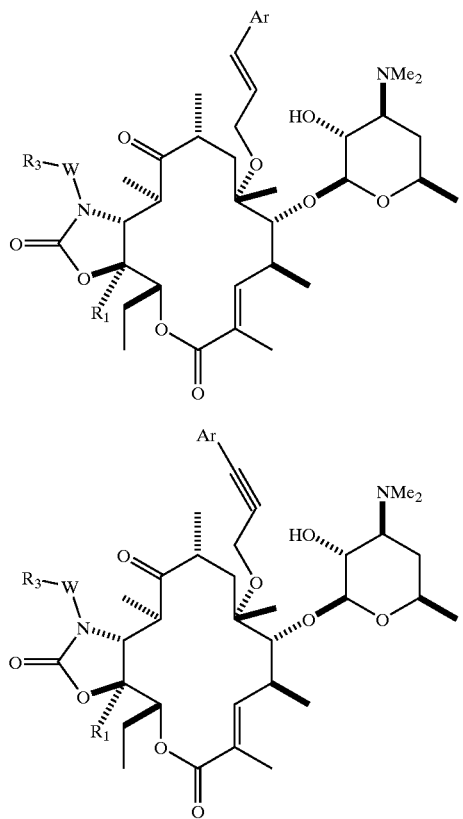

wherein Ar is 2-quinolyl, 3-quinolyl, 4-quinolyl, 5-quinolyl, 6-quinolyl, 7-quinolyl, 8-quinolyl, 1-naphthyl, 2-naphthyl,

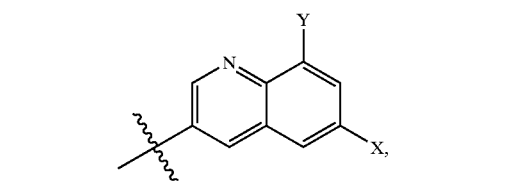

wherein when Y is H, X is F, Cl, OH, CN, $NO_2$, $NH_2$, pyridyl, OR, or Ac; and when X=H, Y=$NO_2$, $NH_2$, $CH_3$, $CF_3$,

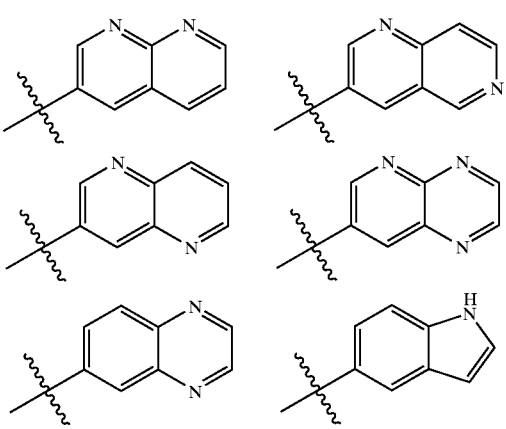

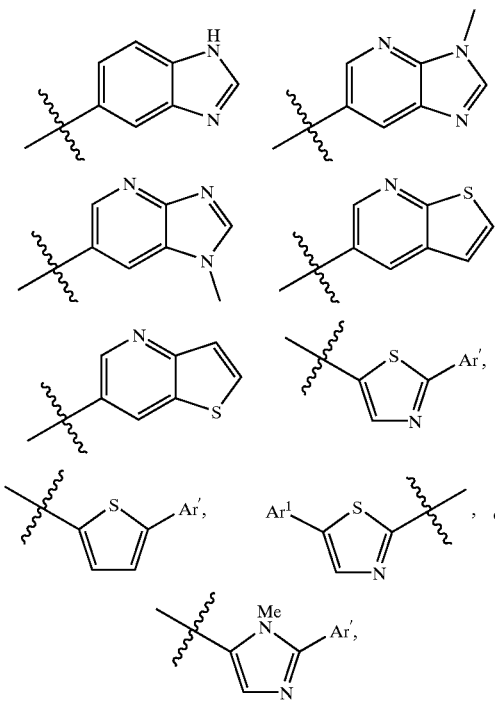

wherein Ar' is pyridyl, substituted-pyridyl, phenyl, substituted phenyl

EXAMPLE 90

Synthesis of 4-Iodo-1-trityl-1H-imidazole

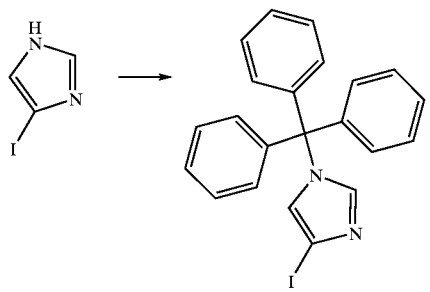

To a solution of 4-iodoimidazole (1 eq) in DMF at room temperature was added triphenylmethyl chloride (1.2 eq). After stirring at room temperature for 24 hours, the solution was poured into ice water and left stirring for 30 minutes. The solid was filtered and pumped on for several hours to yield the crude compound. Ethyl ether was added to the crude compound and the solution was filtered to yield 4-Iodo-1-trityl-1H-imidazole (92%) as a white solid. $MH^+$ (437).

EXAMPLE 91

Synthesis of 5-(1H-Imidazol-4-yl)-2-methyl-pyridine

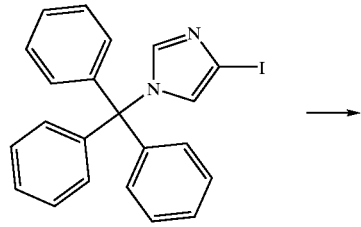

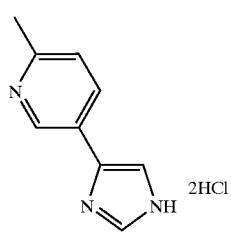

To a solution of 4-Iodo-1-trityl-1H-imidazole (1 eq) in THF at room temperature was added ethylmagnesium bromide (1.2) under dry conditions. After stirring for 90 minutes, zinc chloride (1.2 eq) was added to the reaction mixture. After stirring for another 90 minutes, tetrakis(triphenylphosphine)palladium (10%) and 5-bromo-2-methylpyridine (1.2 eq) were added to the reaction mixture. Following that, the reaction mixture was heated in a 70° C. oil bath overnight. Upon cooling, the reaction was diluted with dichloromethane and washed with a EDTA buffer (at pH~9), NaCl$_{(sat)}$, dried over sodium sulfate, filtered and concentrated. The crude product was dissolved in ethanol and concentrated HCl was added to the solution at room temperature. The reaction mixture was heated in a 50° C. oil bath for 2 hours. Upon cooling, the reaction was filtered and washed with ethyl ether to yield 5-(1H-Imidazol-4-yl)-2-methyl-pyridine (63%). MH$^+$(160).

EXAMPLE 92

Synthesis of Isoindole-1,3-diones

EXAMPLE 92(a)

Synthesis of 2-[4-(6-Methyl-pyridin-3-yl)-imidazol-1-ylmethyl]-isoindole-1,3-dione

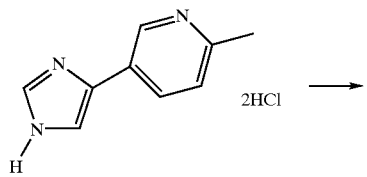

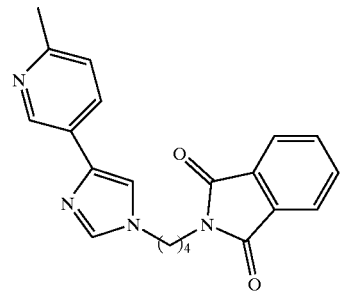

To a solution of 5-(1H-Imidazol-4-yl)-2-methyl-pyridine (1 eq) in DMF was added potassium carbonate (4 eq) at room temperature under dry conditions. After heating the reaction mixture in a 80° C. oil bath for 1 hour, N-(4-bromobutyl)phtalimide (3.9 eq) was added to the mixture. The solution was left stirring in a 80° C. oil bath for 24 hours. Upon cooling, the reaction was filtered and the solid was washed with ethyl acetate. The filterate was diluted with ethyl acetate and washed with NH$_4$Cl$_{(sat)}$, H$_2$O, NaCl$_{(sat)}$, dried over sodium sulfate, filtered and concentrated. The crude product was purified by flash chromatography using an initial solvent gradient of 97% DCM, 3% MeOH and 0.1% TEA (1L) to afford the product (37%). MH$^+$(361).

EXAMPLE 92(b)

Synthesis of 2-Fluoro-5-(1-trityl-1H-imidazol-4-yl)-pyridine

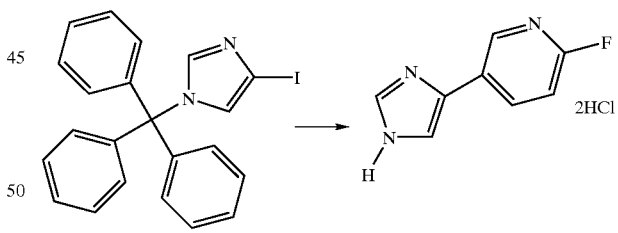

To a solution of 4-Iodo-1-trityl-1H-imidazole (1 eq) in THF at room temperature was added ethylmagnesium bromide (1.2 eq) under dry conditions. After stirring for 90 minutes, zinc chloride (1.2 eq) was added to the reaction mixture. After stirring for another 90 minutes, tetrakis(triphenylphosphine)palladium (10%) and 5-bromo-2-fluoropyridine (1.2 eq) were added to the reaction mixture. Subsequent reaction conditions and work up are as described previously, in Example 73 to afford the solid 2-Fluoro-5-(1H-imidazol-4-yl)-pyridine (46%). MH$^+$(164).

EXAMPLE 92(c)

Synthesis of 2-{4-[4-(6-Fluoro-pyridin-3-yl)-imidazol-1-ylmethyl]-butyl}-isoindole-1,3-dione

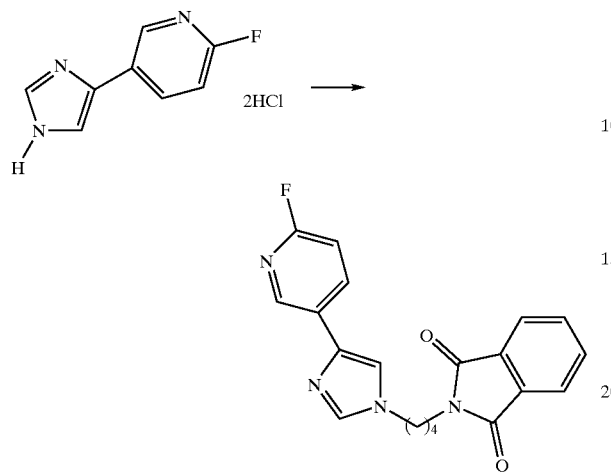

To a solution of 2-Fluoro-5-(1H-imidazol-4-yl)-pyridine (1 eq) in DMF was added potassium carbonate (5 eq) at room temperature under dry conditions. After heating the reaction mixture in a 80° C. oil bath for 1 hour, N-(4-bromobutyl)phtalimide (4 eq) was added to the mixture. The solution was left stirring in a 80° C. oil bath for 24 hours. Upon cooling, the reaction was filtered and the solid was washed with ethyl acetate. The filterate was diluted with ethyl acetate and washed with $NH_4Cl_{(sat)}$, $H_2O$, $NaCl_{(sat)}$, dried over sodium sulfate, filtered and concentrated. The crude product was purified by flash chromatography using an initial solvent gradient of 97% DCM, 3% MeOH and 0.1% TEA (1L) to yield 2-{4-[4-(6-Fluoro-pyridin-3-yl)-imidazol-1-ylmethyl]-butyl}-isoindole-1,3-dione (55%). $MH^+$(365).

EXAMPLE 92(d)

Synthesis of 5-(1-Trityl-1H-imidazol-4-yl)-pyrimidine (A)

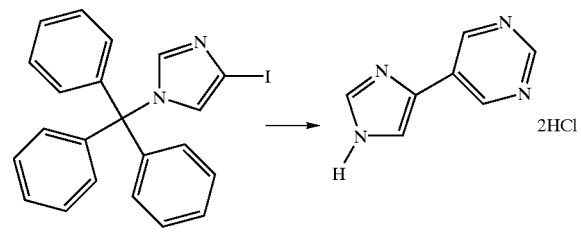

To a solution of 4-Iodo-1-trityl-1H-imidazole (A) (1 eq) in THF (100 mL) at room temperature was added ethylmagnesium bromide (1.2 eq) under dry conditions. After stirring for 90 minutes, zinc chloride (1.2 eq) was added to the reaction mixture. After stirring for another 90 minutes, tetrakis (triphenylphosphine)palladium (10%) and 5-bromopyrimidine (1.2 eq) were added to the reaction mixture. Subsequent reaction conditions and work up are as described previously in Example 73, the resulting solid 5-(1H-Imidazol-4-yl)-pyrimidine (46%) was collected by filtration and used without further purification. $MH^+$(147).

EXAMPLE 92(e)

Synthesis of 2-[4-(4-Pyrimidin-5-yl-imidazol-1-yl)-butyl]-isoindole-1,3-dione

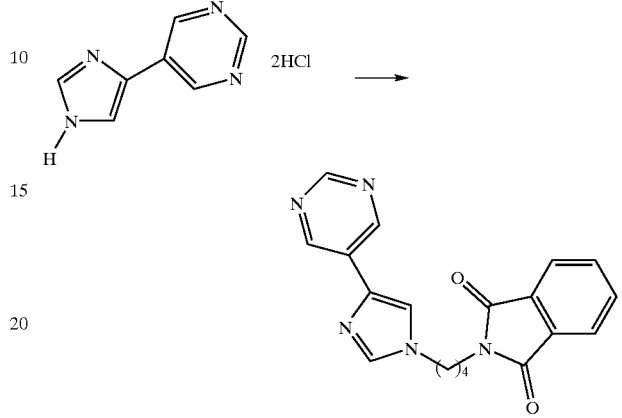

Synthesis was performed as in Example 74, to yield 2-[4-(4-Pyrimidin-5-yl-imidazol-1-yl)-butyl]-isoindole-1,3-dione (48%).

$MH^+$(348).

EXAMPLE 92(f)

Synthesis of 2-(1H-Imidazol-4-yl)-pyrazine

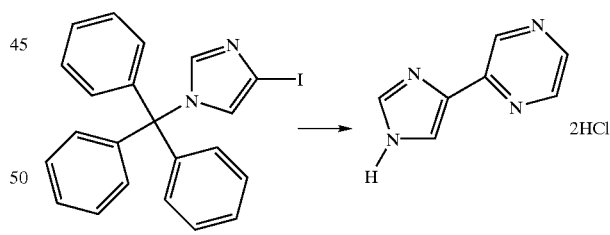

To a solution of 4-Iodo-1-trityl-1H-imidazole (1 eq) in THF at room temperature was added ethylmagnesium bromide (1.2 eq) under dry conditions. After stirring for 90 minutes, zinc chloride (1.2 eq) was added to the reaction mixture. After stirring for another 90 minutes, tetrakis (triphenylphosphine) palladium (10%) and 5-bromopyrazine (1.3 eq) were added to the reaction mixture. Subsequent reaction conditions and work up are as described previously in Example 73, the resulting solid 2-(1H-Imidazol-4-yl)-pyrazine (37%) was collected by filtration. $MH^+$(147).

EXAMPLE 92(g)

Synthesis of 2-[4-(4-Pyrazin-2-yl-imidazol-1-yl)-butyl]-isoindole-1,3-dione

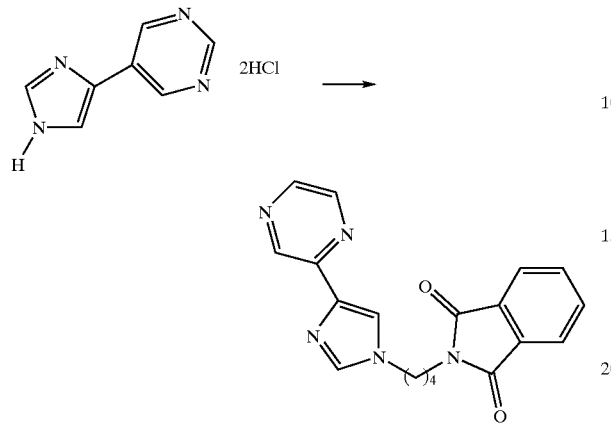

Synthesis was performed as in Example 74, to yield 2-[4-(4-Pyrazin-2-yl-imidazol-1-yl)-butyl]-isoindole-1,3-dione (A) (48%). MH$^+$(348).

EXAMPLE 92(h)

Synthesis of 2-Methoxy-5-(1-trityl-1H-imidazol-4-yl)-pyridine

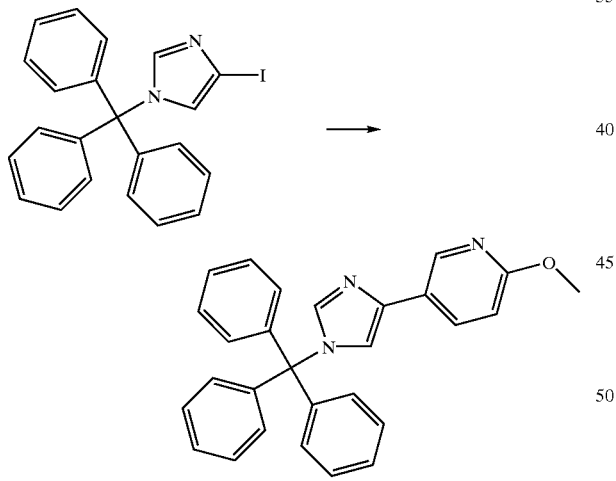

To a solution of 4-Iodo-1-trityl-1H-imidazole (A) (1 eq) in THF at room temperature was added ethylmagnesium bromide (1.2 eq) under dry conditions. After stirring for 90 minutes, zinc chloride (1.2 eq) was added to the reaction mixture. After stirring for another 90 minutes, tetrakis(triphenylphosphine)palladium (10%) and 5-bromo-2-methoxypyridine (1.2 eq) were added to the reaction mixture. Upon cooling, the reaction was diluted with dichloromethane and washed with a EDTA buffer (at pH~9), NaCl$_{(sat)}$, dried over sodium sulfate, filtered and concentrated. MH$^+$(418).

EXAMPLE 92(i)

Synthesis of 3-(5-Methyl-1-trityl-1H-imidazol-4-yl)-pyridine

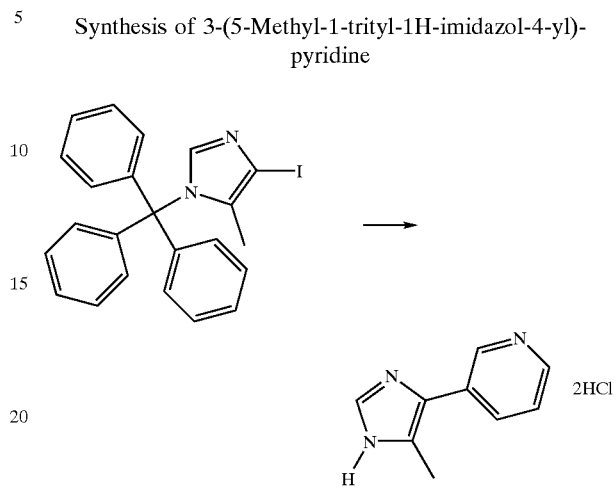

To a solution of 4-Iodo-5-methyl-1-trityl-1H-imidazole (1 eq) in THF at room temperature was added ethylmagnesium bromide (1.2 eq) under dry conditions. After stirring for 90 minutes, zinc chloride (1.2 eq) was added to the reaction mixture. After stirring for another 90 minutes, tetrakis(triphenylphosphine)palladium (10%) and 3-bromopyridine (1.2 eq) were added to the reaction mixture. Subsequent reaction conditions were performed as in Example 73 to give 3-(5-methyl-1H-imidazol-4-yl)-pyridine (92%). MH$^+$(160).

EXAMPLE 92(j)

Synthesis of 2-[4-(5-Methyl-4-pyridin-3-yl-imidazol-1-yl)-butyl]-isoindole-1,3-dione (A), and 2-[4-(4-Methyl-5-pyridin-3-yl-imidazol-1-yl)-butyl]-isoindole-1,3-dione (B)

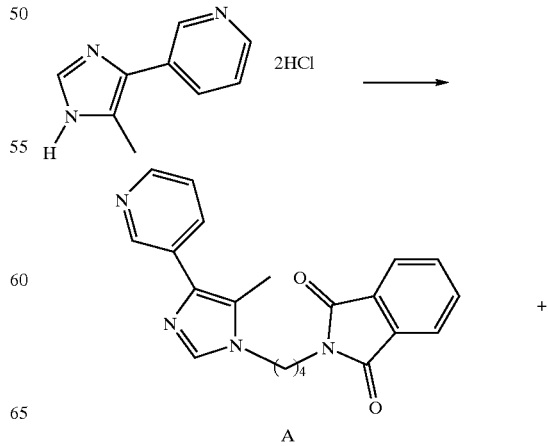

-continued

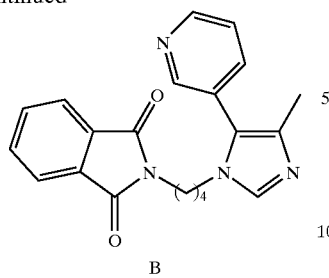

B

To a solution of sodium hydride (4.5 eq) in DMF was added slowly a solution of 3-(5-methyl-1H-imidazol-4-yl)-pyridine (1 eq) in DMF. Once the reaction mixture was left stirring at-room temperature for 30 minutes, N-(4-bromobutyl)phtalimide (2 eq) was added to the mixture. The solution was left stirring in a 80° C. oil bath for 90 minutes. Upon cooling, the reaction was diluted with ethyl acetate and washed with $NH_4Cl_{(sat)}$, $H_2O$, $NaCl_{(sat)}$, dried over sodium sulfate, filtered and concentrated. The crude product was purified by flash chromatography (97% DCM, 3% MeOH and 0.1% TEA) to yield a 6 to 1 mixture of (A) and (B) (28%). $MH^+$(361).

EXAMPLE 92(k)

Synthesis of 3-(2-Methyl-1-trityl-1H-imidazol-4-yl)-pyridine

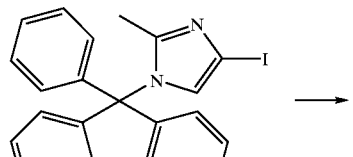

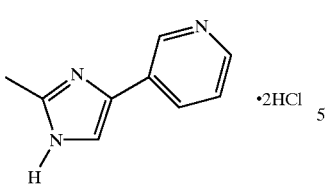

·2HCl

To a solution of 4-Iodo-3-methyl-1-trityl-1H-imidazole (1 eq) in THF at room temperature was added ethylmagnesium bromide (1.2 eq) under dry conditions. After stirring for 90 minutes, zinc chloride (1.2 eq) was added to the reaction mixture. After stirring for another 90 minutes, tetrakis(triphenylphosphine)palladium (10%) and 3-bromopyridine (1.1 eq) were added to the reaction mixture. Subsequent reaction conditions were performed as in Example 91(b) to provide 3-(2-methyl-1H-imidazol-4-yl)-pyridine (88%) $MH^+$(160).

EXAMPLE 92(l)

Synthesis of 2-Methyl-2-(4-pyridin-3-yl-imidazol-1-yl)-propionic acid ethyl ester

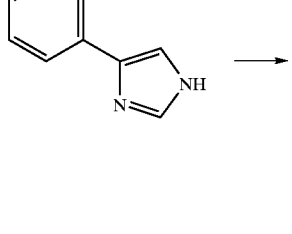

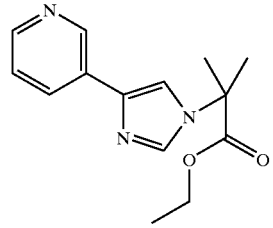

To a solution of 3-(1H-Imidazol-4-yl)-pyridine (1 eq) in DMF was added potassium carbonate (2 eq) under dry condition. After stirring for 1 hour, ethyl 2-bromoisobutyrate (5 eq) was added to the mixture. The solution was left stirring over 36 hours at room temperature. The reaction solvent was removed in vacuo and the solid was diluted with ethyl acetate washed with $H_2O$, $NaCl_{(sat)}$, dried over sodium sulfate, filtered and concentrated. The crude product was purified by flash chromatography using a solvent gradient of 97% DCM, 3% MeOH and 0.1% TEA to yield 2-Methyl-2-(4-pyridin-3-yl-imidazol-1-yl)-propionic acid ethyl ester (33%). $MH^+$(260).

EXAMPLE 92(m)

Synthesis of 2-Methyl-2-(4-pyridin-3-yl-imidazol-1-yl)-propionaldehyde

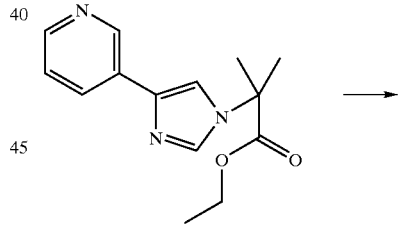

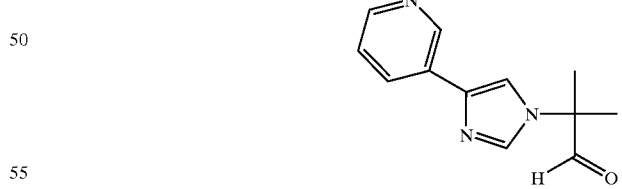

To a solution of 2-Methyl-2-(4-pyridin-3-yl-imidazol-1-yl)-propionic acid ethyl ester (1 eq) in DCM at −78° C. was added diisobutylaluminum hydride (4 eq). After leaving the reaction mixture stir at −78° C. for 3 hours, methanol (4 eq) was added to the reaction mixture at −78° C. and the solution was warmed to room temperature over 60 minutes. Ethyl acetate was added to the solution and after 30 minutes the solution was filtered and concentrated to give 2-Methyl-2-(4-pyridin-3-yl-imidazol-1-yl)-propionaldehyde (70%). $MH^++H_2O$ (234).

EXAMPLE 92(n)

Synthesis of 4-Methyl-4-(4-pyridin-3-yl-imidazol-1-yl)pentanoic acid methyl ester

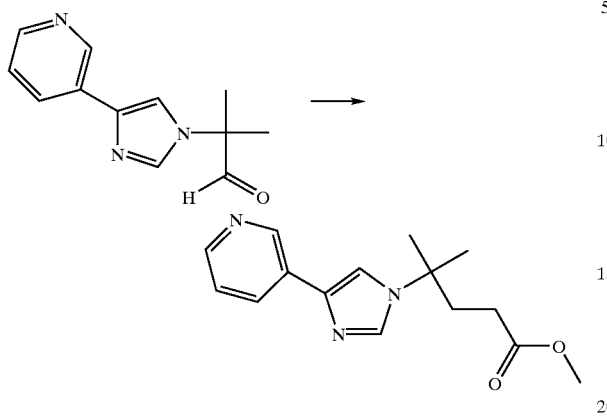

To a solution of sodium hydride (1.2 eq) in THF was added slowly methyl diethylphosphonoacetate (1.2 eq) at 0° C. under dry conditions and the mixture was stirred at room temperature for 30 minutes. A solution of 2-Methyl-2-(4-pyridin-3-yl-imidazol-1-yl)-propionaldehyde (1 eq), in THF was added dropwise at room temperature and the mixture was stirred for 1 hour at the same temperature. The mixture was poured into H$_2$O and the whole was extracted with ethyl acetate. The organic layer was washed with NaCl$_{(sat)}$, dried over sodium sulfate, filtered and concentrated. To a solution of the residue in ethyl acetate, was added Palladium, 10 wt. % on activated carbon and left stirring under 1 atm hydrogen overnight. After the catalyst was filtered off, the filtrate was purified by flash chromatography using a solvent gradient 97% DCM, 3% MeOH and 0.1% TEA to yield 4-Methyl-4-(4-pyridin-3-yl-imidazol-1-yl)pentanoic acid methyl ester (75%). MH$^+$(274).

EXAMPLE 92(o)

Synthesis of 4-Methyl-4-(4-pyridin-3-yl-imidazol-1-yl)-pentan-1-ol

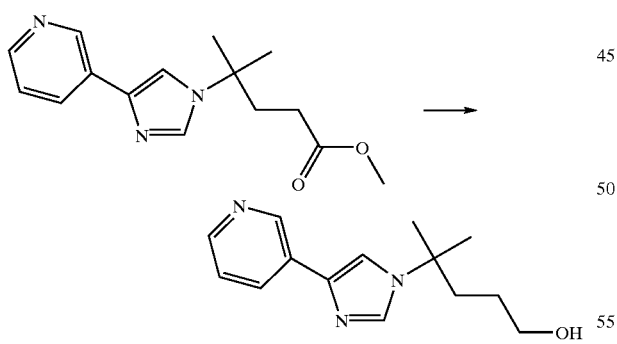

To a solution of 4-Methyl-4-(4-pyridin-3-yl-imidazol-1-yl)pentanoic acid methyl ester (1 eq) in ethanol was added sodium borohydride (4 eq) at room temperature. The reaction mixture was heated in a 50° C. oil bath for 60 minutes and then quenched by addition of H$_2$O. Once the reaction solvent was removed in vacuo, a solution of the residue in dichloromethane was washed with NaCl$_{(sat)}$, dried over sodium sulfate, filtered and concentrated to give 4-Methyl-4-(4-pyridin-3-yl-imidazol-1-yl)-pentan-1-ol (68%). MH$^+$ (246).

EXAMPLE 92(p)

Synthesis of 2-[4-Methyl-4-(4-pyridin-3-yl-imidazol-1-yl)-pentyl]-isoindole-1,3-dione

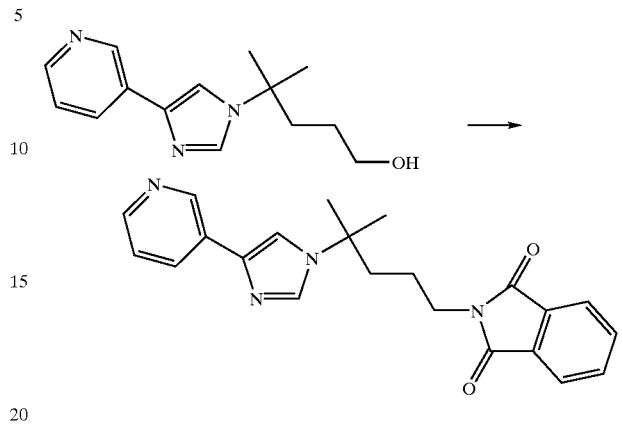

To a solution of 4-Methyl-4-(4-pyridin-3-yl-imidazol-1-yl)-pentan-1-ol (1 eq) in THF (20 mL) was added dropwise diethyl azodicarboxylate (1.1 eq), triphenyl phosphine (1.1 eq) and phtalimide (1.1 eq). The yellow solution was stirred at room temperature overnight and the solution was concentrated. The crude product was directly purified by flash chromatography using a solvent gradient of 97% DCM, 3% MeOH and 0.1% TEA to yield 2-[4-Methyl-4-(4-pyridin-3-yl-imidazol-1-yl)-pentyl]-isoindole-1,3-dione (66%). MH$^+$ (375).

EXAMPLE 92(q)

2-Imidazo[4,5-b]pyridin-1-yl-2-methyl-propionic acid ethyl ester (1) and 2-Imidazo[4,5-b]pyridin-3-yl-2-methyl-propionic acid ethyl ester (2)

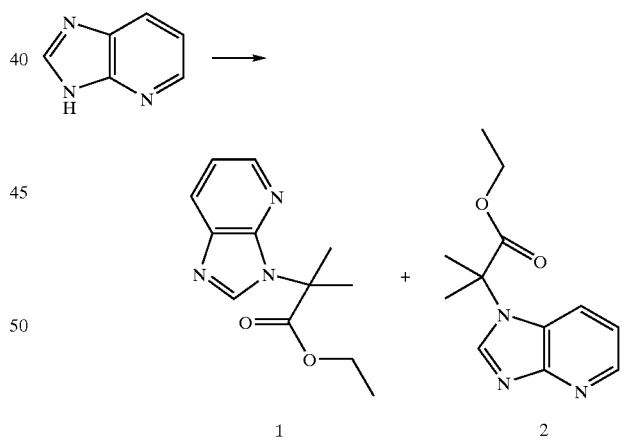

To a solution of 4-azabenzidimazole (1 eq) in DMF was added potassium carbonate (2 eq) under dry condition. After stirring for 1 hour, ethyl 2-bromoisobutyrate (5 eq) was added to the mixture. The solution was left stirring for 7 days at room temperature. The reaction solvent was removed in vacuo and the solid was diluted with dichloromethane, washed with H$_2$O, NaCl$_{(sat)}$, dried over sodium sulfate, filtered and concentrated. The crude product was purified by flash chromatography using a solvent gradient of 98% DCM, 2% MeOH and 0.1% TEA to afford 2-Imidazo[4,5-b]pyridin-3-yl-2-methyl-propionic acid ethyl ester (1)

(33%), and subsequently 2-Imidazo[4,5-b]pyridin-1-yl-2-methyl-propionic acid ethyl ester (2) (66%) as the later spot. MH⁺(234).

EXAMPLE 93

2-Imidazo [4,5-b]pyridin-1-yl-2-methyl-propan-1-ol

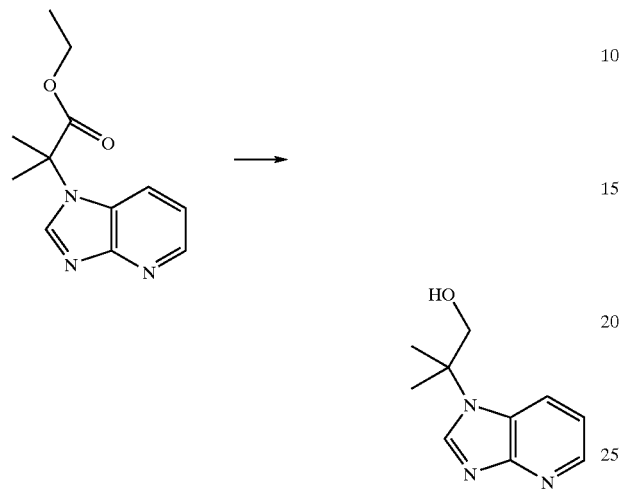

To a solution of 2-Imidazo[4,5-b]pyridin-1-yl-2-methyl-propionic acid ethyl ester (1 eq) in ethanol was added sodium borohydride (4 eq) at room temperature. The reaction mixture was left stirring at room temperature overnight and then quenched by addition of H₂O. Once the reaction solvent was removed in vacuo, the residue was dissolved in dichloromethane, washed with NaCl$_{(sat)}$, dried over sodium sulfate, filtered and concentrated to give compound 2-Imidazo[4,5-b]pyridin-1-yl-2-methyl-propan-1-ol (92%) MH⁺(192).

EXAMPLE 94

4-Imidazo[4,5-b]pyridin-1-yl-4-methyl-pent-2-enoic acid methyl ester

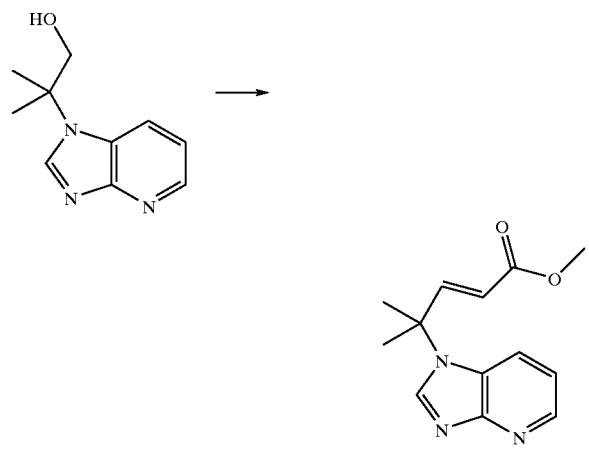

To a –78° C. cooled stirred solution of oxalyl chloride (1 eq) in dichloromethane was added dimethyl sulfoxide (2 eq). After an additional 5 minutes, 2-Imidazo[4,5-b]pyridin-1-yl-2-methyl-propan-1-ol (1 eq) dissolved in dichloromethane was added to the cooled solution via cannula. The resulting heterogeneous mixture was stirred at –78° C. for 30 minutes, and triethylamine (5 eq) was added to produce a thick white slurry. After stirring at –78° C. for 15 minutes, the mixture was allowed to warm slowly to 0° C., diluted with dichloromethane, washed with NaCl$_{(sat)}$, dried over sodium sulfate, filtered and concentrated. Following this, to a solution of sodium hydride (1 eq) in THF was added methyl diethylphosphonoacetate (1 eq) at 0° C. The mixture was stirred at room temperature for 30 minutes and a solution of the latter concentrated residue dissolved in THF was added dropwise to the mixture. The solution was stirred for 1 hour at the same temperature and then poured into H₂O, followed by an extraction with ethyl acetate. The organic layer was washed with NaCl$_{(sat)}$, dried over sodium sulfate, filtered and concentrated. The crude product was purified by flash chromatography using a solvent gradient of 97% DCM, 3% MeOH and 0.1% TEA to yield 4-Imidazo[4,5-b]pyridin-1-yl-4-methyl-pent-2-enoic acid methyl ester (93%). MH⁺(246).

EXAMPLE 95

2-(4-Imidazo[4,5-b]pyridin-1-yl-4-methyl-pentyl)-isoindole-1,3-dione

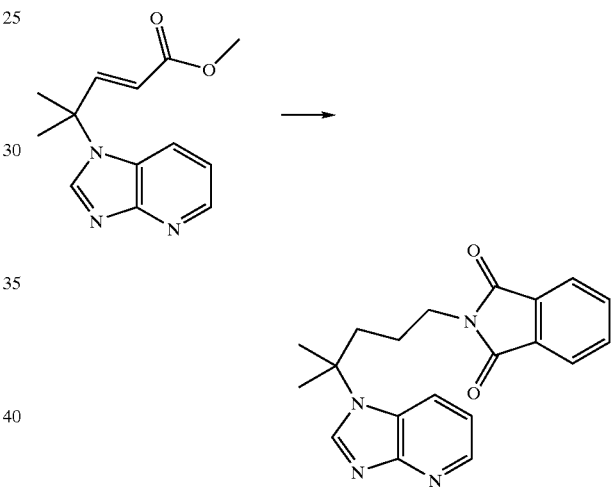

To a solution of 4-Imidazo[4,5-b]pyridin-1-yl-4-methyl-pent-2-enoic acid methyl ester (1 eq) was added Palladium, 10 wt. % on activated carbon, (10%) and left stirring under an atmospheric pressure of hydrogen for 2 days. After the catalyst was filtered off, the mixture was concentrated and dissolved in ethanol. To this solution was added sodium borohydride (4 eq) at room temperature. The reaction mixture was heated in a 50° C. oil bath for 60 minutes and then quenched by addition of H₂O. Once the solvent was removed in vacuo, a solution of the residue in dichloromethane was washed with NaCl$_{(sat)}$, dried over sodium sulfate, filtered and concentrated. To a solution of the residue in THF was added dropwise diethyl azodicarboxylate (1 eq), triphenyl phosphine (1 eq) and phtalimide (1 eq). The yellow solution was stirred at room temperature overnight and the solution was concentrated. The crude solid was treated with 3N HCl and ethyl acetate. Once the aqueous layer was seperated, it was added to ethyl acetate and treated with sodium bicarbonate under vigorous stirring to obtain a basic pH (~7). The organic phase was seperated and washed with NaCl$_{(sat)}$, dried over sodium sulfate, filtered and concentrated to give 2-(4-Imidazol[4,5-b]pyridin-1-yl-4-methyl-pentyl)-isoindole-1,3-dione (40%). MH⁺(349).

EXAMPLE 95(a)
2-Imidazo [4,5-b]pyridin-3-yl-2-methyl-propan-1-ol

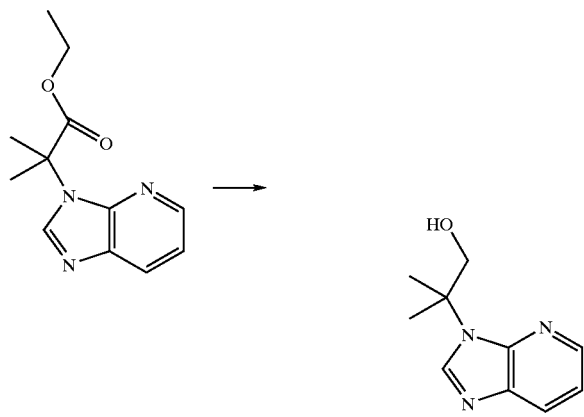

Reduction performed as in Example 93, to give compound 2-Imidazo[4,5-b]pyridin-3-yl-2-methyl-propan-1-ol (A) (16.53 g, 80.7%). MH⁺(192).

EXAMPLE 95(b)
4-Imidazo[4,5-b]pyridin-3-yl-4-methyl-pent-2-enoic acid methyl ester

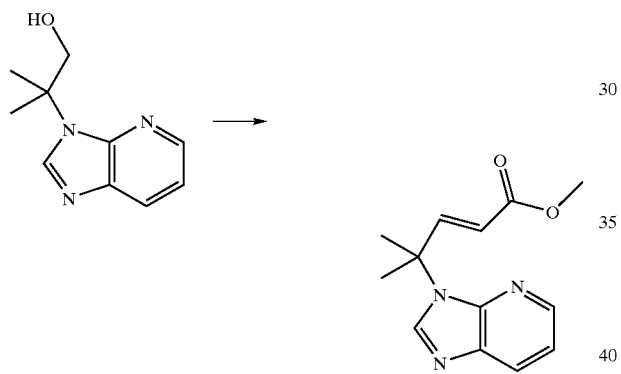

Reaction carried out as in Example 94, to yield 4-Imidazo [4,5-b]pyridin-3-yl-4-methyl-pent-2-enoic acid methyl ester (A) (15.8 g, 75%). MH⁺(246).

EXAMPLE 95(c)
2-(4-Imidazo[4,5-b]pyridin-3-yl-4-methyl-pentyl)-isoindole-1,3-dione

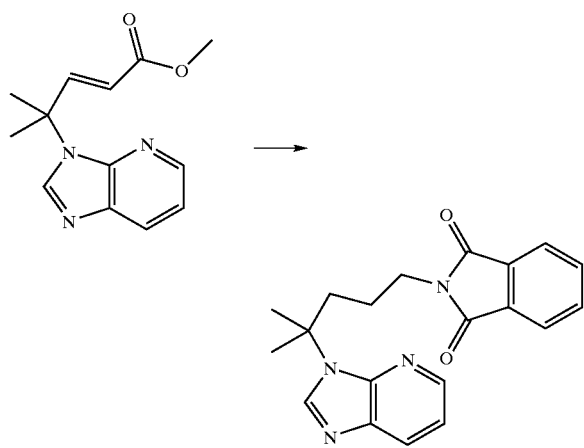

Protection carried out as in Example 95 to give 2-(4-Imidazo[4,5-b]pyridin-3-yl-4-methyl-pentyl)-isoindole-1,3-dione (13.9 g, 77%). MH⁺(349).

EXAMPLE 95(d)
2-[2-(Methyl-pyridin-3-yl-methyl-amino)-ethyl]-isoindole-1,3-dione

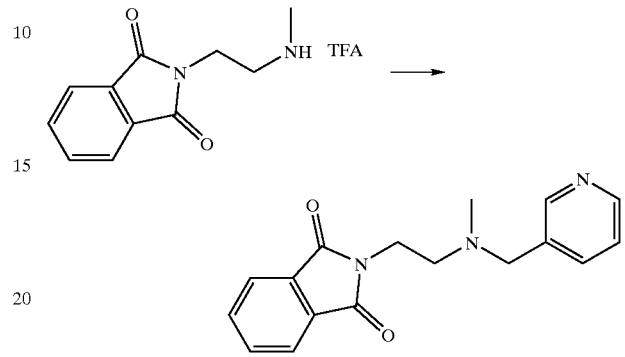

To a solution of 2-(2-methylamino-ethyl)-isoindole-1,3-dione (1 eq) in dichloromethane was added nicotinaldehyde (1.5 eq), sodium acetoborohydride (4.5 eq) and acetic acid (1.5 eq). After stirring at room temperature for 1 hour, NaHCO$_{3(sat)}$ was added to the reaction mixture followed by an extraction with dichloromethane. The organic phase was washed with H$_2$O, NaCl$_{(sat)}$ (50 mL), dried over sodium sulfate, filtered and concentrated. The crude product was purified by flash chromatography using a solvent gradient of 97% DCM, 3% MeOH and 0.1% TEA (2L) to yield 2-[2-methyl-pyridin-3-ylmethyl-amino)-ethyl]-isoindole-1,3-dione (57%). MH⁺(296).

EXAMPLE 95(e)
[3,3']Bipyridinyl-5-carboxylic acid ethyl ester

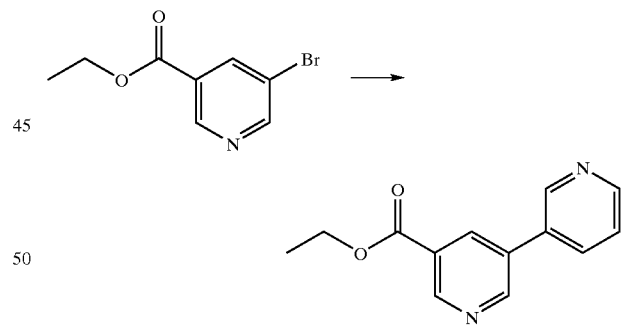

To a solution of 5-Bromo-nicotinic acid ethyl ester (1 eq) in THF was added diethyl(3-pyridyl)borane (2 eq), tetrakis (triphenylphosphine)palladium (10%), potassium carbonate (3 eq) and H$_2$O. The solution was left stirring in a 80° C. oil bath for 60 hours. Upon cooling, the reaction was filtered and concentrated. The crude solid was treated with 3N HCl and ethyl acetate. Once the aqueous layer was seperated, it was added to ethyl acetate and the whole was treated with sodium bicarbonate under vigorous stirring to obtain a basic pH (~7). The organic phase was seperated and washed with NaCl$_{(sat)}$, dried over sodium sulfate, filtered and concentrated to give [3,3']bipyridinyl-5-carboxylic acid ethyl ester (82%) MH⁺(229).

EXAMPLE 95(f)

[3,3']Bipyridinyl-5-yl-methanol

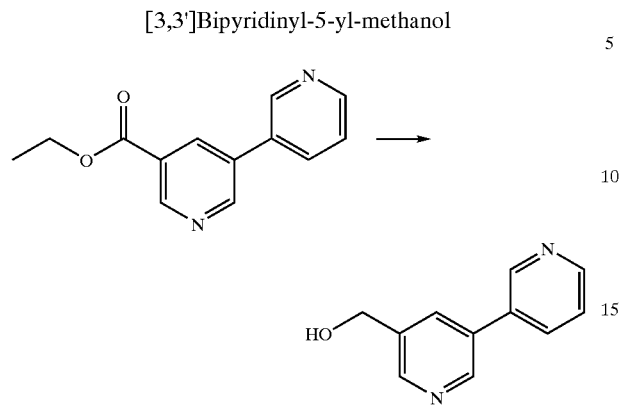

To a solution of [3,3']bipyridinyl-5-carboxylic acid ethyl ester (1 eq) in ethanol was added sodium borohydride (2 eq) at room temperature. The reaction mixture was heated in a 50° C. oil bath for 60 minutes and then quenched by addition of $H_2O$. Once the reaction solvent was removed in vacuo, a solution of the residue in dichloromethane was washed with $NaCl_{(sat)}$, dried over sodium sulfate, filtered and concentrated. The crude solid was purified by flash chromatography using a solvent gradient of 95% DCM, 5% MeOH and 0.1% TEA to yield [3,3']bipyridinyl-5-yl-methanol (34%). $MH^+$ (187).

EXAMPLE 95(g)

2-[2-(2,3']Bipyridinyl-5-ylmethyl-methyl-amino)-ethyl]-isoindole-1,3-dione

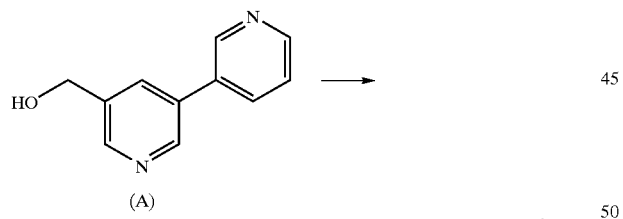

Reaction carried out as in Example 95 to yield 2-[2-(2,3']Bipyridinyl-5-ylmethyl-methyl-amino)-ethyl]-isoindole-1,3-dione (A) (48%). $MH^+$(373).

EXAMPLE 96

2-(2-Methylamino-ethyl)-isoindole-1,3-dione

To the HCl salt of 2-(2-Methylamino-ethyl)-isoindole-1,3-dione (1 eq) in dichloromethane was added quinoline-2-carbaldehyde(1.2 eq), sodium triacetoxyborohydride (2 eq), and acetic acid (1.2 eq) at rt.; the solution was allowed to stir for 16 hours. After concentration, the solution was diluted with ethyl acetate, washed with $NaHCO_{3(sat)}$, $NaCl_{(sat)}$, dried over $MgSO_4$, filtered, concentrated and pumped on. The yellow oil was then purified using flash chromatography (2% methanol/dichloromethane with 0.1% triethylamine) to yield 2-[2-(Methyl-quinolin-2-ylmethyl-amino)-ethyl]-isoindole-1,3-dione as a green solid. $MH^+$(346).

EXAMPLE 96(a)

2-[2-(Methyl-quinolin-2-ylmethyl-amino)-ethyl]-isoindole-1,3-dione

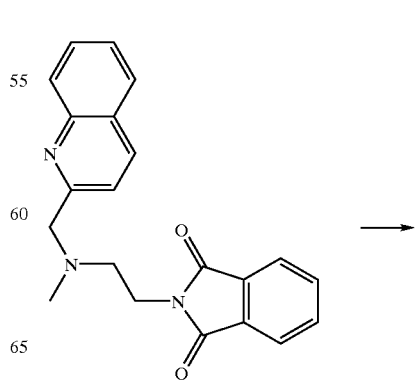

219

-continued

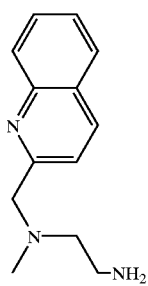

To 2-[2-(Methyl-quinolin-2-ylmethyl-amino)-ethyl]-isoindole-1,3-dione (1 eq) in Ethanol was added hydrazine (2 eq). A Reflux condenser was attached and the solution was heated 65° C. for 19 hours. The solution was then filtered, concentrated, and co-evaporated from toluene to yield N1-Methyl-N1-quinolin-2-ylmethyl-ethane-1,2-diamine in quantitative yield as a dark oil. MH$^+$(216).

EXAMPLE 96(b)

2-(2-Methylamino-ethyl)-isoindole-1,3-dione

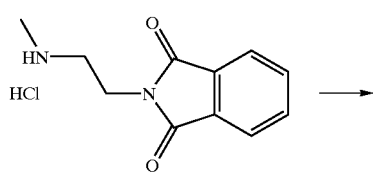

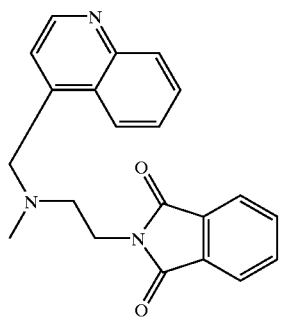

Reaction carried out as in Example 96, to yield 2-[2-(Methyl-quinolin-4-ylmethyl-amino)-ethyl]-isoindole-1,3-dione as an off-white solid. MH+(346).

220

EXAMPLE 96(c)

2-[2-(Methyl-quinolin-4-ylmethyl-amino)-ethyl]-isoindole-1,3-dione

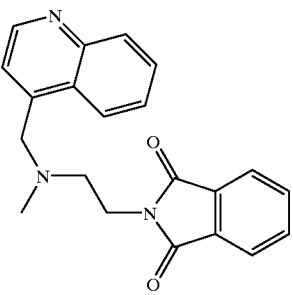

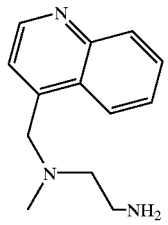

Deprotection was carried out as in Example 96 to yield N1-Methyl-N1-quinolin-4-ylmethyl-ethane-1,2-diamine in quantitative yield as a dark oil. MH$^+$(216).

EXAMPLE 97

Quinolines concentrated in vacuo to give a residue. To the residue was added 2 N NaOH aq. solution. Extracted with dichloromethane, washed with brine, dried over Na$_2$SO$_4$ and

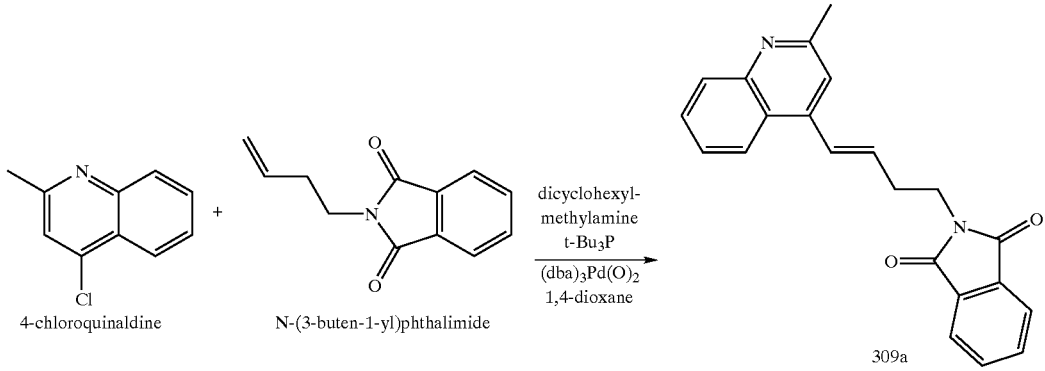

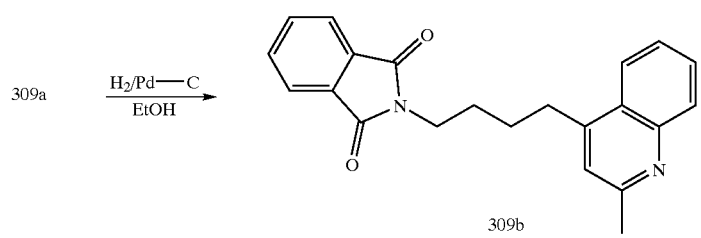

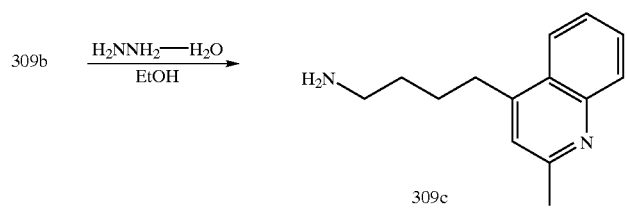

Step 1

A mixture of N-(3-buten-1-yl)phthalimide (1 eq); 4-chloroquinaldine (1 eq); dicyclohexylmethylamine (1.1 eq); and t-Bu3P (0.200 M solution in 1,4-dioxane) in 1,4-dioxane was degassed for 15 min. Tris(dibenzylideneacetone)dipalladium(0) (15%) was added. The mixture was stirred at 90° C. for 46 h. Cooled to rt and diluted with ethyl acetate. The mixture was filtered through a pad of silica gel, concentrated, and purified by silica gel chromatography (eluting with 1:1 EtOAc/hexanes) to afford quinaldine 309a (63%).

Step 2

A solution of compound 309a (1 eq) in EtOH and 10% Pd/C was stirred under $H_2$ (1.0 atm) for 17 h. Filtered through Celite and the filtrate was concentrated to give crude 2 (quantitative yields).

Step 3

The crude material 309b (1 eq) was suspended in EtOH. To this mixture was added hydrazine hydrate (2 eq). The mixture, was heated to 90° C. for 5 h. Cooled to ambient temperature and filtered through Celite. The filtrate was concentrated in vacuo to yield product 309c as a brown oil (79%). ES/MS m/z 215 (MH$^+$), $C_{14}H_{18}N_2$=214 g/mol.

Step 2

Step 3

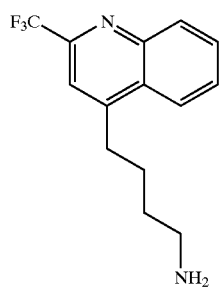

310

Amine 310 was synthesized in the same manner as described above. In step 1,4-chloro-2-trifluoromethylquinoline was used as the starting material. ES/MS m/z 269 (MH$^+$), $C_{14}H_{15}F_3N_2$=268.12 g/mol.

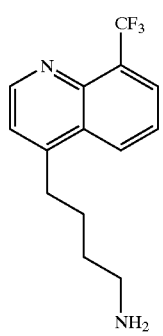

311

Amine 311 was synthesized in the same manner as described above. In step 1,4-chloro-8-trifluoromethylquinoline was used as the starting material. ES/MS m/z 269 (MH$^+$), $C_{14}H_{15}F_3N_2$=268.12 g/mol.

EXAMPLE 98
Thiazoles (Synthesis of 312)
Step 1
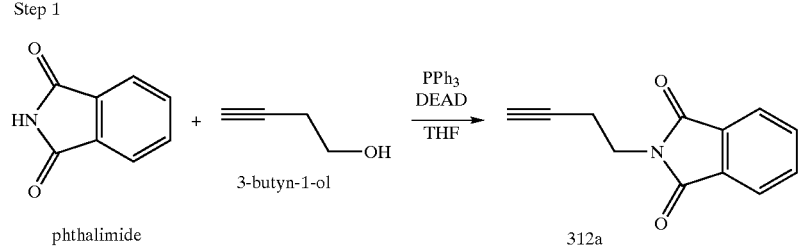
Step 2
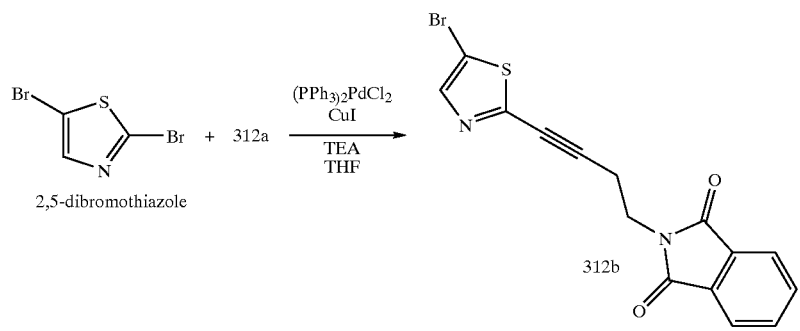
Step 3
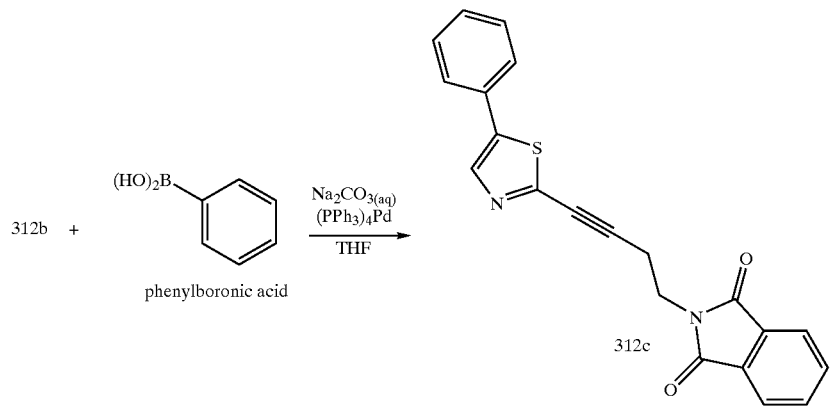
Step 4
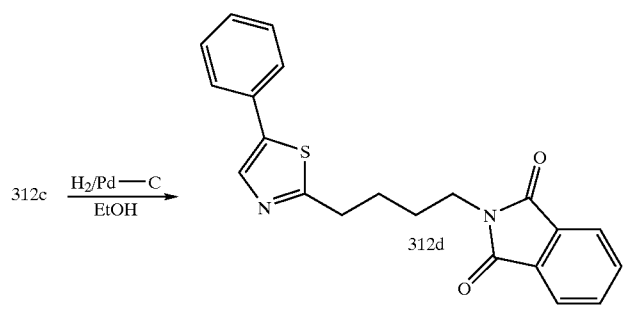

Step 5

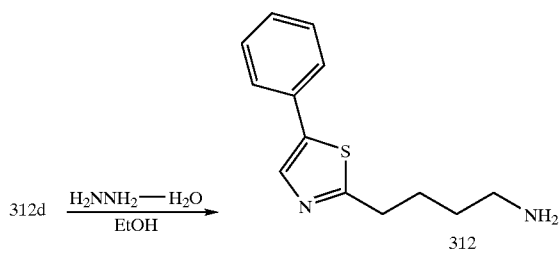

Step 1

A mixture of phthalimide (1 eq); triphenylphosphine (1 eq); and 3-butyn-1-ol (1 eq) in THF was cooled to 0° C. A solution of diethylazodicarboxylate (1 eq) in THF was added over 25 min. The solution was stirred for 5 h at ambient temperature and then poured into 1:1 EtOAc:ether. The solution was washed with water then brine then dried over MgSO4, filtered, and concentrated. The solid was purified by silica gel chromatography (eluting with 1:1 DCM:hexanes) followed by recrystallization from EtOAc/hexanes/DCM to give compound 312a.

Step 2

Only degassed solvents were used under anhydrous conditions. A mixture of 312a (1.5 eq); 2,5-dibromothiazole (1 eq); bis(triphenylphosphine)-palladium(II)chloride (3%); and CuI (3%) 2:1 THF: TEA was stirred at 70° C. for 5 h. Cooled to ambient temperature, filtered through a pad of silica gel, concentrated, and purified by silica gel chromatography (eluting with 3:1:1 hexanes:EtOAc:DCM) to afford 312b (55%).

Step 3

Only degassed solvents were used under anhydrous conditions. A mixture of 312b (1 eq), phenylboronic acid (1 eq), and 10% tetrakis(triphenylphosphine)-palladium(0) in 2:1 THF:2 M Na2CO3 (aq) was stirred at 70° C. for 4 h and then cooled to ambient temperature. Volatiles were removed under reduced pressure. The residue was suspended in DCM; washed sequentially with saturated aqueous NaHCO3 and brine; dried over Na2SO4; filtered; and concentrated. The crude material was purified by silica gel chromatography (eluting with 2:1:1 hexanes:EtOAc:DCM) to give a 58% yield of 312c and a recovery of 20% of unreacted 312b.

Step 4

A solution of compound 312c (1 eq) in EtOH and 10% Pd/C (412 mg) was stirred under $H_2$ (1.0 atm) for 48 h. Filtered through Celite and the filtrate was concentrated to give crude 312d (97%).

Step 5

The crude material 312d (obtained from step 4, 1 eq) was suspended in EtOH. To this mixture was added hydrazine hydrate (2 eq). The mixture was heated at 70° C. for 5 h. Cooled to ambient temperature and filtered through Celite. The filtrate was concentrated in vacuo to give a residue. The residue was re-suspended in 1:1 EtOAc:DCM; filtered through Celite; and concentrated. The residue was concentrated from toluene and left under high-vacuum for 24 h to yield the desired product (312) as a yellow solid (quantitative yields). ES/MS m/z 233 (MH+), $C_{13}H_{16}N_2S$= 232 g/mol.

EXAMPLE 99

Antibacterial Activity

Representative compounds of the present invention were assayed in vitro for antibacterial activity against the bacterial isolates listed in Table 1 as follows:

Strains

The bacterial isolates listed in Table 1 were cultivated from −70° C. frozen stocks by two consecutive overnight passages (P1, P2) at 35° C. on 5% blood agar (Remel, Lenexa, Kans.). Chocolate agar (Remel) is used for *Haemophilus influenzae*. *H. influenzae* and *Streptococcus pneumoniae* are incubated in 5–10% $CO_2$.

Drug Stock Preparation

To determine the amount of solvent to be used to give the desired final concentration, the formula "weight obtained in mg/final concentration in mg/mL" will be used. It will give the amount of solvent in mL needed to be added to give the desired concentration. For example, if 2.5 mg/mL is the desired concentration and the weight of compound is 13.7 mg, then the amount of solvent to be added is 3.94 mL (13.7 mg/2.5 mg/mL=3.94 mLs). Methanol is used as the solvent to dissolve the test compounds. Further dilution of stock is done in sterile, deioinzed water. Drug stocks are kept frozen at −70° C., protected from light.

Susceptibility Testing

MICs are determined by the broth microdilution method in accordance with the NCCLS guidelines. In brief, organism suspensions are adjusted to a 0.5 McFarland standard to yield a final inoculum between $3\times10^5$ and $7\times10^5$ CFU/mL. Drug dilutions and inocula are made in sterile, cation adjusted Mueller-Hinton Broth (CAMHB) (Remel) for all but *S. pneumoniae* [CAMHB with 2–5% lysed horse blood (Remel)] and *H. influenzae* [Haemophilus Test Medium (Remel)]. An inoculum volume of 100 μl is added to wells containing 100 μl of broth with 2-fold serial dilutions of drug. All inoculated microdilution trays are incubated in ambient air at 35° C. for 18–24 hours, except for *S. pneumoniae*, and *H. influenzae* (both at 5–10% $CO_2$).

Following appropriate incubation, the MIC is determined and the MIC is defined as the lowest concentration of the drug that prevented visible growth. The results of this assay, shown below in Table 3 demonstrate the antibacterial activity of representative compounds of the invention shown in Table 1 against the organism strain panel shown in Table 2.

TABLE 1

REPRESENTATIVE COMMPOUNDS

| Cmd. No. | Structure | Cmd. No. | Structure |
|---|---|---|---|
| 5960 | 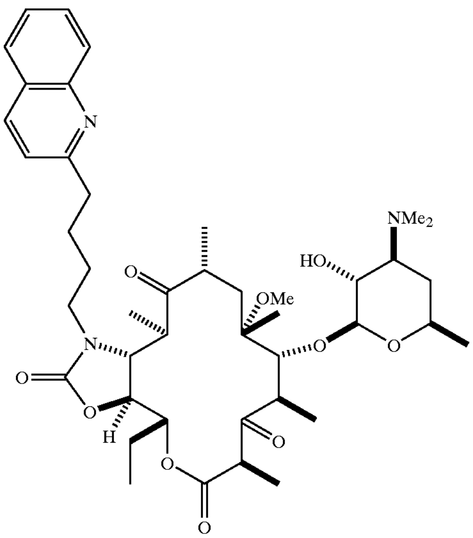 | 4710 | 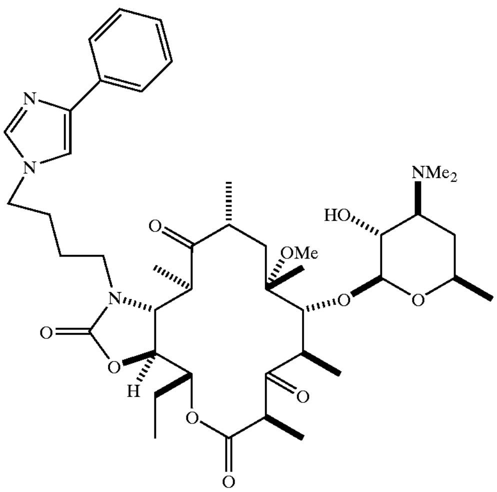 |
| 6220 | 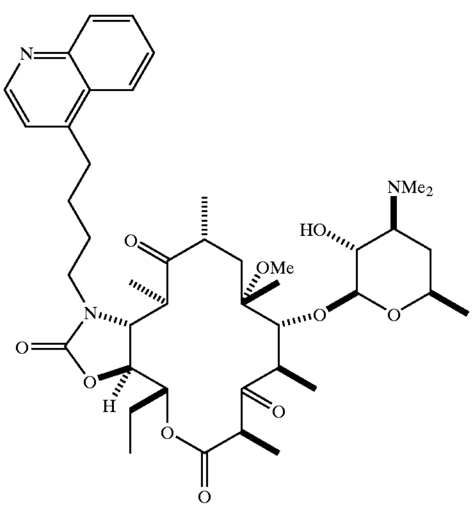 | 4711 | 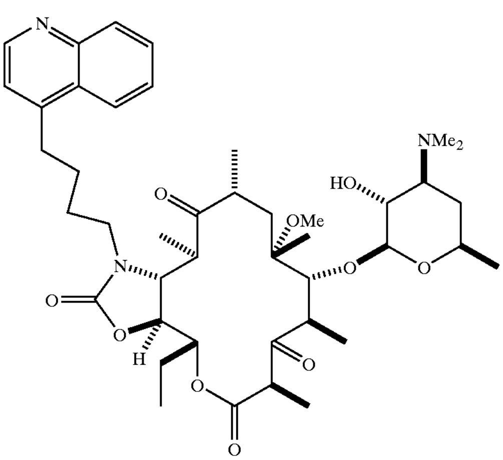 |

TABLE 1-continued

REPRESENTATIVE COMMPOUNDS

| Cmd. No. | Structure | Cmd. No. | Structure |
|---|---|---|---|
| 6221 | 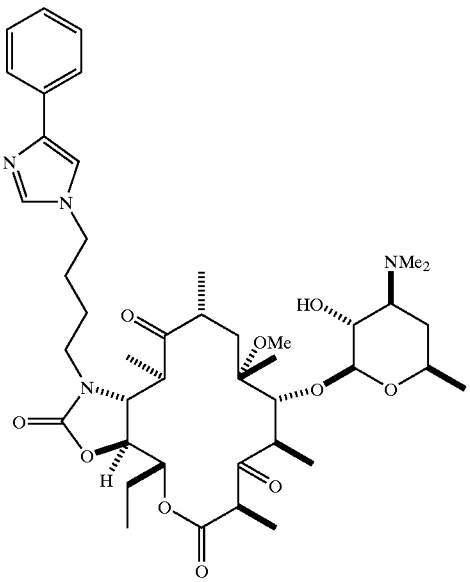 | 4713 | 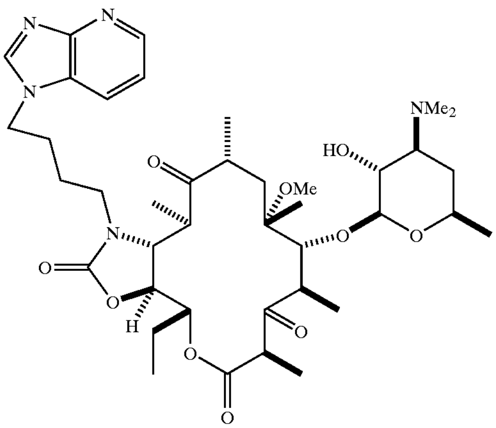 |
| 6222 | 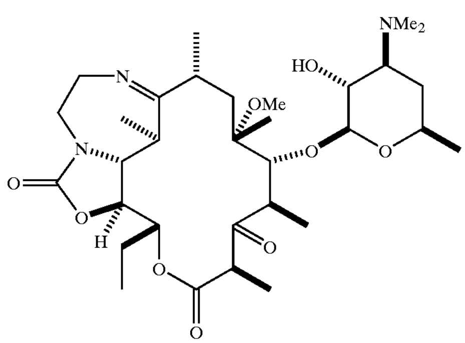 | 4714 | 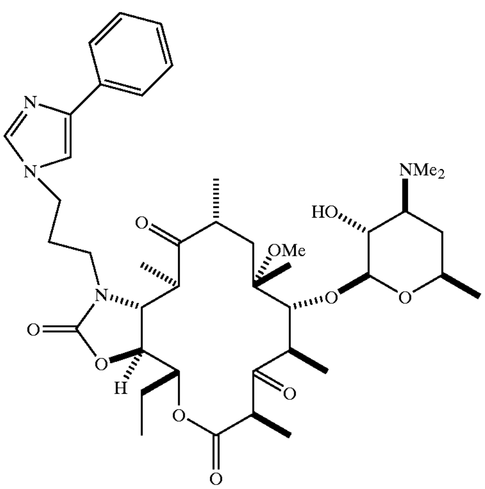 |
| 6223 | 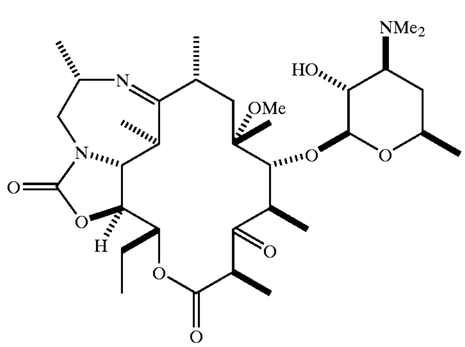 | 4716 | 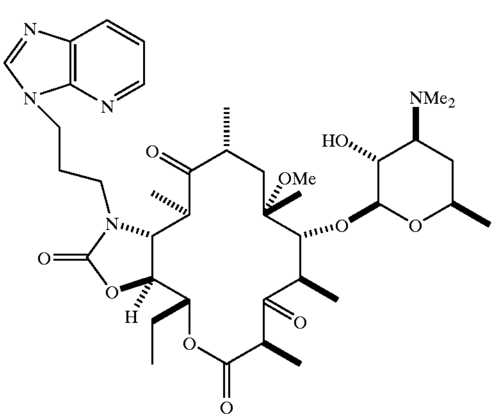 |

TABLE 1-continued

REPRESENTATIVE COMMPOUNDS

| Cmd. No. | Structure | Cmd. No. | Structure |
|---|---|---|---|
| 4265 | 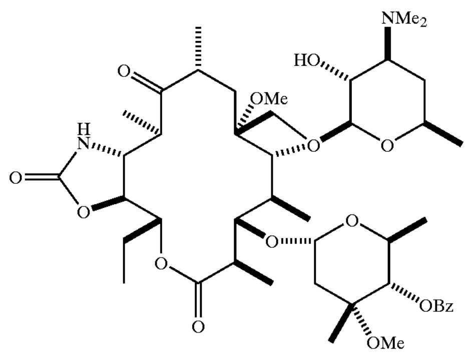 | 4717 | 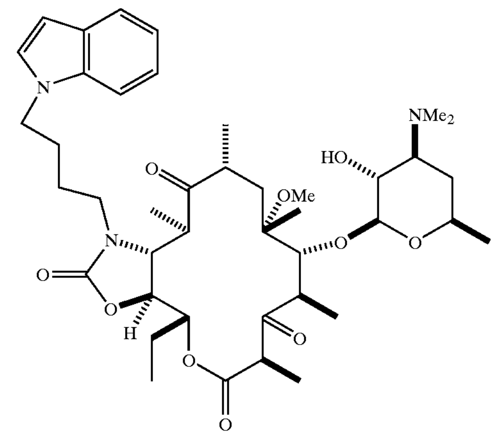 |
| 4266 | 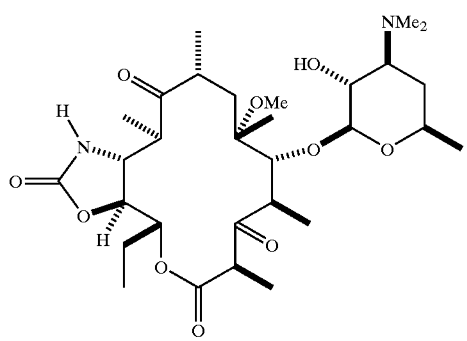 | 7280 | 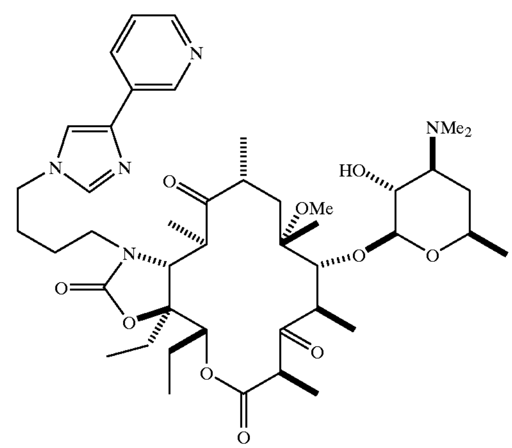 |
| 7281 | 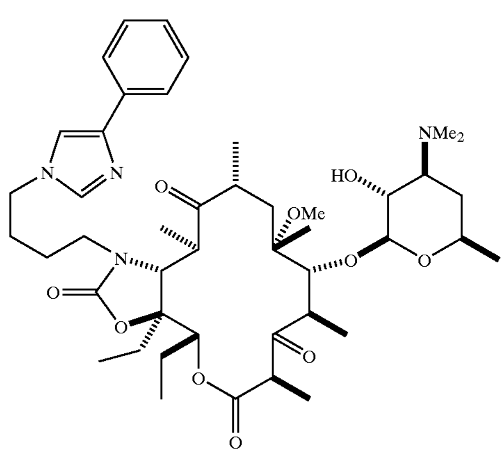 | 7282 | 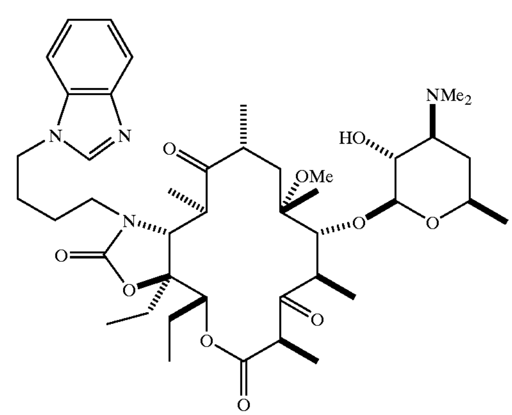 |

TABLE 1-continued

REPRESENTATIVE COMMPOUNDS

| Cmd. No. | Structure | Cmd. No. | Structure |
|---|---|---|---|
| 7283 | (structure) | | |

TABLE 2

STRAINS TESTED

| Strains Tested | Strain ID |
|---|---|
| S. epidermidis Step__14990 | A |
| S. epidermidis Step__f50654 Pen S | B |
| E. faecalis Enfa__29212 | C |
| S. pyogenes Stpy__8668 | D |
| S. pneumoniae Stpn__49619 | E |
| S. pneumoniae Stpn__297-749 Pen R | F |
| S. pneumoniae Stpn__280-962 Pen S | G |
| S. pneumoniae Stpn__Erm 6849 | H |

TABLE 2-continued

STRAINS TESTED

| Strains Tested | Strain ID |
|---|---|
| S. pneumoniae Stpn__Erm S 4297 | I |
| S. pneumoniae Stpn__Mef 5654 | J |
| S. pneumoniae Stpn__Mef S 3427 | K |
| H. influenzae Hain__49247 | L |
| E. coli Esco__25922 | M |

TABLE 3

COMPOUND ACTIVITY

| | Strain ID | | | | | | | | | | | | |
|---|---|---|---|---|---|---|---|---|---|---|---|---|---|
| Cmpd | A | B | C | D | E | F | G | H | I | J | K | L | M |
| Clar. | 0.2 | 0.2 | 0.78 | ≦0.05 | ≦0.05 | ≦0.05 | ≦0.05 | >50 | >50 | 6.25 | 1.56 | 12.5 | 50 |
| 5960 | 0.2 | 0.2 | ≦0.05 | ≦0.05 | ≦0.05 | ≦0.05 | ≦0.05 | 25 | 0.1 | 0.2 | ≦0.05 | 3.13 | 25 |
| 6220 | 0.1 | 0.1 | ≦0.05 | ≦0.05 | ≦0.05 | ≦0.05 | ≦0.05 | 3.13 | 0.1 | 0.4 | ≦0.5 | 1.56 | 6.25 |
| 6221 | 0.1 | 0.1 | ≦0.05 | ≦0.05 | ≦0.05 | ≦0.05 | ≦0.05 | 0.1 | ≦0.05 | 0.4 | ≦0.05 | 3.13 | 25 |
| 6222 | 1.56 | 1.56 | 0.4 | 0.2 | 0.2 | 0.4 | 0.2 | >50 | >50 | 0.78 | 0.4 | 25 | 50 |
| 6223 | 1.56 | 3.13 | 0.78 | 0.2 | 0.2 | 0.2 | 0.2 | >50 | >50 | 0.78 | 0.4 | >50 | 50 |
| 4265 | 3.13 | 6.25 | 3.13 | 0.4 | 0.2 | 0.1 | ≦0.5 | 25 | 1.56 | 1.56 | 0.4 | >50 | >50 |
| 4266 | 3.13 | 3.13 | 1.56 | 0.1 | 0.2 | ≦0.05 | ≦0.05 | >50 | >50 | 0.2 | 0.1 | 25 | >50 |
| 4710 | 0.1 | 0.2 | ≦0.05 | ≦0.5 | ≦0.5 | ≦0.5 | ≦0.5 | 0.2 | ≦0.05 | 0.2 | ≦0.5 | 3.13 | 50 |
| 4711 | 0.1 | 0.1 | ≦0.05 | ≦0.5 | ≦0.5 | ≦0.5 | ≦0.5 | 6.25 | 0.2 | 0.1 | ≦0.5 | 1.56 | 50 |
| 4713 | 0.4 | 0.4 | 0.1 | ≦0.5 | ≦0.5 | ≦0.5 | ≦0.5 | 0.78 | 0.1 | 3.13 | 0.4 | 3.13 | 50 |
| 4714 | 6.25 | 6.25 | 0.4 | 0.1 | ≦0.5 | ≦0.5 | ≦0.5 | >50 | 6.25 | 0.4 | 0.1 | >50 | >50 |
| 4716 | 6.25 | 12.5 | 0.78 | 0.1 | ≦0.5 | ≦0.5 | ≦0.5 | >50 | 25 | 0.78 | 0.4 | 25 | >50 |
| 4717 | 0.2 | 0.4 | 0.1 | ≦0.5 | ≦0.5 | ≦0.5 | ≦0.5 | 6.25 | 0.4 | 0.2 | ≦0.05 | 6.25 | >50 |
| 7280 | 0.2 | 0.2 | 0.1 | ≦0.05 | ≦0.05 | ≦0.05 | ≦0.05 | 0.4 | ≦0.05 | 0.4 | 0.1 | 6.25 | 25 |
| 7281 | 0.2 | 0.1 | 0.1 | ≦0.05 | ≦0.05 | ≦0.05 | ≦0.05 | 0.2 | ≦0.05 | 0.4 | ≦0.05 | 3.13 | 25 |
| 7282 | 0.4 | 0.2 | 0.1 | ≦0.05 | ≦0.05 | ≦0.05 | ≦0.05 | 0.78 | 0.2 | 0.4 | 0.1 | 3.13 | 12.5 |
| 7283 | 0.2 | 0.2 | 0.1 | ≦0.05 | ≦0.05 | ≦0.05 | ≦0.05 | 0.4 | 0.1 | 0.4 | ≦0.05 | 3.13 | 12.5 |

The foregoing procedure is repeated using the strain panel shown in Table 4 demonstrating the antibacterial activity of representative compounds of the invention shown in Table 5.

TABLE 4

STRAINS TESTED

| Strains Tested | Strain ID |
|---|---|
| *S. aureus* Stau__29213 | A |
| *S. epidermidis* Step__14990 | B |
| *S. epidermidis* Step__f50654 | C |
| *E. faecalis* Enfa__29212 | D |
| *S. pyogenes* Stpy__8668 | E |
| *S. pneumoniae* Stpn__49619 | F |
| *S. pneumoniae* Stpn__297-749 | G |
| *S. pneumoniae* Stpn__280-962 | H |
| *S. pneumoniae* Stpn__Erm 6849 | I |
| *S. pneumoniae* Stpn__Erm S 4297 | J |
| *S. pneumoniae* Stpn__Mef 5654 | K |
| *S. pneumoniae* Stpn__Mef S 3427 | L |
| *H. influenzae* Hain__49247 | M |

While the preferred embodiment of the invention has been illustrated and described, it will be appreciated that various changes can be made therein without departing from the spirit and scope of the invention.

What is claimed is:

1. A compound having the formula II:

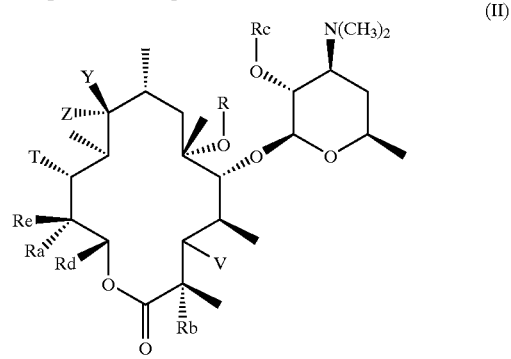

(II)

or a pharmaceutically acceptable salt, ester or prodrug thereof, wherein

TABLE 5

COMPOUND ACTIVITY

| | Strain ID | | | | | | | | | | | | |
|---|---|---|---|---|---|---|---|---|---|---|---|---|---|
| Cmpd Ex. | A | B | C | D | E | F | G | H | I | J | K | L | M |
| 14 | 0.4 | 0.2 | 0.2 | 0.1 | ≦0.05 | ≦0.05 | ≦0.05 | ≦0.05 | 0.4 | 0.1 | 0.4 | ≦0.05 | 3.13 |
| 65(1) | 0.2 | 0.2 | 0.2 | 0.1 | ≦0.05 | ≦0.05 | ≦0.05 | ≦0.05 | ≦0.05 | ≦0.05 | 0.2 | ≦0.05 | 3.13 |
| 15 | 0.4 | 0.2 | 0.4 | 0.1 | ≦0.05 | ≦0.05 | ≦0.05 | ≦0.05 | 1.56 | 0.1 | 0.2 | ≦0.05 | 3.13 |
| 20 | 0.2 | 0.1 | 0.2 | 0.1 | ≦0.05 | ≦0.05 | ≦0.05 | ≦0.05 | ≦0.5 | ≦0.05 | 0.4 | ≦0.05 | 6.25 |
| 48 | 0.2 | 0.2 | 0.2 | 0.1 | ≦0.05 | ≦0.05 | ≦0.05 | ≦0.05 | 0.4 | ≦0.05 | 0.78 | 0.1 | 3.13 |
| 49 | 0.2 | 0.2 | 0.2 | 0.1 | ≦0.05 | ≦0.05 | ≦0.05 | ≦0.05 | 0.1 | ≦0.05 | 0.78 | ≦0.05 | 6.25 |
| 67/20m | 0.2 | 0.1 | 0.2 | ≦0.05 | ≦0.05 | ≦0.05 | ≦0.05 | ≦0.05 | 0.2 | ≦0.05 | 0.2 | ≦0.05 | 1.56 |
| 67/20w | 3.13 | 1.56 | 3.13 | 0.2 | ≦0.05 | ≦0.05 | ≦0.05 | ≦0.05 | 12.5 | 3.13 | 0.4 | 0.1 | 50 |
| 25 | 0.4 | 0.2 | 0.2 | 0.1 | ≦0.05 | ≦0.05 | ≦0.05 | ≦0.05 | 0.1 | 0.1 | 0.4 | 0.1 | 3.13 |
| 27 | 0.1 | 0.1 | 0.1 | 0.05 | ≦0.025 | ≦0.025 | 0.025 | ≦0.025 | 3.13 | 0.1 | 0.4 | 0.1 | 1.56 |
| 67/20r | 3.13 | 3.13 | 1.56 | 1.56 | 0.4 | 0.1 | 0.1 | 0.1 | 25 | 25 | 1.56 | 0.1 | 50 |
| 67/20s | 0.78 | 0.78 | 0.4 | 0.2 | ≦0.05 | ≦0.05 | ≦0.05 | ≦0.05 | 12.5 | 0.2 | 0.78 | ≦0.05 | 3.13 |
| 29 | 0.4 | 0.2 | 0.4 | 0.2 | ≦0.05 | ≦0.05 | ≦0.05 | ≦0.05 | 1.56 | 0.2 | 0.78 | 0.2 | 6.25 |
| 30 | 0.2 | 0.2 | 0.4 | 0.2 | ≦0.05 | ≦0.05 | ≦0.05 | ≦0.05 | 0.4 | 0.1 | 0.78 | 0.1 | 6.25 |
| 33 | 0.4 | 0.2 | 0.2 | 0.1 | ≦0.05 | 3.13 | ≦0.05 | ≦0.05 | ≦0.05 | 0.4 | 0.1 | 0.4 | 0.1 |
| 34 | 0.4 | 0.2 | 0.2 | 0.1 | ≦0.05 | 3.13 | ≦0.05 | ≦0.05 | ≦0.05 | 12.5 | 0.2 | 0.4 | 0.1 |
| 37 | 0.4 | 0.2 | 0.2 | 0.1 | ≦0.05 | ≦0.05 | ≦0.05 | ≦0.05 | 0.4 | 0.1 | 1.56 | 0.2 | 6.25 |
| 50 | 0.4 | 0.4 | 0.2 | 0.2 | ≦0.05 | ≦0.05 | ≦0.05 | ≦0.05 | 0.1 | ≦0.05 | 0.4 | 0.1 | 6.25 |
| 38 | 0.2 | 0.2 | 0.2 | 0.1 | ≦0.05 | ≦0.05 | ≦0.05 | ≦0.05 | 0.4 | 0.1 | 0.78 | 0.1 | 6.25 |
| 22 | 0.4 | 0.4 | 0.4 | 0.2 | ≦0.05 | ≦0.05 | ≦0.05 | ≦0.05 | 0.2 | 0.1 | 0.78 | 0.2 | 3.13 |
| 23 | 1.56 | 0.78 | 0.78 | 0.2 | ≦0.05 | ≦0.05 | ≦0.05 | ≦0.05 | 0.78 | 0.2 | 0.4 | 0.1 | 6.25 |
| 17 | 0.4 | 0.4 | 0.4 | 0.2 | 0.1 | ≦0.05 | ≦0.05 | ≦0.05 | 0.78 | 0.2 | 0.4 | 0.1 | 3.13 |
| 18 | 0.78 | 0.4 | 0.78 | 0.1 | 0.1 | ≦0.05 | ≦0.05 | ≦0.05 | 3.13 | 0.2 | 0.4 | ≦0.05 | 3.13 |
| 19 | 0.4 | 0.4 | 0.4 | 0.4 | 0.1 | ≦0.05 | ≦0.05 | ≦0.05 | 0.78 | 0.2 | 0.4 | 0.1 | 6.25 |
| 21 | 0.4 | 0.4 | 0.4 | 0.1 | ≦0.05 | ≦0.05 | ≦0.05 | ≦0.05 | 0.2 | 0.1 | 0.78 | 0.1 | 12.5 |
| 67/20n | 0.4 | 0.2 | 0.4 | 0.1 | ≦0.05 | ≦0.05 | ≦0.05 | ≦0.05 | 0.4 | 0.1 | 0.2 | 0.1 | 6.25 |
| 67/20o | 0.2 | 0.2 | 0.2 | 0.1 | ≦0.05 | ≦0.05 | ≦0.05 | ≦0.05 | 1.56 | 0.1 | 0.2 | 0.1 | 3.13 |
| 26 | 0.2 | 0.2 | 0.2 | 0.2 | ≦0.05 | ≦0.05 | ≦0.05 | ≦0.05 | 0.2 | ≦0.05 | 0.4 | 0.1 | 3.13 |
| 65(2) | 3.13 | 3.13 | 3.13 | 0.78 | 0.2 | ≦0.05 | ≦0.05 | ≦0.05 | 0.78 | 0.4 | 0.78 | 0.2 | 25 |
| 66 | 0.2 | 0.2 | 0.2 | .01 | ≦0.05 | ≦0.05 | ≦0.05 | ≦0.05 | 0.2 | 0.1 | 0.4 | 0.1 | 6.25 |
| 28 | 0.4 | 0.4 | 0.4 | 0.1 | ≦0.05 | ≦0.05 | ≦0.05 | ≦0.05 | >50 | 0.4 | 0.78 | 0.2 | 3.13 |
| 67/20t | 0.78 | 0.78 | 0.4 | 0.4 | 0.2 | ≦0.05 | ≦0.05 | ≦0.05 | 25 | 1.56 | 1.56 | 0.1 | 12.5 |
| 67/20u | 0.78 | 0.78 | 0.4 | 0.4 | 0.4 | 0.1 | 0.1 | 0.1 | 25 | 12.5 | 1.56 | 0.2 | 25 |
| 67/20v | 0.4 | 0.4 | 0.2 | 0.2 | ≦0.05 | ≦0.05 | ≦0.05 | ≦0.05 | 50 | 0.4 | 0.78 | ≦0.05 | 6.25 |
| 31 | 0.2 | 0.4 | 0.4 | 0.2 | ≦0.05 | ≦0.05 | ≦0.05 | ≦0.05 | 0.4 | 0.2 | 0.78 | 0.2 | 6.25 |
| 32 | 0.2 | 0.4 | 0.4 | .02 | ≦0.05 | ≦0.05 | ≦0.05 | ≦0.05 | 0.2 | ≦0.05 | 0.78 | 0.2 | 6.25 |
| 35 | 0.78 | 0.78 | 0.78 | 0.2 | 0.2 | 6.25 | ≦0.05 | ≦0.05 | ≦0.05 | 3.13 | 0.78 | 0.78 | 0.2 |
| 36 | 6.25 | 1.56 | 0.78 | 0.78 | 0.4 | 25 | 0.1 | 0.1 | 0.1 | 12.5 | 12.5 | 0.78 | 0.2 |
| 40 | 0.2 | 0.2 | 0.2 | 0.1 | ≦0.05 | ≦0.05 | ≦0.05 | ≦0.05 | 0.2 | ≦0.05 | 0.78 | 0.2 | 6.25 |
| 67/20p | 0.4 | 0.2 | 0.4 | 0.2 | 0.1 | 0.1 | ≦0.05 | 0.1 | 6.25 | 0.78 | 0.78 | 0.2 | 6.25 |
| 67/20q | 0.4 | 0.2 | 0.4 | 0.1 | ≦0.05 | ≦0.05 | ≦0.05 | ≦0.05 | 1.56 | 0.2 | 0.4 | 0.1 | 12.5 |

V is —OCOR$_x$, carbonyl, or a cladinose moiety of the formula:

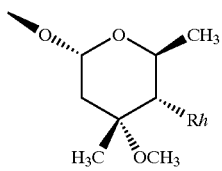

wherein R$_x$ is H, alkyl, —O-alkyl, —N(H)-alkyl, or —N(alkyl)$_2$;

either Y and Z taken together define a group X, wherein X is selected from the group consisting of
(1) =O,
(2) =N—OH,
(3) =N—O—R$^1$ where R$^1$ is selected from the group consisting of
  (a) C$_1$–C$_{12}$-alkyl,
  (b) C$_1$–C$_{12}$-alkyl substituted with alkoxy,
  (c) C$_1$–C$_{12}$-alkyl substituted with aryl,
  (d) C$_1$–C$_{12}$-alkyl substituted with substituted aryl,
  (e) C$_1$–C$_{12}$-alkyl substituted with heteroaryl,
  (f) C$_1$–C$_{12}$-alkyl substituted with substituted heteroaryl,
  (g) C$_3$–C$_{12}$-cycloalkyl, and
  (h) —Si—(R$^2$)(R$^3$)(R$^4$) wherein R$^2$, R$^3$, R$^4$ are each independently selected from C$_1$–C$_{12}$-alkyl and aryl; and
(4) =N—O—C(R$^5$)(R$^6$)—O—R$^1$ wherein R$^1$ is as previously defined and R$^5$ and R$^6$ are each independently selected from the group consisting of
  (a) hydrogen,
  (b) C$_1$–C$_{12}$-alkyl,
  (c) C$_1$–C$_{12}$-alkyl substituted with aryl,
  (d) C$_1$–C$_{12}$-alkyl substituted with substituted aryl,
  (e) C$_1$–C$_{12}$-alkyl substituted with heteroaryl, and
  (f) C$_1$–C$_{12}$-alkyl substituted with substituted heteroaryl;
  or R$^5$ and R$^6$ taken together with the atoms to which they are attached form a C$_3$–C$_{12}$-cycloalkyl ring;
or Y and Z are =N— when taken together with T to form a moiety of the structure:

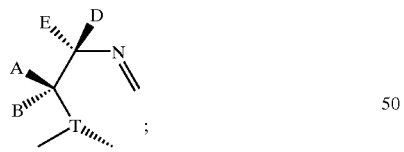

or one of Y and Z is hydrogen and the other is selected from a group consisting of
(1) hydroxy,
(2) protected hydroxy, and
(3) NR$^7$R$^8$ wherein R$^7$ and R$^8$ are independently selected from hydrogen and alkyl, substituted alkyl, or R$^7$ and R$^8$ are taken with the nitrogen atom to which they are connected to form a 3- to 7-membered ring which, when the ring is a 5- to 7-membered ring, may optionally contain a hetero function selected from the group consisting of —O—, —NH, —N(C$_1$–C$_6$-alkyl)-, —N(aryl)-, —N(aryl-C$_1$–C$_6$-alkyl-)-, —N(substituted-aryl-C$_1$–C$_6$-alkyl-)-, —N(heteroaryl)-, —N(heteroaryl-C$_1$–C$_6$-alkyl-)-, —N(substituted-heteroaryl-C$_1$–C$_6$-alkyl-)-, and —S— or S(O)$_n$— wherein n is 1 or 2;

T is selected from the group consisting of —O—Rg, —O—, —NH—, N(W—Rf)-, and —CH(W—Rf)-, wherein
(1) W is absent or is selected from the group consisting of —O—, NH—CO—, —N=CH—, —NH— and —CH$_2$—; and
(2) Rf is selected from the group consisting of
  (a) hydrogen,
  (b) alkyl, alkenyl or alkynyl,
  (c) alkyl, alkenyl or alkynyl substituted with one or more substituents selected from the group consisting of
    (i) aryl,
    (ii) substituted aryl,
    (iii) heteroaryl,
    (iv) substituted heteroaryl,
    (v) hydroxy,
    (vi) C$_1$–C$_6$-alkoxy,
    (vii) —NR$^7$R$^8$ wherein R$^7$ and R$^8$ are as defined previously, and
    (viii) —M—R$^9$, wherein M is selected from the group consisting of:
      (a) —C(O)—NH—,
      (b) —NH—C(O)—,
      (c) —NH—,
      (d) —N=,
      (e) —N(CH$_3$)—,
      (f) —NH—C(O)—O—,
      (g) —NH—C(O)—NH—,
      (h) —O—C(O)—NH—,
      (i) —O—C(O)—O—,
      (j) —O—,
      (k) —S(O)$_n$—, wherein n is 0, 1 or 2,
      (l) —C(O)—O—,
      (m) —O—C(O)—,
      (n) —C(O)—; and
    and R$^9$ is selected from the group consisting of:
      (a) alkyl optionally substituted with a substituent selected from the group consisting of
        (aa) aryl,
        (bb) substituted aryl,
        (cc) heteroaryl, and
        (dd) substituted heteroaryl,
      (b) aryl,
      (c) substituted aryl,
      (d) heteroaryl,
      (e) substituted heteroaryl, and
      (f) heterocycloalkyl, R is selected from the group consisting of
(1) hydrogen;
(2) methyl substituted with a moiety selected from the group consisting of
  (a) CN,
  (b) F,
  (c) —CO$_2$R$^{10}$ wherein R$^{10}$ is C$_1$–C$_3$-alkyl or aryl substituted C$_1$–C$_3$-alkyl, or heteroaryl substituted C$_1$–C$_3$-alkyl,
  (d) —S(O)$_n$R$^{10}$ —, wherein n is 0, 1 or 2 and R$^{10}$ is as previously defined,
  (e) —NH—C(O) R$^{10}$, wherein R$^{10}$ is as previously defined,
  (f) —NH—C(O)N R$^{11}$ R$^{12}$ wherein R$^{11}$ and R$^{12}$ are independently selected from hydrogen, C$_1$–C$_3$-alkyl, C$_1$–C$_3$-alkyl substituted with aryl, substituted aryl, heteroaryl, substituted heteroaryl, (g) aryl,
(h) substituted aryl,
(i) heteroaryl, and
(j) substituted heteroaryl;
(3) alkyl;
(4) $C_2$–$C_{12}$-alkyl substituted with one or more substituents selected from the group consisting of
  (a) halogen,
  (b) hydroxy,
  (c) $C_1$–$C_3$-alkoxy,
  (d) $C_1$–$C_3$-alkoxy- $C_1$–$C_3$-alkoxy,
  (e) oxo,
  (f) O—$SO_2$-(substituted $C_1$–$C_6$-alkyl),
  (g) —$N_3$,
  (h) —CHO,
  (i) —$NR^{13}R^{14}$ wherein $R^{13}$ and $R^{14}$ are selected from the group consisting of
    (i) hydrogen,
    (ii) C1–C12-alkyl,
    (iii) substituted C1–C12-alkyl,
    (iv) C2–C12-alkenyl,
    (v) substituted C2–C12-alkenyl,
    (vi) C2–C12-alkynyl,
    (vii) substituted C2–C12-alkynyl,
    (viii) aryl,
    (ix) C3–C8-cycloalkyl,
    (x) substituted C3–C8-cycloalkyl,
    (xi) substituted aryl,
    (xii) heterocycloalkyl,
    (xiii) substituted heterocycloalkyl,
    (xiv) C1–C12-alkyl substituted with aryl,
    (xv) C1–C12-alkyl substituted with substituted aryl,
    (xvi) C1–C12-alkyl substituted with heterocycloaryl,
    (xvii) C1–C12-alkyl substituted with substituted heterocycloaryl,
    (xviii) C1–C12-alkyl substituted with C3–C8-cycloalkyl,
    (xix) C1–C12-alkyl substituted with substituted C3–C8-cycloalkyl,
    (xx) heteroaryl,
    (xxi) substituted heteroaryl,
    (xxii) C1–C12-alkyl substituted with heteroaryl, and
    (xxiii) C1–C12-alkyl substituted with substituted heteroaryl;
  or $R^{13}$ and $R^{14}$ are taken together with the atom to which they are attached form a 3- to 10-membered heterocycloalkyl ring which may optionally be substituted with one or more substituents independently selected from the group consisting of
    (i) halogen,
    (ii) hydroxy,
    (iii) C1–C3-alkoxy,
    (iv) C1–C3-alkoxy-C1–C3-alkoxy,
    (v) oxo,
    (vi) C1–C3-alkyl,
    (vii) halo-C1–C3-alkyl, and
    (viii) C1–C3-alkoxy-C1–C3-alkyl;
  (j) —$CO_2R^{10}$ wherein $R^{10}$ is as previously defined,
  (k) —$C(O)R^{11}R^{12}$ wherein $R^{11}$ and $R^{12}$ are as previously defined,
  (l) =N—O—$R^{10}$ wherein $R^{10}$ is as previously defined,
  (m) —CN,
  (n) —O—$S(O)_nR^{10}$ wherein n is 0, 1 or 2 and $R^{10}$ is as previously defined,
  (o) aryl,
  (p) substituted aryl,
  (q) heteroaryl,
  (r) substituted heteroaryl,
  (s) $C_3$–$C_8$-cycloalkyl,
  (t) substituted $C_3$–$C_8$-cycloalkyl,
  (u) $C_1$–$C_{12}$-alkyl substituted with heteroaryl,
  (v) heterocycloalkyl,
  (w) substituted heterocycloalkyl,
  (x) —NH—$C(O)R^{10}$ wherein $R^{10}$ is as previously defined,
  (y) —NH—$C(O)NR^{11}R^{12}$ wherein $R^{11}$ and $R^{12}$ are as previously defined,
  (z) =N—$NR^{13}R^{14}$ wherein $R^{13}$ and $R^{14}$ are as previously defined,
  (aa) =N—$R^9$ wherein $R^9$ is as previously defined,
  (bb) =N—NH—$C(O)R^{10}$ wherein $R^{10}$ is as previously defined, and
  (cc) =N—NH—$C(O)NR^{11}R^{12}$ wherein $R^{11}$ and $R^{12}$ are as previously defined;
(5) $C_3$-alkenyl substituted with a moiety selected from the group consisting of
  (a) halogen,
  (b) —CHO,
  (c) —$CO_2R^{10}$ wherein $R^{10}$ is as previously defined,
  (d) —$C(O)NR^{11}R^{12}$ wherein $R^{11}$ and $R^{12}$ are as previously defined,
  (e) —$C(O)R^9$ wherein $R^9$ is as previously defined,
  (f) —CN,
  (g) aryl,
  (h) substituted aryl,
  (i) heteroaryl,
  (j) substituted heteroaryl,
  (k) $C_3$–$C_8$-cycloalkyl, and
  (l) $C_1$–$C_{12}$-alkyl substituted with heteroaryl;
(6) $C_4$–$C_{10}$-alkenyl;
(7) $C_4$–$C_{10}$-alkenyl substituted with one or more substituents selected from the group consisting of
  (a) halogen,
  (b) $C_1$–$C_3$-alkoxy,
  (c) oxo,
  (d) —CHO,
  (e) —$CO_2R^{10}$ wherein $R^{10}$ is as previously defined,
  (f) —$C(O)NR^{11}R^{12}$ wherein $R^{11}$ and $R^{12}$ are as previously defined,
  (g) $NR^{13}R^{14}$ wherein $R^{13}$ and $R^{14}$ are as previously defined,
  (h) =N—O—$R^{10}$ wherein $R^{10}$ is as previously defined,
  (i) —CN,
  (j) —O—$S(O)_nR^{10}$ wherein n is 0, 1 or 2 and $R^{10}$ is as previously defined,
  (k) aryl,
  (l) substituted aryl,
  (m) heteroaryl,
  (n) substituted heteroaryl,
  (o) $C_3$–$C_8$-cycloalkyl,
  (p) $C_1$–$C_{12}$-alkyl substituted with substituted heteroaryl,
  (q) —NH—$C(O)R^{10}$ wherein $R^{10}$ is as previously defined,
  (r) —NH—$C(O)NR^{11}R^{12}$ wherein $R^{11}$ and $R^{12}$ are as previously defined,
  (s) =N—$NR^{13}R^{14}$ wherein $R^{13}$ and $R^{14}$ are as previously defined,
  (t) =N—$R^9$ wherein $R^9$ is as previously defined,
  (u) =N—NH—$C(O)R^{10}$ wherein $R^{10}$ is as previously defined, and (v) =N—NH—C(O)NR$^{11}$R$^{12}$ wherein R$^{11}$ and R$^{12}$ are as previously defined;
(8) C$_3$–C$_{10}$-alkynyl;
(9) C$_3$–C$_{10}$-alkynyl substituted with one or more substituents selected from the group consisting of
  (a) trialkylsilyl,
  (b) aryl,
  (c) substituted aryl,
  (d) heteroaryl, and
  (e) substituted heteroaryl; and
(10) C(O)NR$^7$R$^8$ where R$^7$ and R$^8$ are previously defined;

Ra is selected from a group consisting of
(1) hydrogen;
(2) C$_1$ alkyl further substituted with a one or more substituents selected from a group consisting of
  (a) hydroxyl,
  (b) halogen,
  (c) thiol, which can be further substituted with an alkyl or substituted alkyl group,
  (d) C$_1$–C$_{12}$-alkyl which can be further substituted by halogen, hydroxyl alkoxy, or amino,
  (e) C$_1$–C$_3$-alkoxy,
  (f) C$_1$–C$_3$-thioalkoxy,
  (g) amino,
  (h) alkylamino,
  (i) dialkylamino,
  (j) nitrile,
  (k) nitro,
  (l) amido,
  (m) carboxylic acid,
  (n) ester,
  (o) azido,
  (p) =N—O—R$^{10}$, wherein R$^{10}$ is as previously defined,
  (q) =N—R$^9$, wherein R$^9$ is as previously defined,
  (r) =N—NR$^{13}$R$^{14}$, wherein R$^{13}$ and R$^{14}$ are as previously defined,
  (s) =N—NH—C(O)R$^{10}$, wherein R$^{10}$ is as previously defined, and
  (t) =N—NH—C(O)NR$^{11}$R$^{12}$, wherein R$^{11}$ and R$^{12}$ are as previously defined;
(3) C$_2$–C$_4$-alkenyl, which can be further substituted with C$_1$–C$_{12}$-alkyl and one or more halo groups;
(4) —C$_2$–C$_4$-alkynyl, which can be further substituted with C$_1$–C$_{12}$-alkyl and one or more halo groups;
(5) aryl, which can be further substituted with C$_1$–C$_{12}$-alkyl and one or more halo groups;
(6) CHO;
(7) —CO$_2$H;
(8) —CN;
(9) —CO$_2$R$^{10}$, wherein R$^{10}$ is as previously defined;
(10) —C(O)NR$^{11}$R$^{12}$, wherein R$^{11}$ and R$^{12}$ are as previously defined;
(11) —C(O)R$^9$ wherein R$^9$ is as previously defined; and
(12) thioester;
  with the proviso that in formula II, when Z is amino or substituted amino, then Ra can not be —CH$_2$OH, —NR$^4$R$^6$, or —(CH2)n NR$^4$R$^6$, wherein R$^4$ and R$^6$ are selected from the group consisting of hydrogen, loweralkyl and aralkyl;

Rb is hydrogen, halogen or C$_1$–C$_{12}$-alkyl which can be further substituted by one or more halo groups, or Rb can be taken together with V to form a double bond;

Rc is hydrogen or a hydroxy protecting group;

Rd is selected from the group consisting of
(1) C$_1$–C$_{12}$-alkyl,
(2) C$_1$–C$_{12}$-alkyl substituted with one or more substituents selected from the group consisting of
  (a) halogen,
  (b) hydroxy, and
  (c) C$_1$–C$_3$-alkoxy,
(3) C$_3$–C$_7$-cycloalkyl,
(4) C$_2$–C$_4$-alkenyl, and
(5) C$_2$–C$_4$-alkynyl;

Re is hydroxyl, amino, or alkylamino, provided that when Ra is hydroxymethyl then Re is not hydroxy; or Re and Ra may be taken together to form an epoxide, a carbonyl, an olefin, or a substituted olefin; or Re and Ra when taken together with the atom to which they are attached form a spiro ring consisting of C$_3$–C$_7$-carbocyclic, carbonate or carbamate wherein the nitrogen atom can be unsubstituted or substituted with an alkyl group; or Re and T when taken together with the carbon atoms to which they are attached form a ring of the structure:

wherein L is methylene or carbonyl and P is —O—, —NH— or —NR$^1$— wherein R$^1$ is as previously defined; provided that when L is methylene, T is —O— and P is —O—;

Rg is hydrogen, R where R is as previously defined; or Rg may be taken together with Y, separated by a linker of the formula —C(=O)— or —C(CH$_3$)$_2$—, to form a cyclic moiety;

Rh is selected from the group consisting of
(1) hydrogen,
(2) —ORj, where Rj is hydrogen or a hydroxy protecting group,
(3) halogen,
(4) OC(O)NHRi wherein Ri is selected from a group consisting of
  (a) C$_1$–C$_4$ alkyl,
  (b) C$_1$–C$_4$ aminoalkyl where the amino group is substituted with one or two groups selected from
    (i) C$_1$–C$_4$ alkyl,
    (ii) C$_1$–C$_4$ alkyl substituted with halogen,
    (iii) C$_1$–C$_4$ alkyl substituted with alkoxy,
    (iv) C$_1$–C$_4$ alkyl substituted with hydroxyl,
    (v) C$_1$–C$_4$ alkyl substituted with aryl,
    (vi) C$_1$–C$_4$ alkyl substituted with substituted aryl,
    (vii) C$_1$–C$_4$ alkyl substituted with heteroaryl,
    (viii) C$_1$–C$_4$ alkyl substituted with substituted heteroaryl,
    (ix) C$_3$–C$_6$ cycloalkyl; and A, B, D, and E are independently selected from the group consisting of:
(1) hydrogen;
(2) C$_1$–C$_6$-alkyl optionally substituted with one or more substituents selected from the group consisting of:
  (a) aryl,
  (b) substituted aryl,
  (c) heteroaryl,
  (d) substituted heteroaryl,
  (e) heterocycloalkyl,
  (f) hydroxy,
  (g) C$_1$–C$_6$-alkoxy,
  (h) halogen selected from the group consisting of Br, Cl, F or I, and (i) NR⁷R⁸ where $R^7$ and $R^8$ are as previously defined;
(3) $C_3$–$C_7$-cycloalkyl;
(4) aryl;
(5) substituted aryl;
(6) heteroaryl;
(7) substituted heteroaryl;
(8) heterocycloalkyl; and
(9) a group selected from option (2) above further substituted with —M—$R^9$, wherein M and $R^9$ are as previously defined; or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2, —C(O)—NH, —C(O)—NR$^{12}$, wherein $R^{12}$ is as previously defined, —NH—C(O)—, —NR$^{12}$—C(O)—, wherein $R^{12}$ is as previously defined, and —C(=NH)—NH—;

with the provision that at least two of A, B, D, and E are hydrogen;

or a pharmaceutically acceptable salt, ester or prodrug thereof.

2. A compound of claim 1 having the formula (III):

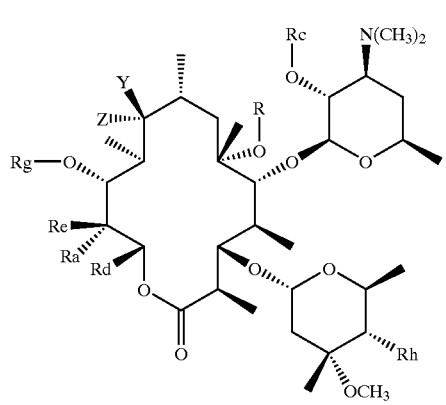

(III)

or a pharmaceutically acceptable salt, ester or prodrug thereof.

3. A compound of claim 1 having the formula (IV):

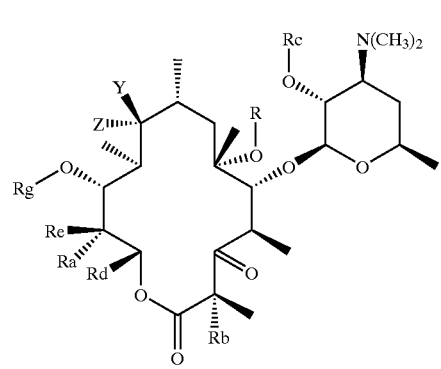

(IV)

or a pharmaceutically acceptable salt, ester or prodrug thereof.

4. A compound of claim 1 having the formula (V):

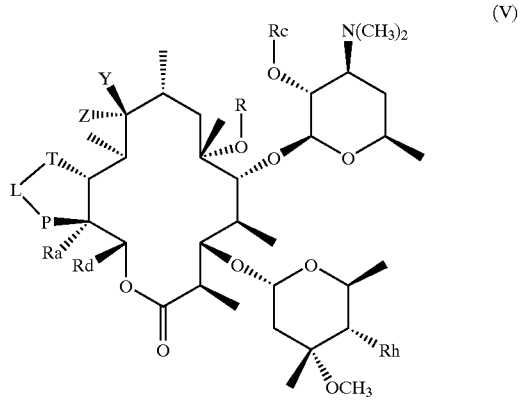

(V)

or a pharmaceutically acceptable salt, ester or prodrug thereof.

5. A compound of claim 1 having the formula (VI):

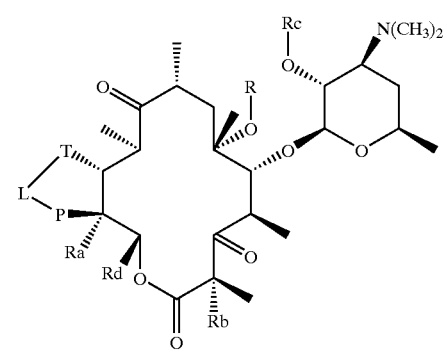

(VI)

or a pharmaceutically acceptable salt, ester or prodrug thereof.

6. A compound of claim 1 having the formula (VII):

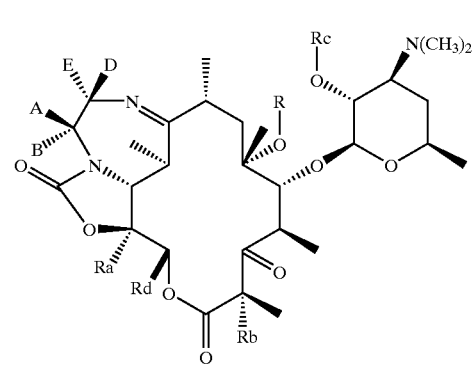

(VII)

or a pharmaceutically acceptable salt, ester or prodrug thereof.

7. A compound of claim 1 having formula (VIII):

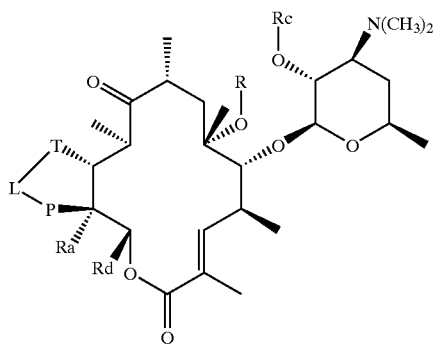

(VIII)

or a pharmaceutically acceptable salt, ester or prodrug thereof.

8. A compound of claim 1 wherein Ra is hydrogen, substituted or unsubstituted $C_1$–$C_{12}$-alkyl, $C_2$–$C_4$-akenyl, —$C_2$–$C_4$-alkynyl, aryl or thioester; X is =O; L is CO; P is =O; T is NH or N(W—Rf) wherein W is absent or is selected from the group consisting of —O—, NH—CO—, —N=CH— and —NH—, and Rf is an alkyl or substituted alkyl group, which may be further substituted by a heteroaryl selected from the group consisting of

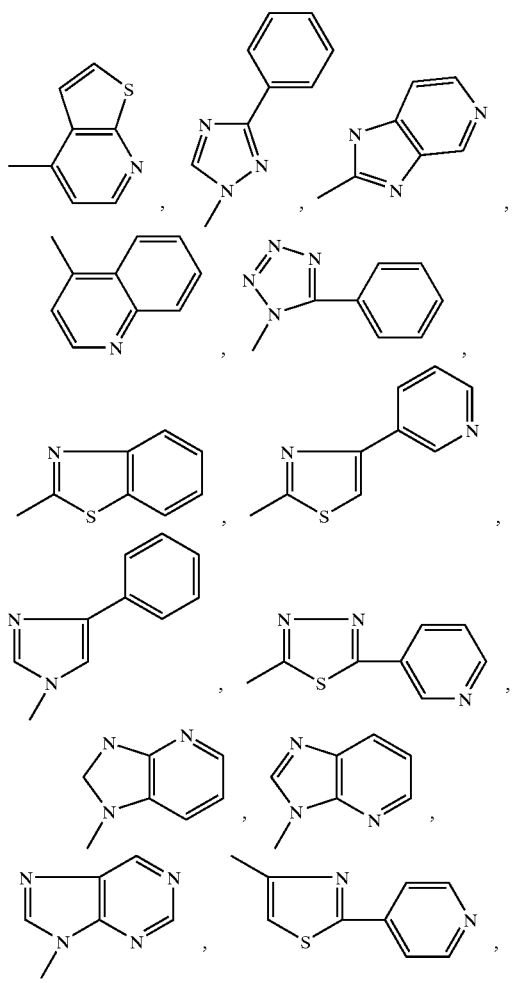

-continued

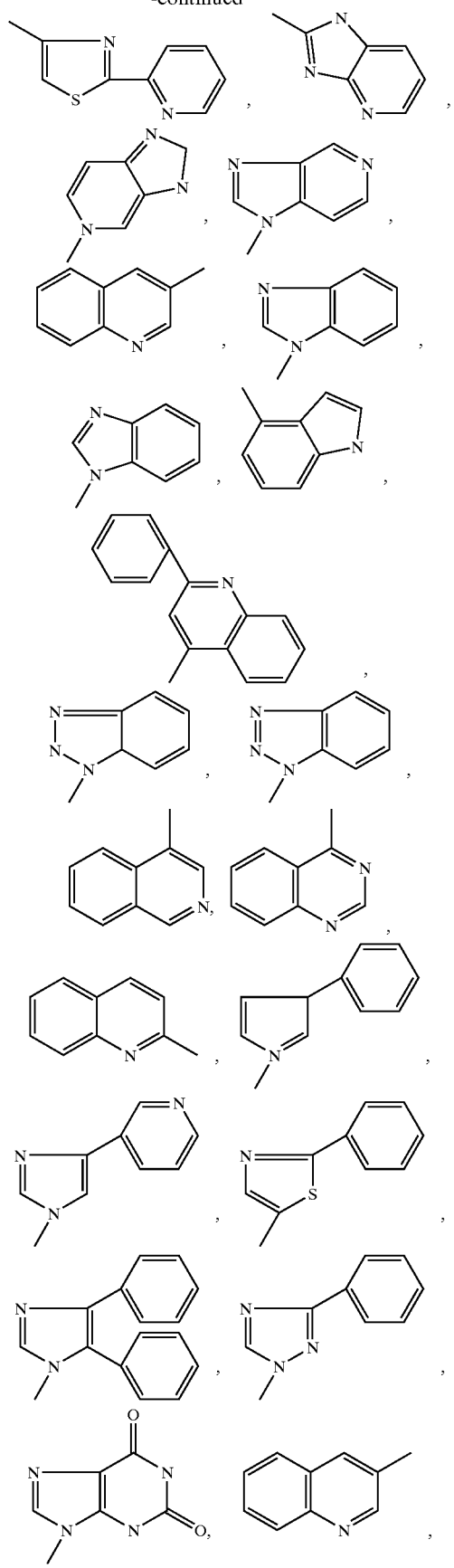

A, B, D, and E are H; and R is selected from the group consisting of methyl, allyl, propyl, —CH₂CHO, —CH₂CH=NOH, —CH₂CH=NOH, —CH₂CN, —CH₂CH₂NH₂, —CH₂CH₂NHCH₂-phenyl, —CH₂CH₂NHCH₂CH₂-phenyl, —CH₂CH₂—NHCH—(CO₂CH₃)CH₂-phenyl, —CH₂CH₂NHCH₂-(4-pyridyl), —CH₂CH₂NHCH₂-(4-quinolyl), —CH₂CH=CH-phenyl, —CH2CH2CH2-phenyl, —CH₂CH=CH-(4-methoxyphenyl), —CH₂CH=CH-(4-chlorophenyl), —CH₂CH=CH-(3-quinolyl), —CH₂CH₂CH₂OH, —CH₂C(O)OH, —CH₂CH₂ HCH₃, —CH₂CH₂NHCH₂OH, —CH₂CH₂N(CH₃)₂, —CH₂CH₂(1-morpholinyl), —CH₂C(O)NH₂, —CH₂NHC(O)NH₂, —CH₂NHC(O)CH₃, —CH₂F, —CH₂CH₂OCH₃, —CH₂CH₃, —CH₂CH=CH(CH₃)₂, —CH₂CH₂CH(CH₃)CH₃, —CH₂CH₂OCH₂CH₂OCH₃, —CH₂SCH₃, -cyclopropyl, —CH₂OCH₃, —CH₂CH₂F, —CH₂-cyclopropyl, —CH₂CH₂CHO, —C(O)CH₂CH₂CH₃, —CH₂-(4-nitrophenyl), —CH₂-(4-chlorophenyl), —CH₂-(4-methoxyphenyl), —CH₂-(4-cyanophenyl), —CH₂CH=CHC(O)OCH₃, —CH₂CH=CHC(O)OCH₂CH₃, —CH₂CH=CHCH₃, —CH₂CH=CHCH₂CH₃, —CH₂CH=CHCH₂CH₂CH₃, —CH₂CH=HSO₂-phenyl, —CH₂C≡C—Si(CH₃)₃, —CH₂C≡CCH₂CH₂CH₂CH₂CH₃, —CH₂C≡CCH₃, —CH₂-(2-pyridyl), —CH₂-(3-pyridyl), —CH₂-(4-pyridyl), —CH₂-(4-quinolyl), —CH₂NO₂, —CH₂C(O)OCH₃, —CH₂C(O)-phenyl, —CH₂C(O)CH₂CH₃, —CH₂Cl, —CH₂S(O)₂-phenyl, —CH₂CH=CHBr, —CH₂CH=CH-(4-quinolyl), —CH₂CH₂CH₂-(4-quinolyl), —CH₂CH=CH-(5-quinolyl), —CH₂CH₂CH₂-(5-quinolyl), —CH₂CH=CH-(4-benzoxazolyl), —CH₂CH=CH-(7-benzimidazolyl), —CH₂-(3-iodophenyl), —CH₂-(2-naphthyl), —CH₂—CH=CH-(4-fluorophenyl) and —CH₂—CH(OH)—CN, —CH₂CH=CH-(quinoxalin-6-yl),—CH₂CH=CH-([1,8]-naphthyridin-3-yl), —CH₂CH=CH-([1,5]-naphthyridin-3-yl), —CH₂CH=CH-(5-pyridin-2-yl-thiophen-2-yl), —CH₂CH=CH-(5-pyridin-3-yl-thiophen-2-yl), —CH₂CH=CH-(5-(6-methylpyridin-3-yl)-thiophen-2-yl), —CH₂CH=CH-(5-thiazol-2-yl-thiophen-2-yl), —CH₂CH=CH-(5-thiazol-5-yl-thiophen-2-yl), —CH₂CH=CH-(5-pyrimidin-2-yl-thiophen-2-yl), —CH₂CH=CH-(5-pyrazin-2-yl-thiophen-2-yl), —CH₂C≡C-(quinolin-3-yl), —CH₂C≡C-(quinoxalin-6-yl), —CH₂C≡C-([1,8]-naphthyridin-3-yl), —CH₂C≡C-([1,5]-naphthyridin-3-yl), —CH₂C≡C-(5-pyridin-2-yl-thiophen-2-yl), —CH₂C≡C-(5-pyridin-3-yl-thiophen-2-yl), —CH₂C≡C-(5-(6-methylpyridin-3-yl)-thiophen-2-yl), —CH₂C≡C-(5-thiazol-2-yl-thiophen-2-yl), —CH₂C≡C-(5-thiazol-5-yl-thiophen-2-yl), —CH₂C≡C-(5-pyrimidin-2-yl-thiophen-2-yl), or —CH₂C≡C-(5-pyrazin-2-yl-thiophen-2-yl); or a pharmaceutically acceptable salt, ester or prodrug thereof.

9. A pharmaceutical composition comprising a therapeutically effective amount of a compound of claim 1, together with a pharmaceutically acceptable carrier.

10. A method of treating a bacterial infection in a mammal in need of such treatment comprising administering to the mammal an antibacterially effective amount of a compound of claim 1 together with a pharmaceutically acceptable carrier.

* * * * *